US009845466B2

(12) United States Patent
Lim et al.

(10) Patent No.: US 9,845,466 B2
(45) Date of Patent: *Dec. 19, 2017

(54) SINGLE-STRANDED RNAI AGENTS CONTAINING AN INTERNAL, NON-NUCLEIC ACID SPACER

(71) Applicant: SIRNA THERAPEUTICS, INC., Cambridge, MA (US)

(72) Inventors: Lee Lim, San Francisco, CA (US); Guillaume Chorn, San Francisco, CA (US); Aarron T. Willingham, San Francisco, CA (US); Lihong Zhao, Walnut Creek, CA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/967,974

(22) Filed: Dec. 14, 2015

(65) Prior Publication Data

US 2016/0222381 A1 Aug. 4, 2016

Related U.S. Application Data

(63) Continuation of application No. 13/818,306, filed as application No. PCT/US2011/048338 on Aug. 19, 2011, now Pat. No. 9,243,246.

(60) Provisional application No. 61/376,471, filed on Aug. 24, 2010.

(51) Int. Cl.
  C12N 15/11 (2006.01)
  C12N 15/113 (2010.01)

(52) U.S. Cl.
  CPC ......... *C12N 15/113* (2013.01); *C12N 15/111* (2013.01); *C12N 15/1138* (2013.01); *C12N 2310/14* (2013.01); *C12N 2310/141* (2013.01); *C12N 2310/318* (2013.01); *C12N 2310/3183* (2013.01); *C12N 2310/344* (2013.01); *C12N 2310/351* (2013.01); *C12N 2310/3515* (2013.01); *C12N 2310/3519* (2013.01)

(58) Field of Classification Search
  CPC .................... C12N 15/113; C12N 2310/14
  See application file for complete search history.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,495,009 A | 2/1996 | Matteucci et al. |
| 5,587,471 A | 12/1996 | Cook et al. |
| 5,627,053 A | 5/1997 | Usman et al. |
| 5,631,360 A | 5/1997 | Usman et al. |
| 5,670,633 A | 9/1997 | Cook et al. |
| 5,716,824 A | 2/1998 | Beigelman et al. |
| 5,804,683 A | 9/1998 | Usman et al. |
| 5,831,071 A | 11/1998 | Usman et al. |
| 5,898,031 A | 4/1999 | Crooke |
| 5,968,909 A | 10/1999 | Agrawal et al. |
| 5,994,517 A | 11/1999 | Ts'o et al. |
| 5,998,203 A | 12/1999 | Matulic-Adamic et al. |
| 6,005,087 A | 12/1999 | Cook et al. |
| 6,107,094 A | 8/2000 | Crooke |
| 6,117,657 A | 9/2000 | Usman et al. |
| 6,248,878 B1 | 6/2001 | Matulic-Adamic et al. |
| 6,348,312 B1 | 2/2002 | Peyman et al. |
| 6,353,098 B1 | 3/2002 | Usman et al. |
| 6,395,713 B1 | 5/2002 | Beigelman et al. |
| 6,437,117 B1 | 8/2002 | Usman et al. |
| 6,469,158 B1 | 10/2002 | Usman et al. |
| 6,528,631 B1 | 3/2003 | Cook et al. |
| 6,906,182 B2 | 6/2005 | Ts'o et al. |
| 7,022,828 B2 | 4/2006 | McSwiggen |
| 7,056,704 B2 | 6/2006 | Tuschl et al. |
| 7,078,196 B2 | 7/2006 | Tuschl et al. |
| 7,109,165 B2 | 9/2006 | Matulic-Adamic et al. |
| 7,262,177 B2 | 8/2007 | Ts'O et al. |
| 7,425,544 B2 | 9/2008 | Dobie et al. |
| 7,432,249 B2 | 10/2008 | Crooke |
| 7,491,805 B2 | 2/2009 | Vargeese et al. |
| 7,833,992 B2 | 11/2010 | Vargeese et al. |
| 7,858,625 B2 | 12/2010 | Matulic-Adamic et al. |
| 7,923,547 B2 | 4/2011 | McSwiggen et al. |

(Continued)

FOREIGN PATENT DOCUMENTS

| | | |
|---|---|---|
| WO | 9207065 A1 | 4/1992 |
| WO | 9315187 A1 | 8/1993 |
| WO | 9323569 A1 | 11/1993 |
| WO | 9401550 A1 | 1/1994 |
| WO | 9402595 A1 | 2/1994 |
| WO | 9504142 A2 | 2/1995 |
| WO | 9511304 A1 | 4/1995 |
| WO | 9511910 A1 | 5/1995 |
| WO | 9618736 A2 | 6/1996 |
| WO | 9726270 A2 | 7/1997 |

(Continued)

OTHER PUBLICATIONS

Bartel, "MicroRNAs: Genomics, Biogenesis, Mechanism, and Function", Cell, vol. 116, pp. 281-297, (2004).
Boffa, et al., Gene Therapy and Molecular Biology, vol. 5, pp. 47-53 (2000), "PNA (peptide nucleic acid) anti-gene/antisense can access intact viable cells and downregulate target genes".
Extended European Search Report from European Application No. 11820420.5 dated Oct. 20, 2014.
Hall et al., "High Potency Silencing by Single-Stranded Boranophosphate siRNA", Nucleic Acids Research, vol. 34, No. 9, May 22, 2006, pp. 2773-2781.

(Continued)

*Primary Examiner* — Brian Whiteman
(74) *Attorney, Agent, or Firm* — Lando & Anastasi, LLP

(57) ABSTRACT

Single-stranded RNA molecules comprise one or more internal, non-nucleotide spacers, covalently linked with nucleotide portions of the molecule are provided. The single-stranded RNA molecules function as guide or antisense strands that are capable of inhibiting gene expression via an RNA interference mechanism, and thus represent single-stranded RNAi agents. The single-stranded RNAi molecules can be used in methods for a variety of therapeutic, diagnostic, target validation, genomic discovery, genetic engineering, and pharmacogenomic applications.

26 Claims, 10 Drawing Sheets

(56) References Cited

U.S. PATENT DOCUMENTS

| | | | |
|---|---|---|---|
| 7,935,812 B2 | 5/2011 | McSwiggen et al. | |
| 7,956,176 B2 | 6/2011 | McSwiggen et al. | |
| 7,964,578 B2 | 6/2011 | Vargeese et al. | |
| 7,989,612 B2 | 8/2011 | McSwiggen et al. | |
| 8,188,247 B2 | 5/2012 | Beigelman et al. | |
| 8,202,979 B2 | 6/2012 | McSwiggen et al. | |
| 8,232,383 B2 | 7/2012 | McSwiggen et al. | |
| 8,236,944 B2 | 8/2012 | Beigelman et al. | |
| 8,242,257 B2 | 8/2012 | Beigelman et al. | |
| 8,268,986 B2 | 9/2012 | Beigelman et al. | |
| 8,273,866 B2 | 9/2012 | McSwiggen et al. | |
| 8,314,227 B2 | 11/2012 | Wengel | |
| 8,329,463 B2 | 12/2012 | Tuschl et al. | |
| 8,362,231 B2 | 1/2013 | Tuschl et al. | |
| 8,372,968 B2 | 2/2013 | Tuschl et al. | |
| 8,394,628 B2 | 3/2013 | Tuschl et al. | |
| 8,420,391 B2 | 4/2013 | Tuschl et al. | |
| 8,445,237 B2 | 5/2013 | Tuschl et al. | |
| 8,461,313 B2 | 6/2013 | Matulic-Adamic et al. | |
| 8,552,171 B2 | 10/2013 | Tuschl et al. | |
| 8,618,277 B2 | 12/2013 | Beigelman et al. | |
| 8,632,997 B2 | 1/2014 | Tuschl et al. | |
| 8,648,185 B2 | 2/2014 | McSwigen et al. | |
| 8,742,092 B2 | 6/2014 | Tuschl et al. | |
| 8,765,930 B2 | 7/2014 | Tuschl et al. | |
| 8,778,902 B2 | 7/2014 | Tuschl et al. | |
| 8,790,922 B2 | 7/2014 | Tuschl et al. | |
| 8,796,016 B2 | 8/2014 | Tuschl et al. | |
| 8,846,894 B2 | 9/2014 | McSwiggen et al. | |
| 9,243,246 B2 * | 1/2016 | Lim | C12N 15/113 |
| 2003/0148507 A1 * | 8/2003 | Fosnaugh | C12N 15/113 435/320.1 |
| 2004/0029275 A1 | 2/2004 | Brown et al. | |
| 2007/0213292 A1 | 9/2007 | Stoffel et al. | |
| 2008/0311040 A1 | 12/2008 | Berry et al. | |
| 2010/0159591 A1 | 6/2010 | Ford et al. | |
| 2010/0215642 A1 | 8/2010 | Lan et al. | |
| 2011/0082186 A1 | 4/2011 | Agrawal et al. | |
| 2012/0107272 A1 | 5/2012 | Manoharan et al. | |

FOREIGN PATENT DOCUMENTS

| | | |
|---|---|---|
| WO | 1997046570 A1 | 12/1997 |
| WO | 9828317 A2 | 7/1998 |
| WO | 9905094 A1 | 2/1999 |
| WO | 199929350 A1 | 6/1999 |
| WO | 9954459 A2 | 10/1999 |
| WO | 9955857 A2 | 11/1999 |
| WO | 9966063 A2 | 12/1999 |
| WO | 200044895 A1 | 8/2000 |
| WO | 0116312 A2 | 3/2001 |
| WO | 200153528 A1 | 7/2001 |
| WO | 0210378 A2 | 2/2002 |
| WO | 0222636 A1 | 3/2002 |
| WO | 02055692 A3 | 7/2002 |
| WO | 02055693 A2 | 7/2002 |
| WO | 2002081494 A1 | 10/2002 |
| WO | 2002094185 A2 | 11/2002 |
| WO | 02096927 A2 | 12/2002 |
| WO | 03070193 A2 | 8/2003 |
| WO | 03070887 A2 | 8/2003 |
| WO | 03070896 A2 | 8/2003 |
| WO | 03070910 A2 | 8/2003 |
| WO | 2003070197 A2 | 8/2003 |
| WO | 2003070742 A1 | 8/2003 |
| WO | 2003070743 A2 | 8/2003 |
| WO | 2003070744 A1 | 8/2003 |
| WO | 2003070750 A2 | 8/2003 |
| WO | 2003070881 A2 | 8/2003 |
| WO | 2003070884 A2 | 8/2003 |
| WO | 2003070886 A2 | 8/2003 |
| WO | 2003070888 A2 | 8/2003 |
| WO | 2003070895 A2 | 8/2003 |
| WO | 2003070897 A2 | 8/2003 |
| WO | 2003070903 A2 | 8/2003 |
| WO | 2003070911 A2 | 8/2003 |
| WO | 2003070912 A2 | 8/2003 |
| WO | 2003070914 A2 | 8/2003 |
| WO | 2003070917 A2 | 8/2003 |
| WO | 2003070918 A2 | 8/2003 |
| WO | 2003070966 A2 | 8/2003 |
| WO | 2003070968 A2 | 8/2003 |
| WO | 2003070969 A2 | 8/2003 |
| WO | 2003070970 A2 | 8/2003 |
| WO | 2003070972 A2 | 8/2003 |
| WO | 2003070983 A1 | 8/2003 |
| WO | 03072590 A1 | 9/2003 |
| WO | 2003072704 A2 | 9/2003 |
| WO | 2003072705 A2 | 9/2003 |
| WO | 2003074654 A2 | 9/2003 |
| WO | 03080638 A2 | 10/2003 |
| WO | 2003106476 A1 | 12/2003 |
| WO | 2004014933 A1 | 2/2004 |
| WO | 2004015107 A2 | 2/2004 |
| WO | 04043977 A2 | 5/2004 |
| WO | 04090105 A2 | 10/2004 |
| WO | 2004097020 A2 | 11/2004 |
| WO | 2005019453 A2 | 3/2005 |
| WO | 2005028649 A1 | 3/2005 |
| WO | 2005028650 A2 | 3/2005 |
| WO | 2005041859 A2 | 5/2005 |
| WO | 2005044981 A2 | 5/2005 |
| WO | 2005045034 A2 | 5/2005 |
| WO | 2005078097 A2 | 8/2005 |
| WO | 2005089268 A2 | 9/2005 |
| WO | 2006102970 A2 | 10/2006 |
| WO | 2007022369 A2 | 2/2007 |
| WO | 2008147824 A2 | 12/2008 |
| WO | 2009073809 A2 | 6/2009 |
| WO | 2009082606 A2 | 7/2009 |
| WO | 2009082607 A2 | 7/2009 |
| WO | 2010006237 A2 | 1/2010 |
| WO | 2010048585 A2 | 4/2010 |
| WO | 2010093705 A2 | 8/2010 |
| WO | 2011028550 A1 | 3/2011 |
| WO | 2011031520 A1 | 3/2011 |
| WO | 2011133876 A2 | 10/2011 |
| WO | 2012068187 A1 | 5/2012 |
| WO | 2013074974 A2 | 5/2013 |
| WO | 2013165816 A2 | 11/2013 |

OTHER PUBLICATIONS

Holen, T et al., Nucleic Acids Research, vol. 31, No. 9, pp. 2401-2407 (2003), "Similar behaviour of single-strand and double-strand siRNAs suggests they act through a common RNAi pathway".

Iwase et al., "Synthesis of Modified Double Stranded RNAs Containing Duplex Regions Between Amide-Linked RNA and RNA at Both Ends and Enhanced Nuclease Resistance", Nucleic Acids Symposium Series No. 53, pp. 119-120 (2009).

Martinez, J et al., Cell, vol. 110, pp. 563-574 (2002), "Single-stranded antisense siRNAs guide target RNA cleavage in RNAi".

Pils, W et al., Nucleic Acids Research, vol. 28, No. 9, pp. 1859-1863 (2000), "Flexible non-nucleotide linkers as loop replacements in short double helical RNAs".

Reynolds, Ma et al., Nucleic Acids Research, vol. 24, No. 4, pp. 760-765 (1996), "Antisense oligonucleotides containing an internal, non-nucletide-based linker promote site-specific cleavage of RNA".

Tijsterman et al., "RNA Helicase MUT-14-Dependent Gene Silencing Triggered in C. elegans by Short Antisense RNAs", Science, vol. 295, (2002).

Ueno et al., "Effect of Incorporation of Alkyl Linkers into siRNAs on RNA Interference", Bioorganic & Medicinal Chemistry Letters, vol. 19, No. 3, Feb. 1, 2009, pp. 875-877.

* cited by examiner

SINGLE-STRANDED RNAI AGENTS CONTAINING AN INTERNAL, NON-NUCLEIC ACID SPACER

CROSS-REFERENCE TO RELATED APPLICATIONS

This application is a continuation of U.S. patent application Ser. No. 13/818,306, filed Aug. 19, 2011, which is a National Stage Entry of PCT Application No. PCT/US2011/048338, filed Aug. 19, 2011 which claims the benefit of U.S. Provisional Application No. 61/376,471, filed Aug. 24, 2010. Each of these prior applications is incorporated herein by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "SIRMIS00133USPCT-SEQLIST-22FEB2013.TXT", creation date of Feb. 14, 2013, and a size of 212 KB. This sequence listing submitted by EFS-Web is part of the specification and is herein incorporated by reference in its entirety.

BACKGROUND OF THE INVENTION

The RNA interference (RNAi) pathway is an evolutionarily conserved mode of gene regulation. The RNAi process is initiated by double-stranded RNA (dsRNA) produced from various exogenous or endogenous sources (e.g., experimental introduction, viral infection). The dsRNA is cleaved by Dicer to generate 20-25 nucleotide small-interfering RNA (siRNA) duplexes. These duplexes are then loaded onto the RNA-induced silencing complex (RISC), and before RISC is activated, the passenger/sense strand of the duplex is removed. The single guide/antisense strand remains associated with RISC and directs cleavage of the target mRNA. Thus, duplexed siRNA have become an important tool for both research and nucleic acid-based therapeutics.

RNAi gene silencing can occur via single-stranded or double-stranded RNA molecules. In the last ten years, it has been reported that single-stranded antisense siRNA are almost as potent as the siRNA duplex (see, e.g., Schwarz et al., 2002, *Mol. Cell.* 10:537-548; Martinez et al., 2002, *Cell* 110:563-574; Amarzguioui et al., 2003, *Nucleic Acids Res.* 31:589-595; and Holen et al., 2003, *Nucleic Acids Res.* 31:2401-2407). There are benefits in utilizing single-stranded RNA molecules, as opposed to duplexed versions, for gene silencing. Their lower molecule weight may make them easier to cross cell membranes. Single-stranded RNA molecules are also half the mass and volume of duplexed siRNA, implicating a manufacturing cost advantage. Thus, there remains a heightened interest in formulating new and advantageous design features suitable for single-stranded RNAi molecules.

SUMMARY OF THE INVENTION

The instant disclosure provides single-stranded RNA molecules which comprise: (a) a nucleic acid portion comprising two or more nucleotide portions, and (b) an internal (as opposed to "terminal") spacer portion comprising one or more non-nucleotide spacer portions, wherein a non-nucleotide spacer portion covalently links two nucleotide portions of the molecule. The nucleotide portions of the single-stranded RNA molecules of the invention are not complementary to each other and, thus, said portions do not form base pairs. The single-stranded RNA molecules of the invention function as guide or antisense strands that are capable of inhibiting gene expression via an RNA interference mechanism and, thus, represent single-stranded RNAi agents.

A single-stranded RNAi molecule of the invention has a single-stranded oligonucleotide structure and mediates RNA interference against a target RNA. A single-stranded RNAi molecule comprises: (a) a nucleic acid portion comprising a first nucleotide portion (N1) and a second nucleotide portion (N2), wherein said nucleic acid portion comprises at least 8 nucleotides that can base pair with a target RNA, and wherein the total number of nucleotides within the nucleic acid portion is from 8 to 26 nucleotides; and, (b) an internal spacer portion comprising at least a first non-nucleotide spacer portion (S1) that covalently links the first and second nucleotide portions. The first and second nucleotide portions are not self complementary. The total number of nucleotides of a single-stranded RNAi molecule of the invention (e.g., 8 to 26) is distributed between the nucleotide portions of the molecule, wherein each nucleotide portion contains at least one nucleotide.

In one embodiment, the nucleic acid portion of a single-stranded RNAi molecule of the invention contains two nucleotide portions, referred to as the first nucleotide portion (N1) and the second nucleotide portion (N2). The first and second nucleotide portions of an RNAi molecule of the invention are covalently attached to a non-nucleotide spacer portion of the molecule. In another embodiment, the nucleic acid portion of a single-stranded RNAi molecule of the invention contains more than one nucleotide portion (e.g., 3, 4, or 5, referred to as third (N3), fourth (N4) or fifth (N5) nucleotide portions, respectively).

In one embodiment, the internal spacer portion of a single-stranded RNAi molecule of the invention contains only one non-nucleotide spacer portion, referred to as the first non-nucleotide spacer portion (S1). The first non-nucleotide spacer portion (S1) of an RNAi molecule of the invention is covalently attached to two nucleotides and/or non-nucleotide substitutes, each located within a distinct nucleotide portion of the single-stranded molecule. In another embodiment, the internal spacer portion of a single-stranded RNAi molecule of the invention contains more than one non-nucleotide spacer portion (e.g., 2, 3, or 4, referred to as second (S2), third (S3) or fourth (S4) non-nucleotide spacer portions, respectively).

A single-stranded RNAi molecule of the invention comprises a nucleotide sequence that is partially, substantially or perfectly complementary to an RNA target site in a cell.

In one embodiment, a single-stranded RNAi molecule of the invention comprises a nucleotide sequence that is partially, substantially, or perfectly homologous to the guide strand of a naturally-occurring miRNA and, thus, functions as a miRNA mimetic. A single-stranded miRNA mimetic of the invention is designed based on a corresponding, naturally-occurring miRNA, wherein at least one non-nucleotide spacer portion is either located between two adjacent nucleotides of the naturally-occurring miRNA guide strand sequence or substituted for from one to about 12 internal (i.e., non-terminal) nucleotides of the naturally-occurring miRNA guide strand sequence.

In another embodiment, a single-stranded RNAi molecule of the invention is an analog of either a single-stranded siRNA or the guide/antisense strand of a duplex siRNA, wherein the single-stranded RNAi molecule comprises a sequence that is partially, substantially, or perfectly homologous to the corresponding single-stranded siRNA or the guide strand of the corresponding duplex siRNA. The corresponding single-stranded siRNA or duplex siRNA may be known to inhibit gene expression via an RNAi mechanism. In this embodiment, the single-stranded RNAi molecule represents a single-stranded siRNA mimetic. A single-stranded siRNA mimetic of the invention is designed based on a corresponding siRNA, wherein at least one non-nucleotide spacer portion is either located between two adjacent nucleotides of the siRNA guide strand sequence or substituted for from one to about 4 nucleotides of the corresponding siRNA guide strand sequence.

A single-stranded RNAi molecule of the invention can comprise substitutions, chemically-modified nucleotides, and non-nucleotides, including substitutions or modifications in the backbone, sugars, bases, or nucleosides. In certain embodiments, the use of substituted or modified single-stranded RNAi molecules of this disclosure can enable achievement of a given therapeutic effect at a lower dose since these molecules may be designed to have an increased half-life in a subject or biological samples (e.g., serum). Furthermore, certain substitutions or modifications can be used to improve the bioavailability of single-stranded RNAi molecules by targeting particular cells or tissues or improving cellular uptake of the single-stranded RNAi molecules.

The internal spacer portion of a single-stranded RNAi molecule of the invention can comprise one or more non-nucleotide spacer portions. A non-nucleotide spacer portion can include any aliphatic or aromatic chemical group that can be further substituted, wherein said spacer portion does not contain a nucleotide. The spacer portion can be substituted with a chemical moiety that provides additional functionality to a single-stranded RNAi molecule. For example, a non-nucleotide spacer portion can be substituted with a moiety that binds specifically to a target molecule of interest or facilitates/enhances cellular delivery of the molecule. In one embodiment of the invention, a non-nucleotide spacer portion includes an alkyl, alkenyl or alkynyl chain of preferably 1 to 20 carbons that can be optionally substituted.

The single-stranded RNAi molecules of the invention are useful reagents, which can be used in methods for a variety of therapeutic, diagnostic, target validation, genomic discovery, genetic engineering, and pharmacogenomic applications. Thus, the prevent invention further includes compositions comprising a single-stranded RNAi molecule of the disclosure and methods for inhibiting expression of one or more corresponding target mRNAs in a cell or organism. This disclosure provides methods and single-stranded RNAi molecule compositions for treating a subject, including a human cell, tissue or individual.

BRIEF DESCRIPTION OF THE DRAWINGS

In FIG. 6A, the inhibition activity shown is against a luciferase reporter with two matches to the miR-124 seed region, representing the miRNA activity of the tested analogs. In FIG. 6B, the inhibition activity shown is against a luciferase reporter with two full-length matches to miR-124, representing the siRNA activity of the tested analogs.

DETAILED DESCRIPTION OF THE INVENTION

A. Terms and Definitions

Figure 1:
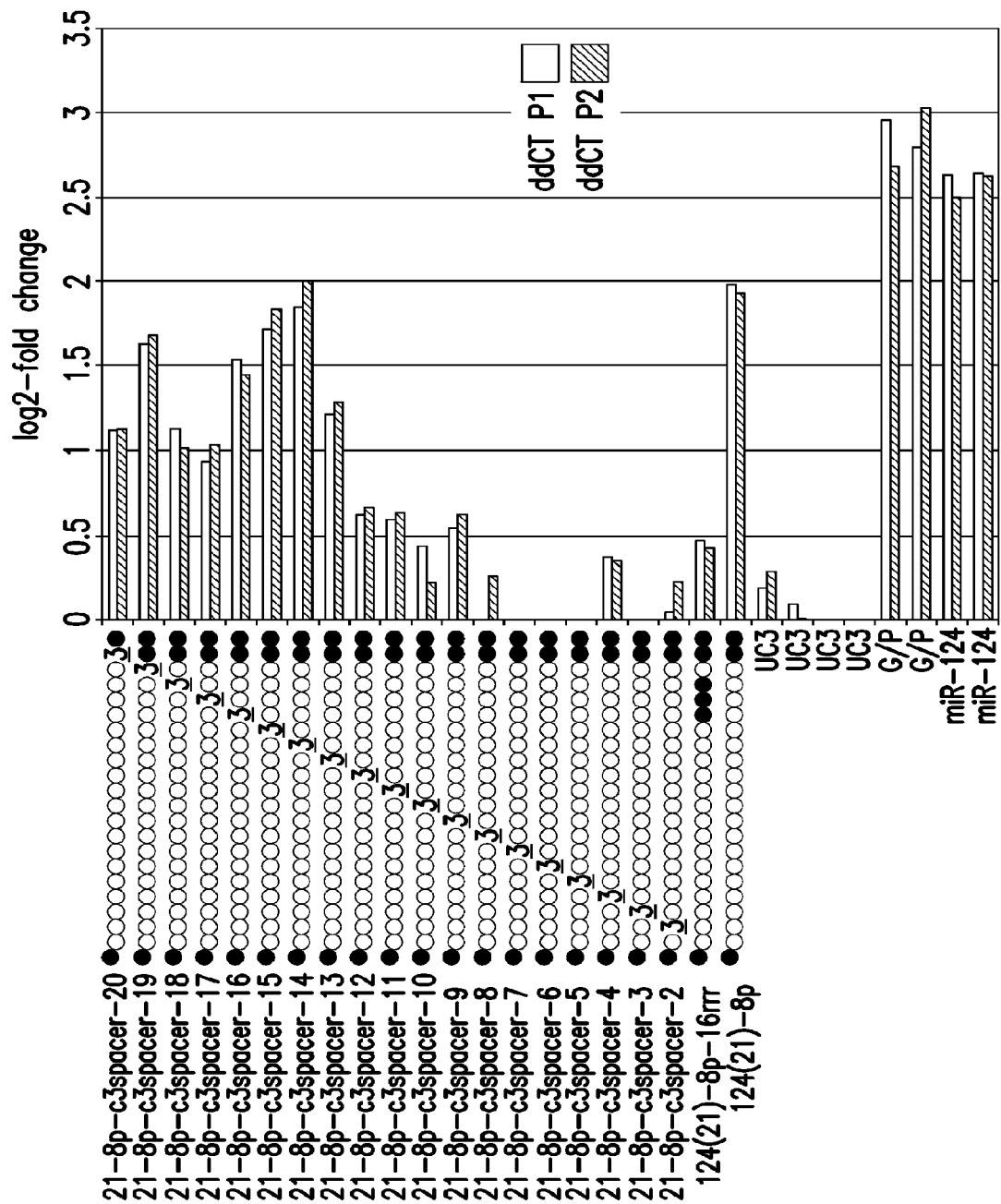
FIG. 1 shows the degree of inhibition of VAMP3 target expression by single-stranded miR-124 analogs containing a C3 spacer using a RT-qPCR assay. The structure and sequence of the analogs are specifically described in Table 2, infra. In the schematic drawings of the miR-124 analogs, the circles represent nucleotides, with the exception of the black circle located at the 5' terminus which represents a 5' phosphate. The open circles represent 2'-deoxy-2'-fluoro nucleotides. The black circles located at the 3' terminus of the schematics represent 2'-O-methyl nucleotides, and the "3" represents the location of the C3 spacer. In the schematic of the "124(21)-8p-16rrr" analog, the three internal black circles represent unmodified ribonucleotides. The longer bars in the graph indicate greater knockdown, and duplicate bars indicate biological replicates.

The following terminology and definitions apply as used in the present application.

As used in this specification and the appended claims, the singular forms "a," "an" and "the" include plural referents unless the content clearly dictates otherwise. Thus, for example, reference to "a cell" includes a combination of two or more cells, and the like.

Any concentration range, percentage range, ratio range, or integer range is to be understood to include the value of any integer within the recited range, and when appropriate, fractions thereof (such as one tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

As used herein, the terms "including" (and any form thereof, such as "includes" and "include), "comprising" (and any form thereof, such as "comprise" and "comprises"), "having" (and any form thereof, such as "has" or "have"), or "containing" (and any form thereof, such as "contains" or "contain") are inclusive and open-ended and do not exclude additional, un-recited elements or method steps.

"Analog" as used herein refers to its meaning as is generally accepted in the art. The term generally refers to a compound or molecule that is structurally similar to a parent compound or molecule (e.g., a nucleotide, a naturally-occurring miRNA), but differs slightly in composition (e.g., one atom or functional group is different, added, or removed). The analog may or may not have different chemical or physical properties than the original parent compound or molecule and may or may not have improved biological or chemical activity. For example, the analog may be more hydrophilic or it may have altered activity of the parent compound/molecule. The analog may be a naturally or non-naturally occurring (e.g., chemically-modified or recombinant) variant of the original parent compound/molecule. An example of an RNA analog is an RNA molecule comprising a nucleotide analog. A nucleotide analog is a nucleotide that is chemically-modified at the sugar, base or nucleoside, as is generally recognized in the art.

As used herein, the term "mimetic" refers to its meaning as is generally accepted in the art. The term generally refers to a molecule that is structurally different from a reference molecule. For example, a reference molecule for purposes of certain embodiments of the present invention can be a naturally-occurring miRNA molecule, or a single-stranded siRNA molecule, that does not contain a non-nucleotide internal spacer. The mimetic is capable of performing one or more or all of the biological, physiological, and/or chemical functions that are within the capabilities of the reference molecule. The mimetic and the reference molecule do not have to be functional equivalents, but the mimetic should be able to perform one or more functions and exhibit at least 5% or more, 10% or more, 20% or more, 30% or more, 40% or more, 50% or more, 60% or more, 70% or more, 80% or more, or 90% or more of the activity of the reference molecule, as measured and compared using assays or parameters that are suitable to represent the shared function(s). The terms "analog" and "mimetic," when describing an RNAi molecule of the disclosure that is structurally different from a reference RNAi molecule, can be used interchangeably.

The term "nucleotide" refers to its meaning as is generally recognized in the art. Nucleotides generally comprise a nucleobase, a sugar, and an internucleoside linkage, e.g., a phosphate. The base can be a natural base (standard), a modified base, or a base analog, as are well known in the art. Such bases are generally located at the 1' position of a nucleotide sugar moiety. Additionally, the nucleotides can be unmodified or modified at the sugar, internucleoside linkage, and/or base moiety (also referred to interchangeably as nucleotide analogs, modified nucleotides, non-natural nucleotides, and non-standard nucleotides); see, for example, U.S. application Ser. No. 12/064,014.

The terms "polynucleotide" and "oligonucleotide" as used herein refer to the meaning as is generally accepted in the art. The terms generally refer to a chain of nucleotides. "Nucleic acids" and "nucleic acid molecules" are polymers of nucleotides. Thus, "nucleic acids," "polynucleotides" and "oligonucleotides" are interchangeable herein. One skilled in the art has the general knowledge that nucleic acids are polynucleotides which can be hydrolyzed into monomeric nucleotides. Monomeric nucleotides can be further hydrolyzed into nucleosides.

By "a contiguous stretch of nucleotides" is meant a continuous series of at least 2 nucleotides. The bonds connecting the nucleotides within the stretch are phosphodiester bonds.

The term "RNA" as used herein refers to its meaning as is generally accepted in the art. The term generally refers to a molecule comprising at least one ribofuranoside residue, such as a ribonucleotide. The term "ribonucleotide" means a nucleotide with a hydroxyl group at the 2' position of a β-D-ribofuranose moiety. The term refers to a double-stranded RNA, a single-stranded RNA, an isolated RNA such as a partially purified RNA, an essentially pure RNA, a synthetic RNA, a recombinantly-produced RNA, or an altered RNA that differs from a naturally-occurring RNA by the addition, deletion, substitution and/or alteration of one or more nucleotides therein. Such alterations can include addition of non-nucleotide material, for example, at one or more non-terminal nucleotides of an RNA molecule. As such, nucleotides in the single-stranded RNA molecules of the invention can comprise non-standard nucleotides, such as non-naturally occurring nucleotides, chemically-synthesized and/or modified nucleotides, or deoxynucleotides. The altered RNA is referred to as a "modified RNA" or a "RNA analog."

The term "pyrimidine" as used herein refers to its meaning as is generally accepted in the art. The term generally refers to conventional pyrimidine bases, including the standard pyrimidine bases uracil, thymidine, and cytosine. In addition, the term pyrimidine is contemplated to embrace non-standard pyrimidine bases or acids, such as 5-methyluracil, 2-thio-5-methyluracil, 4-thiouracil, pseudouracil, dihydrouracil, orotate, 5-methylcytosine, or the like, as well as a chemically-modified bases or "universal bases," which can be used to substitute for a standard pyrimidine within the nucleic acid molecules of this disclosure.

The term "purine" as used herein refers to its meaning as is generally accepted in the art. The term generally refers to conventional purine bases, including the standard purine bases adenine and guanine. In addition, the term "purine" is contemplated to embrace non-standard purine bases or acids, such as $N_2$-methylguanine, inosine, diaminopurine and the like, as well as chemically-modified bases or "universal bases," which can be used to substitute for standard purines herein.

As described herein, a "base pair" can be formed between two nucleotides, a nucleotide and a modified nucleotide, two modified nucleotides, a nucleotide and a nucleotide analog, two nucleotide analogs, a nucleotide and a non-nucleotide substitute moiety, or two non-nucleotide substitute moieties. In a specific embodiment, a non-nucleotide substitute can comprise any chemical moiety that is capable of associating with a component of the cellular RNAi machinery, such as, for example, the PAZ domain, the PIWI domain, and/or other Argonaute protein domains associated with the RISC. Non-traditional Watson-Crick base pairs are also understood as "non-canonical base pairs," which is meant any non-Watson Crick base pair, such as mismatches and/or wobble base pairs, including flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N3-amino(H2), GA sheared, UC 4-carbonyl-amino, UU imino-carbonyl, AC reverse wobble, AU Hoogsteen, AU reverse Watson Crick, CU reverse Watson Crick, GC N3-amino-amino N3, AA N1-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H-N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

As used herein, the term "complementary" (or "complementarity") refers to its meaning as is generally accepted in the art. The term generally refers to the formation or existence of hydrogen bond(s) between one nucleic acid sequence and another nucleic acid sequence by either traditional Watson-Crick or other non-traditional types of bonds as described herein. With reference to exemplary nucleic acid molecules of the invention, complementarity can be found between a single-stranded RNAi of the invention and an RNA target sequence. The binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et at, 1987, *CSH Symp. Quant. Biol.* LII pp. 123-133; Frier et al., 1986, *Proc. Nat. Acad. Sci.* USA 83:9373-9377; Turner et al., 1987, *J. Am. Chem. Soc.* 109:3783-3785).

As used herein, the term "perfectly complementary" (or "perfect complementarity") between a first nucleic acid molecule (e.g., a single-stranded RNAi molecule of the present invention) and the second nucleic acid molecule (e.g., a target RNA sequence) means that all the contiguous residues of the first nucleic acid sequence will hydrogen bond with the same number of contiguous residues in the second nucleic acid sequence. For example, two or more perfectly complementary nucleic acid strands can have the same number of nucleotides (i.e., have the same length and form one double-stranded region with or without an overhang), or have a different number of nucleotides (e.g., one strand may be shorter but fully contained within a second strand). As an example, if a single-stranded RNAi molecule of the invention has a first nucleotide portion of only 1 nucleotide and a second nucleotide portion of 10 contiguous nucleotides, wherein all of the 10 nucleotides in the second nucleotide portion of the molecule base pair with the RNA target sequence, the RNAi molecule is perfectly complementary with the RNA target sequence. The single nucleotide included in the first nucleotide portion is not included when determining the degree of complementarity because it is not within a contiguous chain of nucleotides. However, in this example, if the first nucleotide portion contains 2 nucleotides, the RNAi molecule is perfectly complementary to the RNA target sequence if the 2 nucleotides of the first nucleotide portion and the 10 nucleotides of the second nucleotide portion base pair with the RNA target sequence.

Complementary nucleic acid molecules may have wrongly paired bases—that is, bases that cannot form a traditional Watson-Crick base pair (i.e., forming a hydrogen bond) or other non-traditional types of base pair (i.e., "mismatched" bases, formed or held together by non-traditional forces that are not hydrogen bonds). The term "partially complementary" (or "partial complementarity")

between a first nucleic acid molecule (e.g., a single-stranded RNAi molecule of the present invention) and second nucleic acid molecule (e.g., a target RNA sequence) indicates that various mismatches or non-based paired nucleotides (e.g., 1, 2, 3, 4, 5, 6, 7, 8, 9, 10 or more mismatches or non-based paired nucleotides) occur between the nucleotide sequences, which can result in, for example, in bulges or loops. Such partial complementarity can be represented by a percent (%) complementarity that is determined by the number of base paired nucleotides in relation to the total number of nucleotides involved, e.g., about 50%, 60%, 70%, 80%, 90% etc. For example, a first nucleic acid molecule may have 10 nucleotides and a second nucleic acid molecule may have 10 nucleotides, then base pairing of 5, 6, 7, 8, 9, or 10 nucleotides between the first and second nucleic acid molecules, which may or may not form a contiguous double-stranded region, represents 50%, 60%, 70%, 80%, 90%, or 100% complementarity, respectively. In relation to the present invention, such partial complementarity is permitted to the extent that a single-stranded RNAi molecule of the invention maintains its function, for example the ability to mediate sequence specific RNAi.

A first nucleic acid molecule can be "substantially complementary" to a second nucleic acid. By "substantially complementary" it is meant that a first nucleic acid sequence (e.g., a single-stranded RNAi molecule of the present invention) is at least 50%, 55%, 60%, 65%, 70%, 75%, 80%, 85%, 90%, 95%, 96%, 97%, 98% or 99% complementary to a second nucleic acid sequence (e.g., a RNA target sequence). As used herein, a first nucleic acid molecule can be both "partially complementary" and "substantially complementary" to a second nucleic acid molecule.

As used herein, the term "homologous" (or "homology") refers to its meaning as is generally accepted in the art. The term generally refers to the number of nucleotides of the subject nucleic acid sequence that has been matched to identical nucleotides of a reference nucleic acid sequence, typically as determined by a sequence analysis program (e.g., Karlin and Altschul, 1990, PNAS 87:2264-2268; Karlin and Altschul, 1993, PNAS 90:5873-5877) or by visual inspection. The term "perfect homology" (or "perfectly homologous") as used herein refers to complete (100%) homology or "identity" between a reference sequence and a subject nucleic acid sequence. As used herein, the term "substantially homologous" (or "substantial homology") is meant that the subject sequence shares at least 50% (e.g., at least 55%, 60%, 65%, 70%, 75%, 80%, 85%, 90%, 95%, 96%, 97%, 98% or 99%) homologous nucleotides with the nucleotides of the same nucleotide positions in a reference sequence.

The phrase "chemical modification" as used herein refers to its meaning as is generally accepted in the art. With reference to exemplary nucleic acid molecules of the invention, the term refers to any modification of the chemical structure of the nucleotides that differs from nucleotides of native RNA. The term "chemical modification" encompasses the addition, substitution, or modification of native RNA at the sugar, base, or internucleotide linkage, as described herein or as is otherwise known in the art. In certain embodiments, the teen "chemical modification" can refer to certain forms of RNA that are naturally-occurring in certain biological systems, for example 2'-O-methyl modifications or inosine modifications.

The phrase "modified nucleotide" as used herein refers to its meaning as is generally accepted in the art. The term generally refers a nucleotide that contains a modification in the chemical structure of the base, sugar and/or phosphate of the unmodified (or natural) nucleotide, as is generally known in the art. Non-limiting examples of modified nucleotides are described herein and in U.S. application Ser. No. 12/064,014.

"Percent modification" refers to its meaning as is generally accepted in the art. As used herein, the term generally refers to the number of nucleotides in a single-stranded RNA molecule of the invention that have been modified. The extent of chemical modifications will depend upon various factors well known to one skilled in the art (e.g., target RNA, off-target silencing, degree of endonuclease degradation).

The term "phosphorothioate" refers to its meaning as is generally accepted in the art. The term generally refers to an internucleotide phosphate linkage comprising one or more sulfur atoms in place of an oxygen atom. Hence, the term phosphorothioate refers to both phosphorothioate and phosphorodithioate internucleotide linkages.

As used herein, the term "locked nucleic acid" (LNA) has the structure of the general Formula I:

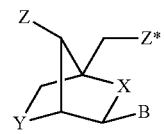

X and Y are independently selected from the group consisting of —O—, —S—, —N(H)—, —N(R)—, —CH$_2$—, or —CH— (if part of a double bond), —CH$_2$—O—, CH$_2$—S—, CH$_2$—N(H)—, —CH$_2$—N(R)—, —CH$_2$—CH$_2$—, and CH$_2$—CH— (if part of a double bond), —CH—CH—, where R is selected from hydrogen and C$_{1-4}$-alkyl; Z and Z* are independently selected from an internucleotide linkage, a terminal group or a protecting group; B constitutes a natural or non-natural nucleobase; and the asymmetric groups may be found in either orientation.

The four chiral centers of Formula I, as shown, are in a fixed configuration, but their configurations are not necessary fixed. As such, the chiral centers can be found in different configurations, such as those represented in Formula II (below). Thus, each chiral center in Formula 1 can exist in either R or S configuration. The definition of R (rectus) and S (sininster) are described in the IUPAC 1974 Recommendations, Section E, Fundamental Stereochemistry: The rules can be found in Pure Appl. Chem. 45, 13-30 (1976) and In "Nomenclature of Organic Chemistry" Pergamon, N.Y., 1979.

The terminal groups are selected independently among from hydrogen, azido, halogen, cyano, nitro, hydroxy, Prot-O-, Act-O-, mercapto, Prot-S-, Act-S-, C$_{1-6}$-alkylthio, amino, Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, monothiophosphate, diphosphate, dithiophosphate triphosphate, trithiophosphate, DNA intercalators, photochemically active groups, thermochemically active groups, chelating groups, reporter groups, ligands, carboxy, sulphono, hydroxymethyl, Prot-O—CH$_2$-, Act-O—CH$_2$—, aminomethyl, Prot-N(R$^H$)—CH$_2$—, Act-N(R$^H$)—CH$_2$—, carboxy methyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl.

The protection groups of hydroxy substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetrahydro-pyranyloxy (mthp), silyloxy such as trimethylsilyloxy (TMS), triisopropylsilyloxy (TIPS)$_7$ tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls.

"Act" designates an activation group for —OH, —SH, and —NH(R$^H$), respectively. Such activation groups are, for example, selected from optionally substituted O-phosphoramidite, optionally substituted O-phosphortriester, optionally substituted O-phosphordiester, optionally substituted H-phosphonate, and optionally substituted O-phosphonate.

B constitutes a natural or non-natural nucleobase and selected among adenine, cytosine, 5-methylcytosine, isocytosine, pseudoisocytosine, guanine, thymine, uracil, 5-bromouracil, 5-propynyluracil, 5-propyny-6-fluoroluracil, 5-methylthiazoleuracil, 6-aminopurine, 2-aminopurine, inosine, diaminopurine, 7-propyne-7-deazaadenine, 7-propyne-7-deazaguanine, and 2-chloro-6-aminopurine.

Preferably, the locked nucleic acid (LNA) used in a single-stranded RNAi molecule of the invention comprises a LNA structure according to any of the Formulas II:

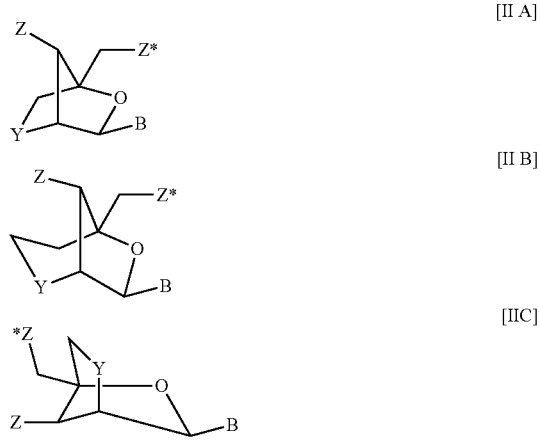

[II A]

[II B]

[IIC]

wherein Y is —O—, —S—, —NH—, or N(R$^H$); Z and Z* are independently selected among an internucleotide linkage, a terminal group or a protecting group; and B constitutes a natural or non-natural nucleobase. These exemplary LNA monomers and others, as well as their preparation are described in WO 99/14226 and subsequent applications, WO 00/56746, WO 00/56748, WO 00/66604, WO 00/125248, WO 02/28875, WO 2002/094250 and WO 2003/006475; the disclosure of all of which are incorporated herein by reference.

The term "universal base" refers to its meaning as is generally accepted in the art. The term generally refers to nucleotide base analogs that form base pairs with each of the standard ANA/RNA bases with little discrimination among them, and is recognized by intracellular enzymes. See, e.g., Loakes et al., 1997, *J. Mol. Bio.* 270:426-435. Non-limiting examples of universal bases include C-phenyl, C-naphthyl and other aromatic derivatives, inosine, azole carbozamides, and nitroazole derivatives such as 3'-nitropyrrole, 4-nitroindole, 5-nitroindole, and 6-nitroindole as known in the art. See, e.g., Loakes, 2001, *Nucleic Acids Res.* 29:2437.

As used herein, the phrase "RNA interference" (also called "RNAi" herein) refers to its meaning as is generally accepted in the art. The term generally refers to the biological process of inhibiting, decreasing, or down-regulating gene expression in a cell, and which is mediated by short interfering nucleic acid molecules (e.g., siRNAs, miRNAs, shRNAs), see for example Zamore and Haley, 2005, *Science* 309:1519-1524; Vaughn and Martienssen, 2005, *Science* 309:1525-1526; Zamore et al., 2000, *Cell* 101:25-33; Bass, 2001, *Nature* 411:428-429; Elbashir et al., 2001, *Nature* 411:494-498; and Kreutzer et al., International PCT Publication No. WO 00/44895; Zernicka-Goetz et al., International PCT Publication No. WO 01/36646; Fire, international PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science* 297:1818-1819; Volpe et al., 2002, *Science* 297:1833-1837; Jenuwein, 2002, *Science* 297:2215-2218; and Hall et al., 2002, *Science* 297:2232-2237; Hutvagner and Zamore, 2002, *Science* 297:2056-60; McManus et al., 2002, *RNA* 8:842-850; Reinhart et al, 2002, *Gene & Dev.* 16:1616-1626; and Reinhart & Bartel, 2002, *Science* 297:1831). Additionally, the term "RNA interference" (or "RNAi") is meant to be equivalent to other terms used to describe sequence-specific RNA interference, such as post-transcriptional gene silencing, translational inhibition, transcriptional inhibition, or epigenetics. For example, single-stranded RNA molecules of the invention can be used to epigenetically silence genes at either the post-transcriptional level or the pre-transcriptional level. In a non-limiting example, epigenetic modulation of gene expression by single-stranded RNA molecules of the invention can result from modification of chromatin structure or methylation patterns to alter gene expression (see, for example, Verdel et al., 2004, *Science* 303:672-676; Pal-Bhadra et al., 2004, *Science* 303:669-672; Allshire, 2002, *Science* 297:1818-1819; Volpe et al., 2002, *Science* 297:1833-1837; Jenuwein, 2002, *Science* 297:2215-2218; and Hall et al., 2002, *Science* 297:2232-2237). In another non-limiting example, modulation of gene expression by single-stranded RNA molecules of the invention can result from cleavage of RNA (either coding or non-coding RNA) via RISC, or via translational inhibition, as is known in the art or modulation can result from transcriptional inhibition (see for example Janowski et al, 2005, *Nature Chemical Biology* 1:216-222).

The terms "inhibit," "down-regulate," "reduce" or "knockdown" as used herein refer to their meanings as are generally accepted in the art. With reference to exemplary single-stranded RNAi molecules of the invention, the terms generally refer to the reduction in the (i) expression of a gene or target sequence and/or the level of RNA molecules encoding one or more proteins or protein subunits, and/or (ii) the activity of one or more proteins or protein subunits, below that observed in the absence of the single-stranded RNAi molecules of the invention. Down-regulation can also be associated with post-transcriptional silencing, such as RNAi-mediated cleavage, or by alteration in DNA methylation patterns or DNA chromatin structure. Inhibition, down-regulation, reduction or knockdown with an RNAi agent can be in reference to an inactive molecule, an attenuated molecule, an RNAi agent with a scrambled sequence, or an RNAi agent with mismatches. The phrase "gene silencing" refers to a partial or complete loss-of-function through targeted inhibition of an endogenous target gene in a cell. As such, the term is used interchangeably with RNAi, "knockdown," "inhibition," "down-regulation," or "reduction" of expression of a target gene.

To determine the extent of inhibition, a test sample (e.g., a biological sample from an organism of interest expressing the target gene(s) or target sequence(s) or a sample of cells in culture expressing the target gene/sequence) can be contacted with an RNAi molecule that silences, reduces, or inhibits expression of a target gene or sequence. Expression of the target gene/sequence in the test sample is compared to expression of the target gene/sequence in a control sample (e.g., a biological sample from an organism of interest expressing the target gene/sequence or a sample of cells in culture expressing the target gene/sequence) that is not contacted with the RNAi molecule. Control samples (i.e., samples expressing the target gene/sequence) are assigned a value of 100%. Silencing, inhibition, or reduction of expression of a target gene/sequence is achieved when the value of the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art, such as dot blots, Northern blots, in situ hybridization, ELBA, microarray hybridization, immunoprecipitation, enzyme function, as well as phenotypic assays known to those of skill in the art.

The phrase "improved RNAi activity" generally refers to an increase in RNAi activity measured in vitro and/or in vivo, where the RNAi activity is a reflection of either or both the ability of the RNAi agent to mediate RNAi and the stability of the RNAi agent.

The term "modulate" as used herein refers to its meaning as is generally accepted in the art. The term generally refers to when the expression of a gene, or level of one or more RNA molecules (coding or non-coding), or activity of one or more RNA molecules or proteins or protein subunits, is up-regulated or down-regulated, such that expression, level, or activity is greater than or less than that observed in the absence of the molecule that effects modulation. For example, the term "modulate" in some embodiments can refer to inhibition and in other embodiments can refer to potentiation or up-regulation, e.g., of gene expression.

The term "RNAi agent" or "RNAi molecule" refers to any nucleic acid molecule capable of inhibiting or down-regulating gene expression or viral replication by mediating RNA interference ("RNAi") or gene silencing in a sequence-specific manner. The RNAi agent can be a double-stranded nucleic acid molecule comprising self-complementary sense (passenger) and antisense (guide) strands, wherein the antisense strand comprises a nucleotide sequence that is complementary to a nucleotide sequence in a target nucleic acid molecule or a portion thereof, and the sense strand comprises a nucleotide sequence corresponding to the target nucleic acid sequence or a portion thereof. An RNAi agent can be a single-stranded polynucleotide. While not wishing to be bound by theory, an RNAi agent may act by one or more of a number of mechanisms, including post-transcriptional cleavage of a target mRNA, or pre-transcriptional or pre-translational mechanisms.

The term "single-stranded RNAi" or "ssRNAi" agent or molecule is an RNAi agent that is a single-stranded, nucleic acid-derived molecule having a nucleotide sequence that is partially, substantially, or perfectly complementary to a nucleotide sequence in a target nucleic acid molecule or a portion thereof. A second nucleotide sequence with which the single-stranded RNAi agent forms base-pairs is not present. A single-stranded RNAi molecule can further comprise a terminal phosphate group located at one or both of the terminal ends, such as a 5'-phosphate or a 5', 3'-diphosphate. An ssRNAi molecule/agent can include a miRNA or a miRNA mimetic. A single-stranded RNAi agent of the invention can be loaded into or otherwise associated with RISC and participate in gene silencing via an RNAi mechanism. A single-stranded RNAi molecule of the invention can comprise substitutions, chemically-modified nucleotides, and non-nucleotides. A single-stranded RNAi molecule of the invention can comprise one or more or all ribonucleotides. Certain embodiments of the invention include single-stranded RNAi molecules that comprise substitutions or modifications in the backbone, sugars, bases, or nucleosides.

The term, "miRNA" or "microRNA" is used herein in accordance with its ordinary meaning in the art and refers to small, non-protein coding RNA molecules that are expressed in a diverse array of eukaryotes, including mammals, and are involved in RNA-based gene regulation. Mature, fully processed miRNAs are about 15 to about 30 nucleotides in length. A representative set of known, endogenous miRNA species is described in the publicly available miRBase sequence database, described in Griffith-Jones et al., *Nucleic Acids Research,* 2004, 32:D109-D111 and Griffith-Jones et al., *Nucleic Acids Research,* 2006, 34:D 140-D144, and accessible on the World Wide Web at the Welcome Trust Sanger Institute website. The mature, fully-processed miRNAs that are publicly available on the miRBase sequence database are each incorporated by reference herein. A representative set of miRNAs is also included herein in Table 1, infra. Each mature miRNA is partially complementary to one or more messenger RNA (mRNA) molecules, which are the targets of the miRNA, thereby regulating the expression of genes associated with the targets.

The term "miRNA mimetic," as used herein, refers to a single-stranded RNA molecule that is a mimetic of a naturally-occurring miRNA in a cell. A miRNA mimetic is typically designed based on a corresponding, endogenous miRNA. A miRNA mimetic is capable of modulating the expression of a target mRNA that is also regulated by a corresponding, naturally-occurring miRNA. A single-stranded RNAi molecule of the present invention that is also a miRNA mimetic can be loaded into or otherwise associated with RISC and participates in gene silencing via an RNAi mechanism. A miRNA mimetic of the invention can comprise substitutions, chemically-modified nucleotides, and non-nucleotides. A miRNA mimetic of the invention can comprise one or more or all ribonucleotides. Certain embodiments of the invention include miRNA mimetics that comprise substitutions or modifications in the backbone, sugars, bases, or nucleosides. A naturally-occurring miRNA in a cell is referred to herein as "the corresponding miRNA," "the endogenous miRNA," or the "naturally-occurring miRNA." A single-stranded miRNA mimetic of the invention that is provided to a cell is also understood to target one or more target mRNAs that are also targeted by a corresponding, naturally-occurring miRNA. It is contemplated that a miRNA mimetic of the present invention introduced to a cell is capable of functioning as a naturally-occurring miRNA under appropriate conditions.

As used herein, the term "seed region" (also referred to herein as a "seed sequence") refers to its meaning as is generally accepted in the art. The term generally refers to at least 6 consecutive nucleotides within nucleotide positions 1 to 10 of the 5'-end of a naturally-occurring mature miRNA, such as one selected from those listed in the publicly available miRBase sequence database (www.mirbase.org) as of the filing date of the present application and/or one selected from those listed in Table 1. The seed sequence nucleotides of positions 1 to 8 are capitalized in the sequences of Table 1. In a naturally-occurring miRNA, the seed region typically determines the target mRNA sequence to which the miRNA may bind and provide gene regulation. As such, multiple naturally-occurring miRNAs can share a seed region or share substantial homology in the seed regions, and these miRNAs are members of the same miRNA family.

The term "siRNA" (also "short interfering RNA" or "small interfering RNA") is given its ordinary meaning accepted in the art, generally referring to a duplex (sense and antisense strands) of complementary RNA oligonucleotides which may or may not comprise 3' overhangs of about 1 to about 4 nucleotides and which mediate RNA interference.

The term "siRNA mimetic" or "single-stranded siRNA mimetic," as used herein, refers to a single-stranded RNAi molecule that is a mimetic of the guide or antisense strand of a corresponding siRNA (either single or double-stranded). A siRNA mimetic is capable of modulating the expression of a target RNA that is also regulated by the corresponding siRNA and, thus, can be loaded into or otherwise associated with RISC and participates in gene silencing via an RNAi mechanism. A single-stranded siRNA mimetic of the invention can comprise substitutions, chemically-modified nucleotides, and non-nucleotides. A siRNA mimetic of the invention can comprise one or more or all ribonucleotides. Certain embodiments of the invention include siRNA nineties that comprise substitutions or modifications in the backbone, sugars, bases, or nucleosides.

The term "gene" as used herein, especially in the context of "target gene" for an RNAi agent, refers to the meaning as is generally accepted in the art. The term generally refers to a nucleic acid (e.g., DNA or RNA) sequence that comprises partial length or entire length coding sequences necessary for the production of a polypeptide. The target gene can also include the UTR (i.e., untranslated region) or non-coding region of the nucleic acid sequence. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for RNA interference in modulating the activity of fRNA or ncRNA involved in functional or regulatory cellular processes. Aberrant fRNA or ncRNA activity leading to disease can therefore be modulated by the RNAi agents of the invention. RNAi agents targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). A target gene can be a gene derived from a cell, an endogenous gene, a transgene, or exogenous genes such as genes of a pathogen, for example a virus, which is present in the cell after infection thereof. A cell containing a target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science* 300:258-260.

The phrases "target site," "target sequence," and "target region," as used herein, refer to their meanings as generally accepted in the art. The terms generally refer to a sequence within a target nucleic acid molecule (e.g., mRNA) that is "targeted," e.g., for cleavage mediated by an RNAi molecule that contains a sequence within its guide/antisense region that is partially, substantially, or perfectly complementary to that target sequence. A "target site" for a single-stranded RNAi molecule of the present invention refers to a nucleic acid sequence that is partially, substantially, or perfectly complementary to the single-stranded RNAi agent. The target site may be within a coding or a non-coding (i.e., untranslated) region of a target RNA. The target site may be the target site for an endogenous miRNA for which the single-stranded RNAi molecule is a mimetic, in which case the "target site" can also be referred to as a "miRNA target site" or a "corresponding miRNA target site."

The phrase "sense region" as used herein refers to its meaning as is generally accepted in the art. The term generally refers to a nucleotide sequence of an RNAi molecule having complementarity to an antisense region of the RNAi molecule. In addition, the sense region of an RNAi molecule can comprise a nucleic acid sequence having homology or sequence identity with a target nucleic acid sequence. The sense region of an RNAi molecule is also referred to as the sense strand or the passenger strand.

The phrase "antisense region" as used herein refers to its meaning as is generally accepted in the art. The term generally refers to a nucleotide sequence of an RNAi molecule having complementarity to a target nucleic acid sequence. In addition, the antisense region of an RNAi molecule can optionally comprise a nucleic acid sequence having complementarity to a sense region of the RNAi molecule. The antisense region of an RNAi molecule is also referred to as the antisense strand or the guide strand.

As used herein, the term "spacer" refers to any chemical group(s) capable of linking either two nucleotides and/or non-nucleotide substitute moieties. As used in the present invention, the "spacer" can connect two nucleotides and/or non-nucleotide substitute moieties by traditional phosphodiester bonds or non-phosphodiester connectors. The spacer is typically an organic entity that is covalently bound to each nucleotide or non-nucleotide substitute and is other than the internucleotide linkages that form the backbone (i.e., the nucleobases which form complementary hybrids).

As used herein, the term "alkyl" is intended to include a saturated aliphatic hydrocarbon group, both branched and straight-chain, having a specified number of carbon atoms. The term "alkyl" also refers to non-aromatic cycloalkyl groups. Preferably, an alkyl group has from 1 to 20 carbons (i.e., $C_1$-$C_{20}$). For example, $C_1$-$C_{10}$, as in "$C_1$-$C_{10}$ alkyl" is defined to include groups having 1, 2, 3, 4, 5, 6, 7, 8, 9 or 10 carbons in a linear, branched or cyclic arrangement (i.e., cycloalkyl). The term "cycloalkyl" means a monocyclic saturated aliphatic hydrocarbon group having the specified number of carbon atoms. For example, "alkyl" specifically includes methyl, ethyl, n-propyl, i-propyl, n-butyl, t-butyl, i-butyl, pentyl, hexyl, heptyl, octyl, nonyl, decyl, and so on, as well as cycloalkyls, including cyclopropyl, methyl-cyclopropyl, 2,2-dimethyl-cyclobutyl, 2-ethyl-cyclopentyl, cyclohexyl, and so on. An alkyl group may be substituted, if indicated.

As used herein, the term "alkenyl" refers to a non-aromatic hydrocarbon radical, straight or branched, containing 2 or more carbon atoms and at least 1 carbon to carbon double bond. The term "alkenyl" also refers to non-aromatic cycloalkenyl groups. Preferably, the alkenyl group has from 1 to 20 carbons (i.e., $C_1$-$C_{20}$). Alkenyl groups include, for example, ethenyl, propenyl, butenyl and cyclohexenyl. An alkenyl group may contain double bonds and may be substituted, if indicated.

As used herein, the term "alkynyl" refers to a non-aromatic hydrocarbon radical, straight, or branched, containing 2 or more carbon atoms and at least 1 carbon to carbon triple bond. The term "alkynyl" also refers to non-aromatic cycloalkynyl groups. Up to 3 carbon-carbon triple bonds may be present. Preferably, the alkynyl group has from 1 to 20 carbons (i.e., $C_1$-$C_{20}$). Alkynyl groups include, for example, ethynyl, propynyl, butyryl and cyclooctynl. An alkynyl group may contain triple bonds and may be substituted, if indicated.

The term "aliphatic" as used herein in reference to a chemical group refers to an organic group composed of carbon and hydrogen which does not contain aromatic rings. Aliphatic structures can be cyclic and/or saturated. The carbon atoms can be joined together in straight chains, branched chains, or non-aromatic rings. They can also be joined by single bonds (alkanes), double bonds (alkenes) or triple bonds (alkynes). Besides hydrogen, other elements can be bound to the carbon chain or substituted for a carbon within the chain, the most common being oxygen, nitrogen, sulfur and chlorine.

The term "aromatic" as used herein in reference to a chemical group refers to an organic group containing a set of covalently-bound atoms with the following specific characteristics: (1) a delocalized conjugated $\pi$ system, most commonly an arrangement of alternating single and double bonds; (2) coplanar structure, with all the contributing atoms in the same plane; (3) contributing atoms arranged in one or more rings; and, (4) a number of delocalized $\pi$ electrons that is even, but not a multiple of 4. An aromatic structure can be composed solely of hydrocarbons (e.g., aryl). Other elements can be bound to or substituted for a carbon of the aromatic structure, the most common being oxygen, nitrogen, sulfur and chlorine (e.g., heteroaryl, substituted aryl, substituted heteroaryl).

The term "substituted" as used in reference to an aliphatic or aromatic organic structure (e.g., an alkyl, alkenyl, alkynyl, aryl) refers to the presence of additional chemical moieties and/or functional groups bound to the carbon chain. For example, a substituted hydrocarbon chain can include a hydrocarbon chain with a heteroatom (e.g., N, O, or S) bound to it. A substituted hydrocarbon chain can also include a hydrocarbon chain that is interrupted with a heteroatom. When substituted, the substituted group(s) is preferably, hydroxyl, halogen, cyano, C1-C4 alkoxy, —O, —S, $NO_2$, SH, $NH_2$, or $NR_1R_2$, where $R_1$ and $R_2$ independently are H or $C_1$-$C_4$ alkyl. A substituted alkyl includes oligomers or polymers of ethylene oxide, including but not limited polyethylene glycol ("PEG").

The term "non-nucleotide" or "non-nucleic acid" refers to any chemical molecule, moiety, group or compound that is not a nucleotide.

As used herein, the term "substitute non-nucleotide moiety" (or "non-nucleotide substitute moiety") refers to a chemical moiety that is capable of substituting for one or more nucleotides in a single-stranded RNAi molecule of the invention. Substitute non-nucleotide moieties are typically those that allow for non-traditional base-pairing (i.e., not forming traditional hydrogen bonds). In certain embodiments, substitute non-nucleotide moieties of the instant disclosure are those that are capable of associating or otherwise interacting with one or more components of the cellular RNAi machinery, including, for example, the PAZ domain, the PIWI domain and/or other Argonaute protein domains associated with the RISC.

The term "synthetic," in certain embodiments herein, refers to nucleic acid molecules that are not produced naturally in a cell. The single-stranded RNAi molecules of the invention are typically synthetic.

In certain embodiments, a single-stranded RNAi molecule of the invention may be isolated. The term "isolated," as used herein in relation to an oligonucleotide, generally refers to a nucleic acid molecule that exists in a physical form differing from any nucleic acid molecules of identical sequence as found in nature. "Isolated" does not require, although it does not prohibit, that the nucleic acid be physically removed from its native environment. For example, a nucleic acid can be said to be "isolated" when it includes nucleotides and/or internucleoside bonds not found in nature. A nucleic acid can be said to be "isolated" when it exists at a purity not found in nature, where purity can be adjudged with respect to the presence of nucleic acids of other sequences, with respect to the presence of proteins, with respect to the presence of lipids, or with respect to the presence of any other component of a biological cell, or when the nucleic acid lacks sequence that flanks an otherwise identical sequence in an organism's genome, or when the nucleic acid possesses sequence not identically present in nature. A single-stranded RNAi molecule of the present invention can be isolated by virtue of its having been synthesized in vitro. It will be understood, however, that isolated nucleic acids may be subsequently mixed or pooled together.

As used herein, "endogenous" refers its meaning as generally accepted in the art. The term generally refers to any material from or produced inside an organism, cell, tissue or system. As used herein, an "endogenous miRNA" is a naturally-occurring miRNA in a cell, tissue, organism, including a mammal, such as, for example, a human. "Exogenous" generally refers to any material introduced from or produced outside an organism, cell, tissue or system.

The term "expression" as used herein refers to its meaning as is generally accepted in the art. The term generally is defined as the transcription and/or translation of a particular nucleotide sequence driven by its promoter.

In some embodiments, it may be useful to know whether a cell expresses a particular miRNA endogenously or whether such expression is affected under particular conditions or when it is in a particular disease state. Thus in some embodiments of the invention, methods include assaying a cell or a sample containing a cell for the presence of one or more marker genes or mRNA or other analyte indicative of the expression level of a gene of interest. Consequently in some embodiments, methods include a step of generating an RNA profile for a sample. The term "RNA profile" or "gene expression profile" refers to a set of data regarding the expression pattern for one or more gene or genetic marker in the sample (e.g., a plurality of nucleic acid probes that identify one or more markers).

By "capable of" is meant that, when RNAi activity is measured by a suitable in vivo or in vitro assay or method, a single-stranded RNAi molecule of the invention demonstrates at least 5% or more of the knockdown effect against a target sequence as compared to the knockdown effect achieved by the corresponding single-stranded RNAi molecule without the internal, non-nucleotide spacer portion(s). Preferably, a single-stranded RNAi molecule of the invention is capable of achieving 25% or more, 35% or more, 50% or more, 55% or more, 60% or more, 65% or more, 70% or more, 75% or more, 80% or more, 85% or more, 90% or more, 95% or more, 99% or more, or even 100% or more (i.e., equal or more potent RNAi activity) knockdown of the target than a corresponding RNAi molecule against the same target (e.g., a naturally-occurring miRNA or previously-identified siRNA guide strand).

A "vector" is a replicon, such as a plasmid, phagemid, cosmid, baculovirus, bacmid, bacterial artificial chromosome (BAC), yeast artificial chromosome (YAC), as well as other bacterial, yeast, or viral vectors, to which another nucleic acid segment may be operatively inserted so as to bring about replication or expression of the inserted segment. "Expression vector" refers to a vector comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses).

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. Non-limiting examples of agents suitable for formulation with the nucleic acid molecules of the instant invention include: Lipid Nanoparticles (see for example Semple et al., 2010, *Nat Biotechnol.* 28(2):172-6.); P-glycoprotein inhibitors (such as Pluronic P85); biodegradable polymers, such as poly (DL-lactide-coglycolide) microspheres for sustained release delivery (Emerich, D F et al, 1999, *Cell Transplant* 8:47-58); and loaded nanoparticles, such as those made of polybutylcyanoacrylate. Other non-limiting examples of delivery strategies for the nucleic acid molecules of the instant invention include material described in Boado et al., 1998*J. Pharm. Sci.* 87:1308-1315; Tyler et aL, 1999, *FEBS Lett.* 421:280-284; Pardridge et al., 1995, *PNAS USA.* 92:5592-5596; Boado, 1995, *Adv. Drug Delivery Rev.*, 15:73-107; Aldrian-Herrada et al., 1998, *Nucleic Acids Res.* 26:4910-4916; and, Tyler et al., 1999, *PNAS* 96:7053-7058. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The terms "patient," "subject," "individual" and the like are used interchangeably herein, and refer to any animal or cells or tissues thereof, whether in vitro or in situ, amendable to the methods described herein. They typically refer to an organism, which is a donor or recipient of the single-stranded RNA molecules of this disclosure. In certain non-limiting embodiments, the patient, subject or individual is a mammal or a mammalian cell. In other non-limiting embodiments, the patient, subject or individual is a human or a human cell.

As used herein, the term "therapeutically effective amount" means an amount of a single-stranded RNAi molecule of the present disclosure that is sufficient to result in a decrease in severity of disease symptoms, an increase in frequency or duration of disease symptom-free periods, or a prevention of impairment or disability due to the disease, in the subject (e.g., a mammal or human) to which it is administered. One of ordinary skill in the art can determine such therapeutically effective amounts based on such factors such as the subject's size, the severity of symptoms, and the particular composition or route of administration selected. For example, a therapeutically effective amount of a single-strand RNAi molecule of the invention, individually, in combination, or in conjunction with other drugs, can be used or administered at a therapeutically effective amount to a subject or by administering to a particular cells under conditions suitable for treatment, to, for example, decrease tumor size, or otherwise ameliorate symptoms associated with a particular disorder in the subject.

The term "therapeutic" as used herein means a treatment and/or prophylaxis. A therapeutic effect is obtained by suppression, remission, or eradication of a disease state. The term "treatment" as used herein is meant to include therapeutic treatment as well as prophylactic, or suppressive measures for diseases or disorders. Thus, for example, the term "treatment" includes the administration of an agent prior to or following the onset of a disease or disorder thereby preventing or removing all signs of the disease or disorder. As another example, administration of the agent after clinical manifestation of the disease to combat the symptoms of the diseases is also comprised by the term "treatment."

The term "parenteral" as used herein refers to its meaning as is generally accepted in the art. The term generally refers methods or techniques of administering a molecule, drug, agent, or compound in a manner other than through the digestive tract, and includes epicutaneous, subcutaneous, intravascular (e.g., intravenous), intramuscular, or intrathecal injection or infusion techniques and the like.

The phrase "systemic administration" as used herein refers to its meaning as is generally accepted in the art. The term generally refers in vivo systemic absorption or accumulation of drugs in the blood stream followed by distribution throughout the entire body.

Other objects, features and advantages of the present invention will become apparent from the detailed description. It should be understood, however, that the detailed description and the specific examples, while indicating specific embodiments of the invention, are given by way of illustration only, since various changes and modifications within the spirit and scope of the invention will become apparent to those skilled in the art from the detailed description.

B. Single-Stranded RNAi Molecules of the Invention

The instant disclosure provides single-stranded RNA molecules comprising at least one internal, non-nucleotide spacer that links together two nucleotide portions of the molecule. Thus, a single-stranded RNA molecule of the present invention is not a continuous stretch of nucleotides but comprises more than one nucleotide portion separated by one or more non-nucleotide spacers, wherein the nucleotide portions contain one or more nucleotides, non-nucleotide substitute moieties, or a combination thereof. A single-stranded RNA molecule of the invention functions as a guide or antisense strand that is capable of inhibiting gene expression via an RNA interference mechanism and, thus, represents an RNAi agent. A single-stranded RNAi molecule of the invention comprises sequence that is partially, substantially or perfectly complementary to one or more RNA target sites in a cell.

A single-stranded RNAi molecule of the invention has a single-stranded oligonucleotide structure comprising (a) a nucleic acid portion separated into two or more nucleotide portions, and (b) an internal (as opposed to "terminal") spacer portion comprising at least one non-nucleotide spacer portion, wherein the non-nucleotide spacer portion(s) covalently links two nucleotides, each within distinct nucleotide portions of the molecule. The nucleotide portions of a single-stranded RNAi molecule of the invention are separated by the non-nucleotide spacer portions, wherein each nucleotide portion contains at least one nucleotide.

In each embodiment of the invention, the nucleic acid portion of a single-stranded RNAi molecule contains at least two nucleotide portions, a first nucleotide portion (N1) (e.g., a 5'-nucleotide portion) and a second nucleotide portion (N2) (e.g., a 3'-nucleotide portion). The nucleic acid portion of a single-stranded RNAi molecule of the invention can comprise more than two nucleotide portions (e.g., a third nucleotide portion (N3), a fourth nucleotide portion (N4) etc.). Within each nucleotide portion of an RNAi molecule of the invention, the nucleotides and/or non-nucleotide moieties are connected by phosphodiester bonds and/or non-phosphodiester connectors. Importantly, the nucleotide portions of a single-stranded RNAi molecule of the invention are not complementary to each other and, thus, said portions do not form significant base-pairing.

In each embodiment of the invention, the internal spacer portion of a single-stranded RNAi molecule contains at least one non-nucleotide spacer portion (S1), referred to here in as a first non-nucleotide spacer portion. In one embodiment of the present invention, a single-stranded RNAi molecule contains one internal, non-nucleotide spacer portion. The internal spacer portion of a single-stranded RNAi molecule of the invention can comprise more than a first non-nucleotide spacer portion (e.g., a second non-nucleotide spacer portion (S2), a third non-nucleotide spacer portion (S3) etc.). In another embodiment, a single-stranded RNAi molecule contains two internal, non-nucleotide spacer portions.

The number of nucleotide portions within the nucleic acid portion of a single-stranded RNAi molecule of the present invention is dependent on the number of non-nucleotide spacer portions within the molecule, and vice versa. For example, if a single-stranded RNAi molecule contains two non-nucleotide spacer portions, it will generally contain three nucleotide portions, as follows: 5'-(first nucleotide portion)-(first non-nucleotide spacer portion)-(second nucleotide portion)-(second non-nucleotide spacer portion)-(third nucleotide portion)-3'. Each non-nucleotide spacer portion of a single-stranded RNAi molecule of the present invention can contain one or more non-nucleotide spacers.

Single-stranded RNAi molecules of the invention have a single-stranded oligonucleotide structure and mediate RNA interference against a target RNA. Single-stranded RNAi molecule of the invention can comprise: (a) a nucleic acid portion comprising a first nucleotide portion (N1) and a second nucleotide portion (N2), wherein said nucleic acid portion comprises at least 8 nucleotides that can base pair with a target site within a target RNA, and wherein the total number of nucleotides within the nucleic acid portion is from 8 to 26 nucleotides; and, (b) an internal spacer portion comprising at least a first non-nucleotide spacer portion (S1) that covalently links the first and second nucleotide portions. The first and second nucleotide portions are not self complementary. All of nucleotides (e.g., 8 to 26) of a single-stranded RNAi molecule of the invention, all located within the nucleic acid portion, are distributed between the nucleotide portions of the molecule, wherein each nucleotide portion contains at least one nucleotide.

In one embodiment, a single-stranded RNAi molecule of the invention comprises a nucleic acid portion containing a total of from 8 to 26 nucleotides or non-nucleotide substitute moieties (e.g., 8, 9, 10, 11, 12, 13, 14, 15, 16, 17, 18, 19, 20, 21, 22, 23, 24, 25, or 26 nucleotides or non-nucleotide substitute moieties) distributed between the nucleotide portions of the oligonucleotide, wherein at least 8 (e.g., 8, 9, 10, 11, 12, 13, 14, 15, 16, 17, 18, 19, 20, 21, 22, 23, 24, 25, or 26) of the nucleotides in the molecule can base pair with a target site within a target RNA. For example, a single-stranded RNAi molecule of the invention may contain 8, 9, 10, 11, 12, 13, 14, 15, 16, 17, 18, 19, 20, 21, 22, 23, 24, 25, or 26 total nucleotides, wherein 8, 9, 10, 11, 12, 13, 14, 15, 16, 17, 18, 19, 20, 21, 22, 23, 24, 25, or 26 of those nucleotides base pair with a target RNA. In one embodiment, the nucleic acid portion of a single-stranded RNAi molecule of the invention contains a total of from 15 to 21 (e.g., 15, 16, 17, 18, 19, 20, or 21) nucleotides. In another embodiment, the nucleic acid portion of a single-stranded RNAi molecule of the invention contains a total of from 18 to 20 (e.g., 18, 19, or 20) nucleotides. In a further embodiment, the nucleic acid portion of a single-stranded RNAi molecule of the invention contains a total of 19 or 20 nucleotides.

The total number of nucleotides or non-nucleotide moieties, or a combination thereof, that make up the nucleotide portions of a single-stranded RNAi molecule of the invention is distributed between those portions of the molecule in any number of ways. As an example, a single-stranded RNAi molecule comprising only one non-nucleotide spacer portion and two nucleotide portions (i.e., the first nucleotide portion and the second nucleotide portion) may have a total of 12 nucleotides. If the first nucleotide portion of the molecule contains a single nucleotide (e.g., at the 5'-terminus of the molecule), the second nucleotide portion of the molecule will contain 11 contiguous nucleotides. Alternatively, if the first nucleotide portion of the molecule contains 5 contiguous nucleotides, the second nucleotide portion of the molecule will contain 7 contiguous nucleotides. In each example, the total number of nucleotides in the molecule is 12. The nucleotides within the nucleotide portions of a single-stranded RNAi molecule of the invention are not complementary to each other and, thus, said portions can not form substantial base-pairing. Within each of the nucleotide portions of the molecule, the nucleotides and/or non-nucleotide moieties are connected by phosphodiester bonds and/or non-phosphodiester connectors.

At least 8 nucleotides within the nucleic acid portion of a single-stranded RNAi molecule of the invention can base pair with a target sequence within a target RNA. Thus, the single-stranded RNAi molecules of the invention comprise a sequence of contiguous nucleotides that is partially, substantially or perfectly complementary to an RNA target site, including a naturally-occurring RNA target site. In one embodiment, all of the contiguous nucleotides within the nucleic acid portion of a single-stranded RNAi molecule of the invention base pair with a target sequence within a target RNA (i.e., perfectly complementary). In another embodiment, at least 50% of the contiguous nucleotides within the nucleic acid portion of a single-stranded RNAi molecule of the invention base pair with a target sequence within a target RNA (i.e., substantially complementary). In another embodiment, 8, 9, 10, 12, 13, 14, 15, 16, 17, 18, 19, 20, 21, 22, 23, 24, 25 or 26 nucleotides within the nucleic acid portion of a single-stranded RNAi molecule of the invention base pair with a target sequence within a target RNA.

In one embodiment, a single-stranded RNAi molecule of the invention has a single-stranded oligonucleotide structure comprising: (a) two nucleotide portions, a first nucleotide portion (N1) and a second nucleotide portion (N2); and, (b) one internal, non-nucleotide spacer portion (S1); wherein the oligonucleotide contains a total of from 8 to 26 nucleotides or non-nucleotide substitute moieties (e.g., 8, 9, 10, 11, 12, 13, 14, 15, 16, 17, 18, 19, 20, 21, 22, 23, 24, 25, or 26 nucleotides or non-nucleotide substitute moieties); and wherein at least 8 of the nucleotides of the molecule can base pair with a target site within a target RNA. The two nucleotide portions of a single-stranded RNAi molecule of this embodiment comprise, in sum, 8 to 26 (e.g., 8, 9, 10, 11, 12, 13, 14, 15, 16, 17, 18, 19, 20, 21, 22, 23, 24, 25 or, 26) nucleotides or non-nucleotide moieties, or a combination thereof, that are distributed between the two nucleotide portions in any number of ways (as described above). In one embodiment, the non-nucleotide spacer portion contains one non-nucleotide spacer. In another embodiment, the non-nucleotide spacer portion contains more than one non-nucleotide spacer (e.g., 2, 3, 4, or more). The spacer portion links the first and second nucleotide portions of the single-stranded RNAi molecule. Thus, the spacer portion is covalently linked to both the 3'-terminal nucleotide or non-nucleotide substitute moiety of the first nucleotide portion of the molecule and the 5'-terminal nucleotide or non-nucleotide substitute moiety of the second nucleotide portion of the molecule. The spacer portion of the molecule can be covalently connected to the phosphate backbone of the nucleotide portions (i.e., through the free phosphate of the two, linked nucleotides) by either traditional phosphodiester bonds or non-phosphodiester connectors.

In one embodiment, a single-stranded RNAi molecule of the invention comprises a contiguous nucleotide sequence that is partially, substantially or perfectly homologous to the guide strand of a naturally-occurring miRNA and, thus, functions as a miRNA mimetic. In another embodiment, a single-stranded RNAi molecule of the invention comprises a contiguous nucleotide sequence that is partially, substantially or perfectly homologous to either a single-stranded siRNA or the guide/antisense strand of a duplex siRNA and, thus, functions as a siRNA mimetic. The single-stranded siRNA or duplex siRNA may be known to inhibit gene expression via an RNAi mechanism.

If a single-stranded RNAi molecule of the present invention is an analog of a naturally-occurring miRNA, the naturally-occurring miRNA is referred to herein as "the corresponding miRNA," and the single-stranded RNAi molecule represents a mimetic of the corresponding miRNA. A single-stranded miRNA mimetic of the present invention is designed based on a corresponding, naturally-occurring miRNA, wherein at least one non-nucleotide spacer portion is either inserted between two nucleotides of the miRNA guide strand sequence or substituted for one or more nucleotides of the miRNA guide strand sequence. A single-stranded miRNA mimetic of the present invention can be an analog of a mature miRNA sequence publicly available in the miRBase database and/or included within Table 1, infra (SEQ ID NOS: 1-1090).

In one embodiment, a single-stranded RNAi molecule as described herein represents a miRNA mimetic, wherein the RNAi molecule comprises a nucleic acid portion of two or more nucleotide portions and an internal spacer portion comprising at least one non-nucleotide spacer portion. As described above, if the nucleic acid portion of the molecule contains only two nucleotide portions (i.e., a first nucleotide portion and a second nucleotide portion), only one non-nucleotide spacer portion will be present. If the nucleic acid portion of the molecule contains three nucleotide portions, two non-nucleotide spacer portions will be present. Each non-nucleotide spacer portion can comprise more than one non-nucleotide spacer (e.g., 2, 3, 4 or more). In one embodiment, the nucleic acid portion of an miRNA mimetic of the invention consists of from 8 to 26 (e.g., 8, 9, 10, 11, 12, 13, 14, 15, 16, 17, 18, 19, 20, 21, 22, 23, 24, 25, or 26) nucleotides or non-nucleotide moieties, or a combination thereof, wherein at least 8 of the nucleotides can base pair with a naturally-occurring miRNA target site. A contiguous nucleotide sequence within the nucleic acid portion of an miRNA mimetic of the invention is partially, substantially or perfectly homologous to a naturally-occurring miRNA guide strand nucleotide sequence. In one embodiment, a contiguous nucleotide sequence within a nucleic acid portion of a single-stranded RNAi molecule of the invention comprises 5 to 8 (i.e., 5, 6, 7, or 8) contiguous nucleotides that are identical (or perfectly homologous) to the whole or a part of a seed sequence of a naturally-occurring miRNA. For example, in one embodiment, an 8 consecutive nucleotide sequence within a nucleotide portion of a single-stranded RNAi molecule is identical to all or a portion of the seed region of a naturally-occurring miRNA (see Table I, infra).

In one embodiment, a miRNA mimetic of the invention has a non-nucleotide spacer portion and two nucleotide portions, wherein the non-nucleotide spacer portion is inserted between two nucleotides of a corresponding, naturally-occurring miRNA sequence, separating the full-length, naturally-occurring miRNA into two distinct nucleotide portions. In another embodiment, more than one non-nucleotide spacer portion is present in a miRNA mimetic of the invention such that the nucleic acid portion of the miRNA mimetic is separated into more than two nucleotide portions. In such cases, the total nucleotide sequence of the miRNA mimetic is perfectly homologous to the corresponding, naturally-occurring miRNA nucleotide sequence. The difference between the naturally-occurring miRNA and the miRNA mimetic in this embodiment is the presence of a non-nucleotide spacer portion.

In another embodiment, a miRNA mimetic of the invention comprises a non-nucleotide spacer portion that substitutes for one or more nucleotides of a naturally-occurring miRNA guide strand sequence. For example, one or more nucleotides may be first deleted from a naturally-occurring miRNA guide strand sequence, leaving a gap in the sequence and producing at least two distinct nucleotide portions. A non-nucleotide spacer portion is then inserted into the gap, covalently linking the distinct nucleotide portions. Thus, in one embodiment, a single-stranded RNAi molecule of the invention represents a miRNA mimetic wherein one or more internal, non-nucleotide spacer portions takes the place of from one to 12 (e.g., 1, 2, 3, 4, 5, 6, 7, 8, 9, 10, 11, or 12) nucleotides of a corresponding, naturally-occurring miRNA sequence (see SEQ ID NOS: 1-1090). A miRNA mimetic may contain more than one non-nucleotide spacer portion.

In one embodiment, a single-stranded miRNA mimetic of the invention comprises at least one non-nucleotide spacer portion in the place of from one to 4 (e.g., 1, 2, 3, or 4) nucleotides of a naturally-occurring miRNA nucleotide sequence. In another embodiment, a single-stranded miRNA mimetic of the invention comprises at least one internal, non-nucleotide spacer portion in the place of one or two nucleotides of a corresponding miRNA nucleotide sequence. The non-nucleotide spacer portion bridges the gap resulting from removal of the one or more nucleotides from a miRNA guide strand sequence, connecting by either traditional phosphodiester bonds or non-phosphodiester connectors to the phosphate backbone of the nucleotide portions of the molecule.

Single-stranded RNAi molecules of the invention can also represent an analog of the guide or antisense strand of a duplex or single-stranded siRNA. The duplex or single-stranded siRNA may be known to inhibit target gene expression, or have the potential of inhibiting target gene expression, via an RNAi mechanism. In such a scenario, the siRNA counterpart, and specifically the guide strand of the siRNA (whether single- or double-stranded), is referred to herein as "the corresponding siRNA" or "the corresponding siRNA guide strand," and the single-stranded RNAi molecule represents a mimetic of the corresponding siRNA guide strand (i.e., "a single-stranded siRNA mimetic"). A single-stranded siRNA mimetic is designed based on the nucleotide sequence of a corresponding siRNA by either inserting one or more internal, non-nucleotide spacer portions within the nucleotide sequence of the corresponding siRNA nucleotide sequence or substituting one or more nucleotides of the corresponding siRNA nucleotide sequence with one or more non-nucleotide spacer portions.

In one embodiment, a single-stranded RNAi molecule of the invention represents a siRNA mimetic, wherein the nucleic acid portion of the single-stranded RNAi molecule comprises two or more nucleotide portions, and the internal spacer portion comprises at least one non-nucleotide spacer portion. As described above, if the nucleic acid portion of the RNAi molecule contains only two nucleotide portions (i.e., a first nucleotide portion and a second nucleotide portion), only one non-nucleotide spacer portion will be present. If the nucleic acid portion of the RNAi molecule contains three nucleotide portions, two non-nucleotide spacer portions will be present. A non-nucleotide spacer portion may comprise more than one non-nucleotide spacer (e.g., 2, 3, 4 or more). In one embodiment, the nucleic acid portion of a siRNA mimetic consists of from 8 to 26 (e.g., 8, 9, 10, 11, 12, 13, 14, 15, 16, 17, 18, 19, 20, 21, 22, 23, 24, 25, or 26) nucleotides or non-nucleotide moieties, or a combination thereof, wherein at least 8 of the nucleotides can base pair with the an RNA target site. The nucleic acid portion of a siRNA mimetic of the invention comprises a contiguous nucleotide sequence that is partially, substantially or perfectly homologous to a corresponding siRNA guide strand nucleotide sequence.

In one embodiment, a siRNA mimetic of the invention has a non-nucleotide spacer portion and two nucleotide portions, wherein the non-nucleotide spacer portion is inserted between two adjacent nucleotides of the corresponding siRNA nucleotide sequence, separating the corresponding siRNA nucleotide sequence into two distinct nucleotide portions. In another embodiment, a siRNA mimetic of the invention can have more than one non-nucleotide spacer portion such that the corresponding siRNA nucleotide sequence is separated into more than two nucleotide portions. In such cases, the total nucleotide sequence of the siRNA mimetic is perfectly homologous to the corresponding siRNA nucleotide sequence. The difference between the corresponding siRNA and the siRNA mimetic in this embodiment is the presence of a non-nucleotide spacer region(s).

In another embodiment, a siRNA mimetic of the invention comprises one or more non-nucleotide spacer portions that substitutes for one or more nucleotides of a corresponding siRNA guide strand nucleotide sequence. For example, one or more nucleotides may be first deleted from a corresponding siRNA nucleotide sequence, leaving a gap in the sequence and producing at least two distinct nucleotide portions. A non-nucleotide spacer portion is then inserted into the gap to link the distinct nucleotide portions. Thus, in one embodiment, a single-stranded RNAi molecule of the present invention represents a siRNA mimetic comprising at least one internal, non-nucleotide spacer portion, wherein said non-nucleotide spacer portion takes the place of from one to 4 (e.g., 1, 2, 3, or 4) nucleotides of a corresponding siRNA nucleotide sequence. The siRNA mimetic may contain more than one non-nucleotide spacer portion. In another embodiment, a single-stranded RNAi molecule of the present invention represents a siRNA mimetic comprising at least one internal, non-nucleotide spacer portion, wherein said non-nucleotide spacer portion takes the place of one or two nucleotides of a corresponding siRNA nucleotide sequence. The non-nucleotide spacer portion(s) bridges the gap resulting from removal of the one or more nucleotides from the siRNA guide strand sequence, connecting by either traditional phosphodiester bonds or non-phosphodiester connectors to the phosphate backbone of the nucleotide portions of the molecule.

In another embodiment, single-stranded RNAi molecules of the invention can be designed de novo for the purpose of knocking down expression of a particular RNA target, including a naturally-occurring RNA target. In this scenario, a target gene is first selected. One of skill in the art then identifies a portion of said gene (i.e., the target site), generally between about 8 and about 26 nucleotides in length, to target with a single-stranded RNAi molecule for gene silencing. In one embodiment of the invention, a contiguous nucleotide sequence within the nucleic acid portion of a single-stranded RNAi molecule described herein is partially, substantially or perfectly complementary to the identified target site sequence and partially, substantially or perfectly homologous to the complement of the corresponding target site sequence. The counterpart sequence of the single-stranded RNAi molecule in this scenario (i.e., a nucleotide sequence that is the complement of the target site sequence) is referred to herein as "the complement of the corresponding target site sequence." The single-stranded RNAi molecule comprises two or more nucleotide portions and at least one internal, non-nucleotide spacer portion, as described in one or more of the embodiments above.

A single-stranded RNAi molecule of the present invention is capable of producing an RNA interference result. In the case of a single-stranded miRNA mimetic of the invention, the molecule is capable of modulating the expression of a target mRNA that is also regulated by a corresponding naturally-occurring miRNA.

The single-stranded RNAi molecules of the disclosure can further comprise a terminal phosphate group located at one or both of the terminal ends, such as a 5'-phosphate or a 5', 3'-diphosphate. In some embodiments, a single-stranded RNAi molecule of the invention can comprise substitutions, chemically-modified nucleotides, and non-nucleotides. In certain other embodiments, a single-stranded RNAi molecule of the invention can comprise one or more or all ribonucleotides. Certain embodiments of the invention include single-stranded RNAi molecules that comprise substitutions or modifications in the backbone, sugars, bases, or nucleosides.

The internal, non-nucleotide spacer portion(s) of the single-stranded RNAi molecules of the disclosure, especially in situations where the total number of nucleotides in the resulting RNAi molecule is reduced compared to a corresponding RNAi agent of which the single-stranded RNAi molecule is an analog (e.g., a naturally-occurring miRNA; the guide strand of a siRNA with gene knockdown capability), reduces the susceptibility of the single-stranded RNAi molecule to endonucleases. The internal, non-nucleotide spacer portion(s) can also limit the damage of exonucleases, ultimately helping to preserve the integrity of the single-stranded RNAi agent. The spacer portion also represents an easily accessible region for connecting one or more moieties of interest to the RNAi molecule (e.g., a chemical moiety that facilitates cellular delivery). Therefore, even if the activity of a single-stranded RNAi molecule of this disclosure is somewhat reduced (e.g., by less than about 20%, or 30%, or even 40%) as compared to a corresponding single-stranded RNAi molecule without the spacer portion (e.g., a naturally-occurring miRNA; the guide strand of a previously identified siRNA with gene knockdown capability), the overall activity of the analog can be greater than that of its counterpart due to improved stability or delivery of the molecule. Additionally, since the yield of synthesis is usually higher for shorter RNA strands, the cost of large-scale synthesis in connection with therapeutic applications may also be substantially reduced using the single-stranded RNAi molecules of the present invention.

In one embodiment, a single-stranded RNAi molecule of the invention can be represented or depicted by Formula III:

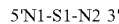

wherein N1, representing a first nucleotide portion, consists of either one nucleotide or a contiguous stretch of nucleotides; S1, representing a non-nucleotide spacer portion, consists of one or more non-nucleotide spacers; and N2, representing a second nucleotide portion, consists of either one nucleotide or a contiguous stretch of nucleotides. The total number of nucleotides in N1 and N2 is from 8 to 26 (e.g., 8, 9, 10, 11, 12, 13, 14, 15, 16, 17, 18, 19, 20, 21, 22, 23, 24, 25, or 26) nucleotides, and at least 8 nucleotides of the molecule can base pair with a target site within a target RNA. The "nucleotide(s)" within N1 and N2 are either nucleotides, modified nucleotides, nucleotide analogs, or non-nucleotides substitute moieties, or a combination thereof. In one embodiment, individually, N1 and N2 can consist of between one and 25 nucleotides, wherein the sum of N1 and N2 is from 8 to 26 (e.g., 8, 9, 10, 11, 12, 13, 14, 15, 16, 17, 18, 19, 20, 21, 22, 23, 24, 25, or 26) nucleotides. N1 and N2 are not self complementary and, thus, cannot participate in substantial base-pairing with each other. Within a contiguous stretches of nucleotides of the molecule, the nucleotides are connected by phosphodiester bonds and/or non-phosphodiester connectors. The spacer portion (S1) is covalently attached to the 3'-terminal nucleotide of the first nucleotide portion (N1) and the 5'-terminal nucleotide of the second nucleotide portion of the molecule (N2). For example, the spacer portion can comprise one or more phosphoramidite spacers attached to the free phosphate group of the adjacent nucleotides by a phosphodiester bond. The spacer portion of the molecule (S1) can consist of a single non-nucleotide spacer or more than one non-nucleotide spacers linked together. If there is more than one non-nucleotide spacer within the S1 portion of the molecule, the spacers can be either the same (i.e., having the same structure) or different (i.e., having different structures). In the case where two non-nucleotide spacers are linked within the S1 portion of the molecule, each spacer is covalently attached to one nucleotide within the N1 and N2 portions of the molecule, respectively. If three non-nucleotide spacers are consecutively linked within the S1 portion of the oligonucleotide, the internal (second) spacer does not form a covalent bond with either the N1 or N2 portions of the molecule. Instead, the internal spacer is covalently attached to the first and third spacers, linking them together.

In another embodiment, a single-stranded RNAi molecule of the invention can be represented or depicted by Formula IV:

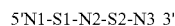

wherein N1, representing a first nucleotide portion, consists of either one nucleotide or a contiguous stretch of nucleotides; S1, representing a first non-nucleotide spacer portion, consists of one or more non-nucleotide spacers; N2, representing a second nucleotide portion, consists of either one nucleotide or a contiguous stretch of nucleotides; S2, representing a second non-nucleotide internal spacer portion, consists of one or more non-nucleotide spacers; and, N3, representing a third nucleotide portion, consists of either one nucleotide or a contiguous stretch of nucleotides. In one embodiment, the total number of nucleotides in N1, N2, and N3 is from 8 to about 26 (e.g., 8, 9, 10, 11, 12, 13, 14, 15, 16, 17, 18, 19, 20, 21, 22, 23, 24, 25, or 26) nucleotides, and at least 8 nucleotides of the molecule can base pair with a target site within a target RNA. The "nucleotide(s)" within N1, N2 and N3 are either nucleotides, modified nucleotides, nucleotide analogs, or non-nucleotides substitute moieties, or a combination thereof. In one embodiment, individually, the nucleotide portions (N1, N2, N3) can consist of between one and 24 nucleotides, wherein the sum of nucleotides within the molecule is from 8 to 26 nucleotides. The nucleotide portions of the RNAi molecule are not self complementary and, thus, cannot participate in substantial base-pairing with each other. Within each of the contiguous stretches of nucleotides, the nucleotides are connected by phosphodiester bonds and/or non-phosphodiester connectors. The spacer portions are covalently attached to terminal nucleotides of the nucleotide portions of the molecule. In one embodiment, a spacer portion comprises one or more phosphoramidite spacers attached to the free phosphate groups of adjacent nucleotides by phosphodiester bonds. Each spacer portion of the molecule can consist of a single non-nucleotide spacer or more than one non-nucleotide spacer linked together. If there is more than one non-nucleotide spacer within a spacer portion of the molecule, the spacers can be either the same (i.e., having the same structure) or different (i.e., having different structures). When two non-nucleotide spacers are linked within a spacer portion of the molecule, each spacer is covalently attached to a terminal nucleotide within the adjacent nucleotide portions of the molecule. If three non-nucleotide spacers are consecutively linked within a spacer portion of the molecule, the internal (second) spacer does not form a covalent bond with a nucleotide portion of the molecule. Instead, the internal spacer is covalently attached to the first and third spacers, linking them together.

In one aspect of the invention, at least one nucleotide portion of a single-stranded RNAi molecule described herein (e.g., N1, N2, or N3, as described in Formulas III and/or IV) is a contiguous stretch of nucleotides that consists of either from 1 to 20 (e.g., 1, 2, 3, 4, 5, 6, 7, 8, 9, 10, 11, 12, 13, 14, 15, 16, 17, 18, 19, or 20) nucleotides, from 5 to 20 (e.g., 5, 6, 7, 8, 9, 10, 11, 12, 13, 14, 15, 16, 17, 18, 19, or 20) nucleotides, from 10 to 20 (e.g., 10, 11, 12, 13, 14, 15, 16, 17, 18, 19, or 20) nucleotides, from 13 to 20 (e.g., 13, 14, 15, 16, 17, 18, 19, or 20) nucleotides, from 5 to 15 (e.g., 5, 6, 7, 8, 9, 10, 11, 12, 13, 14, or 15) nucleotides, or from 1 to 14 (e.g., 1, 2, 3, 4, 5, 6, 7, 8, 9, 10, 11, 12, 13, or 14) nucleotides. In another aspect, the length of at least one nucleotide portion of a single-stranded RNAi molecule of the invention is selected from the group consisting of 18 contiguous nucleotides, 19 contiguous nucleotides, or 20 contiguous nucleotides. In a still further aspect, the length of at least one nucleotide portion of a single-stranded RNAi molecule of the invention is selected from the group consisting of 13 contiguous nucleotides, 14 contiguous nucleotides, or 15 contiguous nucleotides. The length of at least one nucleotide portion of a single-stranded RNAi molecule of the invention can be 18 nucleotides. The length of at least one nucleotide portion of a single-stranded RNAi molecule of the invention can be 19 nucleotides. The length of at least one nucleotide portion of a single-stranded RNAi molecule of the invention can be 20 nucleotides. The length of at least one nucleotide portion of a single-stranded RNAi molecule of the invention can be 21 nucleotides.

In one embodiment, a single-stranded RNAi molecule of the invention is represented by Formula III, wherein N1 consists of 18 contiguous nucleotides; S1 consists of a non-nucleotide spacer; and N2 consists of two contiguous nucleotides. In another embodiment, a single-stranded RNAi molecule of the invention is represented by Formula III, wherein N1 consists of 19 contiguous nucleotides; S1 consists of a non-nucleotide spacer; and N2 consists of one nucleotide. In these embodiments, S1 can be a C3- or C6-alkyl spacer.

In another aspect of the invention, a nucleotide portion of a single-stranded RNAi molecule (e.g., N1, N2, or N3, as described by Formulas III and/or IV) is a contiguous stretch of nucleotides that comprises a sequence of at least 10 (e.g., 10, 11, 12, 13, 14, 15, 16, 17, 18, 19, 20 etc.) nucleotides that is substantially or perfectly complementary to an RNA target region. In another aspect, a nucleotide portion of a single-stranded RNAi molecule comprises a sequence of from 5 to 8 contiguous nucleotides that is substantially or perfectly complementary to a RNA target region. In this portion of the invention, said nucleotide portion of the molecule is a contiguous stretch of nucleotides that consists of either from 1 to 20 nucleotides, from 5 to 20 nucleotides, from 10 to 20 nucleotides, from 13 to 20 nucleotides, from 5 to 15 nucleotides, or from 1 to 14 nucleotides. In another aspect, said nucleotide portion is 18, 19, or 20 contiguous nucleotides in length. In a still further aspect, said nucleotide portion is 13, 14 or 15 contiguous nucleotides in length. In another aspect, the length of said nucleotide portion is selected from the group consisting of 18 contiguous nucleotides, 19 contiguous nucleotides, or 20 contiguous nucleotides. In a still further aspect, the length of said nucleotide portion is selected from the group consisting of 13 contiguous nucleotides, 14 contiguous nucleotides, or 15 contiguous nucleotides. The length of said nucleotide portion can be 18 nucleotides. The length of said nucleotide portion can be 19 nucleotides. The length of said nucleotide portion can be 20 nucleotides. The length of said nucleotide portion can be 21 nucleotides.

In one embodiment, a nucleotide portion of a single-stranded RNAi molecule of the invention comprises from 5 to 8 (e.g., 5, 6, 7, or 8) contiguous nucleotides that are identical (or perfectly homologous) to the whole or a part of a seed sequence of a naturally-occurring miRNA sequence. In one embodiment, the naturally-occurring miRNA sequence is a sequence recited in Table 1, infra. For example, in one embodiment, a 6-nucleotide sequence within a nucleotide portion of a single-stranded RNAi molecule is identical to all or a portion of the seed region of a naturally-occurring miRNA sequence, including a naturally-occurring miRNA sequence selected from Table 1.

In one embodiment, a single-stranded RNAi molecule of the invention can be represented or depicted by Formula III or Formula IV. It should be appreciated that Formulas III and IV represent particular examples of single-stranded RNAi molecules of the present invention. Additional examples encompassed by the present invention include, but are not limited to, RNAi molecules having more than three nucleotide portions.

In one aspect of the present invention, a contiguous nucleotide sequence within the nucleic acid portion of a single-stranded RNAi molecule is partially, substantially, or perfectly homologous to a naturally-occurring endogenous miRNA or to a guide strand of a siRNA. In another aspect of the invention, a contiguous nucleotide sequence within the nucleic acid portion of a single-stranded RNAi molecule is partially, substantially, or perfectly complementary to a target site within a RNA target sequence. In another embodiment, at least one nucleotide portion of a single-strand RNAi molecule of the disclosure is partially, substantially or perfectly homologous to a region of a naturally-occurring endogenous miRNA or the guide strand of a siRNA and/or partially, substantially or perfectly complementary to a target site within a RNA target sequence.

The internal spacer portion of single-stranded RNAi molecules of the invention comprises at least a first non-nucleotide spacer portion. Said non-nucleotide spacer portion comprises a chemical group, typically an organic entity, covalently bound to, and thus linking, at least two nucleotides. The two nucleotides are within distinct nucleotide portions of the molecule. There is no particular limitation in the length of a non-nucleotide spacer portion as long as it does not severely impact the ability of the molecule to form traditional or non-traditional Watson-Crick base pairing with an RNA target sequence and/or to mediate RNAi. A non-nucleotide spacer portion can connect two nucleotides and/or non-nucleotide substitute moieties by traditional phosphodiester bonds or non-phosphodiester connectors. Single-stranded RNAi molecules of the invention comprising non-phosphodiester based connectors linking the nucleotides and/or non-nucleotides to a spacer include, for example, a peptide-based connector, such as one linking the units of an oligo peptide nucleic acid (PNA) (see Boffa et al., 2000, *Gene Ther. Mol. Biol.* 5:47-53).

Various non-nucleotide moieties as are provided herein or otherwise known in the art can be included within the internal spacer portion of the single-stranded RNAi molecules of the invention. The non-nucleotide spacers comprised within the internal spacer portion of a single-stranded RNAi molecule of the invention can include any non-nucleic acid spacer capable of linking either two nucleotides and/or non-nucleotide substitute moieties by either traditional phosphodiester bonds or non-phosphodiester connectors. The spacer is typically an aliphatic or aromatic organic entity and is other than the internucleotide linkages that form the backbone of the oligonucleotide (i.e., the nucleobases which form complementary hybrids).

Non-limiting examples of non-nucleotide spacers include the following: a polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, 1990, *Nucleic Acids Res.* 18:6353; Seela and Kaiser, 1987, *Nucleic Acids Res.* 15:3113; Cload and Schepartz, 1991, *J. Am. Chem. Soc.* 113:6324; Richardson and Schepartz, 1991, *J. Am. Chem. Soc.* 113:5109; Ma et al., 1993, *Nucleic Acids Res.* 27:2585; Ma et al., 1993, *Biochemistry* 32:1751; Durand et al., 1990, *Nucleic Acids Res.* 18:6353; McCurdy et al., 1991, *Nucleosides & Nucleotides* 70:287; Jaschke et al., 1993, *Tetrahedron Lett.* 34:301; Ono et al., 1991, *Biochemistry* 30:9914; and others.

In one embodiment of the invention, a spacer is an alkyl, alkenyl or alkynyl chain of from one to 20 carbons (i.e., C1 to C20), preferably from 1 to 12 carbons (i.e., C1 to C12), that is optionally substituted. The hydrocarbon chains can be substituted with additional chemical and/or functional groups (e.g., a moiety that binds specifically to a target molecule of interest).

A chemical moiety that provides additional functionality (e.g., specifically binds to a target molecule of interest or facilitates/enhances cellular delivery of the molecule) to a single-stranded RNAi molecule may be a part of the spacer or covalently attached or linked thereto (e.g., substituted). For example, an additional functional group can impart therapeutic activity to a single-stranded RNAi molecule by assisting in transferring the RNAi molecule compounds across cellular membranes, altering the pharmacokinetics, and/or modulating the localization of RNAi molecules of the invention.

Examples of specific conjugate molecules that may be incorporated within a non-nucleotide spacer itself and/or covalently attached thereto and are contemplated by the instant disclosure are small molecules, lipids or lipophiles, terpenes, phospholipids, antibodies, toxins, cholesterol, a protein binding agent (e.g., a ligand for a cellular receptor that can facilitate cellular uptake), a vitamin, negatively charged polymers and other polymers, for example proteins (e.g., human serum albumin), peptides, hormones, carbohydrates, polyethylene glycols, or polyamines, and those described in, for example, U.S. Patent Publication No. 2005/0196781, and U.S. Patent Publication No. 2006/0293271, the disclosures of which are incorporated herein by reference. These compounds are expected to improve delivery and/or localization of single-stranded RNAi molecules of the invention into a number of cell types originating from different tissues, in the presence or absence of serum (see Sullenger and Cech, U.S. Pat. No. 5,854,038). For example, a conjugate member can be naproxen, nitroindole (or another conjugate that contributes to stacking interactions), folate, ibuprofen, or a C5 pyrimidine linker. In other embodiments, a conjugate member is a glyceride lipid conjugate (e.g., a dialkyl glyceride derivatives), vitamin E conjugates, or thio-cholesterols. In another embodiment, a conjugate molecule is a peptide that functions, when conjugated to a single-stranded RNAi molecule, to facilitate delivery of the molecule into a target cell, or otherwise enhance delivery, stability, or activity of the molecule when contacted with a biological sample. Exemplary peptide conjugate members for use within these aspects of this disclosure, include peptides PN27, PN28, PN29, PN58, PN61, PN73, PN158, PN159, PN173, PN182, PN202, PN204, PN250, PN361, PN365, PN404, PN453, and PN509 as described, for example, in U.S. Patent Application Publication Nos, 2006/0040882 and 2006/0014289, and U.S. Provisional Patent Application No. 60/939,578, which are all incorporated herein by reference.

In one embodiment, a non-nucleotide spacer comprises a moiety that specifically binds to a target molecule. The target molecule can be any molecule of interest. For example, the target molecule can be a ligand-binding domain of a protein, thereby preventing or competing with the interaction of the naturally-occurring ligand with the protein. This is a non-limiting example and those in the art will recognize that other embodiments can be readily generated using techniques generally known in the art (see, e.g., Gold et al, 1995, *Annu. Rev. Biochem.* 64:163; Brody and Gold, 2000, 1 *Biotechnol.* 74:5; Sun, 2000, *Curr. Opin. Mol. Ther.* 2:100; Kusser, J., 2000, *Biotechnol.* 74:21; Hermann and Patel, 2000, *Science* 257:820; and Jayasena, 1999, *Clinical Chem.* 45:1628). The spacer portion of a single-stranded RNAi molecule of this disclosure can also conveniently be used to introduce functional chemical groups to an RNAi molecule to enhance properties associated with cellular delivery.

In one embodiment, a conjugate molecule or functional chemical moiety attached via a spacer region of a single-stranded RNAi molecule provides the ability to administer said RNAi molecule to specific cell types, such as hepatocytes. For example, the asialoglycoprotein receptor (ASGPr) (Wu and Wu, 1987, *J. Biol. Chem.* 262:4429) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell* 22: 611; Connolly et al., 1982, *J. Biol. Chem.* 257:939). Lee and Lee (1987, *Glycoconjugate J.* 4:317) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpipom et al., 1981, *J. Med. Chem.* 24: 1388). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and pharmacokinetic parameters can be modulated through the use of bioconjugates of this disclosure Conjugate molecules described herein can be attached to a single-stranded RNAi molecule via non-nucleic acid linkers that are biodegradable. The term "biodegradable linker," as used in this context, refers to a non-nucleic acid linker molecule that is designed as a biodegradable linker to connect one molecule to another molecule, for example, connecting a conjugate molecule to a single-stranded RNAi molecule of the invention. The biodegradable linker is designed such that its stability can be modulated for a particular purpose, such as delivery to a particular tissue or cell type. The term "biodegradable," as used herein, refers to degradation in a biological system, for example enzymatic degradation or chemical degradation.

In one embodiment, a single-stranded RNAi molecule of the invention comprises an internal spacer portion comprising one or more non-nucleotide spacer portions, wherein said one or more non-nucleotide spacer portions (e.g., S1 or S2 within Formula III and IV) comprise or consist of a non-nucleotide spacer selected from the group consisting of a C3, a C6, a C9, and a C12 aliphatic spacer. The number after the "C" indicates the number of carbon atoms in the core spacer structure (e.g., if unsubstituted with additional chemical moieties). Said spacers can be alkyl, alkenyl, or alkynyl groups. Said spacers can also contain phosphoramidite moieties to facilitate covalent linkage to the phosphate backbone of the nucleotide portions of the molecule. In one embodiment, the spacer (S) portion is a C3 phosphoramidite spacer. In another embodiment, the spacer is a C6 phosphoramidite spacer. In a further embodiment, the C3, C6, C9, or C12 spacers are optionally substituted (e.g., with a targeting moiety).

One or more or all of the nucleotides within the nucleotide portions of a single-stranded RNAi molecule of the disclosure may be ribonucleotides, modified ribonucleotides, or suitable nucleotide analogs. Incorporation of nucleotide analogs, such as various known sugar, base, and backbone modifications, and LNA monomer units into disrupted strands may significantly enhance serum stability and prolong target knockdown or expression regulatory effects. The single-stranded RNA molecules of the present invention can functionally accommodate and are compatible with various chemical modifications to varying degrees. For example, from 5% to 100% of the ribonucleotides of a single-stranded RNA molecule of the invention may be modified (e.g., 5%, 10%, 15%, 20%, 25%, 30%, 35%, 40%, 45%, 50%, 55%, 60%, 65%, 70%, 75%, 80%, 85%, 90%, 95%, or 100% of the ribonucleotides of the single-stranded RNAi molecules of the invention may be chemically modified or are replaced with nucleotide analog residues). The improved properties conferred by the functionally compatible chemical modifications to the sugar, base and/or backbone, or by including suitable nucleotide analog residues, are of particular importance for application of these single-stranded RNAi molecules in vivo, for example, for use as a therapeutic agent or as a functional genomic tool.

In a further aspect, a single-stranded RNAi molecule of the invention, according to any of the embodiments herein, are capable of participating in RNAi against a RNA target, including an endogenous RNA target. In one embodiment, the endogenous RNA target is the target of a naturally-occurring miRNA. The inhibition of the RNA target may be achieved via the standard RNA-specific interference mechanism, including miRNA-dependent RNA interference. For example, the inhibition of a miRNA target may be by interaction (e.g., base-pairing, binding, etc.) with the untranslated mRNA region, with which a corresponding endogenous miRNA interacts, which effectuates the translational regulation of one or more downstream genes. Alternatively, the inhibition of a miRNA target may be achieved via a siRNA-like interference mechanism wherein the binding of the miRNA target by the single-stranded RNAi molecule of the invention that is a miRNA mimetic results in the cleavage of the untranslated miRNA target. The single-stranded RNAi molecules of the invention may also inhibit mRNA target via a siRNA-like interference mechanism where the binding of the mRNA target in the sequence coding region (rather than in the non-coding untranslated region) by the single-stranded RNAi molecule of the invention results in cleavage of an mRNA target coding sequence.

C. Substituted and/or Modified Single-Stranded RNAi Molecules

The introduction of substituted and modified nucleotides into single-stranded RNAi molecules of the invention provides a tool for overcoming potential limitations of in vivo stability and bioavailability inherent to native RNA molecules (i.e., having standard nucleotides) that are exogenously delivered. In certain embodiments, the use of substituted or modified single-stranded RNAi molecules of this disclosure can enable achievement of a given therapeutic effect at a lower dose since these molecules may be designed to have an increased half-life in a subject or biological samples (e.g., serum). Furthermore, certain substitutions or modifications can be used to improve the bioavailability of single-stranded RNAi molecules by targeting particular cells or tissues or improving cellular uptake of the single-stranded RNAi molecules. Therefore, even if the activity of a single-stranded RNAi molecule of this disclosure is somewhat reduced (e.g., by less than about 20%, or 30%, or even 40%) as compared to an unmodified or unsubstituted RNAi molecule of the same structure, the overall activity of the substituted or modified RNAi molecule can be greater than that of its native counterpart due to improved stability or delivery of the molecule. Substituted and/or modified single-stranded RNAi molecules can also minimize the possibility of activating an interferon response in, for example, humans.

In certain embodiments, single-stranded RNAi molecules of the invention comprise ribonucleotides at about 5% to about 95% of the nucleotide positions. For example, from one to all (e.g., 1, 2, 3, 4, 5, 6, 7, 8, 9, 10, 11, 12, 13, 14, 15, 16, 17, 18, 19, 20, 21, 22, 23, 24, 25 26, or 27) of the ribonucleotides of the single-stranded RNAi molecules of the invention can be modified.

In related embodiments, a single-stranded RNAi molecule according to the instant disclosure comprises one or more natural or synthetic non-standard nucleoside. In related embodiments, the non-standard nucleoside is one or more deoxyuridine, L- or D-locked nucleic acid (LNA) molecule (e.g., a 5-methyluridine LNA) or substituted LNA (e.g., having a pyrene), or a universal-binding nucleotide, or a G clamp, or any combination thereof. In certain embodiments, the universal-binding nucleotide can be C-phenyl, C-naphthyl, inosine, azole carboxamide, 1-β-D-ribofuranosyl-4-nitro indole, 1-β-D-ribofuranosyl-5-nitroindole, 1-β-D-ribofuranosyl-6-nitroindole, or 1-β-D-ribofuranosyl-3-nitropyrrole.

Substituted or modified nucleotides, which can be present in the single-stranded RNAi molecules of the invention, comprise modified or substituted nucleotides having characteristics similar to natural or standard ribonucleotides. For example, this disclosure features single-stranded RNAi molecules comprising nucleotides having a Northern conformation (see, e.g., Northern pseudorotation cycle, Saenger, Springer-Verlag ed., 1984), which are known to potentially impart resistant to nuclease degradation while maintaining the capacity to mediate RNAi, at least when applied to siRNA molecules. Exemplary nucleotides having a Northern configuration include locked nucleic acid (LNA) nucleotides (e.g., 2'-O, 4'-C-methylene-(D-ribofuranosyl) nucleotides), 2'-methoxyethyl (MOE) nucleotides, 2'-methyl-thio-ethyl, 2'-deoxy-2'-fluoro nucleotides, 2'-deoxy-2'-chloro nucleotides, 2'-azido nucleotides, 5-methyluridines, or 2'-O-methyl nucleotides). In any of these embodiments, one or more substituted or modified nucleotides can be a G clamp (e.g., a cytosine analog that forms an additional hydrogen bond to guanine, such as 9-(aminoethoxy)phenoxazine). See, e.g., Lin and Mateucci, 1998, *J. Am. Chem. Soc.* 720:8531.

In certain embodiments, the 5'-terminal end of single-stranded RNAi molecules of the invention is phosphorylated. In any of the embodiments of single-stranded RNAi molecules described herein, the molecule can further comprise a terminal phosphate group, such as a 5'-phosphate (see Martinez et al., 2002, *Cell* 110:563; Schwarz et al., 2002, *Mole. Cell* 70:537) or a 5'3'-diphosphate.

In another aspect, a single-stranded RNAi molecule of the invention comprises one or more 5'- and/or a 3'-cap structure at the terminal ends of the molecule. By "cap structure" is meant chemical modifications, which have been incorporated into the ends of oligonucleotide (see, for example, Matulic-Adamic et al., U.S. Pat. No. 5,998,203, incorporated by reference herein). These terminal modifications can protect certain nucleic acid molecules from exonuclease degradation, and can impart certain advantages in delivery and/or cellular localization. In non-limiting examples: a suitable 5'-cap can be one selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In another non-limiting example, a suitable 3'-cap can be selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. For more details, see Beaucage and Iyer, 1993, *Tetrahedron* 49:1925, which is incorporated by reference herein.

In certain embodiments, this disclosure features modified single-stranded RNAi molecules comprising phosphate backbone modifications, including, for example, one or more phosphorothioate, phosphorodithioate, methylphosphonate, phosphotriester, morpholino, amidate carbamate, carboxymethyl, acetamidate, polyimide, sulfonate, sulfonamide, sulfamate, formacetal, thioformacetal, or alkylsilyl, substitutions. For a review of oligonucleotide backbone modifications, see Hunziker and Leumann, 1995, Nucleic Acid Analogues: Synthesis and Properties, in *Modern Synthetic Methods*, VCH, 331; Mesmaeker et al., 1994, *ACS* 24-39.

In further embodiments, a single-stranded RNAi molecule comprises one or more (e.g., 1, 2, 3, 4, 5, 6, 7, 8, 9, 10, 11, 12, 13, 14, 15, 16, 17, 18, 19, 20, 21, 22, 23, 24, 25, or 26) 2'-sugar substitutions, such as a 2'-deoxy, 2'-O-2-methoxyethyl, 2'-O-methoxyethyl, 2'-O-methyl, 2'-halogen (e.g., 2'-fluoro), 2'-O-allyl, or the like, or any combination thereof. In still further embodiments, a single-stranded RNAi molecule comprises a terminal cap substituent at one or both terminal ends, such as, for example, an alkyl, abasic, deoxy abasic, glyceryl, dinucleotide, acyclic nucleotide, inverted deoxynucleotide moiety, or any combination thereof. In certain embodiments, at least one 5'-terminal-end ribonucleotide has a 2'-sugar substitution.

In other embodiments, a single-stranded RNAi molecule comprises one or more (e.g., 1, 2, 3, 4, 5, 6, 7, 8, 9, 10, 11, 12, 13, 14, 15, 16, 17, 18, 19, 20, 21, 22, 23, 24, 25, or 26) substitutions in the sugar backbone, including any combination of ribosyl, 2'-deoxyribosyl, a tetrafuranosyl (e.g., L-α-threofuranosyl), a hexopyranosyl (e.g., β-allopyranosyl, β-altropyranosyl and β-glucopyranosyl), a pentopyranosyl (e.g., β-ribopyranosyl, α-lyxopyranosyl, β-xylopyranosyl and α-arabinopyranosyl), a carbocyclic analog, a pyranose, a furanose, a morpholino, or analogs or derivatives thereof.

In yet other embodiments, a single-stranded RNAi molecule comprises at least one (e.g., 1, 2, 3, 4, 5, 6, 7, 8, 9, 10, 11, 12, 13, 14, 15, 16, 17, 18, 19, 20, 21, 22, 23, 24, 25, or 26) modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or any combination thereof.

A single-stranded RNAi molecule can comprise one or more modified internucleotide linkages at the 3'-terminal end, the 5'-terminal end, or both of the 3'-terminal and 5'-terminal ends of the molecule. In one embodiment, a single-stranded RNAi molecule of the invention has one modified internucleotide linkage at the 3'-terminal end, such as a phosphorothioate linkage. An exemplary single-stranded RNAi molecule comprises about 1, 2, 3, 4, 5, 6, 7, 8, 9, 10 or more phosphorothioate internucleotide linkages. A further exemplary single-stranded RNAi molecule comprises about 1, 2, 3, 4, 5, 6, 7, 8, 9, 10 or more consecutive phosphorothioate internucleotide linkages at, for example, the 5'-terminal end of the molecule. In yet another exemplary single-stranded RNAi molecule, there can be one or more pyrimidine phosphorothioate internucleotide linkages. In a further exemplary single-stranded RNAi molecule, there can be one or more purine phosphorothioate internucleotide linkages.

Many exemplary modified nucleotide bases or analogs thereof useful in single-stranded RNAi molecules of the instant disclosure include 5-methylcytosine; 5-hydroxymethylcytosine; xanthine; hypoxanthine; 2-aminoadenine; 6-methyl, 2-propyl, or other alkyl derivatives of adenine and guanine; 8-substituted adenines and guanines (e.g., 8-aza, 8-halo, 8-amino, 8-thiol, 8-thioalkyl, 8-hydroxyl, or the like); 7-methyl, 7-deaza, and 3-deaza adenines and guanines; 2-thiouracil; 2-thiothymine; 2-thiocytosine; 5-methyl, 5-propynyl, 5-halo (e.g., 5-bromo or 5-fluoro), 5-trifluoromethyl, or other 5-substituted uracils and cytosines; and 6-azouracil. Further useful nucleotide bases can be found in Kurreck, 2003, *Eur. J. Biochem.* 270:1628; Herdewijn, 2000, *Guide Nucleic Acid Develop.* 10:297; Concise Encyclopedia of Polymer Science and Engineering, pp. 858-859, Kroschwitz, J. L, ed. John Wiley & Sons, 1990; U.S. Pat. No. 3,687,808, and similar references, all of which are incorporated by reference herein.

Certain substituted or modified nucleotide base moieties are also contemplated. These include 5-substituted pyrimidines; 6-azapyrimidines; and N-2, N-6, or 0-6 substituted purines (e.g., 2-aminopropyladenine, 5-propynyluracil and 5-propynylcytosine). Further, for example, 5-methyluridine and 5-methylcytosine substitutions are known to increase nucleic acid duplex stability, which can be combined with 2'-sugar modifications (e.g., 2'-O-methyl or 2'-methoxyethyl) or internucleoside linkages (e.g., phosphorothioate) that provide the desired nuclease resistance to the modified or substituted single-stranded RNAi molecule.

In further embodiments, at least one pyrimidine of a single-stranded RNAi molecule of the invention is a locked nucleic acid (LNA) in the form of a bicyclic sugar. In a related embodiment, the LNA comprises a base substitution, such as a 5-methyluridine LNA or 2-thio-5-methyluridine LNA. In further embodiments, a ribose of the pyrimidine nucleoside or the internucleoside linkage can be optionally modified.

In any of these embodiments, one or more substituted or modified nucleotides can be a G clamp (e.g., a cytosine analog that forms an additional hydrogen bond to guanine, such as 9-(aminoethoxy) phenoxazine). See, e.g., Lin and Mateucci, 1998, *Nucleic Acids Res.* 19:3111.

In any of the embodiments described herein, a single-stranded RNAi molecule may include multiple types of modifications. For example, a single-stranded RNAi molecule having at least one ribothymidine or 2-thioribothymidine can further comprise at least one LNA, 2'-methoxy, 2'-fluoro, 2'-deoxy, phosphorothioate linkage, an inverted base terminal cap, or any combination thereof. In certain exemplary embodiments, a single-stranded RNAi molecule can comprise one or more or all uridines substituted with ribothymidine and have up to about 75% LNA substitutions. In other exemplary embodiments, a single-stranded RNAi molecule can comprise from one or more or all uridines substituted with ribothymidine and have up to about 25% 2'-methoxy substitutions. In still other exemplary embodiments, a single-stranded RNAi molecule can comprise one or more or all uridines substituted with ribothymidine and have up to about 100% 2'-fluoro substitutions.

Within certain aspects, the present disclosure also provides single-stranded RNAi molecules comprising one or more universal base nucleotides. The term "universal base" as used herein refers to nucleotide base analogs that form base pairs or hydrogen bonded nucleotide pairs with more than one types of nucleotides. Non-limiting examples of universal bases include C-phenyl, C-naphthyl and other aromatic derivatives, inosine, azole carboxyamides, and nitroazole derivatives such as 3-nitropyrrole, 4-nitroindole, 5-nitroindole, and 6-nitroindole as known in the art (see, e.g., Loakes, 2001, *Nucleic Acids Research* 29:2437-2447). In certain aspects, a single-stranded RNAi molecule disclosed herein can include about 1 to about 10 universal base nucleotides, so long as the resulting RNAi molecule remains capable of modulating one or more of its endogenous targets.

D. Synthesis of Single-Stranded RNAi Molecules

Exemplary molecules of the instant disclosure can be obtained using a number of techniques known to those of skill in the art. For example, the RNAi molecules of the invention can be chemically synthesized, recombinantly produced (e.g., encoded by plasmid), or a combination thereof.

Oligonucleotides or individual contiguous stretches of nucleotides (e.g., certain modified oligonucleotides or portions of oligonucleotides lacking ribonucleotides) are synthesized using protocols known in the art, for example, as described in Caruthers et al., 1992, *Methods in Enzymol.* 211:3; Thompson et al, PCT Publication No. WO 99/54459; Wincott et al., 1995, *Nucleic Acids Res.* 23:2677; Wincott et al., 1997, *Methods Mol. Bio.* 74:59; Brennan et al., 1998, *Biotechnol. Bioeng.* 67:33; and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end. Synthesis of RNA without modifications, including certain single-stranded RNAi molecules thereof of this disclosure, can be made using the procedure as described in Usman et al., 1987, *J Am. Chem. Soc.* 109:7845; Scaringe et al., 1990, *Nucleic Acids Res.* 18:5433; and Wincott et al., 1995, *Nucleic Acids Res.* 23:2677; and Wincott et al., 1997, *Methods Mol. Bio.* 74:59. In certain embodiments, the nucleotide portions of the single-stranded RNAi molecules of the present disclosure can be synthesized separately and joined together with the non-nucleotide spacer portions post-synthetically, for example, by ligation (Moore et al., 1992, *Science* 256:9923; Draper et al., PCT Publication No. WO 93/23569; Shabarova et al., 1991, *Nucleic Acids Res.* 19:4247; Bellon et al., 1997, *Nucleosides & Nucleotides* 16:951; Belton et al., 1997, *Bioconjugate Chem.* 8:204). In a further embodiment, the nucleotide portion of a single-stranded RNAi molecule of this disclosure can be made as single or multiple transcription products expressed by a polynucleotide (DNA or RNA) vector encoding one or more contiguous stretches of RNAs and directing their expression within host cells. The nucleotide portions are then isolated and joined by ligation with a non-nucleotide spacer portion.

In some embodiments, poi III based constructs are used to express nucleic acid molecules of the invention. Transcription of the single-stranded RNAi molecule sequences can be driven from a promoter for eukaryotic RNA polymerase I (pol I), RNA polymerase II (pol II), or RNA polymerase III (pol III). (see for example, Thompson, U.S. Pat. Nos. 5,902,880 and 6,146,886). (See also, Izant and Weintraub, 1985, *Science*, 229, 345; McGarry and Lindquist, 1986, *Proc. Natl. Acad. Sci., USA* 83, 399; Scanlon et al., 1991, *Proc. Natl. Acad. Sci. USA*, 88, 10591-5; Kashani-Sabet et al., 1992, *Antisense Res. Dev.*, 2, 3-15; Dropulic et al., 1992, *J. Viral.*, 66, 1432-41; Weerasinghe et al., 1991, *J. Virol.*, 65, 5531-4; Ojwang et al., 1992, *Proc. Natl. Acad. Sci.* USA, 89, 10802-6; Chen et al., 1992, *Nucleic Acids Res.*, 20, 4581-9; Sarver et al., 1990 *Science*, 247, 1222-1225; Thompson et al., 1995, *Nucleic Acids Res.*, 23, 2259; Good et at, 1997, *Gene Therapy*, 4, 45. Transcripts from poi II or poi III promoters are expressed at high levels in all cells; the levels of a given poi II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA*, 87, 6743-7; Gao and Huang 1993, *Nucleic Acids Res.*, 21, 2867-72; Lieber et al., 1993, *Methods Enzymol.*, 217, 47-66; Zhou et al., 1990, *Mol. Cell. Biol.*, 10, 4529-37). Several investigators have demonstrated that nucleic acid molecules expressed from such promoters can function in mammalian cells (e.g. Kashani-Sabet et al., 1992, *Antisense Res. Dev.*, 2, 3-15; Ojwang et al., 1992, *Proc. Natl. Acad. Sci. USA*, 89, 10802-6; Chen et al, 1992, *Nucleic Acids Res.*, 20, 4581-9; Yu et al., 1993, *Proc. Natl. Acad. Sci. USA*, 90, 6340-4; L'Huillier et al., 1992, *EMBO J.*, 11, 4411-8; Lisziewicz et al., 1993, *Proc. Natl. Acad. Sci. U S. A*, 90, 8000-4; Thompson et al., 1995, *Nucleic Acids Res.*, 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules (Thompson et al., supra; Couture and Stinchcomb, 1996, supra; Noonberg et at, 1994, *Nucleic Acid Res.*, 22, 2830; Noonberg et al., U.S. Pat. No. 5,624,803; Good et al., 1997, *Gene Ther.*, 4, 45; Beigelman et at, International PCT Publication No. WO 96/18736. The above transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

Chemically synthesizing nucleic acid molecules with substitutions or modifications (base, sugar, phosphate, or any combination thereof) can impart resistance to degradation by serum ribonucleases, which may lead to increased potency and other pharmacological and therapeutic benefits. See, e.g., Eckstein et al., PCT Publication No. WO 92/07065; Perrault et at, 1990, *Nature* 344:565; Pieken et al., 1991, *Science* 253:314; Usman and Cedergren, 1992, *Trends in Biochem. Sci.* 77:334; Usman et al., 1994, *Nucleic Acids Symp. Ser.* 31:163; Beigelman et at, 1995, *J. Biol Chem.* 270:25702; Burlina et at, 1997, *Bioorg. Med. Chem.* 5:1999; Karpeisky et al., 1998, *Tetrahedron Lett.* 39:1131; Earnshaw and Gait, 1998, *Biopolymers* (*Nucleic Acid Sciences*) 48:39; Velma and Eckstein, 1998, *Annu. Rev. Biochem.* 67:99; Herdewijn, 2000, *Guide Nucleic Acid Drug Dev.* 10:291; Kurreck, 2003, *Eur. J. Biochem.* 270:1628; Dorsett and Tuschl, 2004, *Nature Rev. Drug Discov.* 3:318; Rossi et al., PCT Publication No. WO 91/03162; Usman et al., PCT Publication No. WO 93/15187; Beigelman et al., PCT Publication No. WO 97/26270; Woolf et al., PCT Publication No. WO 98/13526; Sproat, U.S. Pat. No. 5,334,711; Usman et al., U.S. Pat. No. 5,627,053; Beigelman et al., U.S. Pat. No. 5,716,824; Otvos et al., U.S. Pat. No. 5,767,264; Gold et al., U.S. Pat. No. 6,300,074. Each of the above references discloses various substitutions and chemical modifications to the base, phosphate, or sugar moieties of nucleic acid molecules, which can be used in the single-stranded RNAi molecules described herein.

E. Methods for Designing a Single-Stranded RNAi Molecule

As described herein, the single-stranded RNA molecules of the present invention are capable of inhibiting the expression of a target sequence via an RNAi mechanism. In one embodiment, the single-stranded RNAi molecules can be designed based on a previously identified RNAi agent possessing a desired knockdown function (e.g., siRNA, miRNA). For example, if a single-stranded RNAi molecule of the present invention is a miRNA mimetic, it is derived from a corresponding, naturally-occurring miRNA molecule (see Table 1) or an analog thereof (e.g., a chemically modified form). As of the filing date of the present application, over 3000 miRNA molecules endogenous to a variety of species can be found in publically available databases (see, e.g., the publicly available miRBase sequence database as described in Griffith-Jones et al., 2004, *Nucleic Acids Research* 32:D109-D111 and Griffith-Jones et al., 2006, *Nucleic Acids Research* 34:D 140-D144, accessible on the World Wide Web at the Wellcome Trust Sanger Institute website). Table 1 herein contains a list of 1090 mature human miRNA sequences (SEQ ID NO: 1-1090). In another example, a single-stranded RNAi molecule of the present invention may be derived from a previously identified siRNA either known to inhibit expression of a target sequence of choice or has the potential of inhibiting expression of a target mRNA sequence. Specifically, a single-stranded RNAi molecule that is derived from a previously identified RNAi molecule (i.e., the reference RNAi molecule) can be designed by introducing one or more internal, non-nucleotide spacers portions within the guide strand of the reference RNAi molecule. In another embodiment, the single-stranded RNAi molecules can be designed de novo (i.e., not based on a known RNAi agent) for the purpose of knocking down expression of a particular target sequence.

The RNAi activity of a given single-stranded RNAi molecule of the invention can be measured using known methods, such as those described generally in Fire et al., PCT Publication No. WO99/32619, and as described in the Examples section infra. In some embodiments, the instant specification provides methods for selecting more efficacious single-stranded RNAi molecule designs by using one or more reporter gene constructs comprising a constitutive promoter, such as a cytomegalovirus (CMV) or phosphoglycerate kinase (PGK) promoter, operably fused to, and capable of altering the expression of one or more reporter genes, such as a luciferase, chloramphenicol (CAT), or β-galactosidase, which, in turn, is operably fused in-frame to a portion of the target sequence that is whole or partially complementary to the ssRNAi to be tested. These reporter gene expression constructs may be co-transfected with one or more ssRNAi molecules and a control (e.g., corresponding miRNA mimetic that does not contain the internal non-nucleotide spacer). The capacity of a given ssRNAi molecule to mediate RNAi of a target mRNA may be determined by comparing the measured reporter gene activity in cells transfected with the ssRNAi molecule and the activity in cells transfected with a negative control (i.e., in cells not transfected with the ssRNAi molecule) and a positive control (e.g., in cells transfected with the corresponding miRNA mimetic that does not contain the internal non-nucleotide spacer). The ssRNAi molecules having at least 20% or more, preferably at least 40% or more, or 60% or more, or 80% or more, of the activity of their corresponding RNAi molecule, for example, that do not contain internal non-nucleotide spacers, are selected.

A person of skill in the art can screen single-stranded RNAi molecules of this disclosure containing various non-nucleotide spacers to determine which of molecules possess improved properties (e.g., pharmacokinetic profile, bioavailability, stability) while maintaining the ability to mediate RNAi in, for example, an animal model as described herein or generally known in the art. Similarly, a person of skill in the art can also screen single-stranded RNAi molecules of this disclosure having various conjugates to determine which of the RNAi molecule-conjugate complexes possess improved properties while maintaining the ability to mediate RNAi.

F. Compositions and Methods of Use

As set forth herein, single-stranded RNA molecules of the invention are RNAi agents preferably capable of participating in the cellular RNAi pathway or otherwise capable of modulating the same or related pathway(s) and resulting in the inhibition of a target gene associated with a pathological or diseased condition. In the case of a single-stranded RNA molecule that represents a miRNA mimetic, the ssRNAi molecule is designed to supplement or take the place of a corresponding, naturally-occurring miRNA, the reduced or otherwise unsuitably low levels of which have been associated with pathological or diseased conditions. The single-stranded RNAi molecules of the invention thus are useful reagents, which can be used in methods for a variety of therapeutic, diagnostic, target validation, genomic discovery, genetic engineering, and pharmacogenomic applications.

A single-stranded RNA molecule of the invention can be introduced to a cell, tissue, organism, in vitro system, or in vivo system to mediate RNAi against a target sequence. That target sequence may be an endogenous target gene or sequence. In one embodiment, the single-stranded RNAi molecules of the invention can be used for treating organisms having a disease characterized by the undesired production of a protein.

In the case of a single-stranded RNAi molecule of the invention that is a miRNA mimetic, the target sequence is the target of a corresponding, naturally-occurring miRNA. In such a case, the single-stranded miRNA mimetic may regulate a number of genes, for example, downstream from its mRNA target, whose expression levels are associated with or otherwise regulated by the corresponding, naturally-occurring miRNA. Because aberrant expression levels of certain naturally-occurring miRNAs have been implicated in various human ailments, including, but not limited to, hyperproliferative, angiogenic, or inflammatory diseases, states, or adverse conditions, the single-stranded miRNA mimetics of the present invention can offer valuable therapeutic opportunities. In this context, a single-stranded miRNA mimetic of this disclosure can regulate (e.g., knockdown or up-regulate) expression of one or more downstream genes of its corresponding endogenous miRNA, such that prevention, alleviation, or reduction of the severity or recurrence of one or more associated disease symptoms can be achieved. Alternatively, for various distinct disease models in which expression of one or more target mRNAs are not necessarily reduced or at a lower-than-normal level as a consequence of diseases or other adverse conditions, introducing exogenous miRNA mimetics, such as one or more single-stranded miRNA mimetics of the invention, may nonetheless result in a therapeutic result by affecting the expression levels of genes associated with the disease pathway.

A single-stranded RNAi molecule of invention can also act similar to a siRNA molecule in targeting the coding region of a target gene, inhibiting the expression that gene and, thus, reducing protein production. The protein that would have been produced if not for introduction of the single-stranded RNAi molecule may be associated with a pathological or diseased condition (e.g., cancer).

In accordance with this disclosure herein, a single-stranded RNAi molecule of the invention, compositions thereof, and methods for inhibiting expression of one or more corresponding target mRNAs in a cell or organism are provided. This disclosure provides methods and single-stranded RNAi molecule compositions for treating a subject, including a human cell, tissue or individual.

(i) Pharmaceutical Compositions and Formulations

The present disclosure includes single-stranded RNAi molecule compositions prepared for storage or administration that include a pharmaceutically effective amount of a desired RNAi molecule in a pharmaceutically acceptable carrier or diluent. The single-stranded RNAi molecule compositions of the disclosure can be effectively employed as pharmaceutically-acceptable formulations. Pharmaceutically-acceptable formulations prevent, alter the occurrence or severity of, or treat (alleviate one or more symptom(s) to a detectable or measurable extent) a disease state or other adverse condition in a subject. Thus, a pharmaceutical composition or formulation refers to a composition or formulation in a form suitable for administration into a cell, or a subject such as a human (e.g., systemic administration). The pharmaceutical compositions of the present disclosure are formulated to allow the single-stranded RNAi molecule(s) contained therein to be bioavailable upon administration to a subject.

In certain embodiments, pharmaceutical compositions of this disclosure can optionally include preservatives, antioxidants, stabilizers, dyes, flavoring agents, or any combination thereof. Exemplary preservatives include sodium benzoate, esters of p-hydroxybenzoic acid, and sorbic acid. A pharmaceutically acceptable formulation includes salts of the above compounds, for example, acid addition salts, such as salts of hydrochloric acid, hydrobromic acid, acetic acid, or benzene sulfonic acid. Acceptable carriers or diluents for therapeutic use are well known in the pharmaceutical art, and are described, for example, in Remington's Pharmaceutical Sciences, Mack Publishing Co., A. R. Gennaro edit., 21st Edition, 2005.

In certain embodiments, aqueous suspensions containing one or more single-stranded RNAi molecules of the invention can be prepared in an admixture with suitable excipients, such as suspending agents or dispersing or wetting agents. Exemplary suspending agents include sodium carboxymethylcellulose, methylcellulose, hydropropyl-methylcellulose, sodium alginate, polyvinylpyrrolidone, gum tragacanth and gum acacia. Representative dispersing or wetting agents include naturally-occurring phosphatides (e.g., lecithin), condensation products of an alkylene oxide with fatty acids (e.g., polyoxyethylene stearate), condensation products of ethylene oxide with long chain aliphatic alcohols (e.g., heptadecaethyleneoxycetanol), condensation products of ethylene oxide with partial esters derived from fatty acids and hexitol (e.g., polyoxyethylene sorbitol monooleate), or condensation products of ethylene oxide with partial esters derived from fatty acids and hexitol anhydrides (e.g., polyethylene sorbitan monooleate). In certain embodiments, the aqueous suspensions can optionally contain one or more preservatives (e.g., ethyl or w-propyl-p-hydroxybenzoate), one or more coloring agents, one or more flavoring agents, or one or more sweetening agents (e.g., sucrose, saccharin). In additional embodiments, dispersible powders and granules suitable for preparation of an aqueous suspension comprising one or more single-stranded RNAi molecules of the invention can be prepared by the addition of water with the single-stranded RNAi molecules in admixture with a dispersing or wetting agent, suspending agent and optionally one or more preservative, coloring agent, flavoring agent, or sweetening agent.

In further embodiments, a single-stranded RNAi molecule of this disclosure can be formulated as oily suspensions or emulsions (e.g., oil-in-water) by suspending the ssRNAi in, for example, a vegetable oil (e.g., arachis oil, olive oil, sesame oil or coconut oil) or a mineral oil (e.g., liquid paraffin). Suitable emulsifying agents can be naturally-occurring gums (e.g., gum acacia or gum tragacanth), naturally-occurring phosphatides (e.g., soy bean, lecithin, esters or partial esters derived from fatty acids and hexitol), anhydrides (e.g., sorbitan monooleate), or condensation products of partial esters with ethylene oxide (e.g., polyoxyethylene sorbitan monooleate). In certain embodiments, the oily suspensions or emulsions can optionally contain a thickening agent, such as beeswax, hard paraffin or cetyl alcohol. In related embodiments, sweetening agents and flavoring agents can optionally be added to provide palatable oral preparations. In yet other embodiments, these compositions can be preserved by the optionally adding an antioxidant, such as ascorbic acid.

In further embodiments, single-stranded RNAi molecules can be formulated as syrups and elixirs with sweetening agents (e.g., glycerol, propylene glycol, sorbitol, glucose or sucrose). Such formulations can also contain a demulcent, preservative, flavoring, coloring agent, or any combination thereof.

In other embodiments, pharmaceutical compositions comprising a single-stranded RNAi molecule of the invention can be in the form of a sterile, injectable aqueous or oleaginous suspension. The sterile, injectable preparation can also be a sterile, injectable solution or suspension in a non-toxic, parenterally-acceptable diluent or solvent (e.g., as a solution in 1,3-butanediol). Among the exemplary acceptable vehicles and solvents useful in the compositions of this disclosure is water, Ringer's solution, or isotonic sodium chloride solution. In addition, sterile, fixed oils may be employed as a solvent or suspending medium. For this purpose, any bland fixed oil can be employed including synthetic mono- or diglycerides. In addition, fatty acids such as oleic acid find use in the preparation of parenteral formulations.

The single-stranded RNAi molecules of the invention can be administered directly, or can be complexed, for example, with cationic lipids or packaged within liposomes, or otherwise delivered to target cells or tissues. Methods for the delivery of nucleic acid molecules are described in Akhtar et al., 1992, *Trends Cell Bio.*, 2:139; *Delivery Strategies for Antisense Oligonucleotide Therapeutics*, ed. Akhtar, 1995; Maurer et al., 1999, *Mol. Membr. Biol.* 16:129-140; Hofland and Huang, 1999, *Handb. Exp. Pharmacol*, 137:165-192; and Lee et al., 2000, *ACS Symp. Ser.* 752:184-192. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example, Gonzalez et al., 1999, *Bioconjugate Chem.*, 10, 1068-1074; Wang et al., International PCT Publication Nos. WO 03/47518 and WO 03/46185), poly (lactic-co-glycolic)acid (PLGA) and PLCA microspheres (see for example U.S. Pat. No. 6,447,796 and US Patent Application Publication No. US2002130430), biodegradable nanocapsules, and bioadhesive microspheres, or by proteinaceous vectors (O'Hare and Normand, International PCT Publication No. WO 00/53722).

(ii) Carrier/Delivery Systems

In one aspect, the present invention provides carrier systems containing the single-stranded RNAi molecules described herein. In some embodiments, the carrier system is a lipid-based carrier system, cationic lipid, or liposome nucleic acid complexes, a liposome, a micelle, a virosome, a lipid nanoparticle or a mixture thereof. In other embodiments, the carrier system is a polymer-based carrier system such as a cationic polymer-nucleic acid complex. In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system in a lipid nanoparticle ("LNP") formulation.

In certain embodiments, the single-stranded RNAi molecules of the invention are formulated with a lipid nanoparticle composition as is described in U.S. patent application Ser. Nos. 11/353,630, 11/586,102, 61/189,295, 61/204,878, 61/235,476, 61/249,807, and 61/298,022. In certain preferred embodiments, the ssRNAi molecules of the invention are formulated with a lipid nanoparticle composition comprising a cationic lipid/Cholesterol/PEG-C-DMA/DSPC in a 40/48/2/10 ratio or a cationic lipid/Cholesterol/PEG-DMG/DSPC in a 40/48/2/10 ratio. In certain other embodiments, the invention features a composition comprising a ssRNAi molecule of the invention formulated with any of the cationic lipid formulations described in U.S. Patent Application Nos. 61/189,295, 61/204,878, 61/235,476, 61/249,807, and 61/298,022.

Within certain embodiments of this disclosure, pharmaceutical compositions and methods are provided that feature the presence or administration of one or more single-stranded RNAi molecule, combined, complexed, or conjugated with functional moiety, optionally formulated with a pharmaceutically-acceptable carrier, such as a diluent, stabilizer, buffer, or the like. Such conjugates and/or complexes can be used to facilitate delivery of RNAi molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. Non-limiting, examples of such conjugates are described in U.S. Publication Nos. US2008/0152661 A1 and US2004/0162260 A1 (e.g., CDM-LBA, CDM-Pip-LBA, CDM-PEG, CDM-NAG, etc.) and U.S. patent application Ser. Nos. 10/427,160 and 10/201,394; and U.S. Pat. Nos. 6,528,631; 6,335,434; 6,235,886; 6,153,737; 5,214,136; and 5,138,045.

A single-stranded RNAi molecule of this disclosure can include a conjugate member on one or more of the nucleotides, at a terminal and/or internal position(s), and/or on the spacer portion of the molecule. The conjugate member can be, for example, a lipophils, a terpene, a protein binding agent, a vitamin, a carbohydrate, or a peptide. For example, the conjugate member can be naproxen, nitroindole (or another conjugate that contributes to stacking interactions), folate, ibuprofen, or a C5 pyrimidine linker. In other embodiments, the conjugate member is a glyceride lipid conjugate (e.g., a dialkyl glyceride derivatives), vitamin E conjugates, or thio-cholesterols. In various embodiments, polyethylene glycol (PEG) can be covalently attached to single-stranded RNAi molecules of the present invention. The attached PEG can be any molecular weight, preferably from about 100 to about 50,000 daltons (Da).

Within certain embodiments of this disclosure, pharmaceutical compositions and methods are provided that feature the presence or administration of one or more single-stranded RNAi molecule, combined, complexed, or conjugated with a polypeptide or peptide, optionally formulated with a pharmaceutically-acceptable carrier, such as a diluent, stabilizer, buffer, or the like. In certain embodiments, when peptide conjugate partners are used to enhance delivery of one or more single-stranded RNAi molecules of this disclosure into a target cell, or otherwise enhance stability or activity of the molecule when contacted with a biological sample. Exemplary peptide conjugate members for use within these aspects of this disclosure, include peptides PN27, PN28, PN29, PN58, PN61, PN73, PN158, PN159, PN173, PN182, PN202, PN204, PN250, PN361, PN365, PN404, PN453, and PN509 as described, for example, in U.S. Patent Application Publication Nos. 2006/0040882 and 2006/0014289, and U.S. Provisional Patent Application No. 60/939,578, which are all incorporated herein by reference.

In one embodiment, this disclosure provides compositions suitable for administering single-stranded RNAi molecules of this disclosure to specific cell types, such as hepatocytes. For example, the asialoglycoprotein receptor (ASGPr) (Wu and Wu, 1987, *J. Biol. Chem.* 262:4429) is unique to hepatocytes and binds branched galactose-terminal glycoproteins, such as asialoorosomucoid (ASOR), Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell* 22: 611; Connolly et al., 1982, *J. Biol. Chem.* 257:939). Lee and Lee (1987, *Glycoconjugate J.* 4:317) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpipom et al., 1981, *J. Med. Chem.* 24: 1388). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and pharmacokinetic parameters can be modulated through the use of bioconjugates of this disclosure.

In still another embodiment, a single-stranded RNAi molecule of the invention may be conjugated to a polypeptide and admixed with one or more non-cationic lipids or a combination of a non-cationic lipid and a cationic lipid to form a composition that enhances intracellular delivery of the RNAi molecule as compared to delivery resulting from contacting the target cells with a naked RNAi molecule without the lipids. In more detailed aspects of this disclosure, the mixture, complex or conjugate comprising a single-stranded RNAi molecule and a polypeptide can be optionally combined with (e.g., admixed or complexed with) a cationic lipid, such as Lipofectine™. To produce these compositions comprised of a polypeptide, a single-stranded RNAi molecule and a cationic lipid, the RNAi molecule and the polypeptide may be mixed together first in a suitable medium such as a cell culture medium, after which the cationic lipid is added to the mixture to form an RNAi molecule/delivery peptide/cationic lipid composition. Optionally, the peptide and cationic lipid can be mixed together first in a suitable medium such as a cell culture medium, followed by the addition of the single-stranded RNAi molecule to form the RNAi molecule/delivery peptide/cationic lipid composition.

This disclosure also features the use of single-stranded RNAi molecule compositions comprising surface-modified liposomes containing poly(ethylene glycol) lipids (PEG-modified, or long-circulating liposomes or stealth liposomes). These formulations may offer increased accumulation of drugs in target tissues (Lasic et al., 1995, *Chem. Rev.* 95:2601; Ishiwata et al., 1995, *Chem. Pharm. Bull.* 43:1005). Such liposomes have been shown to accumulate selectively in tumors, presumably by extravasation and capture in the neovascularized target tissues (Lasic et al., 1995, *Science* 267:1215; Oku et al., 1995, *Biochim. Biophys. Acta* 1238:86). The long-circulating liposomes enhance the pharmacokinetics and pharmacodynamics of nucleic acid molecules as compared to conventional cationic liposomes, which are known to accumulate in tissues of the mononuclear phagocytic system (MPS) (Liu et al., 1995, *J. Biol. Chem.* 42:24864; Choi et al., PCT Publication No. WO 96/10391; Ansell et al., PCT Publication No. WO 96/10390; Holland et al., POT Publication No. WO 96/10392). Long-circulating liposomes may also provide additional protection from nuclease degradation as compared to cationic liposomes, in theory due to avoiding accumulation in metabolically aggressive MPS tissues, such as the liver and spleen.

In some embodiments, the RNAi molecules of the invention can also be formulated or complexed with polyethyleneimine and derivatives thereof; such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in U.S. Patent Application Publication No. 20030077829.

In other embodiments, single-stranded RNAi molecules of the invention are complexed with membrane disruptive agents such as those described in U.S. Patent Application Publication No. 20010007666. In still other embodiments, the membrane disruptive agent or agents and the RNAi molecule are also complexed with a cationic lipid or helper lipid molecule, such as those lipids described in U.S. Pat. No. 6,235,310.

In certain embodiments, single-stranded RNAi molecules of the invention are complexed with delivery systems as described in U.S. Patent Application Publication Nos. 2003077829; 20050287551; 20050164220; 20050191627; 20050118594; 20050153919; 20050085486; and 20030158133; and International PCT Publication Nos. WO 00/03683 and WO 02/087541.

In some embodiments, a liposomal formulation of the invention comprises a RNAi molecule of the invention formulated or complexed with compounds and compositions described in U.S. Pat. Nos. 6,858,224; 6,534,484; 6,287,591; 6,835,395; 6,586,410; 6,858,225; 6,815,432; 6,586,001; 6,120,798; 6,977,223; 6,998,115; 5,981,501; 5,976,567; 5,705,385; and U.S. Patent Application Publication Nos. 2006/0019912; 2006/0019258; 2006/0008909; 2005/0255153; 2005/0079212; 2005/0008689; 2003/0077829, 2005/0064595, 2005/0175682, 2005/0118253; 2004/0071654; 2005/0244504; 2005/0265961 and 2003/0077829.

The present disclosure also features a method for preparing single-stranded RNAi molecule nanoparticles. A first solution containing melamine derivatives is dissolved in an organic solvent such as dimethyl sulfoxide, or dimethyl formamide to which an acid such as HCl has been added. The concentration of HCl would be about 3.3 moles of HCl for every mole of the melamine derivative. The first solution is then mixed with a second solution, which includes a nucleic acid dissolved or suspended in a polar or hydrophilic solvent (e.g., an aqueous buffer solution containing, for instance, ethylenediaminetraacetic acid (EDTA), or tris(hydroxymethyl) aminomethane (TRIS), or combinations thereof. The mixture forms a first emulsion. The mixing can be done using any standard technique such as, for example, sonication, vortexing, or in a micro fluidizer. The resultant nucleic acid particles can be purified and the organic solvent removed using size-exclusion chromatography or dialysis or both. The complexed nucleic acid nanoparticles can then be mixed with an aqueous solution containing either polyarginine or a Gln-Asn polymer, or both, in an aqueous solution.

A preferred molecular weight of each polymer is about 5000 to about 15,000 Daltons. This forms a solution containing nanoparticles of nucleic acid complexed with the melamine derivative and the polyarginine and the Gln-Asn polymers. The mixing steps are carried out in a manner that minimizes shearing of the nucleic acid while producing nanoparticles on average smaller than about 200 nanometers in diameter. It is believed that the polyarginine complexes with the negative charge of the phosphate groups within the minor groove of the nucleic acid, and the polyarginine wraps around the trimeric nucleic acid complex. At either terminus of the polyarginine other moieties, such as the TAT polypeptide, mannose or galactose, can be covalently bound to the polymer to direct binding of the nucleic acid complex to specific tissues, such as to the liver when galactose is used. While not being bound to theory, it is believed that the Gln-Asn polymer complexes with the nucleic acid complex within the major groove of the nucleic acid through hydrogen bonding with the bases of the nucleic acid. The polyarginine and the Gln-Asn polymer should be present at a concentration of 2 moles per every mole of nucleic acid having 20 base pairs. The concentration should be increased proportionally for a nucleic acid having more than 20 base pairs. For example, if the nucleic acid has 25 base pairs, the concentration of the polymers should be 2.5-3 moles per mole of double-stranded nucleic acid. The resultant nanoparticles can be purified by standard means such as size exclusion chromatography followed by dialysis. The purified complexed nanoparticles can then be lyophilized using techniques well known in the art. One embodiment of the present disclosure provides nanoparticles less than 100 nanometers (nm) comprising a single-stranded RNAi molecule.

(iii) Treatment

Subjects (e.g., mammalian, human) amendable for treatment using the single-stranded RNAi molecules of the invention (optionally substituted or modified or conjugated), compositions thereof, and methods of the present disclosure include those suffering from one or more disease or condition mediated, at least in part, by an aberrant expression level of the target gene or sequence, those at risk of developing a disease caused by or associated with the aberrant levels of a target gene/sequence, or those which are amenable to treatment by replenishing or increasing the level of RNAi mediated by the corresponding ssRNAi molecule, including a hyperproliferative (e.g., cancer), angiogenic, metabolic, or inflammatory (e.g., arthritis) disease or disorder or condition.

Compositions and methods disclosed herein are useful in the treatment of a wide variety of target viruses, including retrovirus, such as human immunodeficiency virus (HIV), Hepatitis C Virus, Hepatitis B Virus, Coronavirus, as well as respiratory viruses, including human Respiratory Syncytial Virus, human Metapneumovirus, human Parainfluenza virus, Rhinovirus and Influenza virus.

In other examples, the compositions and methods of this disclosure are useful as therapeutic tools to treat or prevent symptoms of, for example, hyperproliferative disorders. Exemplary hyperproliferative disorders include neoplasms, carcinomas, sarcomas, tumors, or cancer. More exemplary hyperproliferative disorders include oral cancer, throat cancer, laryngeal cancer, esophageal cancer, pharyngeal cancer, nasopharyngeal cancer, oropharyngeal cancer, gastrointestinal tract cancer, gastrointestinal stromal tumors (GIST), small intestine cancer, colon cancer, rectal cancer, colorectal cancer, anal cancer, pancreatic cancer, breast cancer, cervical cancer, uterine cancer, vulvar cancer, vaginal cancer, urinary tract cancer, bladder cancer, kidney cancer, adrenocortical cancer, islet cell carcinoma, gallbladder cancer, stomach cancer, prostate cancer, ovarian cancer, endometrial cancer, trophoblastic tumor, testicular cancer, penial cancer, bone cancer, osteosarcoma, liver cancer, extrahepatic bile duct cancer, skin cancer, basal cell carcinoma (BCC), lung cancer, small cell lung cancer, non-small cell lung cancer (NSCLC), brain cancer, melanoma, Kaposi's sarcoma, eye cancer, head and neck cancer, squamous cell carcinoma of head and neck, tymoma, thymic carcinoma, thyroid cancer, parathyroid cancer, Hippel-Lindau syndrome, leukemia, acute myeloid leukemia, chronic myelogenous leukemia, acute lymphoblastic leukemia, hairy cell leukemia, lymphoma, non-Hodgkin's lymphoma, Burkitt's lymphoma, T-cell lymphoma, multiple myeloma, malignant pleural mesothelioma, Barrett's adenocarcinoma, Wilm's tumor, or the like. In other examples, the compositions and methods of this disclosure are useful as therapeutic tools to regulate expression of one or more target gene to treat or prevent symptoms of, for example, inflammatory disorders. Exemplary inflammatory disorders include diabetes mellitus, rheumatoid arthritis, pannus growth in inflamed synovial lining, collagen-induced arthritis, spondylarthritis, ankylosing spondylitis, multiple sclerosis, encephalomyelitis, inflammatory bowel disease, Chron's disease, psoriasis or psoriatic arthritis, myasthenia gravis, systemic lupus erythematosis, graft-versus-host disease, atherosclerosis, and allergies.

Other exemplary disorders that can be treated with single-stranded RNAi molecules, compositions and methods of the instant disclosure include metabolic disorders, cardiac disease, pulmonary disease, neovascularization, ischemic disorders, age-related macular degeneration, diabetic retinopathy, glomerulonephritis, diabetes, asthma, chronic obstructive pulmonary disease, chronic bronchitis, lymphangiogenesis, and atherosclerosis.

Within additional aspects, combination formulations and methods are provided comprising an effective amount of one or more single-stranded RNAi molecules in combination with one or more secondary or adjunctive active agents that are formulated together or administered coordinately with the single-stranded RNAi molecules of the invention to control one or more target gene-associated disease or condition as described herein. Useful adjunctive therapeutic agents in these combinatorial formulations and coordinate treatment methods include, for example, enzymatic nucleic acid molecules, allosteric nucleic acid molecules, guide, decoy, or aptamer nucleic acid molecules, antibodies such as monoclonal antibodies, small molecules and other organic or inorganic compounds including metals, salts and ions, and other drugs and active agents indicated for treating one or more target gene-associated disease or condition, including chemotherapeutic agents used to treat cancer, steroids, non-steroidal anti-inflammatory drugs (NSAIDs), or the like. Exemplary chemotherapeutic agents include alkylating agents (e.g., cisplatin, oxaliplatin, carboplatin, busulfan, nitrosoureas, nitrogen mustards, uramustine, temozolomide), antimetabolites (e.g., aminopterin, methotrexate, mercaptopurine, fluorouracil, cytarabine), taxanes (e.g., paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin.

To practice the coordinate administration methods of this disclosure, a single-stranded RNAi molecule is administered simultaneously or sequentially in a coordinated treatment protocol with one or more secondary or adjunctive therapeutic agents described herein or known in the art. The coordinate administration may be done in either order, and there may be a time period while only one or both (or all) active therapeutic agents, individually or collectively, exert their biological activities. A distinguishing aspect of all such coordinate treatment methods is that the single-stranded RNAi molecule(s) present in a composition elicits some favorable clinical response, which may or may not be in conjunction with a secondary clinical response provided by the secondary therapeutic agent. For example, the coordinate administration of a single-stranded RNAi molecule with a secondary therapeutic agent as contemplated herein can yield an enhanced (e.g., synergistic) therapeutic response beyond the therapeutic response elicited by either or both the purified single-stranded RNAi molecule and the secondary therapeutic agent alone.

A pharmaceutically effective dose is that dose required to prevent, inhibit the occurrence, or treat (alleviate a symptom to some extent, preferably all of the symptoms) a disease state. The pharmaceutically effective dose depends on the type of disease, the composition used, the route of administration, the type of subject being treated, the physical characteristics of the specific subject under consideration for treatment (e.g., age, body weight, general health, sex, diet), concurrent medication, rate of excretion, drug combination, the severity of the particular disease undergoing therapy, and other factors that those skilled in the medical arts will recognize. For example, an amount between about 0.1 mg/kg and about 140 mg/kg body weight/day of active ingredients may be administered depending on the potency of a single-stranded RNAi molecule of this disclosure (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

Nucleic acid molecules can be administered to cells or organisms by a variety of methods known to those of skill in the art, including administration of formulations that comprise a single-stranded RNAi molecule, or formulations that further comprise one or more additional components, such as a pharmaceutically acceptable carrier, diluent, excipient, adjuvant, emulsifier, buffer, stabilizer, preservative, or the like. In certain embodiments, a single-stranded RNAi molecule of the invention, and/or the polypeptide can be encapsulated in liposomes, administered by iontophoresis, or incorporated into other vehicles, such as hydrogels, cyclodextrins, biodegradable nanocapsules, bioadhesive microspheres, or proteinaceous vectors (see, e.g., PCT Publication No. WO 00/53722). Alternatively, a nucleic acid/peptide/vehicle combination can be locally delivered by direct injection or by use of an infusion pump. Direct injection of the nucleic acid molecules of this disclosure, whether subcutaneous, intramuscular, or intradermal, can take place using standard needle and syringe methodologies, or by needle-free technologies, such as those described in Conroy et al, (1999, Clin. Cancer Res. 5:2330) and PCT Publication No. WO 99/31262.

The formulations of the present disclosure, having an amount of a single-stranded RNAi molecule sufficient to treat or prevent a disorder associated with target gene expression are, for example, suitable for topical (e.g., creams, ointments, skin patches, eye drops, ear drops) application or administration. Other routes of administration include oral, parenteral, sublingual, bladder washout, vaginal, rectal, enteric, suppository, nasal, and inhalation. The term "parenteral," as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The compositions of the present disclosure may also be formulated and used as a tablet, capsule or elixir for oral administration, suppository for rectal administration, sterile solution, or suspension for injectable administration, either with or without other compounds known in the art. For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

Further methods for delivery of nucleic acid molecules, such as single-stranded RNAi molecules of this invention, have been described in, for example, Boado et al., 1998, *J Pharm. Sci* 87:1308; Tyler et al., 1999, *FEBS Lett.* 421:2m; Pardridge et al., 1995, *Proc. Nat'l Acad. Sci. USA* 92:5592; Boado, 1995, *Adv. Drug Delivery Rev.* 15:73; Aldrian-Herrada et al. 1998, *Nucleic Acids Res.* 26:4910; Tyler et al., 1999, *Proc. Nat'l Acad. Sci. USA* 96:7053; Akhtar et al., 1992, *Trends Cell Bio.* 2:139; "Delivery Strategies for Guide Oligonucleotide Therapeutics," ed. Akhtar, 1995, Maurer et al., 1999 Mol. Membr. Biol. 16:129; Lee et al., 2000, *ACS Symp. Ser.* 752:184. In addition to in vivo and therapeutic applications, a skilled person in the art will appreciate that the single-stranded RNAi molecules of the present disclosure are useful in a wide variety of in vitro applications, such as in scientific and commercial research (e.g., elucidation of physiological pathways, drug discovery and development), and medical and veterinary diagnostics.

All U.S. patents, U.S. patent publications, U.S. patent applications, foreign patents, foreign patent applications, non-patent publications, figures, and websites referred to in this specification are expressly incorporated herein by reference, in their entirety.

Table 1 lists certain endogenous human miRNA sequences, wherein the seed sequences, confirmed or projected, are capitalized. All miRNA sequences in Table 1 are shown in 5' to 3' orientation. Other miRNA sequences of the present invention may be found in the miRBase database, the content of which is incorporated by reference herein.

TABLE 1

| miRNA name | miRBase number | Sequence | SEQ ID NO |
|---|---|---|---|
| hsa-let-7a | MIMAT0000062 | UGAGGUAGuagguuguauaguu | 1 |
| hsa-let-7a* | MIMAT0004481 | CUAUACAAucuacugucuuuc | 2 |
| hsa-let-7a-2* | MIMAT0010195 | CUGUACAGccuccuagcuuucc | 3 |
| hsa-let-7b | MIMAT0000063 | UGAGGUAGuagguugugugguu | 4 |
| hsa-let-7b* | MIMAT0004482 | CUAUACAAccuacugccuuccc | 5 |
| hsa-let-7c | MIMAT0000064 | UGAGGUAGuagguuguaugguu | 6 |
| hsa-let-7c* | MIMAT0004483 | UAGAGUUAcacccugggaguua | 7 |
| hsa-let-7d | MIMAT0000065 | AGAGGUAGuagguugcauaguu | 8 |
| hsa-let-7d* | MIMAT0004484 | CUAUACGAccugcugccuuucu | 9 |
| hsa-let-7e | MIMAT0000066 | UGAGGUAGgagguuguauaguu | 10 |
| hsa-let-7e* | MIMAT0004485 | CUAUACGGccuccuagcuuucc | 11 |
| hsa-let-7f | MIMAT0000067 | UGAGGUAGuagauuguauaguu | 12 |
| hsa-let-7f-1* | MIMAT0004486 | CUAUACAAucuauugccuuccc | 13 |
| hsa-let-7f-2* | MIMAT0004487 | CUAUACAGucuacugucuuucc | 14 |
| hsa-miR-15a | MIMAT0000068 | UAGCAGCAcauaaugguuugug | 15 |
| hsa-miR-15a* | MIMAT0004488 | CAGGCCAUauugugcugccuca | 16 |
| hsa-miR-16 | MIMAT0000069 | UAGCAGCAcguaaauauuggcg | 17 |
| hsa-miR-16-1* | MIMAT0004489 | CCAGUAUUaacugugcugcuga | 18 |
| hsa-miR-17 | MIMAT0000070 | CAAAGUGCuuacagugcagguag | 19 |
| hsa-miR-17* | MIMAT0000071 | ACUGCAGUgaaggcacuuguag | 20 |
| hsa-miR-18a | MIMAT0000072 | UAAGGUGCaucuagugcagauag | 21 |
| hsa-miR-18a* | MIMAT0002891 | ACUGCCCUaagugcuccuucugg | 22 |
| hsa-miR-19a* | MIMAT0004490 | AGUUUUGCauaguugcacuaca | 23 |
| hsa-miR-19a | MIMAT0000073 | UGUGCAAucuaugcaaaacuga | 24 |
| hsa-miR-19b-1* | MIMAT0004491 | AGUUUUGCagguuugcauccagc | 25 |
| hsa-miR-19b | MIMAT0000074 | UGUGCAAuccaugcaaaacuga | 26 |
| hsa-miR-19b-2* | MIMAT0004492 | AGUUUUGCagguuugcauuuca | 27 |
| hsa-miR-20a | MIMAT0000075 | UAAAGUGCuuauagugcagguag | 28 |
| hsa-miR-20a* | MIMAT0004493 | ACUGCAUUaugagcacuuaaag | 29 |
| hsa-miR-21 | MIMAT0000076 | UAGCUUAUcagacugauguuga | 30 |
| hsa-miR-21* | MIMAT0004494 | CAACACCAgucgaugggcugu | 31 |
| hsa-miR-22* | MIMAT0004495 | AGUUCUUCaguggcaagcuuua | 32 |
| hsa-miR-22 | MIMAT0000077 | AAGCUGCCaguugaagaacugu | 33 |
| hsa-miR-23a* | MIMAT0004496 | GGGGUUCCuggggaugggauuu | 34 |
| hsa-miR-23a | MIMAT0000078 | AUCACAUUgccagggauuucc | 35 |
| hsa-miR-24-1* | MIMAT0000079 | UGCCUACUgagcugauaucagu | 36 |
| hsa-miR-24 | MIMAT0000080 | UGGCUCAGuucagcaggaacag | 37 |
| hsa-miR-24-2* | MIMAT0004497 | UGCCUACUgagcugaaacacag | 38 |
| hsa-miR-25* | MIMAT0004498 | AGGCGGAGacuugggcaauug | 39 |

TABLE 1-continued

| miRNA name | miRBase number | Sequence | SEQ ID NO |
|---|---|---|---|
| hsa-miR-25 | MIMAT0000081 | CAUUGCACuugucucggucuga | 40 |
| hsa-miR-26a | MIMAT0000082 | UUCAAGUAauccaggauaggcu | 41 |
| hsa-miR-26a-1* | MIMAT0004499 | CCUAUUCUugguuacuugcacg | 42 |
| hsa-miR-26b | MIMAT0000083 | UUCAAGUAauucaggauaggu | 43 |
| hsa-miR-26b* | MIMAT0004500 | CCUGUUCUccauuacuuggcuc | 44 |
| hsa-miR-27a* | MIMAT0004501 | AGGGCUUAgcugcuugugagca | 45 |
| hsa-miR-27a | MIMAT0000084 | UUCACAGUggcuaaguuccgc | 46 |
| hsa-miR-28-5p | MIMAT0000085 | AAGGAGCUcacagucuauugag | 47 |
| hsa-miR-28-3p | MIMAT0004502 | CACUAGAUugugagcuccugga | 48 |
| hsa-miR-29a* | MIMAT0004503 | ACUGAUUUcuuuugguguucag | 49 |
| hsa-miR-29a | MIMAT0000086 | UAGCACCAucugaaaucgguua | 50 |
| hsa-miR-30a | MIMAT0000087 | UGUAAACAuccucgacuggaag | 51 |
| hsa-miR-30a* | MIMAT0000088 | CUUUCAGUcggaugumugcagc | 52 |
| hsa-miR-31 | MIMAT0000089 | AGGCAAGAugcuggcauagcu | 53 |
| hsa-miR-31* | MIMAT0004504 | UGCUAUGCcaacauauugccau | 54 |
| hsa-miR-32 | MIMAT0000090 | UAUUGCACauuacuaaguugca | 55 |
| hsa-miR-32* | MIMAT0004505 | CAAUUUAGugugugugauauuu | 56 |
| hsa-miR-33a | MIMAT0000091 | GUGCAUUGuaguugcauugca | 57 |
| hsa-miR-33a* | MIMAT0004506 | CAAUGUUUccacagugcaucac | 58 |
| hsa-miR-92a-1* | MIMAT0004507 | AGGUUGGGaucgguugcaaugcu | 59 |
| hsa-miR-92a | MIMAT0000092 | UAUUGCACuugucccggccugu | 60 |
| hsa-miR-92a-2* | MIMAT0004508 | GGGUGGGAuuuguugcauuac | 61 |
| hsa-miR-93 | MIMAT0000093 | CAAAGUGCuguucgugcagguag | 62 |
| hsa-miR-93* | MIMAT0004509 | ACUGCUGAgcuagcacuucccg | 63 |
| hsa-miR-95 | MIMAT0000094 | UUCAACGGguauuuauugagca | 64 |
| hsa-miR-96 | MIMAT0000095 | UUUGGCACuagcacauuuugcu | 65 |
| hsa-miR-96* | MIMAT0004510 | AAUCAUGugcagugccaauaug | 66 |
| hsa-miR-98 | MIMAT0000096 | UGAGGUAGuaaguuguauuguu | 67 |
| hsa-miR-99a | MIMAT0000097 | AACCCGUAgauccgaucuugug | 68 |
| hsa-miR-99a* | MIMAT0004511 | CAAGCUCGcuucuaugggucug | 69 |
| hsa-miR-100 | MIMAT0000098 | AACCCGUAgauccgaacuugug | 70 |
| hsa-miR-100* | MIMAT0004512 | CAAGCUUGuaucuauagguaug | 71 |
| hsa-miR-101* | MIMAT0004513 | CAGUUAUCacagugcugaugcu | 72 |
| hsa-miR-101 | MIMAT0000099 | UACAGUACugugauaacugaa | 73 |
| hsa-miR-29b-1* | MIMAT0004514 | GCUGGUUUcauaugguguuuaga | 74 |
| hsa-miR-29b | MIMAT0000100 | UAGCACCAuuugaaaucaguguu | 75 |
| hsa-miR-29b-2* | MIMAT0004515 | CUGGUUUCacauggugcuuag | 76 |
| hsa-miR-103-2* | MIMAT0009196 | AGCUUCUUuacagugcugccuug | 77 |
| hsa-miR-103 | MIMAT0000101 | AGCAGCAUuguacagggcuauga | 78 |

TABLE 1-continued

| miRNA name | miRBase number | Sequence | SEQ ID NO |
|---|---|---|---|
| hsa-miR-105 | MIMAT0000102 | UCAAAUGCucagacuccuguggu | 79 |
| hsa-miR-105* | MIMAT0004516 | ACGGAUGUuugagcaugugcua | 80 |
| hsa-miR-106a | MIMAT0000103 | AAAAGUGCuuacagugcagguag | 81 |
| hsa-miR-106a* | MIMAT0004517 | CUGCAAUGuaagcacuucuuac | 82 |
| hsa-miR-107 | MIMAT0000104 | AGCAGCAUuguacagggcuauca | 83 |
| hsa-miR-16-2* | MIMAT0004518 | CCAAUAUUacugugcugcuuua | 84 |
| hsa-miR-192 | MIMAT0000222 | CUGACCUAugaauugacagcc | 85 |
| hsa-miR-192* | MIMAT0004543 | CUGCCAAUccauaggucacag | 86 |
| hsa-miR-196a | MIMAT0000226 | UAGGUAGUuucauguuguggg | 87 |
| hsa-miR-197 | MIMAT0000227 | UUCACCACcuucuccacccagc | 88 |
| hsa-miR-198 | MIMAT0000228 | GGUCCAGAggggagaugguuc | 89 |
| hsa-miR-199a-5p | MIMAT0000231 | CCCAGUGUucagacuaccuguuc | 90 |
| hsa-miR-199a-3p | MIMAT0000232 | ACAGUAGUcugcacauugguua | 91 |
| hsa-miR-208a | MIMAT0000241 | AUAAGACGagcaaaaagcuugu | 92 |
| hsa-miR-129-5p | MIMAT0000242 | CUUUUUGCggucugggcuugc | 93 |
| hsa-miR-129* | MIMAT0004548 | AAGCCCUUaccccaaaaaguau | 94 |
| hsa-miR-148a* | MIMAT0004549 | AAAGUUCUgagacacuccgacu | 95 |
| hsa-miR-148a | MIMAT0000243 | UCAGUGCAcuacagaacuuugu | 96 |
| hsa-miR-30c | MIMAT0000244 | UGUAAACAuccuacacucucagc | 97 |
| hsa-miR-30c-2* | MIMAT0004550 | CUGGGAGAaggcuguuuacucu | 98 |
| hsa-miR-30d | MIMAT0000245 | UGUAAACAuccccgacuggaag | 99 |
| hsa-miR-30d* | MIMAT0004551 | CUUUCAGUcagauguuugcugc | 100 |
| hsa-miR-139-5p | MIMAT0000250 | UCUACAGUgcacgugucuccag | 101 |
| hsa-miR-139-3p | MIMAT0004552 | GGAGACGCggcccuguuggagu | 102 |
| hsa-miR-147 | MIMAT0000251 | GUGUGUGGaaaugcuucugc | 103 |
| hsa-miR-7 | MIMAT0000252 | UGGAAGACuagugauuuuguugu | 104 |
| hsa-miR-7-1* | MIMAT0004553 | CAACAAAUcacagucugccaua | 105 |
| hsa-miR-7-2* | MIMAT0004554 | CAACAAAUcccagucuaccuaa | 106 |
| hsa-miR-10a | MIMAT0000253 | UACCCUGUagauccgaauuugug | 107 |
| hsa-miR-10a* | MIMAT0004555 | CAAAUUCGuaucuaggggaaua | 108 |
| hsa-miR-10b | MIMAT0000254 | UACCCUGUagaaccgaauuugug | 109 |
| hsa-miR-10b* | MIMAT0004556 | ACAGAUUCgauucuaggggaau | 110 |
| hsa-miR-34a | MIMAT0000255 | UGGCAGUGucuuagcugguugu | 111 |
| hsa-miR-34a* | MIMAT0004557 | CAAUCAGCaaguauacugcccu | 112 |
| hsa-miR-181a | MIMAT0000256 | AACAUUCAacgcugucggugagu | 113 |
| hsa-miR-181a-2* | MIMAT0004558 | ACCACUGAccguugacuguacc | 114 |
| hsa-miR-181b | MIMAT0000257 | AACAUUCAuugcugucgguggu | 115 |
| hsa-miR-181c | MIMAT0000258 | AACAUUCAaccugucggugagu | 116 |
| hsa-miR-181c* | MIMAT0004559 | AACCAUCGaccguugaguggac | 117 |

TABLE 1-continued

| miRNA name | miRBase number | Sequence | SEQ ID NO |
|---|---|---|---|
| hsa-miR-182 | MIMAT0000259 | UUUGGCAAugguagaacucacacu | 118 |
| hsa-miR-182* | MIMAT0000260 | UGGUUCUAgacuugccaacua | 119 |
| hsa-miR-183 | MIMAT0000261 | UAUGGCACugguagaauucacu | 120 |
| hsa-miR-183* | MIMAT0004560 | GUGAAUUAccgaagggccauaa | 121 |
| hsa-miR-187* | MIMAT0004561 | GGCUACAAcacaggacccgggc | 122 |
| hsa-miR-187 | MIMAT0000262 | UCGUGUCUuguguugcagccgg | 123 |
| hsa-miR-196a* | MIMAT0004562 | CGGCAACAagaaacugccugag | 124 |
| hsa-miR-199b-5p | MIMAT0000263 | CCCAGUGUuuagacuaucuguuc | 125 |
| hsa-miR-199b-3p | MIMAT0004563 | ACAGUAGUcugcacauugguua | 91 |
| hsa-miR-203 | MIMAT0000264 | GUGAAAUGuuuaggaccacuag | 126 |
| hsa-miR-204 | MIMAT0000265 | UUCCCUUUgucauccuaugccu | 127 |
| hsa-miR-205 | MIMAT0000266 | UCCUUCAUuccaccggagucug | 128 |
| hsa-miR-205* | MIMAT0009197 | GAUUUCAGuggagugaaguuc | 129 |
| hsa-miR-210 | MIMAT0000267 | CUGUGCGUgugacagcggcuga | 130 |
| hsa-miR-211 | MIMAT0000268 | UUCCCUUUgucauccuucgccu | 131 |
| hsa-miR-212 | MIMAT0000269 | UAACAGUCccagucacggcc | 132 |
| hsa-miR-181a* | MIMAT0000270 | ACCAUCGAccguugauugacc | 133 |
| hsa-miR-214* | MIMAT0004564 | UGCCUGUCuacacuugcugugc | 134 |
| hsa-miR-214 | MIMAT0000271 | ACAGCAGGcacagacaggcagu | 135 |
| hsa-miR-215 | MIMAT0000272 | AUGACCUAugaauugacagac | 136 |
| hsa-miR-216a | MIMAT0000273 | UAAUCUCAgcuggcaacuguga | 137 |
| hsa-miR-217 | MIMAT0000274 | UACUGCAUcaggaacugauugga | 138 |
| hsa-miR-218 | MLMAT0000275 | UUGUGCUUgaucuaaccaugu | 139 |
| hsa-miR-218-1* | MIMAT0004565 | AUGGUUCCgucaagcaccaugg | 140 |
| hsa-miR-218-2* | MIMAT0004566 | CAUGGUUCugucaagcaccgcg | 141 |
| hsa-miR-219-5p | MIMAT0000276 | UGAUUGUCcaaacgcaauucu | 142 |
| hsa-miR-219-1-3p | MIMAT0004567 | AGAGUUGAgucuggacgucccg | 143 |
| hsa-miR-220a | MIMAT0000277 | CCACACCGuaucugacacuuu | 144 |
| hsa-miR-221* | MIMAT0004568 | ACCUGGCAuacaauguagauuu | 145 |
| hsa-miR-221 | MIMAT0000278 | AGCUACAUugucugcugggguuuc | 146 |
| hsa-miR-222* | MIMAT0004569 | CUCAGUAGccaguguagauccu | 147 |
| hsa-miR-222 | MIMAT0000279 | AGCUACAUcuggcuacuggu | 148 |
| hsa-miR-223* | MIMAT0004570 | CGUGUAUUugacaagcugaguu | 149 |
| hsa-miR-223 | MIMAT0000280 | UGUCAGUUugucaaauacccca | 150 |
| hsa-miR-224 | MIMAT0000281 | CAAGUCACuaguguuuccguu | 151 |
| hsa-miR-224* | MIMAT0009198 | AAAAUGGUgcccuagugacuaca | 152 |
| hsa-miR-200b* | MIMAT0004571 | CAUCUUACgggcagcauugga | 153 |
| hsa-miR-200b | MIMAT0000318 | UAAUACUGccugguaaugauga | 154 |
| hsa-let-7g | MIMAT0000414 | UGAGGUAGuaguuuguacaguu | 155 |

TABLE 1-continued

| miRNA name | miRBase number | Sequence | SEQ ID NO |
|---|---|---|---|
| hsa-let-7g* | MIMAT0004584 | CUGUACAGgccacugccuugc | 156 |
| hsa-let-7i | MIMAT0000415 | UGAGGUAGuaguuugugcuguu | 157 |
| hsa-let-7i* | MIMAT0004585 | CUGCGCAAgcuacugccuugcu | 158 |
| hsa-miR-1 | MIMAT0000416 | UGGAAUGUaaagaaguauguau | 159 |
| hsa-miR-15b | MIMAT0000417 | UAGCAGCAcaucaugguuuaca | 160 |
| hsa-miR-15b* | MIMAT0004586 | CGAAUCAUuauuugcugcucua | 161 |
| hsa-miR-23b* | MIMAT0004587 | UGGGUUCCuggcaugcugauuu | 162 |
| hsa-miR-23b | MIMAT0000418 | AUCACAUUgccagggauuacc | 163 |
| hsa-miR-27b* | MIMAT0004588 | AGAGCUUAgcugauuggugaac | 164 |
| hsa-miR-27b | MIMAT0000419 | UUCACAGUggcuaaguucugc | 165 |
| hsa-miR-30b | MIMAT0000420 | UGUAAACAuccuacacucagcu | 166 |
| hsa-miR-30b* | MIMAT0004589 | CUGGGAGGuggauguuuacuuc | 167 |
| hsa-miR-122 | MIMAT0000421 | UGGAGUGUgacaauggguguuug | 168 |
| hsa-miR-122* | MIMAT0004590 | AACGCCAUuaucacacuaaaua | 169 |
| hsa-miR-124* | MIMAT0004591 | CGUGUUCAcagcggaccuugau | 170 |
| hsa-miR-124 | MIMAT0000422 | UAAGGCACgcggugaaugcc | 171 |
| hsa-miR-125b | MIMAT0000423 | UCCCUGAGacccuaacuuguga | 172 |
| hsa-miR-125b-1* | MIMAT0004592 | ACGGGUUAggcucuugggagcu | 173 |
| hsa-miR-128 | MIMAT0000424 | UCACAGUGaaccggucucuuu | 174 |
| hsa-miR-130a* | MIMAT0004593 | UUCACAUUgugcuacugucugc | 175 |
| hsa-miR-130a | MIMAT0000425 | CAGUGCAAuguuaaaagggcau | 176 |
| hsa-miR-132* | MIMAT0004594 | ACCGUGGCuuucgauuguuacu | 177 |
| hsa-miR-132 | MIMAT0000426 | UAACAGUCuacagccauggucg | 178 |
| hsa-miR-133a | MIMAT0000427 | UUUGGUCCccuucaaccagcug | 179 |
| hsa-miR-135a | MIMAT0000428 | UAUGGCUUuuuauuccuauguga | 180 |
| hsa-miR-135a* | MIMAT0004595 | UAUAGGGAuuggagccguggcg | 181 |
| hsa-miR-137 | MIMAT0000429 | UUAUUGCUuaagaauacgcguag | 182 |
| hsa-miR-138 | MIMAT0000430 | AGCUGGUGuugugaaucaggccg | 183 |
| hsa-miR-138-2* | MIMAT0004596 | GCUAUUUCacgacaccagggu | 184 |
| hsa-miR-140-5p | MIMAT0000431 | CAGUGGUUuuacccuaugguag | 185 |
| hsa-miR-140-3p | MIMAT0004597 | UACCACAGgguagaaccacgg | 186 |
| hsa-miR-141* | MIMAT0004598 | CAUCUUCCaguacaguguugga | 187 |
| hsa-miR-141 | MIMAT0000432 | UAACACUGucugguaaagaugg | 188 |
| hsa-miR-142-5p | MIMAT0000433 | CAUAAAGUagaaagcacuacu | 189 |
| hsa-miR-142-3p | MIMAT0000434 | UGUAGUGUuuccuacuuuauga | 190 |
| hsa-miR-143* | MIMAT0004599 | GGUGCAGUgcugcaucucuggu | 191 |
| hsa-miR-143 | MIMAT0000435 | UGAGAUGAagcacuguagcuc | 192 |
| hsa-miR-144* | MIMAT0004600 | GGAUAUCAucauauacuguaag | 193 |
| hsa-miR-144 | MIMAT0000436 | UACAGUAUagaugauguacu | 194 |

TABLE 1-continued

| miRNA name | miRBase number | Sequence | SEQ ID NO |
|---|---|---|---|
| hsa-miR-145 | MIMAT0000437 | GUCCAGUUuucccaggaaucccu | 195 |
| hsa-miR-145* | MIMAT0004601 | GGAUUCCUggaaauacuguucu | 196 |
| hsa-miR-152 | MIMAT0000438 | UCAGUGCAugacagaacuugg | 197 |
| hsa-miR-153 | MIMAT0000439 | UUGCAUAGucacaaaagugauc | 198 |
| hsa-miR-191 | MIMAT0000440 | CAACGGAAucccaaaagcagcug | 199 |
| hsa-miR-191* | MIMAT0001618 | GCUGCGCUuggauuucgucccc | 200 |
| hsa-miR-9 | MIMAT0000441 | UCUUUGGUuaucuagcuguauga | 201 |
| hsa-miR-9* | MIMAT0000442 | AUAAAGCUagauaaccgaaagu | 202 |
| hsa-miR-125a-5p | MIMAT0000443 | UCCCUGAGacccuuuaaccuguga | 203 |
| hsa-miR-125a-3p | MIMAT0004602 | ACAGGUGAgguucuugggagcc | 204 |
| hsa-miR-125b-2* | MIMAT0004603 | UCACAAGUcaggcucuugggac | 205 |
| hsa-miR-126* | MIMAT0000444 | CAUUAUUAcuuuugguacgcg | 206 |
| hsa-miR-126 | MIMAT0000445 | UCGUACCGugaguaauaaugcg | 207 |
| hsa-miR-127-5p | MIMAT0004604 | CUGAAGCUcagagggcucugau | 208 |
| hsa-miR-127-3p | MIMAT0000446 | UCGGAUCCgucugagcuuggcu | 209 |
| hsa-miR-129-3p | MIMAT0004605 | AAGCCCUUaccccaaaaagcau | 210 |
| hsa-miR-134 | MIMAT0000447 | UGUGACUGguugaccagagggg | 211 |
| hsa-miR-136 | MIMAT0000448 | ACUCCAUUuguuuugaugaugga | 212 |
| hsa-miR-136* | MIMAT0004606 | CAUCAUCGucucaaaugagucu | 213 |
| hsa-miR-138-1* | MIMAT0004607 | GCUACUUCacaacaccagggcc | 214 |
| hsa-miR-146a | MIMAT0000449 | UGAGAACUgaauuccauggguu | 215 |
| hsa-miR-146a* | MIMAT0004608 | CCUCUGAAauucaguucuucag | 216 |
| hsa-miR-149 | MIMAT0000450 | UCUGGCUCcgugucuucacuccc | 217 |
| hsa-miR-149* | MIMAT0004609 | AGGGAGGGacggggggcugugc | 218 |
| hsa-miR-150 | MIMAT0000451 | UCUCCCAAcccuuguaccagug | 219 |
| hsa-miR-150* | MIMAT0004610 | CUGGUACAggccuggggggacag | 220 |
| hsa-miR-154 | MIMAT0000452 | UAGGUUAUccguguugccuucg | 221 |
| hsa-miR-154* | MIMAT0004611 | AAUCAUACacgguugaccuauu | 222 |
| hsa-miR-184 | MIMAT0000454 | UGGACGGAgaacugauaagggu | 223 |
| hsa-miR-185 | MIMAT0000455 | UGGAGAGAaaggcaguuccuga | 224 |
| hsa-miR-185* | MIMAT0004611 | AGGGGCUGgcuuuccucugguc | 225 |
| hsa-miR-186 | MIMAT0000456 | CAAAGAAUucuccuuuugggcu | 226 |
| hsa-miR-186* | MIMAT0004612 | GCCCAAAGgugaauuuuuggg | 227 |
| hsa-miR-188-5p | MIMAT0000457 | CAUCCCUUgcauggugga ggg | 228 |
| hsa-miR-188-3p | MIMAT0004613 | CUCCCACAugcagggguuugca | 229 |
| hsa-miR-190 | MIMAT0000458 | UGAUAUGUuugauauauuaggu | 230 |
| hsa-miR-193a-5p | MIMAT0004614 | UGGGUCUUugcgggcgagauga | 231 |
| hsa-miR-193a-3p | MIMAT0000459 | AACUGGCCuacaaaguccc agu | 232 |
| hsa-miR-194 | MIMAT0000460 | UGUAACAGcaacuccaugugga | 233 |

TABLE 1-continued

| miRNA name | miRBase number | Sequence | SEQ ID NO |
|---|---|---|---|
| hsa-miR-195 | MIMAT0000461 | UAGCAGCAcagaaauauugc | 234 |
| hsa-miR-195* | MIMAT0004615 | CCAAUAUUggcugugcugcucc | 235 |
| hsa-miR-206 | MIMAT0000462 | UGGAAUGUaaggaagugugugg | 236 |
| hsa-miR-320a | MIMAT0000510 | AAAAGCUGgguugagagggcga | 237 |
| hsa-miR-200c* | MIMAT0004657 | CGUCUUACccagcaguguuugg | 238 |
| hsa-miR-200c | MIMAT0000617 | UAAUACUGccggguaaugaugga | 239 |
| hsa-miR-155 | MIMAT0000646 | UUAAUGCUaaucgugauaggggu | 240 |
| hsa-miR-155* | MIMAT0004658 | CUCCUACAuauuagcauuaaca | 241 |
| hsa-miR-194* | MIMAT0004671 | CCAGUGGGgcugcuguuaucug | 242 |
| hsa-miR-106b | MIMAT0000680 | UAAAGUGCugacagugcagau | 243 |
| hsa-miR-106b* | MIMAT0004672 | CCGCACUGuggguacuugcugc | 244 |
| hsa-miR-29c* | MIMAT0004673 | UGACCGAUuucuccuggugu uc | 245 |
| hsa-miR-29c | MIMAT0000681 | UAGCACCAuuugaaaucgguua | 246 |
| hsa-miR-30c-1* | MIMAT0004674 | CUGGGAGAgggu ugu uuacucc | 247 |
| hsa-miR-200a* | MIMAT0001620 | CAUCUUACcggacagugcugga | 248 |
| hsa-miR-200a | MIMAT0000682 | UAACACUGucugguaacgaugu | 249 |
| hsa-miR-302a* | MIMAT0000683 | ACUUAAACgugga ugua cuugcu | 250 |
| hsa-miR-302a | MIMAT0000684 | UAAGUGCUuccauguuuggu ga | 251 |
| hsa-miR-219-2-3p | MIMAT0004675 | AGAAUUGUggcuggacaucugu | 252 |
| hsa-miR-34b* | MIMAT0000685 | UAGGCAGUgucauuagcugauug | 253 |
| hsa-miR-34b | MIMAT0004676 | CAAUCACUaacuccacugccau | 254 |
| hsa-miR-34c-5p | MIMAT0000686 | AGGCAGUGuaguuagcugauugc | 255 |
| hsa-miR-34c-3p | MIMAT0004677 | AAUCACUAaccacacggccagg | 256 |
| hsa-miR-299-5p | MIMAT0002890 | UGGUUUACcgucccacauacau | 257 |
| hsa-miR-299-3p | MIMAT0000687 | UAUGUGGGauggu aaaccgcuu | 258 |
| hsa-miR-301a | MIMAT0000688 | CAGUGCAAaguauugucaaagc | 259 |
| hsa-miR-99b | MIMAT0000689 | CACCCGUAgaaccgaccuugcg | 260 |
| hsa-miR-99b* | MIMAT0004678 | CAAGCUCGugucugugggu ccg | 261 |
| hsa-miR-296-5p | MIMAT0000690 | AGGGCCCCcccucaauccugu | 262 |
| hsa-miR-296-3p | MIMAT0004679 | GAGGGUUGgguggaggcucucc | 263 |
| hsa-miR-130b* | MIMAT0004680 | ACUCUUUCccuguugcacuac | 264 |
| hsa-miR-130b | MIMAT0000691 | CAGUGCAAugaugaaagggcau | 265 |
| hsa-miR-30e | MIMAT0000692 | UGUAAACAuccuugacuggaag | 266 |
| hsa-miR-30e* | MIMAT0000693 | CUUUCAGUcggauguuuacagc | 267 |
| hsa-miR-26a-2* | MIMAT0004681 | CCUAUUCUugauuacuuguuuc | 268 |
| hsa-miR-361-5p | MIMAT0000703 | UUAUCAGAaucuccaggggu ac | 269 |
| hsa-miR-361-3p | MIMAT0004682 | UCCCCCAGgugugauucugauuu | 270 |
| hsa-miR-362-5p | MIMAT0000705 | AAUCCUUGgaaccuaggugugagu | 271 |
| hsa-miR-362-3p | MIMAT0004683 | AACACACCuauucaaggauuca | 272 |

TABLE 1-continued

| miRNA name | miRBase number | Sequence | SEQ ID NO |
|---|---|---|---|
| hsa-miR-363* | MIMAT0003385 | CGGGUGGAucacgaugcaauuu | 273 |
| hsa-miR-363 | MIMAT0000707 | AAUUGCACgguauccaucugua | 274 |
| hsa-miR-365 | MIMAT0000710 | UAAUGCCCcuaaaaauccuuau | 275 |
| hsa-miR-365* | MIMAT0009199 | AGGGACUUucaggggcagcugu | 276 |
| hsa-miR-302b* | MIMAT0000714 | ACUUUAACauggaagugcuuuc | 277 |
| hsa-miR-302b | MIMAT0000715 | UAAGUGCUccauguuuuaguag | 278 |
| hsa-miR-302c* | MIMAT0000716 | UUUAACAUggaguaccugcug | 279 |
| hsa-miR-302c | MIMAT0000717 | UAAGUGCUccauguuucagugg | 280 |
| hsa-miR-302d* | MIMAT0004685 | ACUUUAACauggaggcacuugc | 281 |
| hsa-miR-302d | MIMAT0000718 | UAAGUGCUccauguuugagugu | 282 |
| hsa-miR-367* | MIMAT0004686 | ACUGUUGCuaauaugcaacucu | 283 |
| hsa-miR-367 | MIMAT0000719 | AAUUGCACuuuagcaaugguga | 284 |
| hsa-miR-376c | MIMAT0000720 | AACAUAGAggaaauuccacgu | 285 |
| hsa-miR-369-5p | MIMAT0001621 | AGAUCGACcguguuauauucgc | 286 |
| hsa-miR-369-3p | MIMAT0000721 | AAUAAUACaugguugaucuuu | 287 |
| hsa-miR-370 | MIMAT0000722 | GCCUGCUGggguggaaccuggu | 288 |
| hsa-miR-371-5p | MIMAT0004687 | ACUCAAACuguggggggcacu | 289 |
| hsa-miR-371-3p | MIMAT0000723 | AAGUGCCGccaucuuuugagugu | 290 |
| hsa-miR-372 | MIMAT0000724 | AAAGUGCUgcgacauuugagcgu | 291 |
| hsa-miR-373* | MIMAT0000725 | ACUCAAAauggggggcgcuuucc | 292 |
| hsa-miR-373 | MIMAT0000726 | GAAGUGCUucgauuuggggugu | 293 |
| hsa-miR-374a | MIMAT0000727 | UUAUAAUAcaaccugauaagug | 294 |
| hsa-miR-374a* | MIMAT0004688 | CUUAUCAGauuguauuguaauu | 295 |
| hsa-miR-375 | MIMAT0000728 | UUUGUUCGAuucggcucgcguga | 296 |
| hsa-miR-376a* | MIMAT0003386 | GUAGAUUCuccuucuaugagua | 297 |
| hsa-miR-376a | MIMAT0000729 | AUCAUAGAggaaaauccacgu | 298 |
| hsa-miR-377* | MIMAT0004689 | AGAGGUUGcccuuggugaauuc | 299 |
| hsa-miR-377 | MIMAT0000730 | AUCACACAaaggcaacuuuugu | 300 |
| hsa-miR-378* | MIMAT0000731 | CUCCUGACuccagguccugugu | 301 |
| hsa-miR-378 | MIMAT0000732 | ACUGGACUuggagucagaagg | 302 |
| hsa-miR-379 | MIMAT0000733 | UGGUAGACuauggaacguagg | 303 |
| hsa-miR-379* | MIMAT0004690 | UAUGUAACaugguccacuaacu | 304 |
| hsa-miR-380* | MIMAT0000734 | UGGUUGACcauagaacaugcgc | 305 |
| hsa-miR-380 | MIMAT0000735 | UAUGUAAUaugguccacaucuu | 306 |
| hsa-miR-381 | MIMAT0000736 | UAUACAAGggcaagcucucugu | 307 |
| hsa-miR-382 | MIMAT0000737 | GAAGUUGUucguggugauucg | 308 |
| hsa-miR-383 | MIMAT0000738 | AGAUCAGAaggugauuguggcu | 309 |
| hsa-miR-340 | MIMAT0004692 | UUAUAAAGcaaugagacugauu | 310 |
| hsa-miR-340* | MIMAT0000750 | UCCGUCUCaguuacuuuauagc | 311 |

TABLE 1-continued

| miRNA name | miRBase number | Sequence | SEQ ID NO |
|---|---|---|---|
| hsa-miR-330-5p | MIMAT0004693 | UCUCUGGGccugugucuuaggc | 312 |
| hsa-miR-330-3p | MIMAT0000751 | GCAAAGCAcacggccugcagaga | 313 |
| hsa-miR-328 | MIMAT0000752 | CUGGCCCUcucugcccuuccgu | 314 |
| hsa-miR-342-5p | MIMAT0004694 | AGGGGUGCuaucugugauuga | 315 |
| hsa-miR-342-3p | MIMAT0000753 | UCUCACACagaaaucgcacccgu | 316 |
| hsa-miR-337-5p | MIMAT0004695 | GAACGGCUucauacaggaguu | 317 |
| hsa-miR-337-3p | MIMAT0000754 | CUCCUAUAugaugccuuucuuc | 318 |
| hsa-miR-323-5p | MIMAT0004696 | AGGUGGUCcguggcgcguucgc | 319 |
| hsa-miR-323-3p | MIMAT0000755 | CACAUUAcacggucgaccucu | 320 |
| hsa-miR-326 | MIMAT0000756 | CCUCUGGGcccuuccuccag | 321 |
| hsa-miR-151-5p | MIMAT0004697 | UCGAGGAGcucacagucuagu | 322 |
| hsa-miR-151-3p | MIMAT0000757 | CUAGACUGaagcuccuugagg | 323 |
| hsa-miR-135b | MIMAT0000758 | UAUGGCUUuucauuccuauguga | 324 |
| hsa-miR-135b* | MIMAT0004698 | AUGUAGGGcuaaaagccauggg | 325 |
| hsa-miR-148b* | MIMAT0004699 | AAGUUCUGuuauacacucaggc | 326 |
| hsa-miR-148b | MIMAT0000759 | UCAGUGCAucacagaacuuugu | 327 |
| hsa-miR-331-5p | MIMAT0004700 | CUAGGUAUggucccagggaucc | 328 |
| hsa-miR-331-3p | MIMAT0000760 | GCCCCUGGgccuauccuagaa | 329 |
| hsa-miR-324-5p | MIMAT0000761 | CGCAUCCCcuagggcauuggugu | 330 |
| hsa-miR-324-3p | MIMAT0000762 | ACUGCCCCaggugcugcugg | 331 |
| hsa-miR-338-5p | MIMAT0004701 | AACAAUAUccuggugcugagug | 332 |
| hsa-miR-338-3p | MIMAT0000763 | UCCAGCAUcagugauuuuguug | 333 |
| hsa-miR-339-5p | MIMAT0000764 | UCCCUGUCcuccaggagcucacg | 334 |
| hsa-miR-339-3p | MIMAT0004702 | UGAGCGCCucgacgacagagccg | 335 |
| hsa-miR-335 | MIMAT0000765 | UCAAGAGCaauaacgaaaaaugu | 336 |
| hsa-miR-335* | MIMAT0004703 | UUUUUCAUuauugcuccugacc | 337 |
| hsa-miR-133b | MIMAT0000770 | UUUGGUCCccuucaaccagcua | 338 |
| hsa-miR-325 | MIMAT0000771 | CCUAGUAGguguccaguaagugu | 339 |
| hsa-miR-345 | MIMAT0000772 | GCUGACUCcuaguccagggcuc | 340 |
| hsa-miR-346 | MIMAT0000773 | UGUCUGCCcgcaugccugccucu | 341 |
| hsa-miR-384 | MIMAT0001075 | AUUCCUAGaaauuguucaua | 342 |
| hsa-miR-196b | MIMAT0001080 | UAGGUAGUuuccuguuguuggg | 343 |
| hsa-miR-196b* | MIMAT0009201 | UCGACAGCacgacacugccuuc | 344 |
| hsa-miR-422a | MIMAT0001339 | ACUGGACUuaggucagaaggc | 345 |
| hsa-miR-423-5p | MIMAT0004748 | UGAGGGGCagagagcgagacuuu | 346 |
| hsa-miR-423-3p | MIMAT0001340 | AGCUCGGUcugaggccccucagu | 347 |
| hsa-miR-424 | MIMAT0001341 | CAGCAGCAauucauguuuugaa | 348 |
| hsa-miR-424* | MIMAT0004749 | CAAAACGUgaggcgcugcuau | 349 |
| hsa-miR-425 | MIMAT0003393 | AAUGACACgaucacucccguuga | 350 |

TABLE 1-continued

| miRNA name | miRBase number | Sequence | SEQ ID NO |
|---|---|---|---|
| hsa-miR-425* | MIMAT0001343 | AUCGGGAAugucuguccgccc | 351 |
| hsa-miR-18b | MIMAT0001412 | UAAGGUGCaucuagugcaguuag | 352 |
| hsa-miR-18b* | MIMAT0004751 | UGCCCUAAaugcccuucuggc | 353 |
| hsa-miR-20b | MIMAT0001413 | CAAAGUGCucauagugcagguag | 354 |
| hsa-miR-20b* | MIMAT0004752 | ACUGUAGUaugggcacuuccag | 355 |
| hsa-miR-448 | MIMAT0001532 | UUGCAUAUguaggaugucccau | 356 |
| hsa-miR-429 | MIMAT0001536 | UAAUACUGucugguaaaaccgu | 357 |
| hsa-miR-449a | MIMAT0001541 | UGGCAGUGuauuguuagcuggu | 358 |
| hsa-miR-450a | MIMAT0001545 | UUUUGCGAuguguuccuaauau | 359 |
| hsa-miR-431 | MIMAT0001625 | UGUCUUGCaggccgucaugca | 360 |
| hsa-miR-431* | MIMAT0004757 | CAGGUCGUcuugcagggcuucu | 361 |
| hsa-miR-433 | MIMAT0001627 | AUCAUGAUgggcuccucggugu | 362 |
| hsa-miR-329 | MIMAT0001629 | AACACACCugguuaaccucuuu | 363 |
| hsa-miR-451 | MIMAT0001631 | AAACCGUUaccauuacugaguu | 364 |
| hsa-miR-452 | MIMAT0001635 | AACUGUUUgcagaggaaacuga | 365 |
| hsa-miR-452* | MIMAT0001636 | CUCAUCUGcaaagaaguaagug | 366 |
| hsa-miR-409-5p | MIMAT0001638 | AGGUUACCcgagcaacuuugcau | 367 |
| hsa-miR-409-3p | MIMAT0001639 | GAAUGUUGcucggugaaccccu | 368 |
| hsa-miR-412 | MBIAT0002170 | ACUUCACCugguccacuagccgu | 369 |
| hsa-miR-410 | MIMAT0002171 | AAUAUAACacagauggccugu | 370 |
| hsa-miR-376b | MIMAT0002172 | AUCAUAGAggaaaauccauguu | 371 |
| hsa-miR-483-5p | MIMAT0004761 | AAGACGGGaggaaagaagggag | 372 |
| hsa-miR-483-3p | MIMAT0002173 | UCACUCCUcuccucccgucuu | 373 |
| hsa-miR-484 | MIMAT0002174 | UCAGGCUCaguccccucccgau | 374 |
| hsa-miR-485-5p | MIMAT0002175 | AGAGGCUGgccgugaugaauuc | 375 |
| hsa-miR-485-3p | MIMAT0002176 | GUCAUACAcggcucuccucucu | 376 |
| hsa-miR-486-5p | MIMAT0002177 | UCCUGUACugagcugccccgag | 377 |
| hsa-miR-486-3p | MIMAT0004762 | CGGGGCAGcucaguacaggau | 378 |
| hsa-miR-487a | MIMAT0002178 | AAUCAUACagggacauccaguu | 379 |
| hsa-miR-488* | MIMAT0002804 | CCCAGAUAauggcacucucaa | 380 |
| hsa-miR-488 | MIMAT0004763 | UUGAAAGGcuauuucuugguc | 381 |
| hsa-miR-489 | MIMAT0002805 | GUGACAUCcauauacggcagc | 382 |
| hsa-miR-490-5p | MIMAT0004764 | CCAUGGAUcuccaggugggu | 383 |
| hsa-miR-490-3p | MIMAT0002806 | CAACCUGGaggacuccaugcug | 384 |
| hsa-miR-491-5p | MIMAT0002807 | AGUGGGGAacccuuccaugagg | 385 |
| hsa-miR-491-3p | MIMAT0004765 | CUUAUGCAagauucccuucuac | 386 |
| hsa-miR-511 | MIMAT0002808 | GUGUCUUUugcucugcaguca | 387 |
| hsa-miR-146b-5p | MIMAT0002809 | UGAGAACUgaauuccauaggcu | 388 |
| hsa-miR-146b-3p | MIMAT0004766 | UGCCCUGUggacucaguucugg | 389 |

TABLE 1-continued

| miRNA name | miRBase number | Sequence | SEQ ID NO |
|---|---|---|---|
| hsa-miR-202* | MIMAT0002810 | UUCCUAUGcauauacuucuuug | 390 |
| hsa-miR-202 | MIMAT0002811 | AGAGGUAUagggcaugggaa | 391 |
| hsa-miR-492 | MIMAT0002812 | AGGACCUGcgggacaagauucuu | 392 |
| hsa-miR-493* | MIMAT0002813 | UUGUACAUgguaggcuuucauu | 393 |
| hsa-miR-493 | MIMAT0003161 | UGAAGGUCuacugugugccagg | 394 |
| hsa-miR-432 | MIMAT0002814 | UCUUGGAGuaggucauugggugg | 395 |
| hsa-miR-432* | MIMAT0002815 | CUGGAUGGcuccuccaugucu | 396 |
| hsa-miR-494 | MIMAT0002816 | UGAAACAUacacgggaaaccuc | 397 |
| hsa-miR-495 | MIMAT0002817 | AAACAAAcauggugcacuucuu | 398 |
| hsa-miR-496 | MIMAT0002818 | UGAGUAUUacauggccaaucuc | 399 |
| hsa-miR-193b* | MIMAT0004767 | CGGGGUUUugagggcgagauga | 400 |
| hsa-miR-193b | MIMAT0002819 | AACUGGCCcucaaagucccgcu | 401 |
| hsa-miR-497 | MIMAT0002820 | CAGCAGCAcacugugguuugu | 402 |
| hsa-miR-497* | MIMAT0004768 | CAAACCACacugugguguuaga | 403 |
| hsa-miR-181d | MIMAT0002821 | AACAUUCAuuguugucgguggu | 404 |
| hsa-miR-512-5p | MIMAT0002822 | CACUCAGCcuugagggcacuuuc | 405 |
| hsa-miR-512-3p | MIMAT0002823 | AAGUGCUGucauagcugagguc | 406 |
| hsa-miR-498 | MIMAT0002824 | UUUCAAGCcaggggggcguuuuc | 407 |
| hsa-miR-520e | MIMAT0002S25 | AAAGUGCUuccuuuuugaggg | 408 |
| hsa-miR-515-5p | MIMAT0002826 | UUCUCCAAaagaaagcacuuucug | 409 |
| hsa-miR-515-3p | MIMAT0002827 | GAGUGCCUucuuuuggagcguu | 410 |
| hsa-miR-519e* | MIMAT0002828 | UUCUCCAAaagggagcacuuuc | 411 |
| hsa-miR-519e | MIMAT0002829 | AAGUGCCUccuuuuagaguguu | 412 |
| hsa-miR-520f | MIMAT0002830 | AAGUGCUUccuuuuagagggu | 413 |
| hsa-miR-519c-5p | MIMAT0002831 | CUCUAGAGggaagcgcuuucug | 414 |
| hsa-miR-519c-3p | MIMAT0002832 | AAAGUGCAucuuuuuagaggau | 415 |
| hsa-miR-520a-5p | MIMAT0002833 | CUCCAGAGggaaguacuuucu | 416 |
| hsa-miR-520a-3p | MIMAT0002834 | AAAGUGCUuccccuuuggacugu | 417 |
| hsa-miR-526b | MIMAT0002835 | CUCUUGAGggaagcacuuucugu | 418 |
| hsa-miR-526b* | MIMAT0002836 | GAAAGUGCuuccuuuuagaggc | 419 |
| hsa-miR-519b-5p | MIMAT0005454 | CUCUAGAGggaagcgcuuucug | 414 |
| hsa-miR-519b-3p | MIMAT0002837 | AAAGUGCAuccuuuuagagguu | 420 |
| hsa-miR-525-5p | MIMAT0002838 | CUCCAGAGggaugcacuuucu | 421 |
| hsa-miR-525-3p | MIMAT0002839 | GAAGGCGCuucccuuuagagcg | 422 |
| hsa-miR-523* | MIMAT0005449 | CUCUAGAGggaagcgcuuucug | 414 |
| hsa-miR-523 | MIMAT0002840 | GAACGCGCuucccuauagagggu | 423 |
| hsa-miR-518f* | MIMAT0002841 | CUCUAGAGggaagcacuuucuc | 424 |
| hsa-miR-518f | MIMAT0002842 | GAAAGCGCuucucuuuagagg | 425 |
| hsa-miR-520b | MIMAT0002843 | AAAGUGCUuccuuuuagaggg | 426 |

TABLE 1-continued

| miRNA name | miRBase number | Sequence | SEQ ID NO |
|---|---|---|---|
| hsa-miR-518b | MIMAT0002844 | CAAAGCGCuccccuuuagaggu | 427 |
| hsa-miR-526a | MIMAT0002845 | CUCUAGAGggaagcacuuucug | 428 |
| hsa-miR-520c-5p | MIMAT0005455 | CUCUAGAGggaagcacuuucug | 428 |
| hsa-miR-520c-3p | MIMAT0002846 | AAAGUGCUuccuuuuagagggu | 429 |
| hsa-miR-518c* | MIMAT0002847 | UCUCUGGAgggaagcacuuucug | 430 |
| hsa-miR-518c | MIMAT0002848 | CAAAGCGCuucucuuuagagugu | 431 |
| hsa-miR-524-5p | MIMAT0002849 | CUACAAAGggaagcacuuucuc | 432 |
| hsa-miR-524-3p | MIMAT0002850 | GAAGGCGCuucccuuuggagu | 433 |
| hsa-miR-517* | MIMAT0002851 | CCUCUAGAuggaagcacugucu | 434 |
| hsa-miR-517a | MIMAT0002852 | AUCGUGCAuccccuuuagagugu | 435 |
| hsa-miR-519d | MIMAT0002853 | CAAAGUGCcuccccuuuagagug | 436 |
| hsa-miR-521 | MIMAT0002854 | AACGCACUuccccuuuagagugu | 437 |
| hsa-miR-520d-5p | MIMAT0002855 | CUACAAAGggaagcccuuuc | 438 |
| hsa-miR-520d-3p | MIMAT0002856 | AAAGUGCUucucuuuggugggu | 439 |
| hsa-miR-517b | MIMAT0002857 | UCGUGCAUccuuuagaguguu | 440 |
| hsa-miR-520g | MIMAT0002858 | ACAAAGUGcuucccuuuagagugu | 441 |
| hsa-miR-516b | MIMAT0002859 | AUCUGGAGguaagaagcacuuu | 442 |
| hsa-miR-516b* | MIMAT0002860 | UGCUUCCUuuucagagggu | 443 |
| hsa-miR-518e* | MIMAT0005450 | CUCUAGAGggaagcgcuuucug | 414 |
| hsa-miR-518e | MIMAT0002861 | AAAGCGCUuccccuucagagug | 444 |
| hsa-miR-518a-5p | MIMAT0005457 | CUGCAAAGggaagcccuuuc | 445 |
| hsa-miR-518a-3p | MIMAT0002863 | GAAAGCGCuucccuuugcugga | 446 |
| hsa-miR-518d-5p | MIMAT0005456 | CUCUAGAGggaagcacuuucug | 428 |
| hsa-miR-518d-3p | MIMAT0002864 | CAAAGCGCuucccuuuggagc | 447 |
| hsa-miR-517c | MIMAT0002866 | AUCGUGCAuccuuuuagagugu | 448 |
| hsa-miR-520h | MIMAT0002867 | ACAAAGUGcuucccuuuagagu | 449 |
| hsa-miR-522* | MIMAT0005451 | CUCUAGAGggaagcgcuuucug | 414 |
| hsa-miR-522 | MIMAT0002868 | AAAAUGGUucccuuuagagugu | 450 |
| hsa-miR-519a* | MIMAT0005452 | CUCUAGAGggaagcgcuuucug | 414 |
| hsa-miR-519a | MIMAT0002869 | AAAGUGCAuccuuuuagagugu | 451 |
| hsa-miR-527 | MIMAT0002862 | CUGCAAAGggaagcccuuuc | 445 |
| hsa-miR-516a-5p | MIMAT0004770 | UUCUCGAGgaaagaagcacuuuc | 452 |
| hsa-miR-516a-3p | MIMAT0006778 | UGCUUCCUuuucagagggu | 443 |
| hsa-miR-499-5p | MIMAT0002870 | UUAAGACUugcagugauguuu | 453 |
| hsa-miR-499-3p | MIMAT0004772 | AACAUCACagcaagucugugcu | 454 |
| hsa-miR-500 | MIMAT0004773 | UAAUCCUUgcuaccugggugaga | 455 |
| hsa-miR-500* | MIMAT0002871 | AUGCACCUgggcaaggauucug | 456 |
| hsa-miR-501-5p | MIMAT0002872 | AAUCCUUUgucccuggggugaga | 457 |
| hsa-miR-501-3p | MIMAT0004774 | AAUGCACCcgggcaaggauucu | 458 |

TABLE 1-continued

| miRNA name | miRBase number | Sequence | SEQ ID NO |
|---|---|---|---|
| hsa-miR-502-5p | MIMAT0002873 | AUCCUUGcuaucugggugcua | 459 |
| hsa-miR-502-3p | MIMAT0004775 | AAUGCACCugggcaaggauuca | 460 |
| hsa-miR-503 | MIMAT0002874 | UAGCAGCGggaacaguucugcag | 461 |
| hsa-miR-504 | MIMAT0002875 | AGACCCUGgucugcacucuauc | 462 |
| hsa-miR-505* | MIMAT0004776 | GGGAGCCAggaaguauugaugu | 463 |
| hsa-miR-505 | MIMAT0002876 | CGUCAACAcuugcugguuuccu | 464 |
| hsa-miR-513a-5p | MIMAT0002877 | UUCACAGGgaggugucau | 465 |
| hsa-miR-513a-3p | MIMAT0004777 | UAAAUUUCaccuuucugagaagg | 466 |
| hsa-miR-506 | MIMAT0002878 | UAAGGCACccuucugaguaga | 467 |
| hsa-miR-507 | MIMAT0002879 | UUUUGCACcuuuuggagugaa | 468 |
| hsa-miR-508-5p | MIMAT0004778 | UACUCCAGagggcgucacucaug | 469 |
| hsa-miR-508-3p | MIMAT0002880 | UGAUUGUAgccuuuuggaguaga | 470 |
| hsa-miR-509-5p | MIMAT0004779 | UACUGCAGacaguggcaauca | 471 |
| hsa-miR-509-3p | MIMAT0002881 | UGAUUGGUacgucuguggguag | 472 |
| hsa-miR-510 | MIMAT0002882 | UACUCAGGagaguggcaaucac | 473 |
| hsa-miR-514 | MIMAT0002883 | AUUGACACuucugugaguaga | 474 |
| hsa-miR-532-5p | MIMAT0002888 | CAUGCCUUgaguguaggaccgu | 475 |
| hsa-miR-532-3p | MIMAT0004780 | CCUCCCACacccaaggcuugca | 476 |
| hsa-miR-455-5p | MIMAT0003150 | UAUGUGCCuuuggacuacaucg | 477 |
| hsa-miR-455-3p | MIMAT0004784 | GCAGUCCAugggcauauacac | 478 |
| hsa-miR-539 | MIMAT0003163 | GGAGAAAUuauccuuggugugu | 479 |
| hsa-miR-544 | MIMAT0003164 | AUUCUGCAuuuuuagcaaguuc | 480 |
| hsa-miR-545* | MIMAT0004785 | UCAGUAAAuguuuauuagauga | 481 |
| hsa-miR-545 | MIMAT0003165 | UCAGCAAAcauuuauugugugc | 482 |
| hsa-miR-487b | MIMAT0003180 | AAUCGUACagggucauccacuu | 483 |
| hsa-miR-551a | MIMAT0003214 | GCGACCCAcucuuggguuucca | 484 |
| hsa-miR-552 | MIMAT0003215 | AACAGGUGacugguuagacaa | 485 |
| hsa-miR-553 | MIMAT0003216 | AAAACGGUgagauuuuguuuu | 486 |
| hsa-miR-554 | MIMAT0003217 | GCUAGUCCugacucagccagu | 487 |
| hsa-miR-92b* | MIMAT0004792 | AGGGACGGgacgcggugcagug | 488 |
| hsa-miR-92b | MIMAT0003218 | UAUUGCACucgucccggccucc | 489 |
| hsa-miR-555 | MIMAT0003219 | AGGGUAAGcugaaccucugau | 490 |
| hsa-miR-556-5p | MIMAT0003220 | GAUGAGCUcauuguaauaugag | 491 |
| hsa-miR-556-3p | MIMAT0004793 | AUAUUACCauuagcucaucuuu | 492 |
| hsa-miR-557 | MIMAT0003221 | GUUUGCACggguggggccuugcu | 493 |
| hsa-miR-558 | MIMAT0003222 | UGAGCUGCuguaccaaaau | 494 |
| hsa-miR-559 | MIMAT0003223 | UAAAGUAAauaugcaccaaaa | 495 |
| hsa-miR-561 | MIMAT0003225 | CAAAGUUUaagauccuugaagu | 496 |
| hsa-miR-562 | MIMAT0003226 | AAAGUAGCuguaccauuugc | 497 |

TABLE 1-continued

| miRNA name | miRBase number | Sequence | SEQ ID NO |
|---|---|---|---|
| hsa-miR-563 | MIMAT0003227 | AGGUUGACauacguuuccc | 498 |
| hsa-miR-564 | MIMAT0003228 | AGGCACGGugucagcaggc | 499 |
| hsa-miR-566 | MIMAT0003230 | GGGCGCCUgugaucccaac | 500 |
| hsa-miR-567 | MIMAT0003231 | AGUAUGUUcuuccaggacagaac | 501 |
| hsa-miR-568 | MIMAT0003232 | AUGUAUAAauguauacacac | 502 |
| hsa-miR-551b* | MIMAT0004794 | GAAAUCAAgcguggguagagacc | 503 |
| hsa-miR-551b | MIMAT0003233 | GCGACCCAuacuuggguuucag | 504 |
| hsa-miR-569 | MIMAT0003234 | AGUUAAUGaauccuggaaagu | 505 |
| hsa-miR-570 | MIMAT0003235 | CGAAAACAgcaauuaccuuugc | 506 |
| hsa-miR-571 | MIMAT0003236 | UGAGUUGGccaucugagugag | 507 |
| hsa-miR-572 | MIMAT0003237 | GUCCGCUCggcgguggccca | 508 |
| hsa-miR-573 | MIMAT0003238 | CUGAAGUGauguguaacugaucag | 509 |
| hsa-miR-574-5p | MIMAT0004795 | UGAGUGUGugugugugagugugu | 510 |
| hsa-miR-574-3p | MIMAT0003239 | CACGCUCAugcacacacccaca | 511 |
| hsa-miR-575 | MIMAT0003240 | GAGCCAGUuggacaggagc | 512 |
| hsa-miR-576-5p | MIMAT0003241 | AUUCUAAUuucuccacgucuuu | 513 |
| hsa-miR-576-3p | MIMAT0004796 | AAGAUGUGgaaaaauuggaauc | 514 |
| hsa-miR-577 | MIMAT0003242 | UAGAUAAAauauuggguaccug | 515 |
| hsa-miR-578 | MIMAT0003243 | CUUCUUGUgcucuaggauugu | 516 |
| hsa-miR-579 | MIMAT0003244 | UUCAUUUGguauaaaccgcgauu | 517 |
| hsa-miR-580 | MIMAT0003245 | UUGAGAAUgaugaaucauuagg | 518 |
| hsa-miR-581 | MIMAT0003246 | UCUUGUGUucucuagaucagu | 519 |
| hsa-miR-582-5p | MIMAT0003247 | UUACAGUUguucaaccaguuacu | 520 |
| hsa-miR-582-3p | MIMAT0004797 | UAACUGGUugaacaacugaacc | 521 |
| hsa-miR-583 | MIMAT0003248 | CAAAGAGGaaggucccauuac | 522 |
| hsa-miR-584 | MIMAT0003249 | UUAUGGUUugccugggacgag | 523 |
| hsa-miR-585 | MIMAT0003250 | UGGGCGUAucuguaugcua | 524 |
| hsa-miR-548a-3p | MIMAT0003251 | CAAAACUGgcaauuacuuuugc | 525 |
| hsa-miR-586 | MIMAT0003252 | UAUGCAUUguauuuuaggucc | 526 |
| hsa-miR-587 | MIMAT0003253 | UUUCCAUAggugaugagucac | 527 |
| hsa-miR-548b-5p | MIMAT0004798 | AAAAGUAAuugugguuuuggcc | 528 |
| hsa-miR-548b-3p | MIMAT0003254 | CAAGAACCucaguugcuuuugu | 529 |
| hsa-miR-588 | MIMAT0003255 | UUGGCCACaauggguuagaac | 530 |
| hsa-miR-589 | MIMAT0004799 | UGAGAACCacgucugcucugag | 531 |
| hsa-miR-589* | MIMAT0003256 | UCAGAACAaaugccgguucccaga | 532 |
| hsa-miR-550 | MIMAT0004800 | AGUGCCUGagggaguaagagccc | 533 |
| hsa-miR-550* | MIMAT0003257 | UGUCUUACuccccucaggcacau | 534 |
| hsa-miR-590-5p | MIMAT0003258 | GAGCUUAUucauaaaagugcag | 535 |
| hsa-miR-590-3p | MIMAT0004801 | UAAUUUUAuguauaagcuagu | 536 |

TABLE 1-continued

| miRNA name | miRBase number | Sequence | SEQ ID NO |
|---|---|---|---|
| hsa-miR-591 | MIMAT0003259 | AGACCAUGgguucucauugu | 537 |
| hsa-miR-592 | MIMAT0003260 | UUGUGUCAauaugcgaugaugu | 538 |
| hsa-miR-593* | MIMAT0003261 | AGGCACCAgccaggcauugcucagc | 539 |
| hsa-miR-593 | MIMAT0004802 | UGUCUCUGcuggggUUUCU | 540 |
| hsa-miR-595 | MIMAT0003263 | GAAGUGUGccguggugugucu | 541 |
| hsa-miR-596 | MIMAT0003264 | AAGCCUGCccggcuccucggg | 542 |
| hsa-miR-597 | MIMAT0003265 | UGUGUCACucgaugaccacugu | 543 |
| hsa-miR-598 | MIMAT0003266 | UACGUCAUcguugucaucguca | 544 |
| hsa-miR-599 | MIMAT0003267 | GUUGUGUCaguuuaucaaac | 545 |
| hsa-miR-548a-5p | MIMAT0004803 | AAAAGUAAuugcgaguuuuacc | 546 |
| hsa-miR-600 | MIMAT0003268 | ACUUACAGacaagagccuugcuc | 547 |
| hsa-miR-601 | MIMAT0003269 | UGGUCUAGgauuguuggaggag | 548 |
| hsa-miR-602 | MIMAT0003270 | GACACGGGcgacagcugcggccc | 549 |
| hsa-miR-603 | MIMAT0003271 | CACACACUgcaauuacuuuugc | 550 |
| hsa-miR-604 | MIMAT0003272 | AGGCUGCGgaauucaggac | 551 |
| hsa-miR-605 | MIMAT0003273 | UAAAUCCCauggugccuucuccu | 552 |
| hsa-miR-606 | MIMAT0003274 | AAACUACUgaaaaucaaagau | 553 |
| hsa-miR-607 | MIMAT0003275 | GUUCAAAUccagaucuauaac | 554 |
| hsa-miR-608 | MIMAT0003276 | AGGGGUGGuguugggacagcuccgu | 555 |
| hsa-miR-609 | MIMAT0003277 | AGGGUGUUucucucaucucu | 556 |
| hsa-miR-610 | MIMAT0003278 | UGAGCUAAauguguguggga | 557 |
| hsa-miR-611 | MIMAT0003279 | GCGAGGACcccucggggucugac | 558 |
| hsa-miR-612 | MIMAT0003280 | GCUGGGCAgggcuucugagcuccuu | 559 |
| hsa-miR-613 | MIMAT0003281 | AGGAAUGUuccuucuuugcc | 560 |
| hsa-miR-614 | MIMAT0003282 | GAACGCCUguucuugccaggugg | 561 |
| hsa-miR-615-5p | MIMAT0004804 | GGGGGUCCccggugcucggauc | 562 |
| hsa-miR-615-3p | MIMAT0003283 | UCCGAGCCugggucucccucu | 563 |
| hsa-miR-616* | MIMAT0003284 | ACUCAAAAcccuucagugacuu | 564 |
| hsa-miR-616 | MIMAT0004805 | AGUCAUUGgaggguuugagcag | 565 |
| hsa-miR-548c-5p | MIMAT0004806 | AAAAGUAAuugcggauuuuugcc | 566 |
| hsa-miR-548c-3p | MIMAT0003285 | CAAAAAUCucaauuacuuuugc | 567 |
| hsa-miR-617 | MIMAT0003286 | AGACUUCCcauuugaaggugggc | 568 |
| hsa-miR-618 | MIMAT0003287 | AAACUCUAcuugucuucugagu | 569 |
| hsa-miR-619 | MIMAT0003288 | GACCUGGAcauguuugugcccagu | 570 |
| hsa-miR-620 | MIMAT0003289 | AUGGAGAUagauauagaaau | 571 |
| hsa-miR-621 | MIMAT0003290 | GGCUAGCAacagcgcuuaccu | 572 |
| hsa-miR-622 | MIMAT0003291 | ACAGUCUGcugagguuggagc | 573 |
| hsa-miR-623 | MIMAT0003292 | AUCCCUUGcaggggcguugggu | 574 |
| hsa-miR-624* | MIMAT0003293 | UAGUACCAguaccuuguguuca | 575 |

TABLE 1-continued

| miRNA name | miRBase number | Sequence | SEQ ID NO |
|---|---|---|---|
| hsa-miR-624 | MIMAT0004807 | CACAAGGUauuggauauuaccu | 576 |
| hsa-miR-625 | MIMAT0003294 | AGGGGGAAaguucuaagucc | 577 |
| hsa-miR-625* | MIMAT0004808 | GACUAUAGaacuuuccccuca | 578 |
| hsa-miR-626 | MIMAT0003295 | AGCUGUCUgaaaaugucuu | 579 |
| hsa-miR-627 | MIMAT0003296 | GUGAGUCUcuaagaaaagagga | 580 |
| hsa-miR-628-5p | MIMAT0004809 | AUGCUGACauauuuacuagagg | 581 |
| hsa-miR-628-3p | MIMAT0003297 | UCUAGUAAgaguggcagucga | 582 |
| hsa-miR-629 | MIMAT0004810 | UGGGUUUAcguugggagaacu | 583 |
| hsa-miR-629* | MIMAT0003298 | GUUCUCCCaacguaagcccagc | 584 |
| hsa-miR-630 | MIMAT0003299 | AGUAUUCUguaccagggaaggu | 585 |
| hsa-miR-631 | MIMAT0003300 | AGACCUGGcccagaccucagc | 586 |
| hsa-miR-33b | MIMAT0003301 | GUGCAUUGcuguugcauugc | 587 |
| hsa-miR-33b* | MIMAT0004811 | CAGUGCCUcggcagugcagccc | 588 |
| hsa-miR-632 | MIMAT0003302 | GUGUCUGCuuccuguggga | 589 |
| hsa-miR-633 | MIMAT0003303 | CUAAUAGUaucuaccacaauaaa | 590 |
| hsa-miR-634 | MIMAT0003304 | AACCAGCAccccaacuuuggac | 591 |
| hsa-miR-635 | MIMAT0003305 | ACUUGGGCacugaaacaaugucc | 592 |
| hsa-miR-636 | MIMAT0003306 | UGUGCUUGcucgucccgcccgca | 593 |
| hsa-miR-637 | MIMAT0003307 | ACUGGGGGcuuucgggcucugcgu | 594 |
| hsa-miR-638 | MIMAT0003308 | AGGGAUCGcgggcggguggcggccu | 595 |
| hsa-miR-639 | MIMAT0003309 | AUCGCUGCgguugcgagcgcugu | 596 |
| hsa-miR-640 | MIMAT0003310 | AUGAUCCAggaaccugccucu | 597 |
| hsa-miR-641 | MIMAT0003311 | AAAGACAUaggauagagucaccuc | 598 |
| hsa-miR-642 | MIMAT0003312 | GUCCCUCUccaaaugugucuug | 599 |
| hsa-miR-643 | MIMAT0003313 | ACUUGUAUgcuagcucagguag | 600 |
| hsa-miR-644 | MIMAT0003314 | AGUGUGGCuuucuuagagc | 601 |
| hsa-miR-645 | MIMAT0003315 | UCUAGGCUgguacugcuga | 602 |
| hsa-miR-646 | MIMAT0003316 | AAGCAGCUgccucugaggc | 603 |
| hsa-miR-647 | MIMAT0003317 | GUGGCUGCacucacuuccuuc | 604 |
| hsa-miR-648 | MIMAT0003318 | AAGUGUGCagggcacuggu | 605 |
| hsa-miR-649 | MIMAT0003319 | AAACCUGUguuguucaagaguc | 606 |
| hsa-miR-650 | MIMAT0003320 | AGGAGGCAgcgcucucaggac | 607 |
| hsa-miR-651 | MIMAT0003321 | UUUAGGAUaagcuugacuuuug | 608 |
| hsa-miR-652 | MIMAT0003322 | AAUGGCGCcacuagggUUGUG | 609 |
| hsa-miR-548d-5p | MIMAT0004812 | AAAAGUAAuugugguuuuugcc | 610 |
| hsa-miR-548d-3p | MIMAT0003323 | CAAAAACCacaguuucuuuugc | 611 |
| hsa-miR-661 | MIMAT0003324 | UGCCUGGGucucuggccugcgcgu | 612 |
| hsa-miR-662 | MIMAT0003325 | UCCCACGUuguggcccagcag | 613 |
| hsa-miR-663 | MIMAT0003326 | AGGCGGGGcgccgcgggaccgc | 614 |

TABLE 1-continued

| miRNA name | miRBase number | Sequence | SEQ ID NO |
|---|---|---|---|
| hsa-miR-449b | MIMAT0003327 | AGGCAGUGuauuguuagcuggc | 615 |
| hsa-miR-449b* | MIMAT0009203 | CAGCCACAacuacccugccacu | 616 |
| hsa-miR-653 | MIMAT0003328 | GUGUUGAAcaaucucuacug | 617 |
| hsa-miR-411 | MIMAT0003329 | UAGUAGACcguauagcguacg | 618 |
| hsa-miR-411* | MIMAT0004813 | UAUGUAACacgguccacuaacc | 619 |
| hsa-miR-654-5p | MIMAT0003330 | UGGUGGGCcgcagaacaugugc | 620 |
| hsa-miR-654-3p | MIMAT0004814 | UAUGUCUGcugaccaucaccuu | 621 |
| hsa-miR-655 | MIMAT0003331 | AUAAUACAugguuaaccucuuu | 622 |
| hsa-miR-656 | MIMAT0003332 | AAUAUUAUacagucaaccucu | 623 |
| hsa-miR-549 | MIMAT0003333 | UGACAACUauggaugagcucu | 624 |
| hsa-miR-657 | MIMAT0003335 | GGCAGGUUcucacccucucuagg | 625 |
| hsa-miR-658 | MIMAT0003336 | GGCGGAGGgaaguagguccguuggu | 626 |
| hsa-miR-659 | MIMAT0003337 | CUUGGUUCaggagggucccca | 627 |
| hsa-miR-660 | MIMAT0003338 | UACCCAUUgcauaucggaguug | 628 |
| hsa-miR-421 | MIMAT0003339 | AUCAACAGacauuaauugggcgc | 629 |
| hsa-miR-542-5p | MIMAT0003340 | UCGGGGAUcaucaugucacgaga | 630 |
| hsa-miR-542-3p | MIMAT0003389 | UGUGACAGauugauaacugaaa | 631 |
| hsa-miR-758 | MIMAT0003879 | UUUGUGACcugguccacuaacc | 632 |
| hsa-miR-1264 | MIMAT0005791 | CAAGUCUUauuugagcaccuguu | 633 |
| hsa-miR-671-5p | MIMAT0003880 | AGGAAGCCcuggaggggcuggag | 634 |
| hsa-miR-671-3p | MIMAT0004819 | UCCGGUUCucagggcuccacc | 635 |
| hsa-miR-668 | MIMAT0003881 | UGUCACUCggcucggcccacuac | 636 |
| hsa-miR-767-5p | MIMAT0003882 | UGCACCAUgguugucugagcaug | 637 |
| hsa-miR-767-3p | MIMAT0003883 | UCUGCUCAuaccccaugguuucu | 638 |
| hsa-miR-1224-5p | MIMAT0005458 | GUGAGGACucgggaggugg | 639 |
| hsa-miR-1224-3p | MIMAT0005459 | CCCCACCUccucucuccucag | 640 |
| hsa-miR-320b | MIMAT0005792 | AAAAGCUGgguugagagggcaa | 641 |
| hsa-miR-320c | MIMAT0005793 | AAAAGCUGgguugagagggu | 642 |
| hsa-miR-1296 | MIMAT0005794 | UUAGGGCCcuggcuccaucucc | 643 |
| hsa-miR-1468 | MIMAT0006789 | CUCCGUUUgccuguuucgcug | 644 |
| hsa-miR-1323 | MIMAT0005795 | UCAAAACUgaggggcauuuucu | 645 |
| hsa-miR-1271 | MIMAT0005796 | CUUGGCACcuagcaagcacuca | 646 |
| hsa-miR-1301 | MIMAT0005797 | UUGCAGCUgccugggagugacuuc | 647 |
| hsa-miR-454* | MIMAT0003884 | ACCCUAUCaauauugucucugc | 648 |
| hsa-miR-454 | MIMAT0003885 | UAGUGCAAauuugcuuauagggu | 649 |
| hsa-miR-1185 | MIMAT0005798 | AGAGGAUAcccuuuguauguu | 650 |
| hsa-miR-449c | MIMAT0010251 | UAGGCAGUguauugcuagcggcugu | 651 |
| hsa-miR-449c* | MIMAT0013771 | UUGCUAGUugcacuccucucugu | 652 |
| hsa-miR-1283 | MIMAT0005799 | UCUACAAAggaaagcgcuuucu | 653 |

TABLE 1-continued

| miRNA name | miRBase number | Sequence | SEQ ID NO |
|---|---|---|---|
| hsa-miR-769-5p | MIMAT0003886 | UGAGACCUcuggguucugagcu | 654 |
| hsa-miR-769-3p | MIMAT0003887 | CUGGGAUCuccggggucuugguu | 655 |
| hsa-miR-766 | MIMAT0003888 | ACUCCAGCcccacagccucagc | 656 |
| hsa-miR-762 | MIMAT0010313 | GGGGCUGGggccggggccgagc | 657 |
| hsa-miR-802 | MIMAT0004185 | CAGUAACAaagauucauccuugu | 658 |
| hsa-miR-670 | MIMAT0010357 | GUCCCUGAguguaugugguug | 659 |
| hsa-miR-1298 | MIMAT0005800 | UUCAUUCGgcuguccagaugua | 660 |
| hsa-miR-2113 | MIMAT0009206 | AUUUGUGCuuggcucugucac | 661 |
| hsa-miR-761 | MIMAT0010364 | GCAGCAGGgugaaacugacaca | 662 |
| hsa-miR-764 | MIMAT0010367 | GCAGGUGCucacuuguccuccu | 663 |
| hsa-miR-759 | MIMAT0010497 | GCAGAGUGcaaacaauuuugac | 664 |
| hsa-miR-765 | MIMAT0003945 | UGGAGGAGaaggaaggugaug | 665 |
| hsa-miR-770-5p | MIMAT0003948 | UCCAGUACcacgugucagggcca | 666 |
| hsa-miR-675 | MIMAT0004284 | UGGUGCGGagagggcccacagug | 667 |
| hsa-miR-675* | MIMAT0006790 | CUGUAUGCccucaccgcuca | 668 |
| hsa-miR-298 | MIMAT0004901 | AGCAGAAGcagggagguucuccca | 669 |
| hsa-miR-891a | MIMAT0004902 | UGCAACGAaccuaccacuga | 670 |
| hsa-miR-300 | MIMAT0004903 | UAUACAAGggcagacucucucu | 671 |
| hsa-miR-886-5p | MIMAT0004905 | CGGGUCGGaguuagcucaagcgg | 672 |
| hsa-miR-886-3p | MIMAT0004906 | CGCGGGUGcuuacugacccuu | 673 |
| hsa-miR-892a | MIMAT0004907 | CACUGUGUccuuucugcguag | 674 |
| hsa-miR-220b | MIMAT0004908 | CCACCACCgugucugacacuu | 675 |
| hsa-miR-450b-5p | MIMAT0004909 | UUUUGCAAuauguccugaaua | 676 |
| hsa-miR-450b-3p | MIMAT0004910 | UUGGGAUCauuuugcauccaua | 677 |
| hsa-miR-874 | MIMAT0004911 | CUGCCCUGgcccgagggaccga | 678 |
| hsa-miR-890 | MIMAT0004912 | UACUUGGAaaggcaucaguug | 679 |
| hsa-miR-891b | MIMAT0004913 | UGCAACUUaccugagucauuga | 680 |
| hsa-miR-220c | MIMAT0004915 | ACACAGGGcuguugugaagacu | 681 |
| hsa-miR-888 | MIMAT0004916 | UACUCAAAagcugucaguca | 682 |
| hsa-miR-888* | MIMAT0004917 | GACUGACAccucuuugggugaa | 683 |
| hsa-miR-892b | MIMAT0004918 | CACUGGCUccuuucggguaga | 684 |
| hsa-miR-541* | MIMAT0004919 | AAAGGAUUcugcugucggucccacu | 685 |
| hsa-miR-541 | MIMAT0004920 | UGGUGGGCacagaaucuggacu | 686 |
| hsa-miR-889 | MIMAT0004921 | UUAAUAUCggacaaccauugu | 687 |
| hsa-miR-875-5p | MIMAT0004922 | UAUACCUCaguuuuaucaggug | 688 |
| hsa-miR-875-3p | MIMAT0004923 | CCUGGAAAcacugagguugug | 689 |
| hsa-miR-876-5p | MIMAT0004924 | UGGAUUUCuuugugaaucacca | 690 |
| hsa-miR-876-3p | MIMAT0004925 | UGGUGGUUuacaaaguaauuca | 691 |
| hsa-miR-708 | MIMAT0004926 | AAGGAGCUuacaaucuagcuggg | 692 |

TABLE 1-continued

| miRNA name | miRBase number | Sequence | SEQ ID NO |
|---|---|---|---|
| hsa-miR-708* | MIMAT0004927 | CAACUAGAcugugagcuucuag | 693 |
| hsa-miR-147b | MIMAT0004928 | GUGUGCGGaaaugcuucugcua | 694 |
| hsa-miR-190b | MIMAT0004929 | UGAUAUGUuugauauugggu | 695 |
| hsa-miR-744 | MIMAT0004945 | UGCGGGGCuagggcuaacagca | 696 |
| hsa-miR-744* | MIMAT0004946 | CUGUUGCCacuaaccucaaccu | 697 |
| hsa-miR-885-5p | MIMAT0004947 | UCCAUUACacuacccugccucu | 698 |
| hsa-miR-885-3p | MIMAT0004948 | AGGCAGCGggguguaguggaua | 699 |
| hsa-miR-877 | MIMAT0004949 | GUAGAGGAgauggcgcaggg | 700 |
| hsa-miR-877* | MIMAT0004950 | UCCUCUUCucccuccucccag | 701 |
| hsa-miR-887 | MIMAT0004951 | GUGAACGGagcgccaucccgagg | 702 |
| hsa-miR-665 | MIMAT0004952 | ACCAGGAGgcugaggccccu | 703 |
| hsa-miR-873 | MIMAT0004953 | GCAGGAACuugugagucuccu | 704 |
| hsa-miR-543 | MIMAT0004954 | AAACAUUCgcggugcacuucuu | 705 |
| hsa-miR-374b | MIMAT0004955 | AUAUAAUAcaaccugcuaagug | 706 |
| hsa-miR-374b* | MIMAT0004956 | CUUAGCAGuuguauuaucauu | 707 |
| hsa-miR-760 | MIMAT0004957 | CGGCUCUGggucugugggga | 708 |
| hsa-miR-301b | MIMAT0004958 | CAGUGCAAugauauugucaaagc | 709 |
| hsa-miR-216b | MIMAT0004959 | AAAUCUCUgcaggcaaauguga | 710 |
| hsa-miR-208b | MIMAT0004960 | AUAAGACGaacaaaagguuugu | 711 |
| hsa-miR-920 | MIMAT0004970 | GGGGAGCUguggaagcagua | 712 |
| hsa-miR-921 | MIMAT0004971 | CUAGUGAGggacagaaccaggauuc | 713 |
| hsa-miR-922 | MIMAT0004972 | GCAGCAGAgaauaggacuacguc | 714 |
| hsa-miR-924 | MIMAT0004974 | AGAGUCUUgugaugucuugc | 715 |
| hsa-miR-509-3-5p | MIMAT0004975 | UACUGCAGacguggcaaucaug | 716 |
| hsa-miR-933 | MIMAT0004976 | UGUGCGCAgggagaccucuccc | 717 |
| hsa-miR-934 | MIMAT0004977 | UGUCUACUacuggagacacugg | 718 |
| hsa-miR-935 | MIMAT0004978 | CCAGUUACcgcuuccgcuaccgc | 719 |
| hsa-miR-936 | MIMAT0004979 | ACAGUAGAgggaggaaucgcag | 720 |
| hsa-miR-937 | MIMAT0004980 | AUCCGCGCucugacucucugcc | 721 |
| hsa-miR-938 | MIMAT0004981 | UGCCCUUAaaggugaacccagu | 722 |
| hsa-miR-939 | MIMAT0004982 | UGGGGAGCugaggcucuggggug | 723 |
| hsa-miR-940 | MIMAT0004983 | AAGGCAGGcccccgcucccc | 724 |
| hsa-miR-941 | MIMAT0004984 | CACCCGGCugugugcacaugugc | 725 |
| hsa-miR-942 | MIMAT0004985 | UCUUCUCUguuuuggccaugug | 726 |
| hsa-miR-943 | MIMAT0004986 | CUGACUGUugccguccucag | 727 |
| hsa-miR-944 | MIMAT0004987 | AAAUUAUUguacaucggaugag | 728 |
| hsa-miR-297 | MIMAT0004450 | AUGUAUGUgugcaugugcaug | 729 |
| hsa-miR-1178 | MIMAT0005823 | UUGCUCACuguucuucccuag | 730 |
| hsa-miR-1179 | MIMAT0005824 | AAGCAUUCuuucauugguugg | 731 |

TABLE 1-continued

| miRNA name | miRBase number | Sequence | SEQ ID NO |
|---|---|---|---|
| hsa-miR-1180 | MIMAT0005825 | UUUCCGGCucgcgugggugugu | 732 |
| hsa-miR-1181 | MIMAT0005826 | CCGUCGCCgccacccgagccg | 733 |
| hsa-miR-1182 | MLMAT0005827 | GAGGGUCUugggagggaugugac | 734 |
| hsa-miR-1183 | MIMAT0005828 | CACUGUAGgugauggugagagugggca | 735 |
| hsa-miR-1184 | MIMAT0005829 | CCUGCAGCgacuugauggcuucc | 736 |
| hsa-miR-1225-5p | MIMAT0005572 | GUGGGUACggcccagugggggg | 737 |
| hsa-miR-1225-3p | MIMAT0005573 | UGAGCCCCugugccgcccccag | 738 |
| hsa-miR-1226* | MIMAT0005576 | GUGAGGGCaugcaggccuggaugggg | 739 |
| hsa-miR-1226 | MIMAT0005577 | UCACCAGCccuguguucccuag | 740 |
| hsa-miR-1227 | MIMAT0005580 | CGUGCCACccuuuuccccag | 741 |
| hsa-miR-1228* | MIMAT0005582 | GUGGGCGGgggcaggugugug | 742 |
| hsa-miR-1228 | MIMAT0005583 | UCACACCUgccucgcccccc | 743 |
| hsa-miR-1229 | MIMAT0005584 | CUCUCACCacugcccucccacag | 744 |
| hsa-miR-1231 | MIMAT0005586 | GUGUCUGGgcggacagcugc | 745 |
| hsa-miR-1233 | MLMAT0005588 | UGAGCCCUguccucccgcag | 746 |
| hsa-miR-1234 | MIMAT0005589 | UCGGCCUGaccacccaccccac | 747 |
| hsa-miR-1236 | MIMAT0005591 | CCUCUUCCccuugucucuccag | 748 |
| hsa-miR-1237 | MIMAT0005592 | UCCUUCUGcuccgucccccag | 749 |
| hsa-miR-1238 | MIMAT0005593 | CUUCCUCGucugucugcccc | 750 |
| hsa-miR-1200 | MIMAT0005863 | CUCCUGAGccauucugagccuc | 751 |
| hsa-miR-1201 | MIMAT0005864 | AGCCUGAUuaaacacaugcucuga | 752 |
| hsa-miR-1202 | MIMAT0005865 | GUGCCAGCugcagugggggag | 753 |
| hsa-miR-1203 | MIMAT0005866 | CCCGGAGCcaggaugcagcuc | 754 |
| hsa-miR-663b | MIMAT0005867 | GGUGGCCCggccgugccugagg | 755 |
| hsa-miR-1204 | MIMAT0005868 | UCGUGGCCuggucuccauuau | 756 |
| hsa-miR-1205 | MIMAT0005869 | UCUGCAGGguuugcuuugag | 757 |
| hsa-miR-1206 | MIMAT0005870 | UGUUCAUGuagauguuuaagc | 758 |
| hsa-miR-1207-5p | MIMAT0005871 | UGGCAGGGaggcugggagggg | 759 |
| hsa-miR-1207-3p | MIMAT0005872 | UCAGCUGGcccucauuuc | 760 |
| hsa-miR-1208 | MIMAT0005873 | UCACUGUUcagacaggcgga | 761 |
| hsa-miR-548e | MIMAT0005874 | AAAAACUGagacuacuuuugca | 762 |
| hsa-miR-548j | MIMAT0005875 | AAAAGUAAuugcggucuuuggu | 763 |
| hsa-miR-1285 | MIMAT0005876 | UCUGGGCAacaaagugagaccu | 764 |
| hsa-miR-1286 | MIMAT0005877 | UGCAGGACcaagaugagcccu | 765 |
| hsa-miR-1287 | MIMAT0005878 | UGCUGGAUcagugguucgaguc | 766 |
| hsa-miR-1289 | MIMAT0005879 | UGGAGUCCaggaaucugcauuuu | 767 |
| hsa-miR-1290 | MIMAT0005880 | UGGAUUUUuggaucaggga | 768 |
| hsa-miR-1291 | MIMAT0005881 | UGGCCCUGacugaagaccagcagu | 769 |
| hsa-miR-548k | MIMAT0005882 | AAAAGUACuugcggauuuugcu | 770 |

TABLE 1-continued

| miRNA name | miRBase number | Sequence | SEQ ID NO |
|---|---|---|---|
| hsa-miR-1293 | MIMAT0005883 | UGGGUGGUcuggagauuugugc | 771 |
| hsa-miR-1294 | MIMAT0005884 | UGUGAGGUuggcauuguugucu | 772 |
| hsa-miR-1295 | MIMAT0005885 | UUAGGCCGcagaucuggguga | 773 |
| hsa-miR-1297 | MIMAT0005886 | UUCAAGUAauucaggug | 774 |
| hsa-miR-1299 | MIMAT0005887 | UUCUGGAAuucugugugaggga | 775 |
| hsa-miR-5481 | MIMAT0005889 | AAAAGUAUuugcggguuuuguc | 776 |
| hsa-miR-1302 | MIMAT0005890 | UUGGGACAuacuuaugcuaaa | 777 |
| hsa-miR-1303 | MIMAT0005891 | UUUAGAGAcgggucuugcucu | 778 |
| hsa-miR-1304 | MIMAT0005892 | UUUGAGGCuacagugagaugug | 779 |
| hsa-miR-1305 | MIMAT0005893 | UUUUCAACucuaaugggagaga | 780 |
| hsa-miR-1243 | MIMAT0005894 | AACUGGAUcaauuauaggagug | 781 |
| hsa-miR-548f | MIMAT0005895 | AAAAACUGuaauuacuuuu | 782 |
| hsa-miR-1244 | MIMAT0005896 | AAGUAGUUgguuuguaugagaugguu | 783 |
| hsa-miR-1245 | MIMAT0005897 | AAGUGAUCuaaaggccuacau | 784 |
| hsa-miR-1246 | MIMAT0005898 | AAUGGAUUuuuggagcagg | 785 |
| hsa-miR-1247 | MIMAT0005899 | ACCCGUCCcguucgucccccgga | 786 |
| hsa-miR-1248 | MIMAT0005900 | ACCUUCUUguauaagcacugugcuaaa | 787 |
| hsa-miR-1249 | MIMAT0005901 | ACGCCCUUccccccuucuuca | 788 |
| hsa-miR-1250 | MIMAT0005902 | ACGGUGCUggauguggccuuu | 789 |
| hsa-miR-1251 | MIMAT0005903 | ACUCUAGCugccaaaggcgcu | 790 |
| hsa-miR-1253 | MIMAT0005904 | AGAGAAGAagaucagccugca | 791 |
| hsa-miR-1254 | MIMAT0005905 | AGCCUGGAagcuggagccugcagu | 792 |
| hsa-miR-1255a | MIMAT0005906 | AGGAUGAGcaaagaaaguagauu | 793 |
| hsa-miR-1256 | MIMAT0005907 | AGGCAUUGacuucucacuagcu | 794 |
| hsa-miR-1257 | MIMAT0005908 | AGUGAAUGauggguucugacc | 795 |
| hsa-miR-1258 | MIMAT0005909 | AGUUAGGAuuaggucguggaa | 796 |
| hsa-miR-1259 | MIMAT0005910 | AUAUAUGAugacuuagcuuuu | 797 |
| hsa-miR-1260 | MIMAT0005911 | AUCCCACCucugccacca | 798 |
| hsa-miR-548g | MIMAT0005912 | AAAACUGUaauuacuuuuguac | 799 |
| hsa-miR-1261 | MIMAT0005913 | AUGGAUAAggcuuuggcuu | 800 |
| hsa-miR-1262 | MIMAT0005914 | AUGGGUGAauuuguagaaggau | 801 |
| hsa-miR-1263 | MIMAT0005915 | AUGGUACCcuggcauacugagu | 802 |
| hsa-miR-548n | MIMAT0005916 | CAAAAGUAauuguggauuuugu | 803 |
| hsa-miR-548m | MIMAT0005917 | CAAAGGUAuuuguggguuuug | 804 |
| hsa-miR-1265 | MIMAT0005918 | CAGGAUGUggucaaguguugu | 805 |
| hsa-miR-548o | MIMAT0005919 | CCAAAACUgcaguuacuuuugc | 806 |
| hsa-miR-1266 | MIMAT0005920 | CCUCAGGGcuguagaacagggcu | 807 |
| hsa-miR-1267 | MIMAT0005921 | CCUGUUGAaguguaaucccca | 808 |
| hsa-miR-1268 | MIMAT0005922 | CGGGCGUGgugguggggg | 809 |

TABLE 1-continued

| miRNA name | miRBase number | Sequence | SEQ ID NO |
|---|---|---|---|
| hsa-miR-1269 | MIMAT0005923 | CUGGACUGagccgugcuacugg | 810 |
| hsa-miR-1270 | MIMAT0005924 | CUGGAGAUauggaagagcugugu | 811 |
| hsa-miR-1272 | MIMAT0005925 | GAUGAUGAuggcagcaaauucugaaa | 812 |
| hsa-miR-1273 | MIMAT0005926 | GGGCGACAaagcaagacucuuucuu | 813 |
| hsa-miR-1274a | MIMAT0005927 | GUCCCUGUucaggcgcca | 814 |
| hsa-miR-548h | MIMAT0005928 | AAAAGUAAucgcgguuuuuguc | 815 |
| hsa-miR-1275 | MIMAT0005929 | GUGGGGGAgaggcuguc | 816 |
| hsa-miR-1276 | MIMAT0005930 | UAAAGAGCccuguggagaca | 817 |
| hsa-miR-302e | MIMAT0005931 | UAAGUGCUuccaugcuu | 818 |
| hsa-miR-302f | MIMAT0005932 | UAAUUGCUuccauguuu | 819 |
| hsa-miR-1277 | MIMAT0005933 | UACGUAGAuauauauguauuuu | 820 |
| hsa-miR-548p | MIMAT0005934 | UAGCAAAAacugcaguuacuuu | 821 |
| hsa-miR-548i | MIMAT0005935 | AAAAGUAAuugcggauuuugcc | 822 |
| hsa-miR-1278 | MIMAT0005936 | UAGUACUGugcauaucaucuau | 823 |
| hsa-miR-1279 | MIMAT0005937 | UCAUAUUGcuucuuucu | 824 |
| hsa-miR-1274b | MIMAT0005938 | UCCCUGUUcgggcgcca | 825 |
| hsa-miR-1281 | MIMAT0005939 | UCGCCUCCuccucuccc | 826 |
| hsa-miR-1282 | MIMAT0005940 | UCGUUUGCcuuuuucugcuu | 827 |
| hsa-miR-1284 | MIMAT0005941 | UCUAUACAgacccuggcuuuuc | 828 |
| hsa-miR-1288 | MIMAT0005942 | UGGACUGCccugaucuggaga | 829 |
| hsa-miR-1292 | MIMAT0005943 | UGGGAACGgguuccggcagacgcug | 830 |
| hsa-miR-1252 | MIMAT0005944 | AGAAGGAAauugaauucauuua | 831 |
| hsa-miR-1255b | MIMAT0005945 | CGGAUGAGcaaagaaagugguu | 832 |
| hsa-miR-1280 | MIMAT0005946 | UCCCACCGcugccaccc | 833 |
| hsa-miR-1308 | MIMAT0005947 | GCAUGGGUgguucagugg | 834 |
| hsa-miR-664* | MIMAT0005948 | ACUGGCUAgggauaaugauuggau | 835 |
| hsa-miR-664 | MIMAT0005949 | UAUUCAUUuauccccagccuaca | 836 |
| hsa-miR-1306 | MIMAT0005950 | ACGUUGGCucuggugguug | 837 |
| hsa-miR-1307 | MIMAT0005951 | ACUCGGCGuggcgucggucgug | 838 |
| hsa-miR-513b | MIMAT0005788 | UUCACAAGgaggugucauuuau | 839 |
| hsa-miR-513c | MIMAT0005789 | UUCUCAAGgaggugucguuuau | 840 |
| hsa-miR-1321 | MIMAT0005952 | CAGGGAGGugaaugugau | 841 |
| hsa-miR-1322 | MIMAT0005953 | GAUGAUGCugcugaugcug | 842 |
| hsa-miR-720 | MIMAT0005954 | UCUCCCUGgggccucca | 843 |
| hsa-miR-1197 | MIMAT0005955 | UAGGACACauggucuacuucu | 844 |
| hsa-miR-1324 | MIMAT0005956 | CCAGACAGaauucuaugcacuuuc | 845 |
| hsa-miR-1469 | MIMAT0007347 | CUCGGCGCggggcgcgggcucc | 846 |
| hsa-miR-1470 | MIMAT0007348 | GCCCUCCGcccgugcacccg | 847 |
| hsa-miR-1471 | MIMAT0007349 | GCCCGCGUguggagccaggugu | 848 |

TABLE 1-continued

| miRNA name | miRBase number | Sequence | SEQ ID NO |
|---|---|---|---|
| hsa-miR-1537 | MIMAT0007399 | AAAACCGUcuaguuacaguugu | 849 |
| hsa-miR-1538 | MIMAT0007400 | CGGCCCGGgcugcugcuguuccu | 850 |
| hsa-miR-1539 | MIMAT0007401 | UCCUGCGCgucccagaugccc | 851 |
| hsa-miR-103-as | MIMAT0007402 | UCAUAGCCcuguacaaugcugcu | 852 |
| hsa-miR-320d | MIMAT0006764 | AAAAGCUGgguugagagga | 853 |
| hsa-miR-1825 | MIMAT0006765 | UCCAGUGCccuccucucc | 854 |
| hsa-miR-1826 | MIMAT0006766 | AUUGAUCAucgacacuucgaacgcaau | 855 |
| hsa-miR-1827 | MIMAT0006767 | UGAGGCAGuagauugaau | 856 |
| hsa-miR-1908 | MIMAT0007881 | CGGCGGGGacggcgauugguc | 857 |
| hsa-miR-1909* | MIMAT0007882 | UGAGUGCCggugccugcccug | 858 |
| hsa-miR-1909 | MIMAT0007883 | CGCAGGGGccgggugcucaccg | 859 |
| hsa-miR-1910 | MIMAT0007884 | CCAGUCCGugugccugccgccu | 860 |
| hsa-miR-1911 | MIMAT0007885 | UGAGUACCgccaugucuguuggg | 861 |
| hsa-miR-1911* | MIMAT0007886 | CACCAGGCauuguggucucc | 862 |
| hsa-miR-1912 | MIMAT0007887 | UACCCAGAgcaugcagugugaa | 863 |
| hsa-miR-1913 | MIMAT0007888 | UCUGCCCCcuccgcugcugcca | 864 |
| hsa-miR-1914 | MIMAT0007889 | CCCUGUGCccggcccacuucug | 865 |
| hsa-miR-1914* | MIMAT0007890 | GGAGGGGUcccgcacugggagg | 866 |
| hsa-miR-1915* | MIMAT0007891 | ACCUUGCCuugcugcccgggcc | 867 |
| hsa-miR-1915 | MIMAT0007892 | CCCCAGGGcgacgcggcggg | 868 |
| hsa-miR-1972 | MIMAT0009447 | UCAGGCCAggcacaguggcuca | 869 |
| hsa-miR-1973 | MIMAT0009448 | ACCGUGCAaagguagcaua | 870 |
| hsa-miR-1975 | MIMAT0009450 | CCCCCACAaccgcgcuugacuagcu | 871 |
| hsa-miR-1976 | MIMAT0009451 | CCUCCUGCccuccuugcugu | 872 |
| hsa-miR-1979 | MIMAT0009454 | CUCCCACUgcuucacuugacua | 873 |
| hsa-miR-2052 | MIMAT0009977 | UGUUUUGAuaacaguaaugu | 874 |
| hsa-miR-2053 | MIMAT0009978 | GUGUUAAUuaaaccucuauuuac | 875 |
| hsa-miR-2054 | MIMAT0009979 | CUGUAAUUaaaauuuaauuauu | 876 |
| hsa-miR-2110 | MIMAT0010133 | UUGGGGAAacggccgcugagug | 877 |
| hsa-miR-2114 | MIMAT0011156 | UAGUCCCUuccuugaagcgguc | 878 |
| hsa-miR-2114* | MIMAT0011157 | CGAGCCUCaagcaagggacuu | 879 |
| hsa-miR-2115 | MIMAT0011158 | AGCUUCCAugacuccugaugga | 880 |
| hsa-miR-2115* | MIMAT0411159 | CAUCAGAAuucauggaggcuag | 881 |
| hsa-miR-2116 | MIMAT0011160 | GGUUCUUAgcauaggaggucu | 882 |
| hsa-miR-2116* | MIMAT0011161 | CCUCCCAUgccaagaacuccc | 883 |
| hsa-miR-2117 | MIMAT0011162 | UGUUCUCUuugccaaggacag | 884 |
| hsa-miR-548q | MIMAT0011163 | GCUGGUGCaaaaguaauggcgg | 885 |

TABLE 1-continued

| miRNA name | miRBase number | Sequence | SEQ ID NO |
|---|---|---|---|
| hsa-miR-2276 | MIMAT0011775 | UCUGCAAgugucagaggcgagg | 886 |
| hsa-miR-2277 | MIMAT0011777 | UGACAGCGcccugccuggcuc | 887 |
| hsa-miR-2278 | MIMAT0011778 | GAGAGCAGugugug uugccugg | 888 |
| hsa-miR-711 | MIMAT0012734 | GGGACCCAgggagagacguaag | 889 |
| hsa-miR-718 | MIMAT0012735 | CUUCCGCCccgccgggcgucg | 890 |
| hsa-miR-2861 | MIMAT0013802 | GGGGCCUGgcggugggcgg | 891 |
| hsa-miR-2909 | MIMAT0013863 | GUUAGGGCcaacaucucuugg | 892 |
| hsa-miR-3115 | MIMAT0014977 | AUAUGGGUuuacuaguuggu | 893 |
| hsa-miR-3116 | MIMAT0014978 | UGCCUGGAacauaguagggacu | 894 |
| hsa-miR-3117 | MIMAT0014979 | AUAGGACUcauauagugccag | 895 |
| hsa-miR-3118 | MIMAT0014980 | UGUGACUGcauuauaaaauucu | 896 |
| hsa-miR-3119 | MIMAT0014981 | UGGCUUUUaacuuugauggc | 897 |
| hsa-miR-3120 | MIMAT0014982 | CACAGCAAguguagacaggca | 898 |
| hsa-miR-3121 | MIMAT0014983 | UAAAUAGAguaggcaaaggaca | 899 |
| hsa-miR-3122 | MIMAT0014984 | GUUGGGACaagaggacggucuu | 900 |
| hsa-miR-3123 | MIMAT0014985 | CAGAGAAUuguuuaauc | 901 |
| hsa-miR-3124 | MIMAT0014986 | UUCGCGGGcgaaggcaaaguc | 902 |
| hsa-miR-548s | MIMAT0014987 | AUGGCCAAaacugcaguuauuuu | 903 |
| hsa-miR-3125 | MIMAT0014988 | UAGAGGAAgcuguggagaga | 904 |
| hsa-miR-3126-5p | MIMAT0014989 | UGAGGGACagaugccagaagca | 905 |
| hsa-miR-3126-3p | MIMAT0015377 | CAUCUGGCauccgucacacaga | 906 |
| hsa-miR-3127 | MIMAT0014990 | AUCAGGGCuugugg aaugggaag | 907 |
| hsa-miR-3128 | MIMAT0014991 | UCUGGCAAguaaaaaacucucau | 908 |
| hsa-miR-3129 | MIMAT0014992 | GCAGUAGUguagagauugguuu | 909 |
| hsa-miR-3130-5p | MIMAT0014995 | UACCCAGUcuccggugcagcc | 910 |
| hsa-miR-3130-3p | MIMAT0014994 | GCUGCACCggagacuggguaa | 911 |
| hsa-miR-3131 | MIMAT0014996 | UCGAGGACuggug gaagggccuu | 912 |
| hsa-miR-3132 | MIMAT0014997 | UGGGUAGAgaaggagcucagagga | 913 |
| hsa-miR-3133 | MIMAT0014998 | UAAAGAACucuuaaaacccaau | 914 |
| hsa-miR-378b | MIMAT0014999 | ACUGGACUuggaggcagaa | 915 |
| hsa-miR-3134 | MIMAT0015000 | UGAUGGAUaaaagacuacauauu | 916 |
| hsa-miR-3135 | MIMAT0015001 | UGCCUAGGcugagacugcagug | 917 |
| hsa-miR-466 | MIMAT0015002 | AUACACAUacacgcaacacacau | 918 |
| hsa-miR-3136 | MIMAT0015003 | CUGACUGAauaggua gggucauu | 919 |
| hsa-miR-544b | MIMAT0015004 | ACCUGAGGuugugcauuucuaa | 920 |
| hsa-miR-3137 | MIMAT0015005 | UCUGUAGCcugggagcaauggggu | 921 |
| hsa-miR-3138 | MIMAT0015006 | UGUGGACAgugagguagagggagu | 922 |
| hsa-miR-3139 | MIMAT0015007 | UAGGAGCUcaacagaugccuguu | 923 |
| hsa-miR-3140 | MIMAT0015008 | AGCUUUUGggaauucaggu agu | 924 |

TABLE 1-continued

| miRNA name | miRBase number | Sequence | SEQ ID NO |
|---|---|---|---|
| hsa-miR-548t | MIMAT0015009 | CAAAAGUGaucgugguuuuug | 925 |
| hsa-miR-3141 | MIMAT0015010 | GAGGGCGGguggaggagga | 926 |
| hsa-miR-3142 | MIMAT0015011 | AAGGCCUUucugaaccuucaga | 927 |
| hsa-miR-3143 | MIMAT0015012 | AUAACAUUguaaagcgcuucuuucg | 928 |
| hsa-miR-548u | MIMAT0015013 | CAAAGACUgcaauuacuuuugcg | 929 |
| hsa-miR-3144-5p | MIMAT0015014 | AGGGGACCaaagagauauauag | 930 |
| hsa-miR-3144-3p | MIMAT0015015 | AUAUACCUguucggucucuuua | 931 |
| hsa-miR-3145 | MIMAT0015016 | AGAUAUUUugaguguuuggaauug | 932 |
| hsa-miR-1273c | MIMAT0015017 | GGCGACAAaacgagacccuguc | 933 |
| hsa-miR-3146 | MIMAT0015018 | CAUGCUAGgauagaaagaaugg | 934 |
| Hsa-miR-3147 | MIMAT0015019 | GGUUGGGCagugaggaggguguga | 935 |
| hsa-miR-548v | MIMAT0015020 | AGCUACAGuuacuuuugcacca | 936 |
| hsa-miR-3148 | MIMAT0015021 | UGGAAAAAacuggugugugcuu | 937 |
| hsa-miR-3149 | MIMAT0015022 | UUUGUAUGgauaugugugugugu | 938 |
| hsa-miR-3150 | MIMAT0015023 | CUGGGGAGauccucgagguugg | 939 |
| hsa-miR-3151 | MIMAT0015024 | GGUGGGGCaaugggaucaggu | 940 |
| hsa-miR-3152 | MIMAT0015025 | UGUGUUAGaauaggggcaauaa | 941 |
| hsa-miR-3153 | MIMAT0015026 | GGGGAAAGcgaguagggacauuu | 942 |
| hsa-miR-3074 | MIMAT0015027 | GAUAUCAGcucaguaggcaccg | 943 |
| hsa-miR-3154 | MIMAT0015028 | CAGAAGGGgaguugggagcaga | 944 |
| hsa-miR-3155 | MIMAT0015029 | CCAGGCUCugcagugggaacu | 945 |
| hsa-miR-3156 | MIMAT0015030 | AAAGAUCUggaaaugggagaca | 946 |
| hsa-miR-3157 | MIMAT0015031 | UUCAGCCAggcuagugcagucu | 947 |
| hsa-miR-3158 | MIMAT0015032 | AAGGGCUUccucucugcaggac | 948 |
| hsa-miR-3159 | MIMAT0015033 | UAGGAUUAcaagugucggccac | 949 |
| hsa-miR-3160 | MIMAT0015034 | AGAGCUGAgacuagaaagccca | 950 |
| hsa-miR-3161 | MIMAT0015035 | CUGAUAAGaacagagaggcccagau | 951 |
| hsa-miR-3162 | MIMAT0015036 | UUAGGGAGuagaagggugggag | 952 |
| hsa-miR-3163 | MIMAT0015037 | UAUAAAAUgagggcaguaagac | 953 |
| hsa-miR-3164 | MIMAT0015038 | UGUGACUUaagggaaauggcg | 954 |
| hsa-miR-3165 | MIMAT0015039 | AGGUGGAUgcaaugugaccuca | 955 |
| hsa-miR-3166 | MIMAT0015040 | CGCAGACAaugccuacuggccua | 956 |
| hsa-miR-1260b | MIMAT0015041 | AUCCCACCacugccaccau | 957 |
| hsa-miR-3167 | MIMAT0015042 | AGGAUUUCagaaauacuggugu | 958 |
| hsa-miR-3168 | MIMAT0015043 | GAGUUCUAcagucagac | 959 |
| hsa-miR-3169 | MIMAT0015044 | UAGGACUGugcuuggcacauag | 960 |
| hsa-miR-3170 | MIMAT0015045 | CUGGGGUUcugagacagacagu | 961 |
| hsa-miR-3171 | MIMAT0015046 | AGAUGUAUggaaucuguauauac | 962 |
| hsa-miR-3172 | MIMAT0015047 | UGGGGUUUugcaguccuua | 963 |

TABLE 1-continued

| miRNA name | miRBase number | Sequence | SEQ ID NO |
|---|---|---|---|
| hsa-miR-3173 | MIMAT0015048 | AAAGGAGGaaauaggcaggcca | 964 |
| hsa-miR-1193 | MIMAT0015049 | GGGAUGGUagaccggugacgugc | 965 |
| hsa-miR-323b-5p | MIMAT0001630 | AGGUUGUCcguggugaguucgca | 966 |
| hsa-miR-323b-3p | MIMAT0015050 | CCCAAUACacggucgaccucuu | 967 |
| hsa-miR-3174 | MIMAT0015051 | UAGUGAGUuagagaugcagagcc | 968 |
| hsa-miR-3175 | MIMAT0015052 | CGGGGAGAgaacgcagugacgu | 969 |
| hsa-miR-3176 | MIMAT0015053 | ACUGGCCUgggacuaccgg | 970 |
| hsa-miR-3177 | MIMAT0015054 | UGCACGGCacuggggacacgu | 971 |
| hsa-miR-3178 | MIMAT0015055 | GGGGCGCGgccggaucg | 972 |
| hsa-miR-3179 | MIMAT0015056 | AGAAGGGUgaaauuuaaacgu | 973 |
| hsa-miR-3180-5p | MIMAT0015057 | CUUCCAGAcgcuccgccccacgucg | 974 |
| hsa-miR-3180-3p | MIMAT0015058 | UGGGGCGGagcuuccggaggcc | 975 |
| hsa-miR-548w | MIMAT0015060 | AAAAGUAAcugcgguuuuugccu | 976 |
| hsa-miR-3181 | MIMAT0015061 | AUCGGGCCcucggcgccgg | 977 |
| hsa-miR-3182 | MIMAT0015062 | GCUUCUGUaguguaguc | 978 |
| hsa-miR-3183 | MIMAT0015063 | GCCUCUCUcggagucgcucgga | 979 |
| hsa-miR-3184 | MIMAT0015064 | UGAGGGGCcucagaccgagcuuuu | 980 |
| hsa-miR-3185 | MIMAT0015065 | AGAAGAAGcggucggucugcgg | 981 |
| hsa-miR-3065-5p | MIMAT0015066 | UCAACAAAaucacugaugcugga | 982 |
| hsa-miR-3065-3p | MIMAT0015378 | UCAGCACCaggauauuguuggag | 983 |
| hsa-miR-3186-5p | MIMAT0015067 | CAGGCGUCugucuacguggcuu | 984 |
| hsa-miR-3186-3p | MIMAT0015068 | UCACGCGGagagauggcuuug | 985 |
| hsa-miR-3187 | MIMAT0015069 | UUGGCCAUggggcugcgcgg | 986 |
| hsa-miR-3188 | MIMAT0015070 | AGAGGCUUugugcggauacgggg | 987 |
| hsa-miR-3189 | MIMAT0015071 | CCCUUGGGucugauggguag | 988 |
| hsa-miR-320e | MIMAT0015072 | AAAGCUGGguugagaagg | 989 |
| hsa-miR-3190-5p | MIMAT0015073 | UGUGGAAGguagacggccagaga | 990 |
| hsa-miR-3190-3p | MIMAT0015074 | UGGAAGGUagacggccagagag | 991 |
| hsa-miR-3191 | MIMAT0015075 | UGGGGACGuagcuggccagacag | 992 |
| hsa-miR-3192 | MIMAT0015076 | UCUGGGAGguuguagcaguggaa | 993 |
| hsa-miR-3193 | MIMAT0015077 | UCCUGCGUaggaucugaggagu | 994 |
| hsa-miR-3194 | MIMAT0015078 | GGCCAGCCaccaggagggcug | 995 |
| hsa-miR-3195 | MIMAT0015079 | CGCGCCGGgcccggguu | 996 |
| hsa-miR-3196 | MIMAT0015080 | CGGGGCGGcaggggccuc | 997 |
| hsa-miR-548x | MIMAT0015081 | UAAAACUgcaauuacuuuca | 998 |
| hsa-miR-3197 | MIMAT0015082 | GGAGGCGCaggcucggaaaggcg | 999 |
| hsa-miR-3198 | MIMAT0015083 | GUGGAGUCcuggggaauggaga | 1000 |
| hsa-miR-3199 | MIMAT0015084 | AGGGACUGccuuaggagaaaguu | 1001 |
| hsa-miR-3200 | MIMAT0015085 | CACCUUGCgcuacucaggucug | 1002 |

TABLE 1-continued

| miRNA name | miRBase number | Sequence | SEQ ID NO |
|---|---|---|---|
| hsa-miR-3201 | MIMAT0015086 | GGGAUAUGaagaaaaau | 1003 |
| hsa-miR-514b-5p | MIMAT0015087 | UUCUCAAGagggaggcaaucau | 1004 |
| hsa-miR-514b-3p | MIMAT0015088 | AUUGACACcucugugagugga | 1005 |
| hsa-miR-3202 | MIMAT0015089 | UGGAAGGGagaagagcuuuaau | 1006 |
| hsa-miR-1273d | MIMAT0015090 | GAACCCAUgagguugaggcugcagu | 1007 |
| hsa-miR-4295 | MIMAT0016844 | CAGUGCAAuguuuuccuu | 1008 |
| hsa-miR-4296 | MIMAT0016845 | AUGUGGGCucaggcuca | 1009 |
| hsa-miR-4297 | MIMAT0016846 | UGCCUUCCugucugug | 1010 |
| hsa-miR-378c | MIMAT0016847 | ACUGGACUuggagucagaagagugg | 1011 |
| hsa-miR-4293 | MIMAT0016848 | CAGCCUGAcaggaacag | 1012 |
| hsa-miR-4294 | MIMAT0016849 | GGGAGUCUacagcaggg | 1013 |
| hsa-miR-4301 | MIMAT0016850 | UCCCACUAcuucacuuguga | 1014 |
| hsa-miR-4299 | MIMAT0016851 | GCUGGUGAcaugagaggc | 1015 |
| hsa-miR-4298 | MIMAT0016852 | CUGGGACAggaggaggaggcag | 1016 |
| hsa-miR-4300 | MIMAT0016853 | UGGGAGCUggacuacuuc | 1017 |
| hsa-miR-4304 | MIMAT0016854 | CCGGCAUGuccagggca | 1018 |
| hsa-miR-4302 | MIMAT0016855 | CCAGUGUGgcucagcgag | 1019 |
| hsa-miR-4303 | MIMAT0016856 | UUCUGAGCugaggacag | 1020 |
| hsa-miR-4305 | MIMAT0016857 | CCUAGACAccuccaguuc | 1021 |
| hsa-miR-4306 | MIMAT0016858 | UGGAGAGAaaggcagua | 1022 |
| hsa-miR-4309 | MIMAT0016859 | CUGGAGUCuaggauucca | 1023 |
| hsa-miR-4307 | MIMAT0016860 | AAUGUUUUuuccuguuucc | 1024 |
| hsa-miR-4308 | MIMAT0016861 | UCCCUGGAguuucuucuu | 1025 |
| hsa-miR-4310 | MIMAT0016862 | GCAGCAUUcauguccc | 1026 |
| hsa-miR-4311 | MIMAT0016863 | GAAAGAGAgcugagugug | 1027 |
| hsa-miR-4312 | MIMAT0016864 | GGCCUUGUuccugucccca | 1028 |
| hsa-miR-4313 | MIMAT0016865 | AGCCCCUggccccaaaccc | 1029 |
| hsa-miR-4315 | MIMAT0016866 | CCGCUUUCugagcuggac | 1030 |
| hsa-miR-4316 | MIMAT0016867 | GGUGAGGCuagcuggug | 1031 |
| hsa-miR-4314 | MIMAT0016868 | CUCUGGGAaaugggacag | 1032 |
| hsa-miR-4318 | MIMAT0016869 | CACUGUGGguacaugcu | 1033 |
| hsa-miR-4319 | MIMAT0016870 | UCCCUGAGcaaagccac | 1034 |
| hsa-miR-4320 | MIMAT0016871 | GGGAUUCUguagcuuccu | 1035 |
| hsa-miR-4317 | MIMAT0016872 | ACAUUGCCagggaguuu | 1036 |
| hsa-miR-4322 | MIMAT0016873 | CUGUGGGCucagcgcgugggg | 1037 |
| hsa-miR-4321 | MIMAT0016874 | UUAGCGGUggaccgcccugcg | 1038 |
| hsa-miR-4323 | MIMAT0016875 | CAGCCCCAcagcucaga | 1039 |
| hsa-miR-4324 | MIMAT0016876 | CCCUGAGAcccuaaccuuaa | 1040 |
| hsa-miR-4256 | MIMAT0016877 | AUCUGACCugaugaaggu | 1041 |

TABLE 1-continued

| miRNA name | miRBase number | Sequence | SEQ ID NO |
|---|---|---|---|
| hsa-miR-4257 | MIMAT0016878 | CCAGAGGUggggacugag | 1042 |
| hsa-miR-4258 | MIMAT0016879 | CCCCGCCAccgccuugg | 1043 |
| hsa-miR-4259 | MIMAT0016880 | CAGUUGGGucuaggggucagga | 1044 |
| hsa-miR-4260 | MIMAT0016881 | CUUGGGGCauggaguccca | 1045 |
| hsa-miR-4253 | MIMAT0016882 | AGGGCAUGuccagggggu | 1046 |
| hsa-miR-4251 | MIMAT0016883 | CCUGAGAAaagggccaa | 1047 |
| hsa-miR-4254 | MIMAT0016884 | GCCUGGAGcuacuccaccaucuc | 1048 |
| hsa-miR-4255 | MIMAT0016885 | CAGUGUUCagagaugga | 1049 |
| hsa-miR-4252 | MIMAT0016886 | GGCCACUGagucagcacca | 1050 |
| hsa-miR-4325 | MIMAT0016887 | UUGCACUUgucucaguga | 1051 |
| hsa-miR-4326 | MIMAT0016888 | UGUUCCUCugucucccagac | 1052 |
| hsa-miR-4327 | MIMAT0016889 | GGCUUGCAuggggacugg | 1053 |
| hsa-miR-4261 | MIMAT0016890 | AGGAAACAgggaccca | 1054 |
| hsa-miR-4265 | MIMAT0016891 | CUGUGGGCucagcucuggg | 1055 |
| hsa-miR-4266 | MIMAT0016892 | CUAGGAGGccuuggcc | 1056 |
| hsa-miR-4267 | MIMAT0016893 | UCCAGCUCgguggcac | 1057 |
| hsa-miR-4262 | MIMAT0016894 | GACAUUCAgacuaccug | 1058 |
| hsa-miR-2355 | MIMAT0016895 | AUCCCCAGauacaauggacaa | 1059 |
| hsa-miR-4268 | MIMAT0016896 | GGCUCCUCcucucaggaugug | 1060 |
| hsa-miR-4269 | MIMAT0016897 | GCAGGCACagacagcccuggc | 1061 |
| hsa-miR-4263 | MIMAT0016898 | AUUCUAAGugccuuggcc | 1062 |
| hsa-miR-4264 | MIMAT0016899 | ACUCAGUCauggucauu | 1063 |
| hsa-miR-4270 | MIMAT0016900 | UCAGGGAGucagggagggc | 1064 |
| hsa-miR-4271 | MIMAT0016901 | GGGGGAAGaaaaggugggg | 1065 |
| hsa-miR-4272 | MIMAT0016902 | CAUUCAACuagugauugu | 1066 |
| hsa-miR-4273 | MIMAT0416903 | GUGUUCUCugauggacag | 1067 |
| hsa-miR-4276 | MIMAT0016904 | CUCAGUGAcucaugugc | 1068 |
| hsa-miR-4275 | MIMAT0016905 | CCAAUUACcacuucuuu | 1069 |
| hsa-miR-4274 | MIMAT0016906 | CAGCAGUCccuccccug | 1070 |
| hsa-miR-4281 | MIMAT0016907 | GGGUCCCGgggaggggg | 1071 |
| hsa-miR-4277 | MIMAT0016908 | GCAGUUCUgagcacaguacac | 1072 |
| hsa-miR-4279 | MIMAT0016909 | CUCUCCUCccggcuuc | 1073 |
| hsa-miR-4278 | MIMAT0016910 | CUAGGGGuuugcccuug | 1074 |
| hsa-miR-4280 | MIMAT0016911 | GAGUGUAGuucugagcagagc | 1075 |
| hsa-miR-4282 | MIMAT0016912 | UAAAAUUUgcauccagga | 1076 |
| hsa-miR-4285 | MIMAT0016913 | GCGGCGAGuccgacucau | 1077 |
| hsa-miR-4283 | MIMAT0016914 | UGGGGCUCagcgaguuu | 1078 |
| hsa-miR-4284 | MIMAT0016915 | GGGCUCACaucaccccau | 1079 |
| hsa-miR-4286 | MIMAT0016916 | ACCCCACUccugguacc | 1080 |

TABLE 1-continued

| miRNA name | miRBase number | Sequence | SEQ ID NO |
|---|---|---|---|
| hsa-miR-4287 | MIMAT0016917 | UCUCCCUUgagggcacuuu | 1081 |
| hsa-miR-4288 | MIMAT0016918 | UUGUCUGCugaguuucc | 1082 |
| hsa-miR-4292 | MIMAT0016919 | CCCCUGGGccggccuugg | 1083 |
| hsa-miR-4289 | MIMAT0016920 | GCAUUGUGcagggcuauca | 1084 |
| hsa-miR-4290 | MIMAT0016921 | UGCCCUCCuuucuucccuc | 1085 |
| hsa-miR-4291 | MIMAT0016922 | UUCAGCAGgaacagcu | 1086 |
| hsa-miR-4329 | MIMAT0016923 | CCUGAGACccuaguuccac | 1087 |
| hsa-miR-4330 | MIMAT0016924 | CCUCAGAUcagagccuugc | 1088 |
| hsa-miR-500b | MIMAT0016925 | AAUCCUUGcuaccugggu | 1089 |
| hsa-miR-4328 | MIMAT0016926 | CCAGUUUUcccaggauu | 1090 |

EXAMPLE 1

Inhibition of VAMP3 Expression by Single Stranded miR-124 Analogs

RT-qPCR Assays—

HCT-116 cells were cultured in McCoy's 5A Medium (Mediatech Inc.) supplemented with 10% fetal bovine serum and 1% penicillin-streptomycin. These cells were plated in 96-well culture plates at a density of 6000 cells/well 24 hours prior to transfection.

Figure 2:
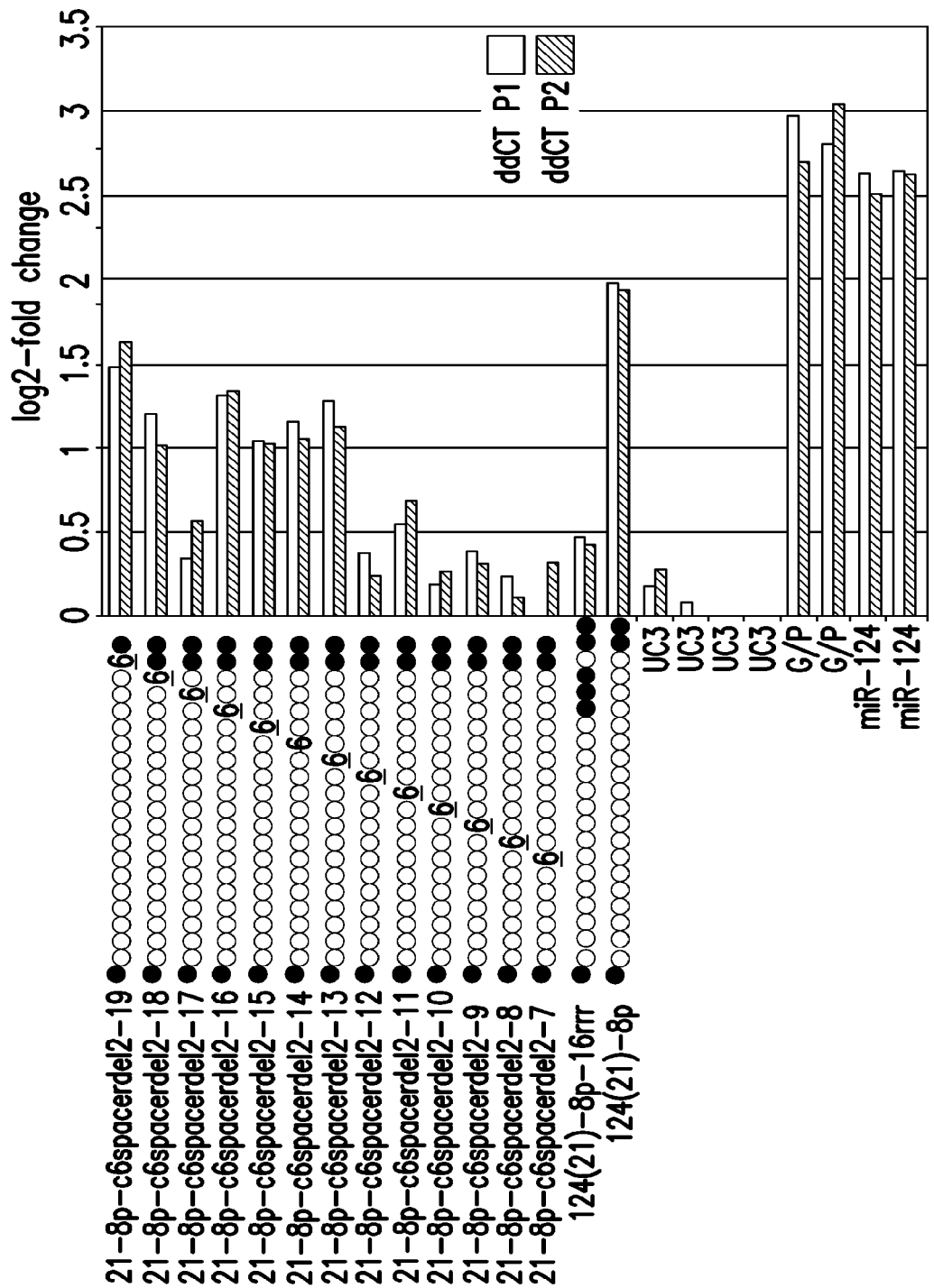
FIG. 2 shows the degree of inhibition of VAMP3 target expression by single-stranded miR-124 analogs containing a C6 spacer using a RT-qPCR assay. The structure and sequence of the analogs are specifically described in Table 2, infra. In the schematic drawings of the miR-124 analogs, the circles represent nucleotides, with the exception of the black circle located at the 5' terminus which represents a 5' phosphate. The open circles represent 2'-deoxy-2'-fluoro nucleotides. The black circles located at the 3' terminus of the schematics represent 2'-O-methyl nucleotides, and the "6" represents the location of the C6 spacer. In the schematic of the "124(21)-8p-16rrr" analog, the three internal black circles represent unmodified ribonucleotides. The longer bars in the graph indicate greater knockdown, and duplicate bars indicate biological replicates.
Figure 3:
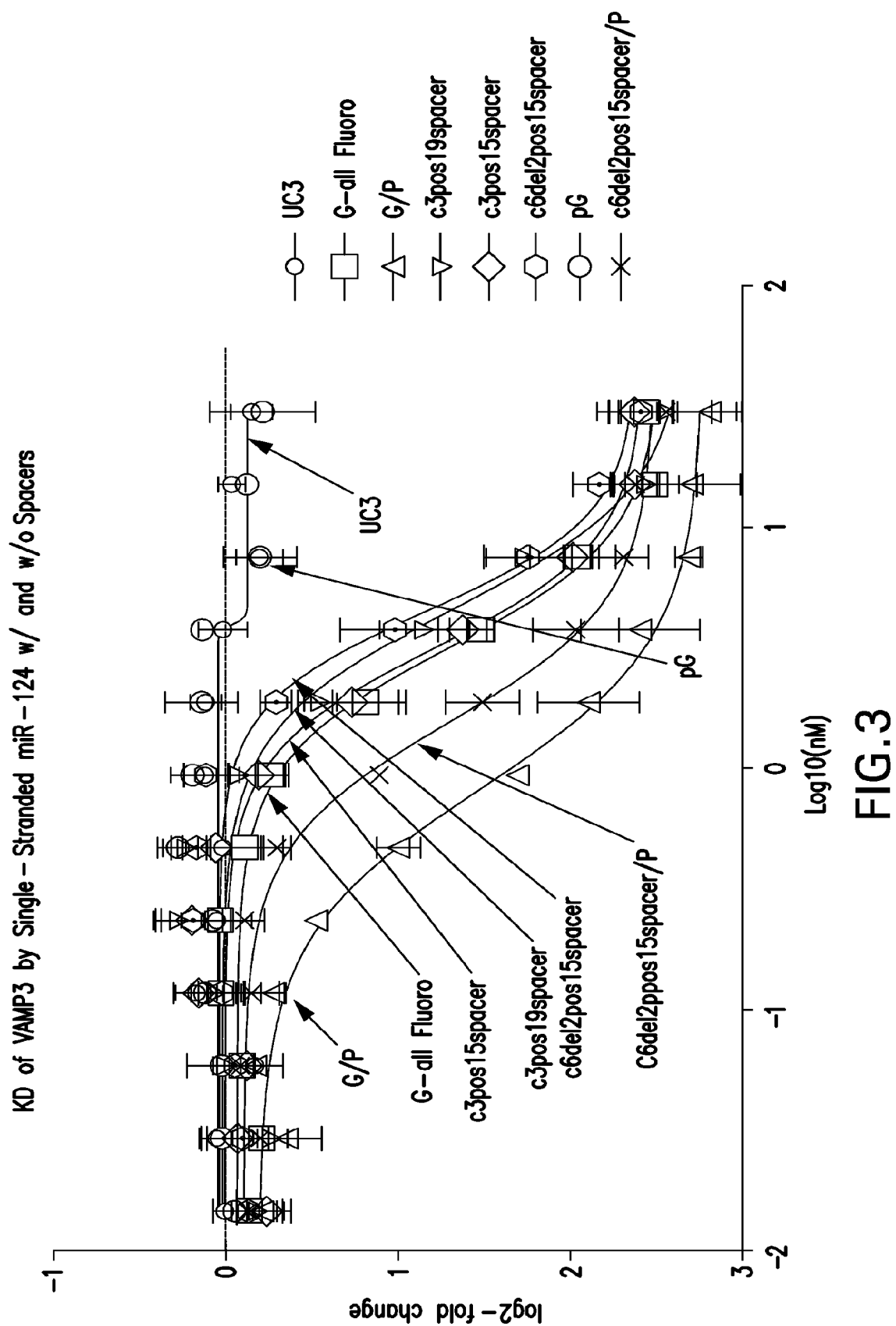
FIG. 3 shows the dose-dependent response of VAMP3 expression for a subset of the analogs tested in FIGS. 1 and 2. VAMP3 expression is depicted along the y-axis. The dose of the miR-124 analog tested (see Table 2, infra, for structure and sequences) is depicted along the x-axis, ranging from the lowest doses on the left to the highest doses on the right.

Transfection was carried out using Opti-MEM I Reduced Serum Media (Gibco) and Lipofectamine RNAiMax (Invitrogen) with a final miRNA concentration of 10 nM for the data in FIGS. 1 and 2, and ranging from 30 nM down to 0.01 nM along a 12-point titration curve for the data in FIG. 3.

24 hours after transfection, cells were washed with phosphate-buffered saline and processed using the TaqMan® Gene Expression Cells-to-CT™ Kit (Applied Biosystems/Ambion) to extract RNA, synthesize cDNA, and perform RT-qPCR using a VAMP3-specific probe (Applied Biosystems) on an ABI Prism 7900HT Sequence Detector.

Reverse transcription conditions were as follows: 60 minutes at 37° C., followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization. Knockdown of VAMP3 was calculated as the two-fold change in VAMP3 cDNA measured in experimentally-treated cells relative to the VAMP3 eDNA measured in non-targeting control-treated cells.

Reporter Assays—

HCT-116 cells were cultured in McCoy's 5A Medium (Mediatech Inc.) supplemented with 10% fetal bovine serum and 1% penicillin-streptomycin. These cells were plated in 96-well culture plates at a density of 25,000 cells/well 24 hours prior to transfection.

Figure 4:
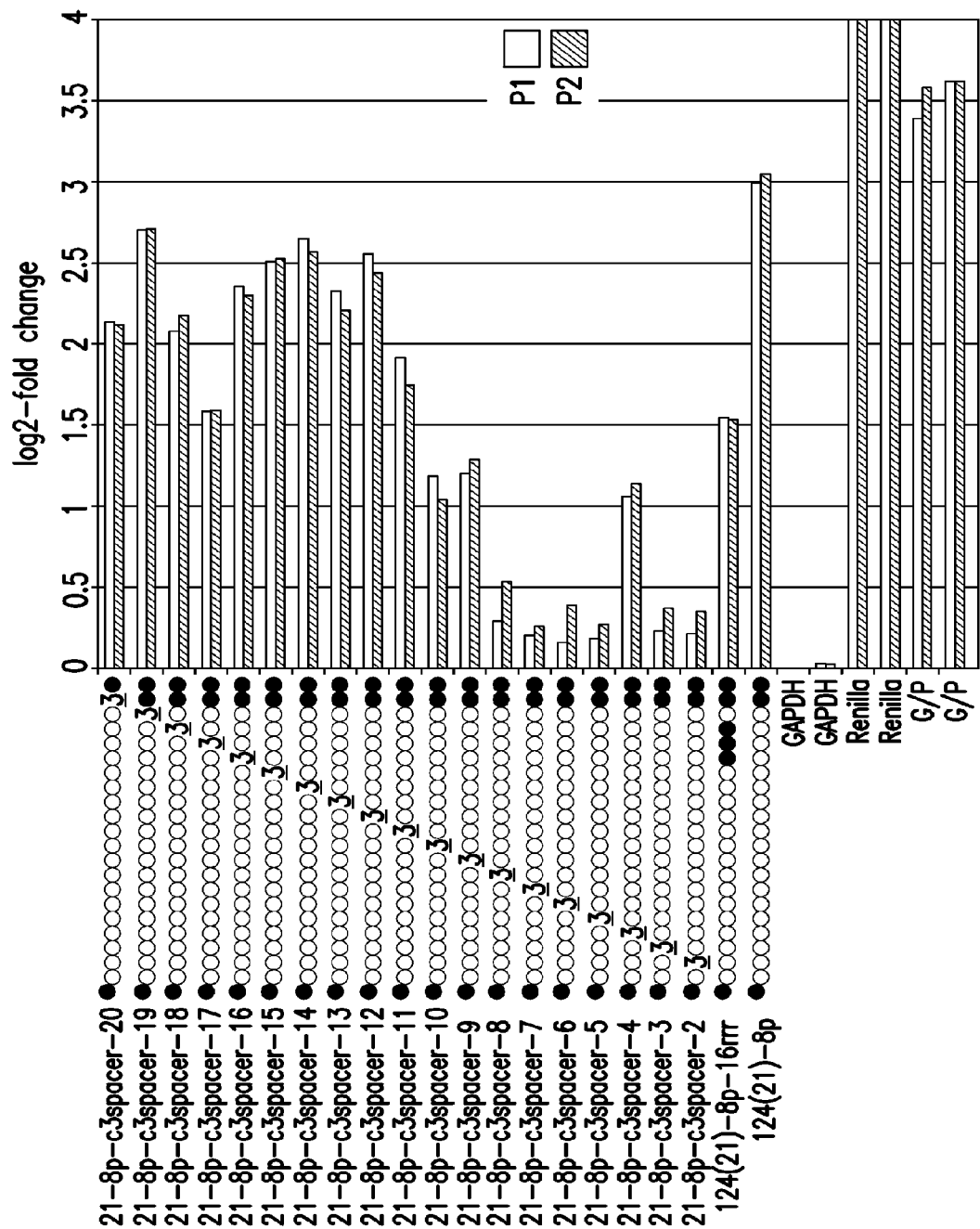
FIG. 4 shows the degree of inhibition by single-stranded miR-124 analogs containing a C3 spacer using a reporter assay that measures knockdown of a co-transfected luciferase reporter that carries two target sites matching the seed region of miR-124. The structure and sequence of the analogs are specifically described in Table 2, infra. In the schematic drawings of the miR-124 analogs, the circles represent nucleotides, with the exception of the black circle located at the 5' terminus which represents a 5' phosphate. The open circles represent 2'-deoxy-2'-fluoro nucleotides. The black circles located at the 3' terminus of the schematics represent 2'-O-methyl nucleotides, and the "3" represents the location of the C3 spacer. In the schematic of the "124(21)-8p-16rrr" analog, the three internal black circles represent unmodified ribonucleotides. The duplicate bars of the graph indicate biological replicates, and longer bars indicate greater inhibition.
Figure 5:
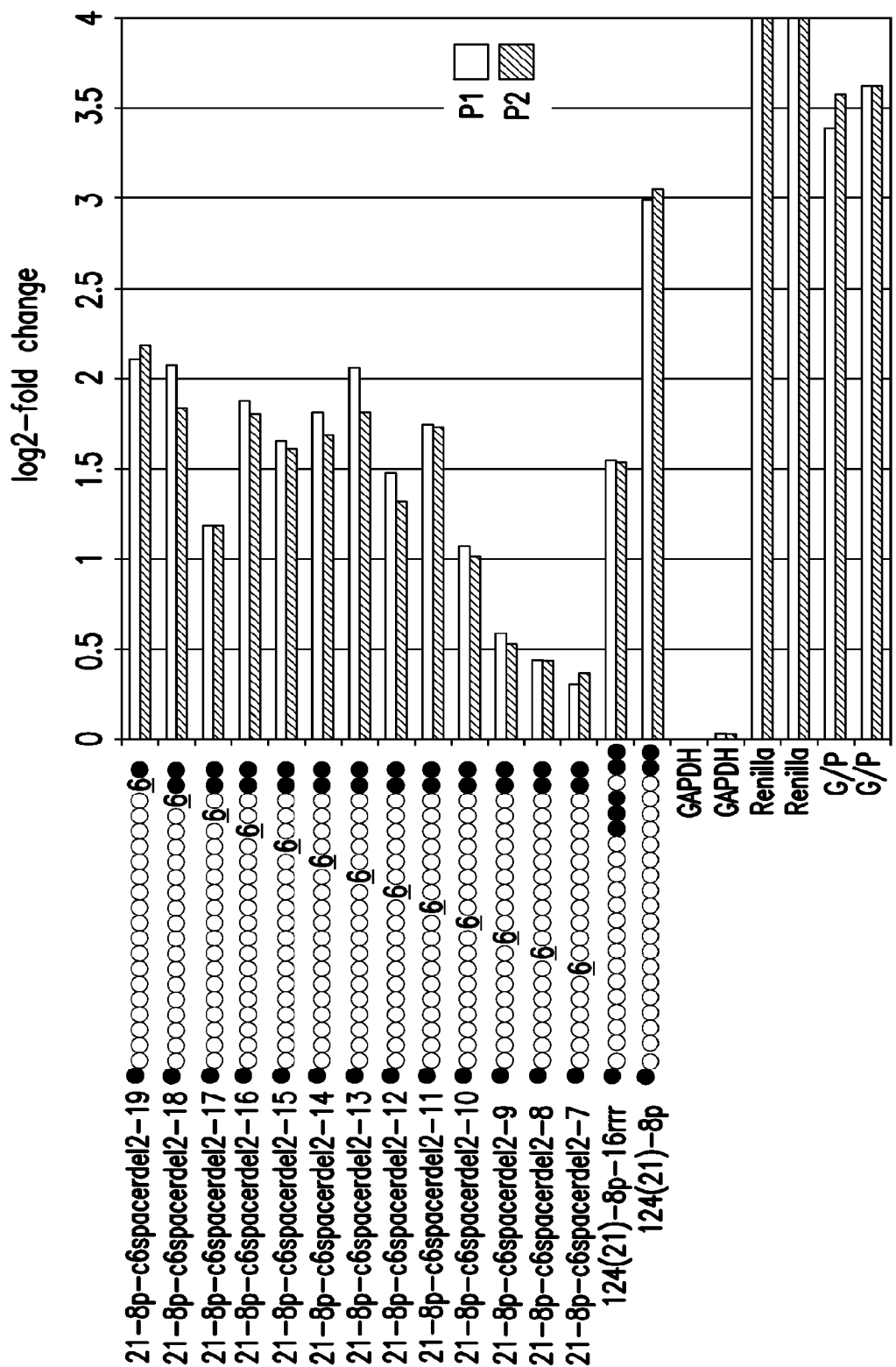
FIG. 5 shows the degree of inhibition by single-stranded miR-124 analogs containing a C6 spacer using a reporter assay that measures knockdown of a co-transfected luciferase reporter that carries two target sites matching the seed region of miR-124. The structure and sequence of the analogs are specifically described in Table 2, infra. In the schematic drawings of the miR-124 analogs, the circles represent nucleotides, with the exception of the black circle located at the 5' terminus which represents a 5' phosphate. The open circles represent 2'-deoxy-2'-fluoro nucleotides. The black circles located at the 3' terminus of the schematics represent 2'-O-methyl nucleotides, and the "6" represents the location of the C6 spacer. In the schematic of the "124(21)-8p-16rrr" analog, the three internal black circles represent unmodified ribonucleotides. The duplicate bars indicate biological replicates, and longer bars indicate greater inhibition.
Figure 6A:
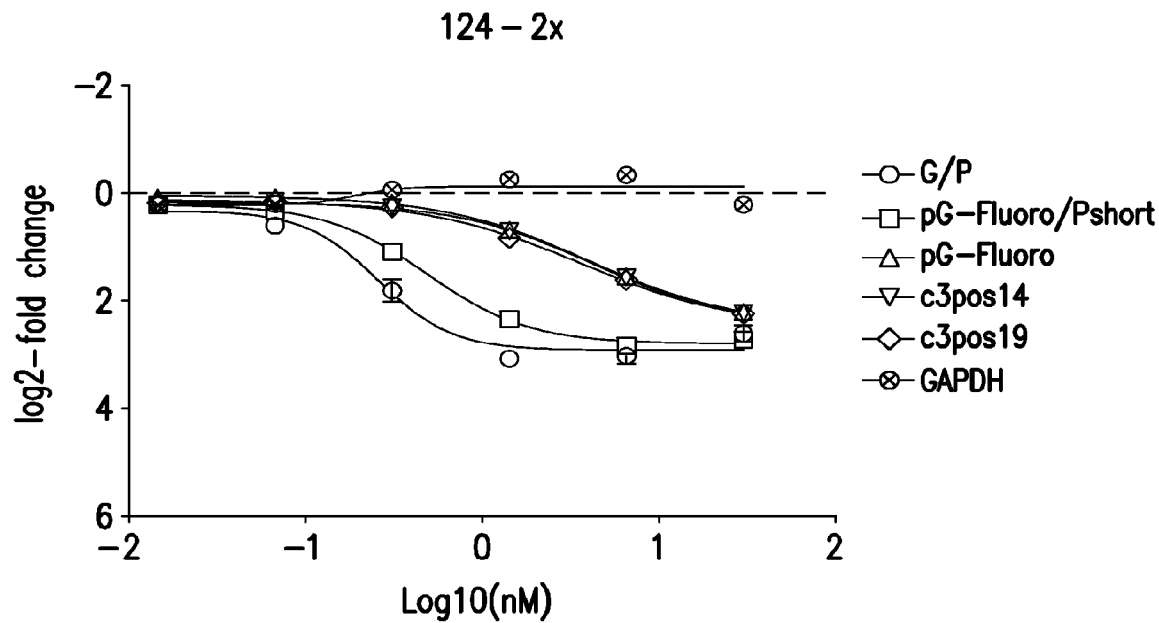
FIGS. 6A and 6B show the dose-dependent response of target expression inhibition of two different luciferase reporters for a subset of the single-stranded miR-124 analogs tested in FIG. 3.
Figure 6B:
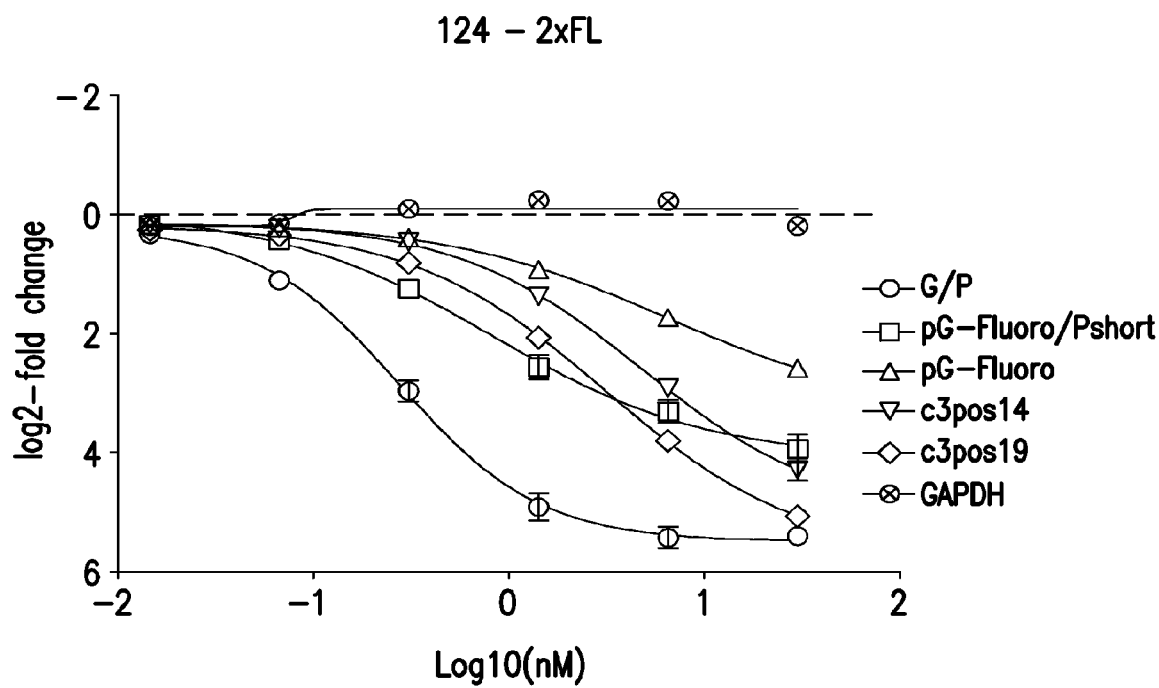

Transfection was carried out using Opti-MEM I Reduced Serum Media (Gibco) and Lipofectamine 2000 (Invitrogen) with a final miRNA concentration of 10 nM for the data in FIGS. 4 and 5, and ranging from 30 nM down to 0.01 nM along a 6-point titration curve for the data in FIG. 6. miRNAs were co-transfected with siCHECK2 vectors (Genscript) containing cloned target inserts consisting of a tandem repeat of a seed match to miR-124 (2×; FIG. 6A) or a full-length match to miR-124 (2×FL; FIG. 6B).

Twenty-four hours after transfection, transfection medium was replaced with fresh growth medium. Forty-eight hours after transfection, cells were lysed and both Firefly- and Renilla-Luciferase activity were measured using the Dual-Glo™ Luciferase Assay System (Promega) on a Wallac EnVision 2103 Multilabel Reader (PerkinElmer). Firefly-Luciferase activity was used to normalize Renilla-Luciferase activity, and the final data was calculated as two-fold change of the Renilla-Luciferase signal in experimentally-treated cells relative to non-targeting control-treated cells.

Oligonucleotide Synthesis—

Oligonucleotides were synthesized using protocols well known in the art (solid phase synthesis) using commercially available phosphoramidites, then purified by reversed phase solid phase extraction (SPE). The C3 ($C_{33}H_{43}N_2O_5P$) and C6 ($C_{36}H_{49}N_2O_5P$) phosphoramidites were purchased from ChemGenes.

Briefly, the single strand oligonucleotides were synthesized using phosphoramidite chemistry on an automated solid-phase synthesizer, using procedures as are generally known in the art (see, for example, U.S. application Ser. No. 12/064,014, published as US 20090176725). A synthesis column was packed with solid support derivatized with the first nucleoside residue (natural or chemically modified). Synthesis was initiated by detritylation of the acid labile 5'-O-dimethoxytrityl group to release the 5'-hydroxyl. A suitably protected phosphoramidite and a suitable activator in acetonitrile were delivered simultaneously to the synthesis column resulting in coupling of the amidite to the 5'-hydroxyl. The column was then washed with a solvent, such as acetonitrile. An oxidizing solution, such as an iodine solution was pumped through the column to oxidize the phosphite triester linkage P(III) to its phosphotriester P(V) analog. Unreacted 5'-hydroxyl groups were capped using reagents such as acetic anhydride in the presence of 2,6-lutidine and N-methylimidazole. The elongation cycle was resumed with the detritylation step for the next phosphoramidite incorporation. This process was repeated until the desired sequence was synthesized. The synthesis concluded with the final 5'-terminus protecting group (trityl or 5'-O-dimethoxytrityl).

Upon completion of the synthesis, the solid-support and associated oligonucleotide were dried under argon pressure or vacuum. Aqueous base was added and the mixture was heated to effect cleavage of the succinyl linkage, removal of the cyanoethyl phosphate protecting group, and deprotection of the exocyclic amine protection.

The following process was performed on single strands that do not contain ribonucleotides. After treating the solid support with the aqueous base, the mixture was filtered to separate the solid support from the deprotected crude synthesis material. The solid support was then rinsed with DMSO, which is combined with the filtrate. The resultant basic solution allows for retention of the 5'-O-dimethoxytrityl group to remain on the 5' terminal position (trityl-on).

For single strands that contain ribonucleotides, the following process was performed. After treating the solid support with the aqueous base, the mixture was filtered to separate the solid support from the deprotected crude synthesis material. The solid support was then rinsed with dimethylsulfoxide (DMSO), which was combined with the filtrate. Fluoride reagent, such as triethylamine trihydrofluoride, was added to the mixture, and the solution was heated. The reaction was quenched with suitable buffer to provide a solution of crude single strand with the 5'-O-dimethoxytrityl group on the final 5' terminal position.

The trityl—on solution of each crude single strand was purified using chromatographic purification, such as SPE RPC purification. The hydrophobic nature of the trityl group permits stronger retention of the desired full-length oligo than the non-tritylated truncated failure sequences. The failure sequences were selectively washed from the resin with a suitable solvent, such as low percent acetonitrile. Retained oligonucleotides were then detritylated on-column with trifluoroacetic acid to remove the acid-labile trityl group. Residual acid was washed from the column, a salt exchange was performed, and a final desalting of the material commenced. The full-length oligo was recovered in a purified form with an aqueous-organic solvent. The final product was then analyzed for purity (HPLC), identity (Maldi-TOF MS), and yield (UV $A_{260}$). The oligos were dried via lyophilization or vacuum condensation.

Results—

The ability of single-stranded miR-124 analogs to inhibit expression of a known target, VAMP3, was tested, wherein the miR-124 analogs comprise either a C3 spacer substituted for one nucleotide, or a C6 spacer substituted for two nucleotides, at various positions along the strand.

The passenger strand sequence of the miR-124 used in this study is 5'-GCAUUCACCGCGUGCCUUAAAU-3' (SEQ ID NO: 1091), and the guide strand sequence is 5'UUAAGGCACGCGGUGAAUGCCA-3' (SEQ ID NO: 1092). The miR-124 analogs tested, as well as control molecules, are described in Table 2 and below.

TABLE 2

| Name | Sequence (5' → 3')* |
|---|---|
| G/P | (guide) UUAAGGCACGCGGUGAAUGCCA (SEQ ID NO: 1092)<br>(passenger) GCAUUCACCGCGUGCCUUAAAU (SEQ ID NO: 1091) |
| 21-8p-c3spacer-20 | (guide) UAAGGCACGCGGUGAAUGC(C3-spacer)A (SEQ ID NO: 1093) |
| 21-8p-c3spacer-19<br>(FIGS. 1, 3)<br><br>c3pos19spacer (FIG. 2)<br><br>c3pos19 (FIG. 4) | (guide) UAAGGCACGCGGUGAAUG(C3-spacer)CA (SEQ ID NO: 1094) |
| 21-8p-c3spacer-18 | (guide) UAAGGCACGCGGUGAAU(C3-spacer)CCA (SEQ ID NO: 1095) |
| 21-8p-c3spacer-17 | (guide) UAAGGCACGCGGUGAA(C3-spacer)GCCA (SEQ ID NO: 1096) |
| 21-8p-c3spacer-16 | (guide) UAAGGCACGCGGUGA(C3-spacer)UGCCA (SEQ ID NO: 1097) |
| 21-8p-c3spacer-15<br>(FIGS. 1, 3)<br><br>c3pos15spacer (FIG. 2) | (guide) UAAGGCACGCGGUG(C3-spacer)AUGCCA (SEQ ID NO: 1098) |
| 21-8p-c3spacer-14<br>(FIGS. 1, 3)<br><br>c3pos14 (FIG. 4) | (guide) UAAGGCACGCGGU(C3-spacer)AAUGCCA (SEQ ID NO: 1099) |
| 21-8p-c3spacer-3 | (guide) UAAGGCACGCGG(C3-spacer)GAAUGCCA (SEQ ID NO: 1100) |
| 21-8p-c3spacer-12 | (guide) UAAGGCACGCG(C3-spacer)UGAAUGCCA (SEQ ID NO: 1101) |
| 21-8p-c3spacer-11 | (guide) UAAGGCACGC(C3-spacer)GUGAAUGCCA (SEQ ID NO: 1102) |
| 21-8p-c3spacer-10 | (guide) UAAGGCACG(C3-spacer)GGUGAAUGCCA (SEQ ID NO: 1103) |
| 21-8p-c3spacer-9 | (guide) UAAGGCAC(C3-spacer)CGGUGAAUGCCA (SEQ ID NO: 1104) |
| 21-8p-c3spacer-8 | (guide) UAAGGCA(C3-spacer)GCGGUGAAUGCCA (SEQ ID NO: 1105) |

TABLE 2-continued

| Name | Sequence (5' → 3')* |
|---|---|
| 21-8p-c3space-7 | (guide) *UAAGGC*(C3-spacer)*CGCGGUGAAUGC<u>CA</u>* (SEQ ID NO: 1106) |
| 21-8p-c3spacer-6 | (guide) *UAAGG*(C3-spacer)*ACGCGGUGAAUGC<u>CA</u>* (SEQ ID NO: 1107) |
| 21-8p-c3spacer-5 | (guide) *UAAG*(C3-spacer)*CACGCGGUGAAUGC<u>CA</u>* (SEQ ID NO: 1108) |
| 21-8p-c3spacer-4 | (guide) *UAA*(C3-spacer)*GCACGCGGUGAAUGC<u>CA</u>* (SEQ ID NO: 1109) |
| 21-8p-c3spacer-3 | (guide) *UA*(C3-spacer)*GGCACGCGGUGAAUGC<u>CA</u>* (SEQ ID NO: 1110) |
| 21-8p-c3spacer-2 | (guide) *U*(C3-spacer)*AGGCACGCGGUGAAUGC<u>CA</u>* (SEQ ID NO: 1111) |
| 21-8p-c6spacerdel2-19 | (guide) *UAAGGCACGCGGUGAAUG*(C6-spacer)<u>A</u> (SEQ ID NO: 1112) |
| 21-8p-c6spacerdel2-18 | (guide) *UAAGGCACGCGGUGAAU*(C6-spacer)<u>CA</u> (SEQ ID NO: 1113) |
| 21-8p-c6spacerdel2-17 | (guide) *UAAGGCACGCGGUGAA*(C6-spacer)<u>C</u>*C*<u>A</u> (SEQ ID NO: 1114) |
| 21-8p-c6spacerdel2-16 | (guide) *UAAGGCACGCGGUGA*(C6-spacer)*G*<u>CC</u><u>A</u> (SEQ ID NO: 1115) |
| 21-8p-c6spacerdel2-15 (FIGS. 1, 3) c6del2pos15spacer (FIG. 2) | (guide) *UAAGGCACGCGGUG*(C6-spacer)*UGC<u>CA</u>* (SEQ ID NO: 1116) |
| 21-8p-c6spacerdel2-14 | (guide) *UAAGGCACGCGGU*(C6-spacer)*AUGC<u>CA</u>* (SEQ ID NO: 1117) |
| 21-8p-c6spacerdel2-13 | (guide) *UAAGGCACGCGG*(C6-spacer)*AAUGC<u>CA</u>* (SEQ ID NO: 1118) |
| 21-8p-c6spacerdel2-12 | (guide) *UAAGGCACGCG*(C6-spacer)*GAAUGC<u>CA</u>* (SEQ ID NO: 1119) |
| 21-8p-c6spacerdel2-11 | (guide) *UAAGGCACGC*(C6-spacer)*UGAAUGC<u>CA</u>* (SEQ ID NO: 1120) |
| 21-8p-c6spacerdel2-10 | (guide) *UAAGGCACG*(C6-spacer)*GUGAAUGC<u>CA</u>* (SEQ ID NO: 1121) |
| 21-8p-c6spacerdel2-9 | (guide) *UAAGGCAC*(C6-spacer)*GGUGAAUGC<u>CA</u>* (SEQ ID NO: 1122) |
| 21-8p-c6spacerdel2-8 | (guide) *UAAGGCA*(C6-spacer)*CGGUGAAUGC<u>CA</u>* (SEQ ID NO: 1123) |
| 21-8p-c6spacerdel2-7 | (guide) *UAAGGC*(C6-spacer)*GCGGUGAAUGC<u>CA</u>* (SEQ ID NO: 1124) |
| UC3 | (passenger) B g*U*a*U*ga*CC*ga*C<u>U</u>*a*C*g*C*g*U*att B (SEQ ID NO: 1125) <br> (guide) *UAC<u>G</u>C<u>GU</u>AG<u>U</u>C<u>GG</u>UC<u>AUA</u>CUU* SEQ ID NO: 1126) |
| miR-124 (FIG. 1) pG (FIG. 2) | (guide) UUAAGGCACGCGGUGAAUGCCA (SEQ ID NO: 1127) |
| 124(21)-8p-16rrr 124(21)-8p (FIG. 1) | (guide) *UAAGGCACGCGGUGAAUGC<u>CA</u>* (SEQ ID NO: 1128) |
| G-all-Fluoro (FIG. 2) pG-Fluoro (FIG. 4) | (guide) *UAAGGCACGCGGUGAAUGCCA* (SEQ ID NO: 1129) |
| GAPDH | (guide) AAG*UU*G*U<u>C</u>*A*U*GG*A<u>U</u>*GA*CC*UU (SEQ ID NO: 1131) <br> (passenger) B agg*U<u>C</u>*a*U<u>CC</u>*a*U*ga*C*aa*C<u>U</u>U*tt B (SEQ ID NO: 1130) |
| Renilla | (guide) UAGUUGCGGACAAUCUGGAtt (SEQ ID NO: 1133) <br> (passenger) UCCAGAUUGUCCGCAACUAtt (SEQ ID NO: 1132) |
| C6delpos15spacer/P | (guide) *UAAGGCACGCGGUG*(C6-spacer)*UGC<u>CA</u>* (SEQ ID NO: 1116) <br> (passenger) GCAUUCACCGCGUGCCUUAAAU (SEQ ID NO: 1091) |
| pG-Fluoro/Pshort | (guide) *UAAGGCACGCGGUGAAUGC<u>CA</u>* (SEQ ID NO: 1129) <br> (passenger) GCAUUCACCGCGUGCCUUAAAU (SEQ ID NO: 1134) |

*A, U, C, and G = 2'-deoxy-2'-fluoro A, U, C, and G
<u>A</u>, <u>U</u>, <u>C</u>, and <u>G</u> = 2'-O-methyl (2'-OMe) A, U, C, and G
a, g, c and u = deoxy A, U, C, and G
t = thymidine
A, C, G, and U = ribose A, C, G or U
B = inverted abasic All of the single-stranded molecules in Table 2 contain a 5' phosphate cap.

"G/P" represents double-stranded miR-124, wherein the duplex has two nucleotide overhangs on the 3' ends of the passenger and guide strands. The guide strand of the G/P duplex is 22 nucleotides in length.

SEQ ID NOs: 1093-1124 represent analogs of the single-stranded miR-124 guide strand. Each of these molecules are a 21-nucleotide version of the miR-124 guide strand that is present in the G/P duplex, missing the 5'-uracil nucleotide that is present in the 22-nucleotide G/P miR-124 guide strand. All of the nucleotides in these 21-mer analogs, with the exception of the 3' adenosine, and the adjacent cytosine (if present), are chemically modified on the ribose moiety with 2'-fluoro (depicted as italicized nucleotides in Table 2). The 3' adenosine, and the adjacent cytosine (if present), are chemically modified on the ribose moiety with 2'-O-methyl (depicted as underlined nucleotides in Table 2). Finally, the 21-mer analogs of the miR-124 guide strand contain either a C3-spacer substituted for one nucleotide (the "c3spacer" analogs) or a C6-spacer substituted for two nucleotides (the "c6spacerdel2" analogs) at the various denoted positions along the strand. For example "21-8p-c3spacer-20" represents a 21-mer miR-124 guide strand analog containing an ethylene glycol spacer in the place of the nucleotide at position 20 within the 21-nucleotide miR-124 guide strand, linking the nucleotides at position 19 and position 21. As another example, the analog labeled "21-Sp-c6spacerdel2-19" represents a 21-met miR-124 guide strand analog containing a hexane spacer in the place of the nucleotides at positions 19 and 20 within the 21-nucleotide miR-124 guide strand, linking the nucleotides at positions 18 and 21. Some of the 21-nucleotide miR-124 guide strand analogs have different names in accompanying Figures, as noted in Table 2. For example, the 21-mer miR-124 guide strand analog represented by SEQ ID NO: 1116 is called "21-8p-c6spacerdel2-15" in FIGS. 1 and 3 and "c6del2pos15spacer" in FIG. 2.

"UC3" represents a non-targeting, chemically-modified duplex.

"124(21)-8p-16rrr" represents an analog of the 21-nucleotide version of the miR-124 guide strand. This molecule does not contain an internal spacer. All of the nucleotides are modified with 2'-fluoro, with the exception of nucleotides 16-18, which are RNA, and nucleotides 21 and 22, which are modified with 2'-O-methyl.

"124(21)-8p" represents a 21-nucleotide version of the miR-124 guide, wherein nucleotides 1-20 are modified with 2'-fluoro and nucleotides 20 and 21 are modified with 2'-O-methyl.

"124(21)-8p" is the name of this analog in FIG. 1; "G-all Fluoro" is the name of this analog in FIG. 2; and, "pG-Fluoro" is the name of this analog in FIG. 4.

"miR-124" is the single-stranded guide strand of the G/P duplex. It is 22 nucleotides in length and unmodified.

"C6delpos15spacer/P" represents a double-stranded miR-124 duplex, wherein the guide strand has the structure of "21-Sp-c6spacerdel2-15" (SEQ ID NO: 1116), and the passenger strand is the 22-nucleotide miR-124 passenger strand (SEQ ID NO: 1091).

FIGS. 1 and 2 show the degree of inhibition of VAMP3 target expression by the single-stranded miR-124 analogs described in Table 2 using the RT-qPCR assay described above. FIG. 1 shows the degree of inhibition by the single-stranded miR-124 analogs containing a C3 spacer. FIG. 2 shows the degree of inhibition by the single-stranded miR-124 analogs containing a C6 spacer. The longer bars in each figure indicate greater knockdown of VAMP3. The duplicate bars indicate biological replicates, each representing data from a separate well of cells (on two separate plates) transfected with the indicated nucleic acid molecules. The spacer appears to be most well-tolerated at position 19, and in the vicinity of position 15, of the miR-124 analogs.

The graph in FIG. 3 depicts the dose-dependent response of VAMP3 expression to a subset of the analogs tested in FIGS. 1 and 2 (see Table 2 for sequences). VAMP3 expression is depicted along the y-axis, thus data points with lower values along this axis indicate greater VAMP3 expression knockdown. The dose of the miR-124 analog tested is depicted along the x-axis, ranging from the lowest doses on the left to the highest doses on the right. Although the double stranded versions (G/P and c6del2pos15spacer/P) are more potent than the single-stranded analogs, it is worth noting that the single-stranded "G-all Fluoro" analog (no internal spacer, nucleotides 1-20 are 2'-fluoro, nucleotides 20 and 21 are 2'O-methyl) behaves almost identically to comparable single-stranded analogs with a C3 spacer replacing position 15 (c3pos15spacer) or position 19 (c3pos19spacer).

FIGS. 4 and 5 show data from a screen of the same single-stranded miR-124 analogs tested in FIGS. 1 and 2, measuring knockdown of a co-transfected luciferase reporter that carries two target sites matching the seed region of miR-124. Thus, the data from this assay is a representation of the miRNA activity of the tested analogs. FIG. 4 shows the degree of inhibition by the single-stranded miR-124 analogs that contain a C3 spacer. FIG. 5 shows the degree of inhibition by the single-stranded miR-124 analogs that contain a C6 spacer. The duplicate bars indicate biological replicates, each representing data from a separate well of cells (on two separate plates) transfected with the indicated molecules. Again, the longer bars indicate greater inhibition, showing that the analogs that contain a spacer at position 19, or in the vicinity of position 15, have the greatest knockdown activity.

The graphs in FIG. 6 depict the dose-dependent response of target expression inhibition of two different luciferase reporters to a subset of the analogs tested in FIG. 3. In FIG. 6A, the inhibition activity shown is against a luciferase reporter with two matches to the miR-124 seed region. Thus, this is a representation of the miRNA activity of the tested analogs. In FIG. 6B, the inhibition activity shown is against a luciferase reporter with two full-length matches to miR-124 and, thus, represents the siRNA activity of the tested analogs. In both A and B, the G/P curves represent activity by a miR-124 duplex made up entirely of RNA. The pG-Fluoro/Pshort curves represent activity by a guide strand that is predominantly modified with 2'-fluoro nucleotides duplexed to an all-RNA passenger strand. The pG-Fluoro curves represent the activity of a single-stranded miR-124 guide strand analog that is predominantly modified with 2'-fluoro nucleotides. The c3pos14 and c3pos19 curves represent the activity of analogs of pG-Fluoro, only differing from pG-Fluoro by containing a 3-carbon spacer (C3-spacer) substituted for position 14 ("c3pos14") or position 19 ("c3pos19"). All of the single-stranded analogs show less potency than either duplexes against the reporter with only seed matches, but they are effectively equivalent to each other across all concentrations and show similar activity to the duplexes at the highest concentration (FIG. 6A). Against the reporter with full-length matches, the all-RNA duplex ("G/P") was still the strongest performer, but the spacer-containing single-stranded analogs had activity as strong as or stronger than the duplex with the 2'-fluoro guide strand ("pG-Fluoro/Pshort") and the single-strand ("pG-Fluoro").

EXAMPLE 2

Single-Strand RNAi Knockdown of ApoB mRNA

RT-qPCR Assays (Primary Screens and Dose-Response Curves)—

Hepa1-6 cells were cultured in Dulbecco's Modified Eagle Medium supplemented with 10% fetal bovine serum, 1% penicillin-steptomycin, and 1% sodium bicarbonate. These cells were plated in a 96-well culture plates at a density of 3000 cells/well 24 hours prior to transfection.

Transfections were performed using Opti-MEM I Reduced Serum Media and Lipofectamine RNAiMAX per the manufacturer's directions. Final single-stranded siRNA concentrations were 100 nM and 10 nM.

Twenty-four hours post-transfection, cells were washed with phosphate-buffered saline and processed using the TaqMan Gene Expression Cells-to-CT™ Kit, per manufacturer's instructions, to extract RNA, synthesize cDNA, and perform RT-qPCR using an ApoB specific Taqman primer/probe set on an ABI Prism 7900HT Sequence Detector.

Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GADPH mRNA levels were used for data normalization.

Knockdown of ApoB was calculated as the two-fold change in ApoB cDNA measured in experimentally-treated cells relative to the ApoB cDNA measured in non-targeting, control-treated cells.

Results—

Figure 7:
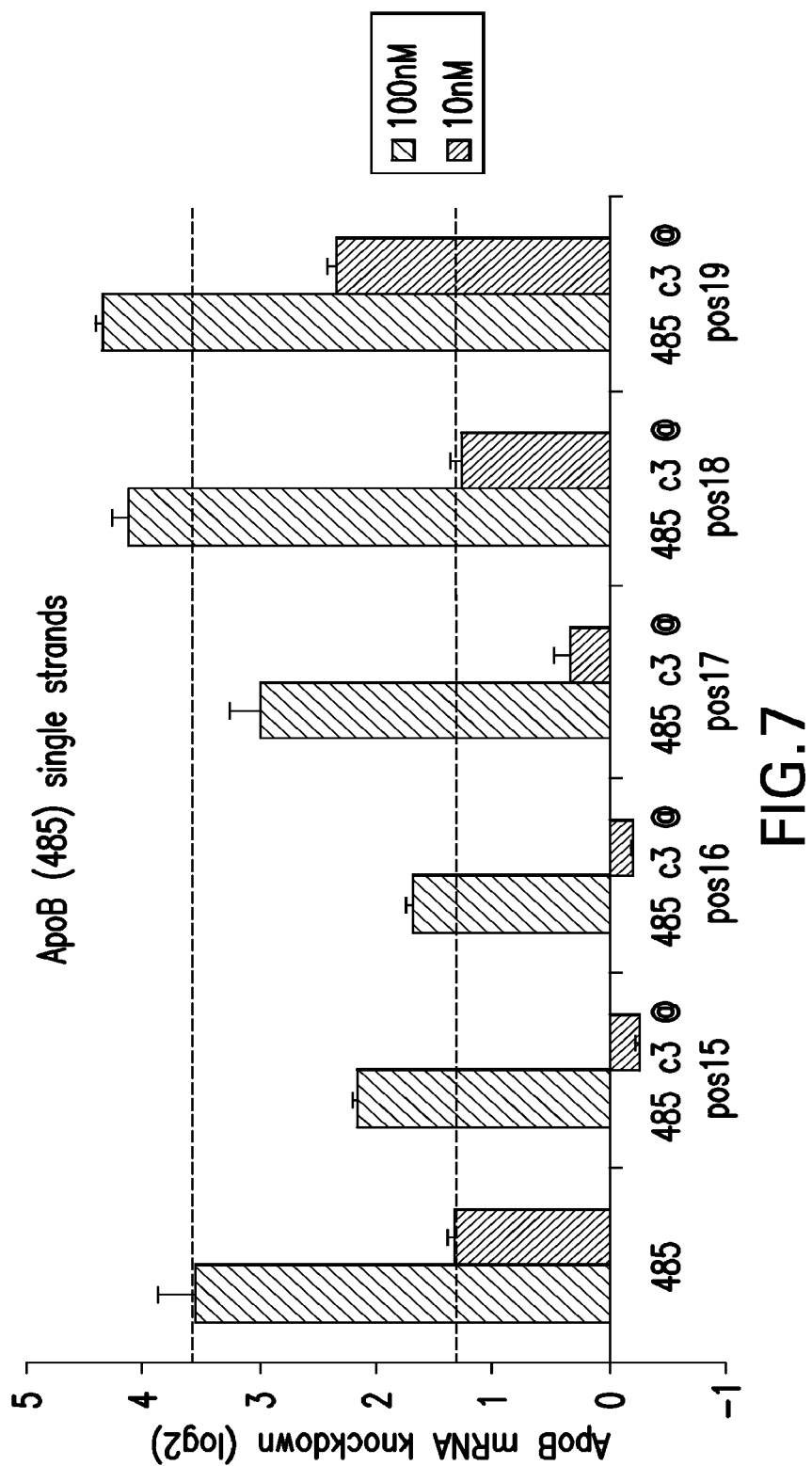
FIG. 7 compares the knockdown of ApoB mRNA using ApoB-targeted single stranded (guide strand) oligonucleotides having a C3 spacer incorporated at either position 15 ("485 c3@pos15"), 16 ("485 c3@pos16"), 17 ("485 c3@pos17"), 18 ("485 c3@pos185"), or 19 ("485 c3@pos19") (relative to the 5' of the oligo) to the corresponding single stranded oligonucleotide without the spacer ("485") at two different concentrations (100 nM and 10 nM). All of the single stranded molecules are composed of 2'-deoxy-2'-fluoro nucleotides at both pyrimidine and purine nucleotides, a 5' phosphate, and two 2'-O-methyl nucleotides at the 3' terminus.

The knockdown of ApoB mRNA was measured using single strand (guide strand) oligonucleotides with a C3 spacer incorporated at either position 15, 16, 17, 18, or 19 (relative to the 5' of the oligo) at two different concentrations (100 nM and 10 nM). The results are shown in FIG. 7. All of the single strand molecules tested are composed of 2'-deoxy-2'-fluoro nucleotides at both pyrimidine and purine nucleotides and a 5' phosphate. The two 3' terminal nucleotides of each molecule are 2'-O-methyl nucleotides. Single strand molecule "485" (see FIG. 7; 5'-UUAAGAGAAGC-CUUACUGGUU-3' (SEQ ID NO: 1135)) is a 21-nucleotide molecule that does not contain a C3 spacer and targets ApoB mRNA at nucleotide position 485. A C3 spacer is incorporated into molecule 485 at positions 15 ("485 c3@pos15"; SEQ ID NO: 1136), 16 ("485 c3@pos16"; SEQ ID NO: 1137), 17 ("485 c3@pos17"; SEQ ID NO: 1138), 18 ("485 c3@pos18"; SEQ ID NO: 1139) or 19 ("485 c3@pos19"; SEQ ID NO: 1140) (i.e., the spacer takes the place of the indicated nucleotide of the 485 molecule). For example, signal strand molecule "485 c3@pos15" is represented by: 5'-UUAAGAGAAGCCUU(C3-spacer)CUGGUU-3'; SEQ ID NO: 1136). As shown in FIG. 7, inclusion of the C3 spacer at positions 18 or 19 is both well tolerated and improves mRNA knockdown at two different concentrations (100 nM and 10 nM). This data indicates that incorporation of a non-nucleotide C3 carbon spacer at the 3' end of a single strand RNA interference oligonucleotide improves the potency of mRNA knockdown (FIG. 7).

Figure 8:
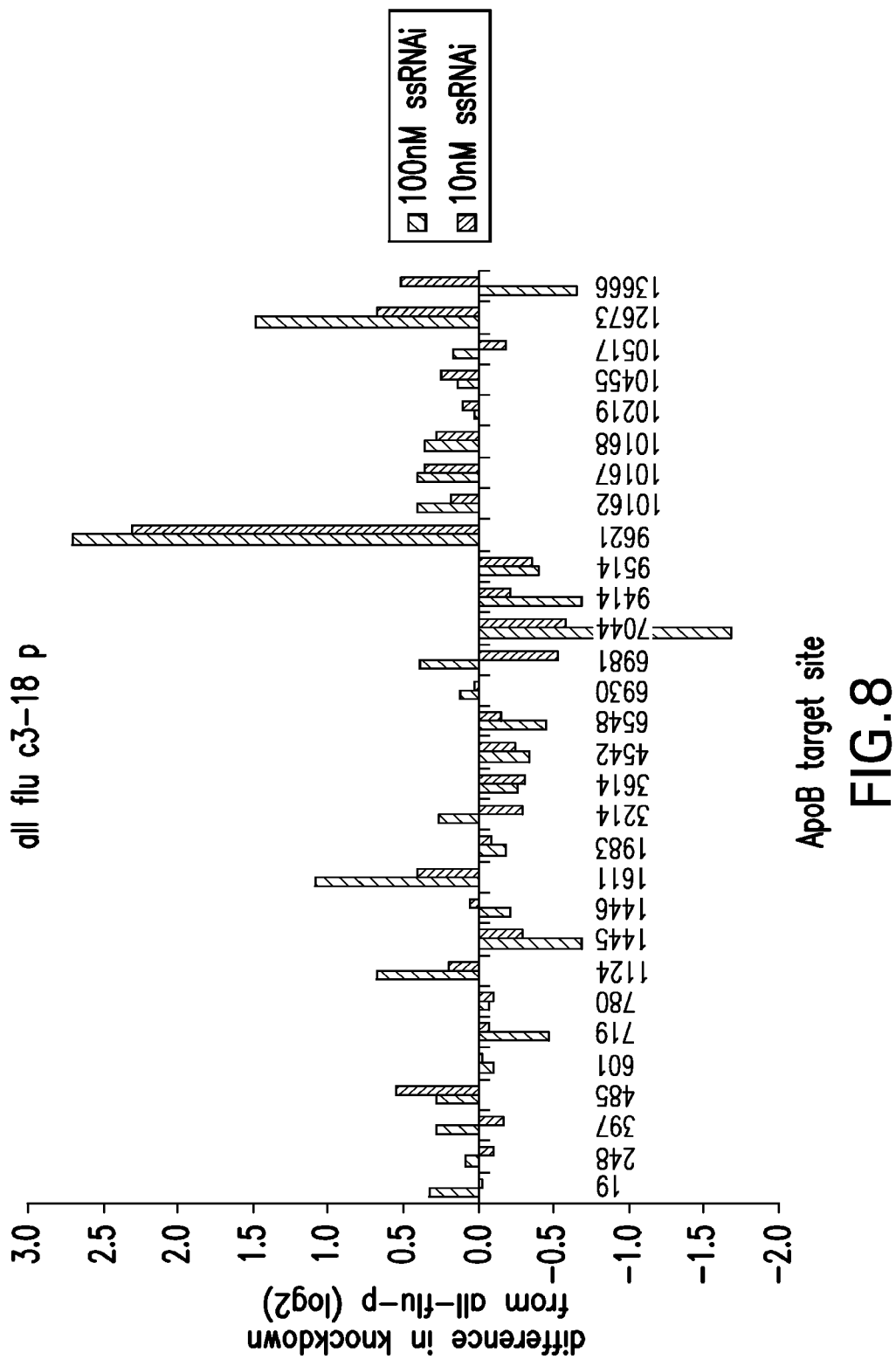
FIGS. 8 and 9 compares ApoB mRNA knockdown using 30 different single strand sequences targeting ApoB with C3 spacer at either position 18 (FIG. 8) or position 19 (FIG. 9) at two concentrations (100 nM and 10 nM). Single strands are notated on the x-axis by the position within the ApoB mRNA which they target. All of the single stranded molecules are composed of 2'-deoxy-2'-fluoro nucleotides at both pyrimidine and purine nucleotides, a 5' phosphate, and two 2'-O-methyl nucleotides at the 3' terminus.
Figure 9:
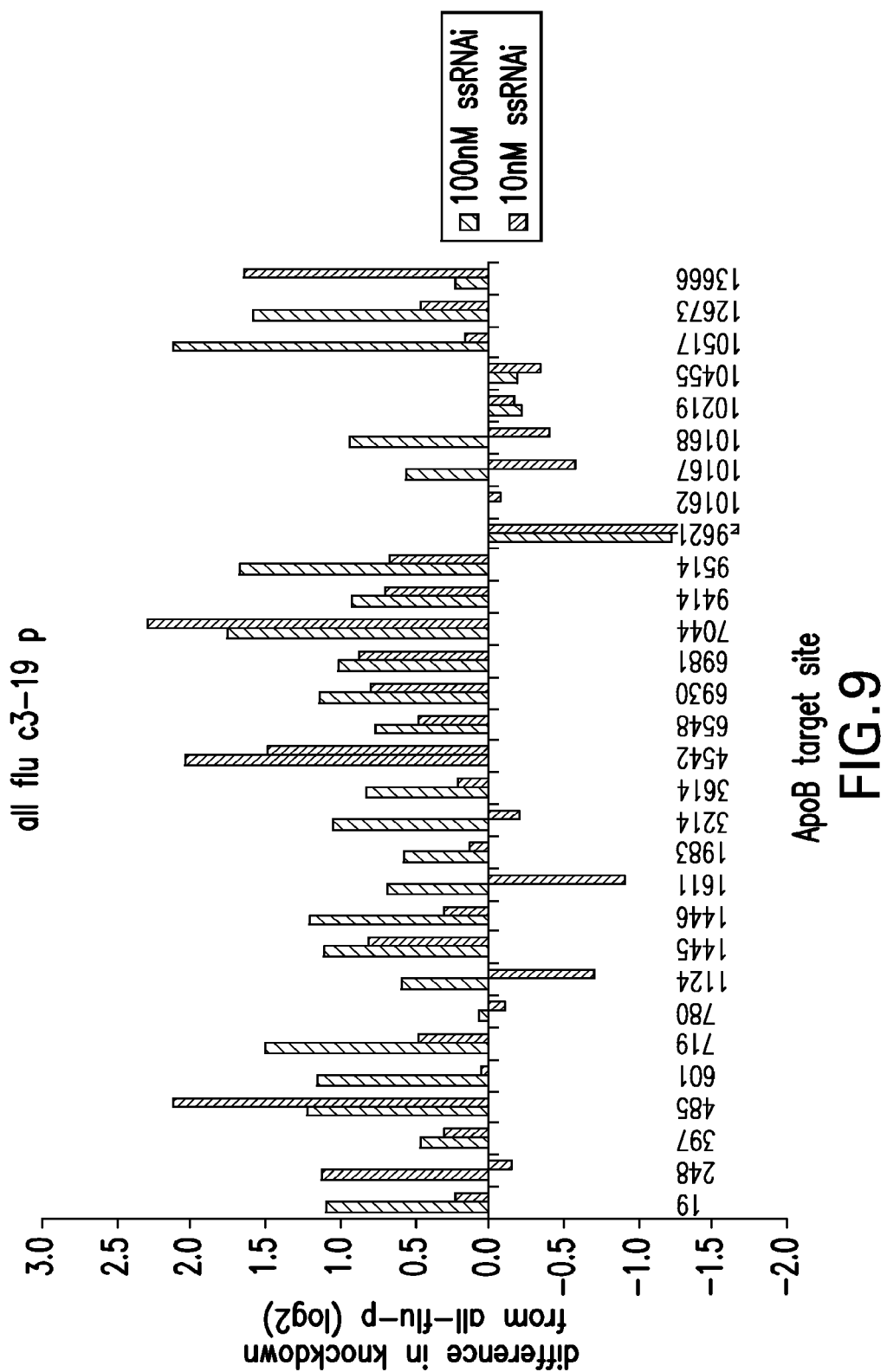

To evaluate whether the incorporation of a C3 spacer in single strands was more broadly applicable, 30 different single strand sequences targeting ApoB, each with a C3 spacer at either position 18 (FIG. 8) or position 19 (FIG. 9), were evaluated at two concentrations (100 nM and 10 nM). In FIGS. 8 and 9, the single-stranded molecules are notated by the position within the ApoB mRNA which they target. All of the single-stranded molecules tested are composed of 2'-deoxy-2'-fluoro nucleotides at both pyrimidine and purine nucleotides and a 5' phosphate. The two 3' terminal nucleotides of each molecule are 2'-O-methyl nucleotides. The sequence identifiers (SEQ ID NOs:) of the single stranded RNAi molecules evaluated in FIGS. 8 and 9 are listed in Table 3.

TABLE 3

| ApoB Target Region | C3-position 18 (FIGS. 8 and 10) | C3-position 19 (FIGS. 9 and 10) | No spacer (FIG. 10) |
|---|---|---|---|
| 19 | SEQ ID NO: 1141 | SEQ ID NO: 1170 | SEQ ID NO: 1199 |
| 248 | SEQ ID NO: 1142 | SEQ ID NO: 1171 | SEQ ID NO: 1200 |
| 397 | SEQ ID NO: 1143 | SEQ ID NO: 1172 | SEQ ID NO: 1201 |
| 485 | SEQ ID NO: 1139 | SEQ ID NO: 1140 | SEQ ID NO: 1135 |

TABLE 3-continued

| ApoB Target Region | C3-position 18 (FIGS. 8 and 10) | C3-position 19 (FIGS. 9 and 10) | No spacer (FIG. 10) |
|---|---|---|---|
| 601 | SEQ ID NO: 1144 | SEQ ID NO: 1173 | SEQ ID NO: 1202 |
| 719 | SEQ ID NO: 1145 | SEQ ID NO: 1174 | SEQ ID NO: 1203 |
| 780 | SEQ ID NO: 1146 | SEQ ID NO: 1175 | SEQ ID NO: 1204 |
| 1124 | SEQ ID NO: 1147 | SEQ ID NO: 1176 | SEQ ID NO: 1205 |
| 1445 | SEQ ID NO: 1148 | SEQ ID NO: 1177 | SEQ ID NO: 1206 |
| 1446 | SEQ ID NO: 1149 | SEQ ID NO: 1178 | SEQ ID NO: 1207 |
| 1611 | SEQ ID NO: 1150 | SEQ ID NO: 1179 | SEQ ID NO: 1208 |
| 1983 | SEQ ID NO: 1151 | SEQ ID NO: 1180 | SEQ ID NO: 1209 |
| 3214 | SEQ ID NO: 1152 | SEQ ID NO: 1181 | SEQ ID NO: 1210 |
| 3614 | SEQ ID NO: 1153 | SEQ ID NO: 1182 | SEQ ID NO: 1211 |
| 4542 | SEQ ID NO: 1154 | SEQ ID NO: 1183 | SEQ ID NO: 1212 |
| 6548 | SEQ ID NO: 1155 | SEQ ID NO: 1184 | SEQ ID NO: 1213 |
| 6930 | SEQ ID NO: 1156 | SEQ ID NO: 1185 | SEQ ID NO: 1214 |
| 6981 | SEQ ID NO: 1157 | SEQ ID NO: 1186 | SEQ ID NO: 1215 |
| 7044 | SEQ ID NO: 1158 | SEQ ID NO: 1187 | SEQ ID NO: 1216 |
| 9414 | SEQ ID NO: 1159 | SEQ ID NO: 1188 | SEQ ID NO: 1217 |
| 9514 | SEQ ID NO: 1160 | SEQ ID NO: 1189 | SEQ ID NO: 1218 |
| 9621 | SEQ ID NO: 1161 | SEQ ID NO: 1190 | SEQ ID NO: 1219 |
| 10162 | SEQ ID NO: 1162 | SEQ ID NO: 1191 | SEQ ID NO: 1220 |
| 10167 | SEQ ID NO: 1163 | SEQ ID NO: 1192 | SEQ ID NO: 1221 |
| 10168 | SEQ ID NO: 1164 | SEQ ID NO: 1193 | SEQ ID NO: 1222 |
| 10219 | SEQ ID NO: 1165 | SEQ ID NO: 1194 | SEQ ID NO: 1223 |
| 10455 | SEQ ID NO: 1166 | SEQ ID NO: 1195 | SEQ ID NO: 1224 |
| 10517 | SEQ ID NO: 1167 | SEQ ID NO: 1196 | SEQ ID NO: 1225 |
| 12673 | SEQ ID NO: 1168 | SEQ ID NO: 1197 | SEQ ID NO: 1226 |
| 13666 | SEQ ID NO: 1169 | SEQ ID NO: 1198 | SEQ ID NO: 1227 |

In FIGS. 8 and 9, the data was normalized to the corresponding single-stranded molecule without the C3 spacer. Knockdown amounts that are equivalent to the single-stranded controls (without C3 spacer) would be centered at 0, while positive values indicate that incorporation of the C3 spacer confers an improvement in mRNA knockdown. Negative values indicate a deleterious effect of C3 spacer inclusion. Note that due to experimental variation with in vitro assays, only values greater than +0.5 or less than −0.5 are considered significant. For example, inclusion of the C3 spacer in ApoB molecule 485 at position 18 does not have a significant improvement over the single strand control since the difference in knockdown shown in the FIG. 8 is less than 0.5. However, inclusion of the C3 spacer in the same single strand guide molecule at position 19 has a significant improvement in knockdown (see FIG. 9). Overall, inclusion of the C3 spacer at position 19 is preferred as incorporation at this position seems to improve the potency of mRNA knockdown for the majority of the 30 different sequences tested (73%).

Figure 10:
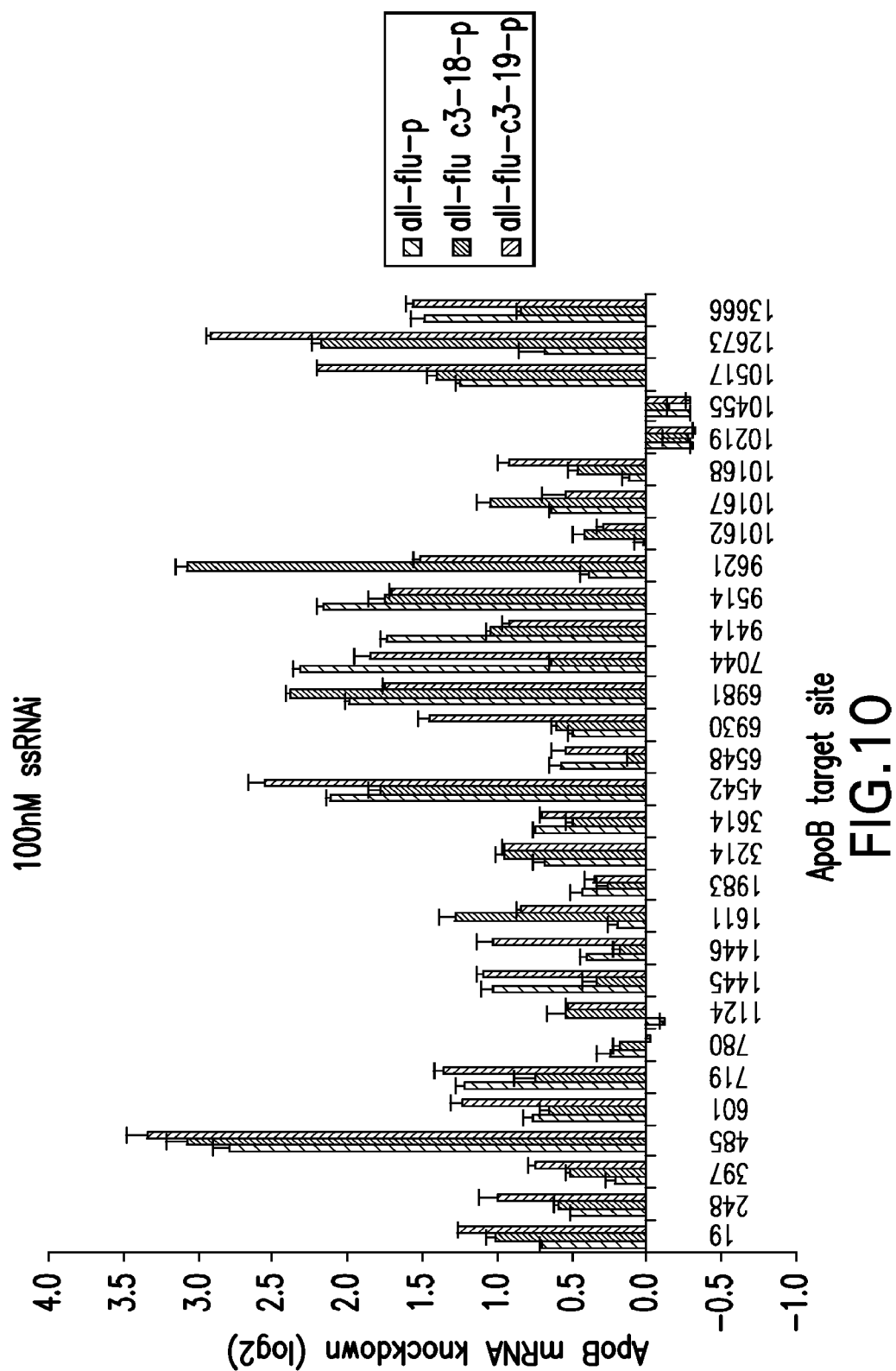
FIG. 10 compares ApoB mRNA knockdown at 100 nM concentration using single stranded molecules targeting each of the 30 different ApoB target sites tested in FIGS. 8 and 9—single strands without a C3 spacer ("all-flu-p"), with a C3 spacer at position 18 ("all-flu-c3-18-p"), and with a C3 spacer at position 19 ("all-flu-c3-19-p"). All of the single stranded molecules are composed of 2'-deoxy-2'-fluoro nucleotides at both pyrimidine and purine nucleotides, a 5' phosphate, and two 2'-O-methyl nucleotides at the 3' terminus.

In FIG. 10, ApoB mRNA knockdown at 100 nM concentration using single stranded molecules targeting each of the 30 different ApoB target sites tested in FIGS. 8 and 9 were compared—single strands without C3 spacer ("all-flu-p"), with C3 spacer at position 18 ("all-flu-c3-18-p"), and with C3 spacer at position 19 ("all-flu-c3-19-p"). All of the single-stranded molecules tested are composed of 2'-deoxy-2'-fluoro nucleotides at both pyrimidine and purine nucleotides and a 5' phosphate. The two 3' terminal nucleotides of each molecule are 2'-O-methyl nucleotides. The sequence identifiers (SEQ ID NOs:) of the single stranded RNAi molecules evaluated in FIG. 10 are listed in Table 3. FIG. 10 demonstrates the range in overall efficacy of mRNA knockdown for different single-stranded sequences. For example, single strand molecules targeting ApoB target site 485 is maximally effective, while others like those targeting ApoB target site 780 or 10219 have limited mRNA knockdown. For each of the 30 different sequences, the mRNA knockdown shown in FIG. 10 was normalized to the corresponding strands which do not contain the C3 spacer ("all-flu-p").

What is claimed:

1. A single-stranded RNA molecule that mediates RNA interference against a target RNA, wherein said single-stranded RNA molecule comprises:
   (a) a nucleic acid portion comprising a first nucleotide portion (N1) and a second nucleotide portion (N2) that are not self complementary, wherein said nucleic acid portion comprises at least 8 nucleotides that can base pair with a target site of the target RNA, and wherein the total number of nucleotides within the nucleic acid portion is from 8 to 26 nucleotides;
   (b) an internal spacer portion, wherein said spacer portion comprises at least a first non-nucleotide spacer portion (S1) that covalently links the first and second nucleotide portions wherein said single-stranded RNA molecule comprises the following structure:

5'N1-S1-N2 3' wherein:
   (i) N1 contains either one nucleotide or a contiguous stretch of nucleotides;
   (ii) S1 contains one or more non-nucleotide spacers covalently linking N1 and N2;
   (iii) N2 contains either one nucleotide or a contiguous stretch of nucleotides;
   (iv) S1 is at the 3' end of N1 and at the 5' end of N2; and
   (v) wherein said single-stranded RNA molecule has one 3' end; and
   (c) a ligand.

2. The molecule of claim 1, wherein S1 is an aliphatic or aromatic organic group.

3. The molecule of claim 2, wherein S1 is a $C_1$-$C_{12}$ alkyl chain that is optionally substituted.

4. The molecule of claim 3, wherein said alkyl chain is optionally substituted with cholesterol.

5. The molecule of claim 2, wherein S1 is selected from a group consisting of a C3 alkyl, a C6 alkyl, and polyethylene glycol.

6. The molecule of claim 1, wherein N1 is 13 to 20 nucleotides long.

7. The molecule of claim 1, wherein the total number of nucleotides within the nucleic acid portion is about 19 to about 21 nucleotides.

8. The molecule of claim 1, wherein the target site is within a untranslated region of the target RNA.

9. The molecule of claim 8, wherein the at least 8 nucleotides that can base pair with the target site is the whole or a part of a seed sequence of a naturally-occurring, endogenous miRNA nucleotide sequence.

10. The molecule of claim 9, wherein S1 takes the place of from one to 4 internal nucleotides of the naturally-occurring, endogenous miRNA nucleotide sequence.

11. The molecule of claim 10, wherein the nucleic acid portion of the molecule is at least 50% homologous to the naturally-occurring, endogenous miRNA nucleotide sequence.

12. The molecule of claim 1, wherein the target site is within a gene coding region of the target RNA.

13. The molecule of claim 1, wherein the nucleic acid portion of the molecule is at least 90% complementary to the target site.

14. The molecule of claim 1, wherein the nucleic acid portion comprises at least 20 nucleotides that can base pair with the target site.

15. The molecule of claim 1, wherein the nucleic acid portion further comprises a third nucleotide portion (N3) and the internal spacer portion further comprises a second non-nucleotide spacer portion (S2).

16. The molecule of claim 1, wherein at least one nucleotide has a modified sugar.

17. The molecule of claim 1, wherein at least one nucleotide has a modified internucleoside linkage.

18. The molecule of claim 1, having a terminal cap at the 5'-end, the 3'-end, or both the 5'- and 3'-ends.

19. The molecule of claim 1, wherein the ligand is a terminal group.

20. The molecule of claim 1, wherein the ligand is a ligand for a cellular receptor.

21. The molecule of claim 20, wherein the ligand is a carbohydrate.

22. The molecule of claim 21, wherein the carbohydrate is an N-acetyl-D-galactosamine.

23. The molecule of claim 1, wherein the ligand is attached by a linker.

24. A composition comprising the single-stranded RNA molecule of claim 1 and a pharmaceutically acceptable carrier.

25. The composition of claim 24, further comprising a liposome, a hydrogel, a cyclodextrin, a biodegradable nanocapsule, a bioadhesive microsphere, or a proteinaceous vector.

26. A method of reducing the expression of an endogenous RNA target gene in a cell comprising administering a composition of claim 24.

* * * * *

SEQUENCE LISTING

```
<160> NUMBER OF SEQ ID NOS: 1227

<210> SEQ ID NO 1
<211> LENGTH: 22
<212> TYPE: RNA
<213> ORGANISM: Homo sapiens

<400> SEQUENCE: 1
ugagguagua gguuguauag uu                                                  22

<210> SEQ ID NO 2
<211> LENGTH: 21
<212> TYPE: RNA
<213> ORGANISM: Homo sapiens

<400> SEQUENCE: 2
cuauacaauc uacugucuuu c                                                   21

<210> SEQ ID NO 3
<211> LENGTH: 22
<212> TYPE: RNA
<213> ORGANISM: Homo sapiens

<400> SEQUENCE: 3
cuguacagcc uccuagcuuu cc                                                  22

<210> SEQ ID NO 4
<211> LENGTH: 22
<212> TYPE: RNA
<213> ORGANISM: Homo sapiens

<400> SEQUENCE: 4
ugagguagua gguugugugg uu                                                  22

<210> SEQ ID NO 5
<211> LENGTH: 22
<212> TYPE: RNA
<213> ORGANISM: Homo sapiens

<400> SEQUENCE: 5
cuauacaacc uacugccuuc cc                                                  22

<210> SEQ ID NO 6
<211> LENGTH: 22
<212> TYPE: RNA
<213> ORGANISM: Homo sapiens

<400> SEQUENCE: 6
ugagguagua gguuguaugg uu                                                  22

<210> SEQ ID NO 7
<211> LENGTH: 22
<212> TYPE: RNA
<213> ORGANISM: Homo sapiens

<400> SEQUENCE: 7
uagaguuaca cccugggagu ua                                                  22

<210> SEQ ID NO 8
<211> LENGTH: 22
<212> TYPE: RNA
<213> ORGANISM: Homo sapiens

<400> SEQUENCE: 8
```
agagguagua gguugcauag uu                                              22

<210> SEQ ID NO 9
<211> LENGTH: 22
<212> TYPE: RNA
<213> ORGANISM: Homo sapiens

<400> SEQUENCE: 9
cuauacgacc ugcugccuuu cu                                              22

<210> SEQ ID NO 10
<211> LENGTH: 22
<212> TYPE: RNA
<213> ORGANISM: Homo sapiens

<400> SEQUENCE: 10
ugagguagga gguuguauag uu                                              22

<210> SEQ ID NO 11
<211> LENGTH: 22
<212> TYPE: RNA
<213> ORGANISM: Homo sapiens

<400> SEQUENCE: 11
cuauacggcc uccuagcuuu cc                                              22

<210> SEQ ID NO 12
<211> LENGTH: 22
<212> TYPE: RNA
<213> ORGANISM: Homo sapiens

<400> SEQUENCE: 12
ugagguagua gauuguauag uu                                              22

<210> SEQ ID NO 13
<211> LENGTH: 22
<212> TYPE: RNA
<213> ORGANISM: Homo sapiens

<400> SEQUENCE: 13
cuauacaauc uauugccuuc cc                                              22

<210> SEQ ID NO 14
<211> LENGTH: 22
<212> TYPE: RNA
<213> ORGANISM: Homo sapiens

<400> SEQUENCE: 14
cuauacaguc uacugucuuu cc                                              22

<210> SEQ ID NO 15
<211> LENGTH: 22
<212> TYPE: RNA
<213> ORGANISM: Homo sapiens

<400> SEQUENCE: 15
uagcagcaca uaaugguuug ug                                              22

<210> SEQ ID NO 16
<211> LENGTH: 22
<212> TYPE: RNA
<213> ORGANISM: Homo sapiens

```
<400> SEQUENCE: 16
caggccauau ugugcugccu ca                                    22

<210> SEQ ID NO 17
<211> LENGTH: 22
<212> TYPE: RNA
<213> ORGANISM: Homo sapiens

<400> SEQUENCE: 17
uagcagcacg uaaauauugg cg                                    22

<210> SEQ ID NO 18
<211> LENGTH: 22
<212> TYPE: RNA
<213> ORGANISM: Homo sapiens

<400> SEQUENCE: 18
ccaguauuaa cugugcugcu ga                                    22

<210> SEQ ID NO 19
<211> LENGTH: 23
<212> TYPE: RNA
<213> ORGANISM: Homo sapiens

<400> SEQUENCE: 19
caaagugcuu acagugcagg uag                                   23

<210> SEQ ID NO 20
<211> LENGTH: 22
<212> TYPE: RNA
<213> ORGANISM: Homo sapiens

<400> SEQUENCE: 20
acugcaguga aggcacuugu ag                                    22

<210> SEQ ID NO 21
<211> LENGTH: 23
<212> TYPE: RNA
<213> ORGANISM: Homo sapiens

<400> SEQUENCE: 21
uaaggugcau cuagugcaga uag                                   23

<210> SEQ ID NO 22
<211> LENGTH: 23
<212> TYPE: RNA
<213> ORGANISM: Homo sapiens

<400> SEQUENCE: 22
acugcccuaa gugcuccuuc ugg                                   23

<210> SEQ ID NO 23
<211> LENGTH: 22
<212> TYPE: RNA
<213> ORGANISM: Homo sapiens

<400> SEQUENCE: 23
aguuuugcau aguugcacua ca                                    22

<210> SEQ ID NO 24
<211> LENGTH: 23
<212> TYPE: RNA
<213> ORGANISM: Homo sapiens
```

```
<400> SEQUENCE: 24
ugugcaaauc uaugcaaaac uga                                           23

<210> SEQ ID NO 25
<211> LENGTH: 23
<212> TYPE: RNA
<213> ORGANISM: Homo sapiens

<400> SEQUENCE: 25
aguuuugcag guuugcaucc agc                                           23

<210> SEQ ID NO 26
<211> LENGTH: 23
<212> TYPE: RNA
<213> ORGANISM: Homo sapiens

<400> SEQUENCE: 26
ugugcaaauc caugcaaaac uga                                           23

<210> SEQ ID NO 27
<211> LENGTH: 22
<212> TYPE: RNA
<213> ORGANISM: Homo sapiens

<400> SEQUENCE: 27
aguuuugcag guuugcauuu ca                                            22

<210> SEQ ID NO 28
<211> LENGTH: 23
<212> TYPE: RNA
<213> ORGANISM: Homo sapiens

<400> SEQUENCE: 28
uaaagugcuu auagugcagg uag                                           23

<210> SEQ ID NO 29
<211> LENGTH: 22
<212> TYPE: RNA
<213> ORGANISM: Homo sapiens

<400> SEQUENCE: 29
acugcauuau gagcacuuaa ag                                            22

<210> SEQ ID NO 30
<211> LENGTH: 22
<212> TYPE: RNA
<213> ORGANISM: Homo sapiens

<400> SEQUENCE: 30
uagcuuauca gacugauguu ga                                            22

<210> SEQ ID NO 31
<211> LENGTH: 21
<212> TYPE: RNA
<213> ORGANISM: Homo sapiens

<400> SEQUENCE: 31
caacaccagu cgaugggcug u                                             21

<210> SEQ ID NO 32
<211> LENGTH: 22
<212> TYPE: RNA
```

```
<213> ORGANISM: Homo sapiens

<400> SEQUENCE: 32
aguucuucag uggcaagcuu ua                                              22

<210> SEQ ID NO 33
<211> LENGTH: 22
<212> TYPE: RNA
<213> ORGANISM: Homo sapiens

<400> SEQUENCE: 33
aagcugccag uugaagaacu gu                                              22

<210> SEQ ID NO 34
<211> LENGTH: 22
<212> TYPE: RNA
<213> ORGANISM: Homo sapiens

<400> SEQUENCE: 34
gggguuccug gggaugggau uu                                              22

<210> SEQ ID NO 35
<211> LENGTH: 21
<212> TYPE: RNA
<213> ORGANISM: Homo sapiens

<400> SEQUENCE: 35
aucacauugc cagggauuuc c                                               21

<210> SEQ ID NO 36
<211> LENGTH: 22
<212> TYPE: RNA
<213> ORGANISM: Homo sapiens

<400> SEQUENCE: 36
ugccuacuga gcugauauca gu                                              22

<210> SEQ ID NO 37
<211> LENGTH: 22
<212> TYPE: RNA
<213> ORGANISM: Homo sapiens

<400> SEQUENCE: 37
uggcucaguu cagcaggaac ag                                              22

<210> SEQ ID NO 38
<211> LENGTH: 22
<212> TYPE: RNA
<213> ORGANISM: Homo sapiens

<400> SEQUENCE: 38
ugccuacuga gcugaaacac ag                                              22

<210> SEQ ID NO 39
<211> LENGTH: 21
<212> TYPE: RNA
<213> ORGANISM: Homo sapiens

<400> SEQUENCE: 39
aggcggagac uugggcaauu g                                               21

<210> SEQ ID NO 40
<211> LENGTH: 22
```

```
<212> TYPE: RNA
<213> ORGANISM: Homo sapiens

<400> SEQUENCE: 40
cauugcacuu gucucggucu ga                                           22

<210> SEQ ID NO 41
<211> LENGTH: 22
<212> TYPE: RNA
<213> ORGANISM: Homo sapiens

<400> SEQUENCE: 41
uucaaguaau ccaggauagg cu                                           22

<210> SEQ ID NO 42
<211> LENGTH: 22
<212> TYPE: RNA
<213> ORGANISM: Homo sapiens

<400> SEQUENCE: 42
ccuauucuug guuacuugca cg                                           22

<210> SEQ ID NO 43
<211> LENGTH: 21
<212> TYPE: RNA
<213> ORGANISM: Homo sapiens

<400> SEQUENCE: 43
uucaaguaau ucaggauagg u                                            21

<210> SEQ ID NO 44
<211> LENGTH: 22
<212> TYPE: RNA
<213> ORGANISM: Homo sapiens

<400> SEQUENCE: 44
ccuguucucc auuacuuggc uc                                           22

<210> SEQ ID NO 45
<211> LENGTH: 22
<212> TYPE: RNA
<213> ORGANISM: Homo sapiens

<400> SEQUENCE: 45
agggcuuagc ugcuugugag ca                                           22

<210> SEQ ID NO 46
<211> LENGTH: 21
<212> TYPE: RNA
<213> ORGANISM: Homo sapiens

<400> SEQUENCE: 46
uucacagugg cuaaguuccg c                                            21

<210> SEQ ID NO 47
<211> LENGTH: 22
<212> TYPE: RNA
<213> ORGANISM: Homo sapiens

<400> SEQUENCE: 47
aaggagcuca cagucuauug ag                                           22

<210> SEQ ID NO 48
```

```
<211> LENGTH: 22
<212> TYPE: RNA
<213> ORGANISM: Homo sapiens

<400> SEQUENCE: 48
cacuagauug ugagcccug ga                                              22

<210> SEQ ID NO 49
<211> LENGTH: 22
<212> TYPE: RNA
<213> ORGANISM: Homo sapiens

<400> SEQUENCE: 49
acugauuucu uuugguguuc ag                                             22

<210> SEQ ID NO 50
<211> LENGTH: 22
<212> TYPE: RNA
<213> ORGANISM: Homo sapiens

<400> SEQUENCE: 50
uagcaccauc ugaaaucggu ua                                             22

<210> SEQ ID NO 51
<211> LENGTH: 22
<212> TYPE: RNA
<213> ORGANISM: Homo sapiens

<400> SEQUENCE: 51
uguaaacauc cucgacugga ag                                             22

<210> SEQ ID NO 52
<211> LENGTH: 22
<212> TYPE: RNA
<213> ORGANISM: Homo sapiens

<400> SEQUENCE: 52
cuuucagucg gauguuugca gc                                             22

<210> SEQ ID NO 53
<211> LENGTH: 21
<212> TYPE: RNA
<213> ORGANISM: Homo sapiens

<400> SEQUENCE: 53
aggcaagaug cuggcauagc u                                              21

<210> SEQ ID NO 54
<211> LENGTH: 22
<212> TYPE: RNA
<213> ORGANISM: Homo sapiens

<400> SEQUENCE: 54
ugcuaugcca acauauugcc au                                             22

<210> SEQ ID NO 55
<211> LENGTH: 22
<212> TYPE: RNA
<213> ORGANISM: Homo sapiens

<400> SEQUENCE: 55
uauugcacau uacuaaguug ca                                             22
```

```
<210> SEQ ID NO 56
<211> LENGTH: 22
<212> TYPE: RNA
<213> ORGANISM: Homo sapiens

<400> SEQUENCE: 56
caauuuagug ugugugauau uu                                              22

<210> SEQ ID NO 57
<211> LENGTH: 21
<212> TYPE: RNA
<213> ORGANISM: Homo sapiens

<400> SEQUENCE: 57
gugcauugua guugcauugc a                                               21

<210> SEQ ID NO 58
<211> LENGTH: 22
<212> TYPE: RNA
<213> ORGANISM: Homo sapiens

<400> SEQUENCE: 58
caauguuucc acagugcauc ac                                              22

<210> SEQ ID NO 59
<211> LENGTH: 23
<212> TYPE: RNA
<213> ORGANISM: Homo sapiens

<400> SEQUENCE: 59
agguugggau cgguugcaau gcu                                             23

<210> SEQ ID NO 60
<211> LENGTH: 22
<212> TYPE: RNA
<213> ORGANISM: Homo sapiens

<400> SEQUENCE: 60
uauugcacuu gucccggccu gu                                              22

<210> SEQ ID NO 61
<211> LENGTH: 22
<212> TYPE: RNA
<213> ORGANISM: Homo sapiens

<400> SEQUENCE: 61 gggugggau uuguugcauu ac                                               22

<210> SEQ ID NO 62
<211> LENGTH: 23
<212> TYPE: RNA
<213> ORGANISM: Homo sapiens

<400> SEQUENCE: 62
caaagugcug uucgugcagg uag                                             23

<210> SEQ ID NO 63
<211> LENGTH: 22
<212> TYPE: RNA
<213> ORGANISM: Homo sapiens

<400> SEQUENCE: 63
acugcugagc uagcacuucc cg                                              22
```

```
<210> SEQ ID NO 64
<211> LENGTH: 22
<212> TYPE: RNA
<213> ORGANISM: Homo sapiens

<400> SEQUENCE: 64
uucaacgggu auuuauugag ca                                              22

<210> SEQ ID NO 65
<211> LENGTH: 23
<212> TYPE: RNA
<213> ORGANISM: Homo sapiens

<400> SEQUENCE: 65
uuuggcacua gcacauuuuu gcu                                             23

<210> SEQ ID NO 66
<211> LENGTH: 22
<212> TYPE: RNA
<213> ORGANISM: Homo sapiens

<400> SEQUENCE: 66
aaucaugugc agugccaaua ug                                              22

<210> SEQ ID NO 67
<211> LENGTH: 22
<212> TYPE: RNA
<213> ORGANISM: Homo sapiens

<400> SEQUENCE: 67
ugagguagua aguuguauug uu                                              22

<210> SEQ ID NO 68
<211> LENGTH: 22
<212> TYPE: RNA
<213> ORGANISM: Homo sapiens

<400> SEQUENCE: 68
aacccguaga uccgaucuug ug                                              22

<210> SEQ ID NO 69
<211> LENGTH: 22
<212> TYPE: RNA
<213> ORGANISM: Homo sapiens

<400> SEQUENCE: 69
caagcucgcu ucuaugdgguc ug                                             22

<210> SEQ ID NO 70
<211> LENGTH: 22
<212> TYPE: RNA
<213> ORGANISM: Homo sapiens

<400> SEQUENCE: 70
aacccguaga uccgaacuug ug                                              22

<210> SEQ ID NO 71
<211> LENGTH: 22
<212> TYPE: RNA
<213> ORGANISM: Homo sapiens

<400> SEQUENCE: 71
caagcuugua ucuauaggua ug                                              22
```

```
<210> SEQ ID NO 72
<211> LENGTH: 22
<212> TYPE: RNA
<213> ORGANISM: Homo sapiens

<400> SEQUENCE: 72
caguuaucac agugcugaug cu                                        22

<210> SEQ ID NO 73
<211> LENGTH: 21
<212> TYPE: RNA
<213> ORGANISM: Homo sapiens

<400> SEQUENCE: 73
uacaguacug ugauaacuga a                                         21

<210> SEQ ID NO 74
<211> LENGTH: 24
<212> TYPE: RNA
<213> ORGANISM: Homo sapiens

<400> SEQUENCE: 74
gcugguuuca uauggugguu uaga                                      24

<210> SEQ ID NO 75
<211> LENGTH: 23
<212> TYPE: RNA
<213> ORGANISM: Homo sapiens

<400> SEQUENCE: 75
uagcaccauu ugaaaucagu guu                                       23

<210> SEQ ID NO 76
<211> LENGTH: 22
<212> TYPE: RNA
<213> ORGANISM: Homo sapiens

<400> SEQUENCE: 76
cugguuucac augguggcuu ag                                        22

<210> SEQ ID NO 77
<211> LENGTH: 23
<212> TYPE: RNA
<213> ORGANISM: Homo sapiens

<400> SEQUENCE: 77
agcuucuuua cagugcugcc uug                                       23

<210> SEQ ID NO 78
<211> LENGTH: 23
<212> TYPE: RNA
<213> ORGANISM: Homo sapiens

<400> SEQUENCE: 78
agcagcauug uacagggcua uga                                       23

<210> SEQ ID NO 79
<211> LENGTH: 23
<212> TYPE: RNA
<213> ORGANISM: Homo sapiens

<400> SEQUENCE: 79
```
ucaaaugcuc agacuccugu ggu                                          23

<210> SEQ ID NO 80
<211> LENGTH: 22
<212> TYPE: RNA
<213> ORGANISM: Homo sapiens

<400> SEQUENCE: 80
acggauguuu gagcaugugc ua                                           22

<210> SEQ ID NO 81
<211> LENGTH: 23
<212> TYPE: RNA
<213> ORGANISM: Homo sapiens

<400> SEQUENCE: 81
aaaagugcuu acagugcagg uag                                          23

<210> SEQ ID NO 82
<211> LENGTH: 22
<212> TYPE: RNA
<213> ORGANISM: Homo sapiens

<400> SEQUENCE: 82
cugcaaugua agcacuucuu ac                                           22

<210> SEQ ID NO 83
<211> LENGTH: 23
<212> TYPE: RNA
<213> ORGANISM: Homo sapiens

<400> SEQUENCE: 83
agcagcauug uacagggcua uca                                          23

<210> SEQ ID NO 84
<211> LENGTH: 22
<212> TYPE: RNA
<213> ORGANISM: Homo sapiens

<400> SEQUENCE: 84
ccaauauuac ugugcugcuu ua                                           22

<210> SEQ ID NO 85
<211> LENGTH: 21
<212> TYPE: RNA
<213> ORGANISM: Homo sapiens

<400> SEQUENCE: 85
cugaccuaug aauugacagc c                                            21

<210> SEQ ID NO 86
<211> LENGTH: 22
<212> TYPE: RNA
<213> ORGANISM: Homo sapiens

<400> SEQUENCE: 86
cugccaauuc cauaggucac ag                                           22

<210> SEQ ID NO 87
<211> LENGTH: 22
<212> TYPE: RNA
<213> ORGANISM: Homo sapiens

<400> SEQUENCE: 87
uagguaguuu cauguuguug gg                                          22

<210> SEQ ID NO 88
<211> LENGTH: 22
<212> TYPE: RNA
<213> ORGANISM: Homo sapiens

<400> SEQUENCE: 88
uucaccaccu ucuccaccca gc                                          22

<210> SEQ ID NO 89
<211> LENGTH: 22
<212> TYPE: RNA
<213> ORGANISM: Homo sapiens

<400> SEQUENCE: 89
gguccagagg ggagauaggu uc                                          22

<210> SEQ ID NO 90
<211> LENGTH: 23
<212> TYPE: RNA
<213> ORGANISM: Homo sapiens

<400> SEQUENCE: 90
cccaguguuc agacuaccug uuc                                         23

<210> SEQ ID NO 91
<211> LENGTH: 22
<212> TYPE: RNA
<213> ORGANISM: Homo sapiens

<400> SEQUENCE: 91
acaguagucu gcacauuggu ua                                          22

<210> SEQ ID NO 92
<211> LENGTH: 22
<212> TYPE: RNA
<213> ORGANISM: Homo sapiens

<400> SEQUENCE: 92
auaagacgag caaaaagcuu gu                                          22

<210> SEQ ID NO 93
<211> LENGTH: 21
<212> TYPE: RNA
<213> ORGANISM: Homo sapiens

<400> SEQUENCE: 93
cuuuuugcgg ucugggcuug c                                           21

<210> SEQ ID NO 94
<211> LENGTH: 22
<212> TYPE: RNA
<213> ORGANISM: Homo sapiens

<400> SEQUENCE: 94
aagcccuuac cccaaaaagu au                                          22

<210> SEQ ID NO 95
<211> LENGTH: 22
<212> TYPE: RNA
<213> ORGANISM: Homo sapiens

```
<400> SEQUENCE: 95
aaaguucuga gacacuccga cu                                              22

<210> SEQ ID NO 96
<211> LENGTH: 22
<212> TYPE: RNA
<213> ORGANISM: Homo sapiens

<400> SEQUENCE: 96
ucagugcacu acagaacuuu gu                                              22

<210> SEQ ID NO 97
<211> LENGTH: 23
<212> TYPE: RNA
<213> ORGANISM: Homo sapiens

<400> SEQUENCE: 97
uguaaacauc cuacacucuc agc                                             23

<210> SEQ ID NO 98
<211> LENGTH: 22
<212> TYPE: RNA
<213> ORGANISM: Homo sapiens

<400> SEQUENCE: 98
cugggagaag gcuguuuacu cu                                              22

<210> SEQ ID NO 99
<211> LENGTH: 22
<212> TYPE: RNA
<213> ORGANISM: Homo sapiens

<400> SEQUENCE: 99
uguaaacauc cccgacugga ag                                              22

<210> SEQ ID NO 100
<211> LENGTH: 22
<212> TYPE: RNA
<213> ORGANISM: Homo sapiens

<400> SEQUENCE: 100
cuuucaguca gauguuugcu gc                                              22

<210> SEQ ID NO 101
<211> LENGTH: 22
<212> TYPE: RNA
<213> ORGANISM: Homo sapiens

<400> SEQUENCE: 101
ucuacagugc acgugucucc ag                                              22

<210> SEQ ID NO 102
<211> LENGTH: 22
<212> TYPE: RNA
<213> ORGANISM: Homo sapiens

<400> SEQUENCE: 102
ggagacgcgg cccuguugga gu                                              22

<210> SEQ ID NO 103
<211> LENGTH: 20
<212> TYPE: RNA
<213> ORGANISM: Homo sapiens
```

```
<400> SEQUENCE: 103
guguguggaa augcuucugc                                         20

<210> SEQ ID NO 104
<211> LENGTH: 23
<212> TYPE: RNA
<213> ORGANISM: Homo sapiens

<400> SEQUENCE: 104
uggaagacua gugauuugu ugu                                      23

<210> SEQ ID NO 105
<211> LENGTH: 22
<212> TYPE: RNA
<213> ORGANISM: Homo sapiens

<400> SEQUENCE: 105
caacaaauca cagucugcca ua                                      22

<210> SEQ ID NO 106
<211> LENGTH: 22
<212> TYPE: RNA
<213> ORGANISM: Homo sapiens

<400> SEQUENCE: 106
caacaaaucc cagucuaccu aa                                      22

<210> SEQ ID NO 107
<211> LENGTH: 23
<212> TYPE: RNA
<213> ORGANISM: Homo sapiens

<400> SEQUENCE: 107
uacccuguag auccgaauuu gug                                     23

<210> SEQ ID NO 108
<211> LENGTH: 22
<212> TYPE: RNA
<213> ORGANISM: Homo sapiens

<400> SEQUENCE: 108
caaauucgua ucuaggggaa ua                                      22

<210> SEQ ID NO 109
<211> LENGTH: 23
<212> TYPE: RNA
<213> ORGANISM: Homo sapiens

<400> SEQUENCE: 109
uacccuguag aaccgaauuu gug                                     23

<210> SEQ ID NO 110
<211> LENGTH: 22
<212> TYPE: RNA
<213> ORGANISM: Homo sapiens

<400> SEQUENCE: 110
acagauucga uucuagggga au                                      22

<210> SEQ ID NO 111
<211> LENGTH: 22
<212> TYPE: RNA
```

```
<213> ORGANISM: Homo sapiens

<400> SEQUENCE: 111
uggcaguguc uuagcugguu gu                                              22

<210> SEQ ID NO 112
<211> LENGTH: 22
<212> TYPE: RNA
<213> ORGANISM: Homo sapiens

<400> SEQUENCE: 112
caaucagcaa guauacugcc cu                                              22

<210> SEQ ID NO 113
<211> LENGTH: 23
<212> TYPE: RNA
<213> ORGANISM: Homo sapiens

<400> SEQUENCE: 113
aacauucaac gcugucggug agu                                             23

<210> SEQ ID NO 114
<211> LENGTH: 22
<212> TYPE: RNA
<213> ORGANISM: Homo sapiens

<400> SEQUENCE: 114
accacugacc guugacugua cc                                              22

<210> SEQ ID NO 115
<211> LENGTH: 23
<212> TYPE: RNA
<213> ORGANISM: Homo sapiens

<400> SEQUENCE: 115
aacauucauu gcugucggug ggu                                             23

<210> SEQ ID NO 116
<211> LENGTH: 22
<212> TYPE: RNA
<213> ORGANISM: Homo sapiens

<400> SEQUENCE: 116
aacauucaac cugucgguga gu                                              22

<210> SEQ ID NO 117
<211> LENGTH: 22
<212> TYPE: RNA
<213> ORGANISM: Homo sapiens

<400> SEQUENCE: 117
aaccaucgac cguugagugg ac                                              22

<210> SEQ ID NO 118
<211> LENGTH: 24
<212> TYPE: RNA
<213> ORGANISM: Homo sapiens

<400> SEQUENCE: 118
uuuggcaaug guagaacuca cacu                                            24

<210> SEQ ID NO 119
<211> LENGTH: 21
```

-continued

<212> TYPE: RNA
<213> ORGANISM: Homo sapiens

<400> SEQUENCE: 119 gguucuaga cuugccaacu a                                    21

<210> SEQ ID NO 120
<211> LENGTH: 22
<212> TYPE: RNA
<213> ORGANISM: Homo sapiens

<400> SEQUENCE: 120
uauggcacug guagaauuca cu                                  22

<210> SEQ ID NO 121
<211> LENGTH: 22
<212> TYPE: RNA
<213> ORGANISM: Homo sapiens

<400> SEQUENCE: 121
gugaauuacc gaagggccau aa                                  22

<210> SEQ ID NO 122
<211> LENGTH: 22
<212> TYPE: RNA
<213> ORGANISM: Homo sapiens

<400> SEQUENCE: 122
ggcuacaaca caggacccgg gc                                  22

<210> SEQ ID NO 123
<211> LENGTH: 22
<212> TYPE: RNA
<213> ORGANISM: Homo sapiens

<400> SEQUENCE: 123
ucgugucuug uguugcagcc gg                                  22

<210> SEQ ID NO 124
<211> LENGTH: 22
<212> TYPE: RNA
<213> ORGANISM: Homo sapiens

<400> SEQUENCE: 124
cggcaacaag aaacugccug ag                                  22

<210> SEQ ID NO 125
<211> LENGTH: 23
<212> TYPE: RNA
<213> ORGANISM: Homo sapiens

<400> SEQUENCE: 125
cccaguguuu agacuaucug uuc                                 23

<210> SEQ ID NO 126
<211> LENGTH: 22
<212> TYPE: RNA
<213> ORGANISM: Homo sapiens

<400> SEQUENCE: 126
gugaaauguu uaggaccacu ag                                  22

<210> SEQ ID NO 127

```
<211> LENGTH: 22
<212> TYPE: RNA
<213> ORGANISM: Homo sapiens

<400> SEQUENCE: 127
uucccuuugu cauccuaugc cu                                              22

<210> SEQ ID NO 128
<211> LENGTH: 22
<212> TYPE: RNA
<213> ORGANISM: Homo sapiens

<400> SEQUENCE: 128
uccuucauuc caccggaguc ug                                              22

<210> SEQ ID NO 129
<211> LENGTH: 21
<212> TYPE: RNA
<213> ORGANISM: Homo sapiens

<400> SEQUENCE: 129
gauuucagug gagugaaguu c                                               21

<210> SEQ ID NO 130
<211> LENGTH: 22
<212> TYPE: RNA
<213> ORGANISM: Homo sapiens

<400> SEQUENCE: 130
cugugcgugu gacagcggcu ga                                              22

<210> SEQ ID NO 131
<211> LENGTH: 22
<212> TYPE: RNA
<213> ORGANISM: Homo sapiens

<400> SEQUENCE: 131
uucccuuugu cauccuucgc cu                                              22

<210> SEQ ID NO 132
<211> LENGTH: 21
<212> TYPE: RNA
<213> ORGANISM: Homo sapiens

<400> SEQUENCE: 132
uaacagucuc cagucacggc c                                               21

<210> SEQ ID NO 133
<211> LENGTH: 22
<212> TYPE: RNA
<213> ORGANISM: Homo sapiens

<400> SEQUENCE: 133
accaucgacc guugauugua cc                                              22

<210> SEQ ID NO 134
<211> LENGTH: 22
<212> TYPE: RNA
<213> ORGANISM: Homo sapiens

<400> SEQUENCE: 134
ugccugucua cacuugcugu gc                                              22
```

```
<210> SEQ ID NO 135
<211> LENGTH: 22
<212> TYPE: RNA
<213> ORGANISM: Homo sapiens

<400> SEQUENCE: 135
acagcaggca cagacaggca gu                                              22

<210> SEQ ID NO 136
<211> LENGTH: 21
<212> TYPE: RNA
<213> ORGANISM: Homo sapiens

<400> SEQUENCE: 136
augaccuaug aauugacaga c                                               21

<210> SEQ ID NO 137
<211> LENGTH: 22
<212> TYPE: RNA
<213> ORGANISM: Homo sapiens

<400> SEQUENCE: 137
uaaucucagc uggcaacugu ga                                              22

<210> SEQ ID NO 138
<211> LENGTH: 23
<212> TYPE: RNA
<213> ORGANISM: Homo sapiens

<400> SEQUENCE: 138
uacugcauca ggaacugauu gga                                             23

<210> SEQ ID NO 139
<211> LENGTH: 21
<212> TYPE: RNA
<213> ORGANISM: Homo sapiens

<400> SEQUENCE: 139
uugugcuuga ucuaaccaug u                                               21

<210> SEQ ID NO 140
<211> LENGTH: 22
<212> TYPE: RNA
<213> ORGANISM: Homo sapiens

<400> SEQUENCE: 140
augguuccgu caagcaccau gg                                              22

<210> SEQ ID NO 141
<211> LENGTH: 22
<212> TYPE: RNA
<213> ORGANISM: Homo sapiens

<400> SEQUENCE: 141 cauguucug ucaagcaccg cg                                               22

<210> SEQ ID NO 142
<211> LENGTH: 21
<212> TYPE: RNA
<213> ORGANISM: Homo sapiens

<400> SEQUENCE: 142
ugauugucca aacgcaauuc u                                               21
```

```
<210> SEQ ID NO 143
<211> LENGTH: 22
<212> TYPE: RNA
<213> ORGANISM: Homo sapiens

<400> SEQUENCE: 143
agaguugagu cuggacgucc cg                                           22

<210> SEQ ID NO 144
<211> LENGTH: 21
<212> TYPE: RNA
<213> ORGANISM: Homo sapiens

<400> SEQUENCE: 144
ccacaccgua ucugacacuu u                                            21

<210> SEQ ID NO 145
<211> LENGTH: 22
<212> TYPE: RNA
<213> ORGANISM: Homo sapiens

<400> SEQUENCE: 145
accuggcaua caauguagau uu                                           22

<210> SEQ ID NO 146
<211> LENGTH: 23
<212> TYPE: RNA
<213> ORGANISM: Homo sapiens

<400> SEQUENCE: 146
agcuacauug ucugcugggu uuc                                          23

<210> SEQ ID NO 147
<211> LENGTH: 22
<212> TYPE: RNA
<213> ORGANISM: Homo sapiens

<400> SEQUENCE: 147
cucaguagcc aguguagauc cu                                           22

<210> SEQ ID NO 148
<211> LENGTH: 21
<212> TYPE: RNA
<213> ORGANISM: Homo sapiens

<400> SEQUENCE: 148
agcuacaucu ggcuacuggg u                                            21

<210> SEQ ID NO 149
<211> LENGTH: 22
<212> TYPE: RNA
<213> ORGANISM: Homo sapiens

<400> SEQUENCE: 149
cguguauuug acaagcugag uu                                           22

<210> SEQ ID NO 150
<211> LENGTH: 22
<212> TYPE: RNA
<213> ORGANISM: Homo sapiens

<400> SEQUENCE: 150
ugucaguuug ucaaauaccc ca                                           22
```

```
<210> SEQ ID NO 151
<211> LENGTH: 21
<212> TYPE: RNA
<213> ORGANISM: Homo sapiens

<400> SEQUENCE: 151
caagucacua gugguuccgu u                                               21

<210> SEQ ID NO 152
<211> LENGTH: 23
<212> TYPE: RNA
<213> ORGANISM: Homo sapiens

<400> SEQUENCE: 152
aaaauggugc ccuagugacu aca                                             23

<210> SEQ ID NO 153
<211> LENGTH: 22
<212> TYPE: RNA
<213> ORGANISM: Homo sapiens

<400> SEQUENCE: 153
caucuuacug ggcagcauug ga                                              22

<210> SEQ ID NO 154
<211> LENGTH: 22
<212> TYPE: RNA
<213> ORGANISM: Homo sapiens

<400> SEQUENCE: 154
uaauacugcc ugguaaugau ga                                              22

<210> SEQ ID NO 155
<211> LENGTH: 22
<212> TYPE: RNA
<213> ORGANISM: Homo sapiens

<400> SEQUENCE: 155
ugagguagua guuguacag uu                                               22

<210> SEQ ID NO 156
<211> LENGTH: 21
<212> TYPE: RNA
<213> ORGANISM: Homo sapiens

<400> SEQUENCE: 156
cuguacaggc cacugccuug c                                               21

<210> SEQ ID NO 157
<211> LENGTH: 22
<212> TYPE: RNA
<213> ORGANISM: Homo sapiens

<400> SEQUENCE: 157
ugagguagua guuugugcug uu                                              22

<210> SEQ ID NO 158
<211> LENGTH: 22
<212> TYPE: RNA
<213> ORGANISM: Homo sapiens

<400> SEQUENCE: 158
```
cugcgcaagc uacugccuug cu                                          22

<210> SEQ ID NO 159
<211> LENGTH: 22
<212> TYPE: RNA
<213> ORGANISM: Homo sapiens

<400> SEQUENCE: 159
uggaauguaa agaaguaugu au                                          22

<210> SEQ ID NO 160
<211> LENGTH: 22
<212> TYPE: RNA
<213> ORGANISM: Homo sapiens

<400> SEQUENCE: 160
uagcagcaca ucaugguuua ca                                          22

<210> SEQ ID NO 161
<211> LENGTH: 22
<212> TYPE: RNA
<213> ORGANISM: Homo sapiens

<400> SEQUENCE: 161
cgaaucauua uuugcugcuc ua                                          22

<210> SEQ ID NO 162
<211> LENGTH: 22
<212> TYPE: RNA
<213> ORGANISM: Homo sapiens

<400> SEQUENCE: 162
uggguuccug gcaugcugau uu                                          22

<210> SEQ ID NO 163
<211> LENGTH: 21
<212> TYPE: RNA
<213> ORGANISM: Homo sapiens

<400> SEQUENCE: 163
aucacauugc cagggauuac c                                           21

<210> SEQ ID NO 164
<211> LENGTH: 22
<212> TYPE: RNA
<213> ORGANISM: Homo sapiens

<400> SEQUENCE: 164
agagcuuagc ugauugguga ac                                          22

<210> SEQ ID NO 165
<211> LENGTH: 21
<212> TYPE: RNA
<213> ORGANISM: Homo sapiens

<400> SEQUENCE: 165
uucacagugg cuaaguucug c                                           21

<210> SEQ ID NO 166
<211> LENGTH: 22
<212> TYPE: RNA
<213> ORGANISM: Homo sapiens

<400> SEQUENCE: 166
uguaaacauc cuacacucag cu						22

<210> SEQ ID NO 167
<211> LENGTH: 22
<212> TYPE: RNA
<213> ORGANISM: Homo sapiens

<400> SEQUENCE: 167
cugggaggug gauguuuacu uc						22

<210> SEQ ID NO 168
<211> LENGTH: 22
<212> TYPE: RNA
<213> ORGANISM: Homo sapiens

<400> SEQUENCE: 168
uggaguguga caauguguu ug						22

<210> SEQ ID NO 169
<211> LENGTH: 22
<212> TYPE: RNA
<213> ORGANISM: Homo sapiens

<400> SEQUENCE: 169
aacgccauua ucacacuaaa ua						22

<210> SEQ ID NO 170
<211> LENGTH: 22
<212> TYPE: RNA
<213> ORGANISM: Homo sapiens

<400> SEQUENCE: 170
cguguucaca gcggaccuug au						22

<210> SEQ ID NO 171
<211> LENGTH: 20
<212> TYPE: RNA
<213> ORGANISM: Homo sapiens

<400> SEQUENCE: 171
uaaggcacgc ggugaaugcc						20

<210> SEQ ID NO 172
<211> LENGTH: 22
<212> TYPE: RNA
<213> ORGANISM: Homo sapiens

<400> SEQUENCE: 172
ucccugagac ccuaacuugu ga						22

<210> SEQ ID NO 173
<211> LENGTH: 22
<212> TYPE: RNA
<213> ORGANISM: Homo sapiens

<400> SEQUENCE: 173
acggguuagg cucuugggag cu						22

<210> SEQ ID NO 174
<211> LENGTH: 21
<212> TYPE: RNA
<213> ORGANISM: Homo sapiens

```
<400> SEQUENCE: 174
ucacagugaa ccggucucuu u                                             21

<210> SEQ ID NO 175
<211> LENGTH: 22
<212> TYPE: RNA
<213> ORGANISM: Homo sapiens

<400> SEQUENCE: 175
uucacauugu gcuacugucu gc                                            22

<210> SEQ ID NO 176
<211> LENGTH: 22
<212> TYPE: RNA
<213> ORGANISM: Homo sapiens

<400> SEQUENCE: 176
cagugcaaug uuaaaagggc au                                            22

<210> SEQ ID NO 177
<211> LENGTH: 22
<212> TYPE: RNA
<213> ORGANISM: Homo sapiens

<400> SEQUENCE: 177
accguggcuu ucgauuguua cu                                            22

<210> SEQ ID NO 178
<211> LENGTH: 22
<212> TYPE: RNA
<213> ORGANISM: Homo sapiens

<400> SEQUENCE: 178
uaacagucua cagccauggu cg                                            22

<210> SEQ ID NO 179
<211> LENGTH: 22
<212> TYPE: RNA
<213> ORGANISM: Homo sapiens

<400> SEQUENCE: 179
uuuggucccc uucaaccagc ug                                            22

<210> SEQ ID NO 180
<211> LENGTH: 23
<212> TYPE: RNA
<213> ORGANISM: Homo sapiens

<400> SEQUENCE: 180
uauggcuuuu uauuccuaug uga                                           23

<210> SEQ ID NO 181
<211> LENGTH: 22
<212> TYPE: RNA
<213> ORGANISM: Homo sapiens

<400> SEQUENCE: 181
uauagggauu ggagccgugg cg                                            22

<210> SEQ ID NO 182
<211> LENGTH: 23
<212> TYPE: RNA
<213> ORGANISM: Homo sapiens
```

```
<400> SEQUENCE: 182
uuauugcuua agaauacgcg uag                                          23

<210> SEQ ID NO 183
<211> LENGTH: 23
<212> TYPE: RNA
<213> ORGANISM: Homo sapiens

<400> SEQUENCE: 183
agcugguguu gugaaucagg ccg                                          23

<210> SEQ ID NO 184
<211> LENGTH: 22
<212> TYPE: RNA
<213> ORGANISM: Homo sapiens

<400> SEQUENCE: 184
gcuauuucac gacaccaggg uu                                           22

<210> SEQ ID NO 185
<211> LENGTH: 22
<212> TYPE: RNA
<213> ORGANISM: Homo sapiens

<400> SEQUENCE: 185
cagugguuuu acccuauggu ag                                           22

<210> SEQ ID NO 186
<211> LENGTH: 21
<212> TYPE: RNA
<213> ORGANISM: Homo sapiens

<400> SEQUENCE: 186
uaccacaggg uagaaccacg g                                            21

<210> SEQ ID NO 187
<211> LENGTH: 22
<212> TYPE: RNA
<213> ORGANISM: Homo sapiens

<400> SEQUENCE: 187
caucuuccag uacaguguug ga                                           22

<210> SEQ ID NO 188
<211> LENGTH: 22
<212> TYPE: RNA
<213> ORGANISM: Homo sapiens

<400> SEQUENCE: 188
uaacacuguc ugguaaagau gg                                           22

<210> SEQ ID NO 189
<211> LENGTH: 21
<212> TYPE: RNA
<213> ORGANISM: Homo sapiens

<400> SEQUENCE: 189
cauaaaguag aaagcacuac u                                            21

<210> SEQ ID NO 190
<211> LENGTH: 23
<212> TYPE: RNA
```

<213> ORGANISM: Homo sapiens

<400> SEQUENCE: 190
uguaguguuu ccuacuuuau gga                                          23

<210> SEQ ID NO 191
<211> LENGTH: 22
<212> TYPE: RNA
<213> ORGANISM: Homo sapiens

<400> SEQUENCE: 191
ggugcagugc ugcaucucug gu                                           22

<210> SEQ ID NO 192
<211> LENGTH: 21
<212> TYPE: RNA
<213> ORGANISM: Homo sapiens

<400> SEQUENCE: 192
ugagaugaag cacuguagcu c                                            21

<210> SEQ ID NO 193
<211> LENGTH: 22
<212> TYPE: RNA
<213> ORGANISM: Homo sapiens

<400> SEQUENCE: 193
ggauaucauc auauacugua ag                                           22

<210> SEQ ID NO 194
<211> LENGTH: 20
<212> TYPE: RNA
<213> ORGANISM: Homo sapiens

<400> SEQUENCE: 194
uacaguauag augauguacu                                              20

<210> SEQ ID NO 195
<211> LENGTH: 23
<212> TYPE: RNA
<213> ORGANISM: Homo sapiens

<400> SEQUENCE: 195
guccaguuuu cccaggaauc ccu                                          23

<210> SEQ ID NO 196
<211> LENGTH: 22
<212> TYPE: RNA
<213> ORGANISM: Homo sapiens

<400> SEQUENCE: 196
ggauuccugg aaauacuguu cu                                           22

<210> SEQ ID NO 197
<211> LENGTH: 21
<212> TYPE: RNA
<213> ORGANISM: Homo sapiens

<400> SEQUENCE: 197
ucagugcaug acagaacuug g                                            21

<210> SEQ ID NO 198
<211> LENGTH: 22

```
<212> TYPE: RNA
<213> ORGANISM: Homo sapiens

<400> SEQUENCE: 198
uugcauaguc acaaaaguga uc                                           22

<210> SEQ ID NO 199
<211> LENGTH: 23
<212> TYPE: RNA
<213> ORGANISM: Homo sapiens

<400> SEQUENCE: 199
caacggaauc ccaaaagcag cug                                          23

<210> SEQ ID NO 200
<211> LENGTH: 22
<212> TYPE: RNA
<213> ORGANISM: Homo sapiens

<400> SEQUENCE: 200
gcugcgcuug gauuucgucc cc                                           22

<210> SEQ ID NO 201
<211> LENGTH: 23
<212> TYPE: RNA
<213> ORGANISM: Homo sapiens

<400> SEQUENCE: 201
ucuuugguua ucuagcugua uga                                          23

<210> SEQ ID NO 202
<211> LENGTH: 22
<212> TYPE: RNA
<213> ORGANISM: Homo sapiens

<400> SEQUENCE: 202
auaaagcuag auaaccgaaa gu                                           22

<210> SEQ ID NO 203
<211> LENGTH: 24
<212> TYPE: RNA
<213> ORGANISM: Homo sapiens

<400> SEQUENCE: 203
ucccugagac ccuuuaaccu guga                                         24

<210> SEQ ID NO 204
<211> LENGTH: 22
<212> TYPE: RNA
<213> ORGANISM: Homo sapiens

<400> SEQUENCE: 204
acaggugagg uucuugggag cc                                           22

<210> SEQ ID NO 205
<211> LENGTH: 22
<212> TYPE: RNA
<213> ORGANISM: Homo sapiens

<400> SEQUENCE: 205
ucacaaguca ggcucuuggg ac                                           22

<210> SEQ ID NO 206
```

```
<211> LENGTH: 21
<212> TYPE: RNA
<213> ORGANISM: Homo sapiens

<400> SEQUENCE: 206
cauuauuacu uuugguacgc g                                              21

<210> SEQ ID NO 207
<211> LENGTH: 22
<212> TYPE: RNA
<213> ORGANISM: Homo sapiens

<400> SEQUENCE: 207
ucguaccgug aguaauaaug cg                                             22

<210> SEQ ID NO 208
<211> LENGTH: 22
<212> TYPE: RNA
<213> ORGANISM: Homo sapiens

<400> SEQUENCE: 208
cugaagcuca gagggcucug au                                             22

<210> SEQ ID NO 209
<211> LENGTH: 22
<212> TYPE: RNA
<213> ORGANISM: Homo sapiens

<400> SEQUENCE: 209
ucggauccgu cugagcuugg cu                                             22

<210> SEQ ID NO 210
<211> LENGTH: 22
<212> TYPE: RNA
<213> ORGANISM: Homo sapiens

<400> SEQUENCE: 210
aagcccuuac cccaaaaagc au                                             22

<210> SEQ ID NO 211
<211> LENGTH: 22
<212> TYPE: RNA
<213> ORGANISM: Homo sapiens

<400> SEQUENCE: 211
ugugacuggu ugaccagagg gg                                             22

<210> SEQ ID NO 212
<211> LENGTH: 23
<212> TYPE: RNA
<213> ORGANISM: Homo sapiens

<400> SEQUENCE: 212
acuccauuug uuuugaugau gga                                            23

<210> SEQ ID NO 213
<211> LENGTH: 22
<212> TYPE: RNA
<213> ORGANISM: Homo sapiens

<400> SEQUENCE: 213
caucaucguc ucaaaugagu cu                                             22
```

```
<210> SEQ ID NO 214
<211> LENGTH: 22
<212> TYPE: RNA
<213> ORGANISM: Homo sapiens

<400> SEQUENCE: 214
gcuacuucac aacaccaggg cc                                              22

<210> SEQ ID NO 215
<211> LENGTH: 22
<212> TYPE: RNA
<213> ORGANISM: Homo sapiens

<400> SEQUENCE: 215
ugagaacuga auuccauggg uu                                              22

<210> SEQ ID NO 216
<211> LENGTH: 22
<212> TYPE: RNA
<213> ORGANISM: Homo sapiens

<400> SEQUENCE: 216
ccucugaaau ucaguucuuc ag                                              22

<210> SEQ ID NO 217
<211> LENGTH: 23
<212> TYPE: RNA
<213> ORGANISM: Homo sapiens

<400> SEQUENCE: 217
ucuggcuccg ugucuucacu ccc                                             23

<210> SEQ ID NO 218
<211> LENGTH: 21
<212> TYPE: RNA
<213> ORGANISM: Homo sapiens

<400> SEQUENCE: 218
agggagggac gggggcugug c                                               21

<210> SEQ ID NO 219
<211> LENGTH: 22
<212> TYPE: RNA
<213> ORGANISM: Homo sapiens

<400> SEQUENCE: 219
ucucccaacc cuuguaccag ug                                              22

<210> SEQ ID NO 220
<211> LENGTH: 22
<212> TYPE: RNA
<213> ORGANISM: Homo sapiens

<400> SEQUENCE: 220
cugguacagg ccuggggac ag                                               22

<210> SEQ ID NO 221
<211> LENGTH: 22
<212> TYPE: RNA
<213> ORGANISM: Homo sapiens

<400> SEQUENCE: 221
uagguuaucc guguugccuu cg                                              22
```

```
<210> SEQ ID NO 222
<211> LENGTH: 22
<212> TYPE: RNA
<213> ORGANISM: Homo sapiens

<400> SEQUENCE: 222
aaucauacac gguugaccua uu                                              22

<210> SEQ ID NO 223
<211> LENGTH: 22
<212> TYPE: RNA
<213> ORGANISM: Homo sapiens

<400> SEQUENCE: 223
uggacggaga acugauaagg gu                                              22

<210> SEQ ID NO 224
<211> LENGTH: 22
<212> TYPE: RNA
<213> ORGANISM: Homo sapiens

<400> SEQUENCE: 224
uggagagaaa ggcaguuccu ga                                              22

<210> SEQ ID NO 225
<211> LENGTH: 22
<212> TYPE: RNA
<213> ORGANISM: Homo sapiens

<400> SEQUENCE: 225
aggggcuggc uuuccucugg uc                                              22

<210> SEQ ID NO 226
<211> LENGTH: 22
<212> TYPE: RNA
<213> ORGANISM: Homo sapiens

<400> SEQUENCE: 226
caaagaauuc uccuuuuggg cu                                              22

<210> SEQ ID NO 227
<211> LENGTH: 22
<212> TYPE: RNA
<213> ORGANISM: Homo sapiens

<400> SEQUENCE: 227
gcccaaaggu gaauuuuuug gg                                              22

<210> SEQ ID NO 228
<211> LENGTH: 21
<212> TYPE: RNA
<213> ORGANISM: Homo sapiens

<400> SEQUENCE: 228
caucccuugc augguggagg g                                               21

<210> SEQ ID NO 229
<211> LENGTH: 21
<212> TYPE: RNA
<213> ORGANISM: Homo sapiens

<400> SEQUENCE: 229
cucccacaug caggguuugc a                                               21
```

<210> SEQ ID NO 230
<211> LENGTH: 22
<212> TYPE: RNA
<213> ORGANISM: Homo sapiens

<400> SEQUENCE: 230
ugauauguuu gauauauuag gu                                            22

<210> SEQ ID NO 231
<211> LENGTH: 22
<212> TYPE: RNA
<213> ORGANISM: Homo sapiens

<400> SEQUENCE: 231
ugggucuuug cgggcgagau ga                                            22

<210> SEQ ID NO 232
<211> LENGTH: 22
<212> TYPE: RNA
<213> ORGANISM: Homo sapiens

<400> SEQUENCE: 232
aacuggccua caaaguccca gu                                            22

<210> SEQ ID NO 233
<211> LENGTH: 22
<212> TYPE: RNA
<213> ORGANISM: Homo sapiens

<400> SEQUENCE: 233
uguaacagca acuccaugug ga                                            22

<210> SEQ ID NO 234
<211> LENGTH: 21
<212> TYPE: RNA
<213> ORGANISM: Homo sapiens

<400> SEQUENCE: 234
uagcagcaca gaaauauugg c                                             21

<210> SEQ ID NO 235
<211> LENGTH: 22
<212> TYPE: RNA
<213> ORGANISM: Homo sapiens

<400> SEQUENCE: 235
ccaauauugg cugugcugcu cc                                            22

<210> SEQ ID NO 236
<211> LENGTH: 22
<212> TYPE: RNA
<213> ORGANISM: Homo sapiens

<400> SEQUENCE: 236
uggaauguaa ggaagugugu gg                                            22

<210> SEQ ID NO 237
<211> LENGTH: 22
<212> TYPE: RNA
<213> ORGANISM: Homo sapiens

<400> SEQUENCE: 237

```
aaaagcuggg uugagagggc ga                                                22

<210> SEQ ID NO 238
<211> LENGTH: 22
<212> TYPE: RNA
<213> ORGANISM: Homo sapiens

<400> SEQUENCE: 238
cgucuuaccc agcaguguuu gg                                                22

<210> SEQ ID NO 239
<211> LENGTH: 23
<212> TYPE: RNA
<213> ORGANISM: Homo sapiens

<400> SEQUENCE: 239
uaauacugcc ggguaaugau gga                                               23

<210> SEQ ID NO 240
<211> LENGTH: 23
<212> TYPE: RNA
<213> ORGANISM: Homo sapiens

<400> SEQUENCE: 240
uuaaugcuaa ucgugauagg ggu                                               23

<210> SEQ ID NO 241
<211> LENGTH: 22
<212> TYPE: RNA
<213> ORGANISM: Homo sapiens

<400> SEQUENCE: 241
cuccuacaua uuagcauuaa ca                                                22

<210> SEQ ID NO 242
<211> LENGTH: 22
<212> TYPE: RNA
<213> ORGANISM: Homo sapiens

<400> SEQUENCE: 242 ccagugggge ugcuguuauc ug                                                22

<210> SEQ ID NO 243
<211> LENGTH: 21
<212> TYPE: RNA
<213> ORGANISM: Homo sapiens

<400> SEQUENCE: 243
uaaagugcug acagugcaga u                                                 21

<210> SEQ ID NO 244
<211> LENGTH: 22
<212> TYPE: RNA
<213> ORGANISM: Homo sapiens

<400> SEQUENCE: 244
ccgcacugug gguacuugcu gc                                                22

<210> SEQ ID NO 245
<211> LENGTH: 22
<212> TYPE: RNA
<213> ORGANISM: Homo sapiens

<400> SEQUENCE: 245
```
ugaccgauuu cuccuggugu uc                                                    22

<210> SEQ ID NO 246
<211> LENGTH: 22
<212> TYPE: RNA
<213> ORGANISM: Homo sapiens

<400> SEQUENCE: 246
uagcaccauu ugaaaucggu ua                                                    22

<210> SEQ ID NO 247
<211> LENGTH: 22
<212> TYPE: RNA
<213> ORGANISM: Homo sapiens

<400> SEQUENCE: 247
cugggagagg guuguuuacu cc                                                    22

<210> SEQ ID NO 248
<211> LENGTH: 22
<212> TYPE: RNA
<213> ORGANISM: Homo sapiens

<400> SEQUENCE: 248
caucuuaccg gacagugcug ga                                                    22

<210> SEQ ID NO 249
<211> LENGTH: 22
<212> TYPE: RNA
<213> ORGANISM: Homo sapiens

<400> SEQUENCE: 249
uaacacuguc ugguaacgau gu                                                    22

<210> SEQ ID NO 250
<211> LENGTH: 23
<212> TYPE: RNA
<213> ORGANISM: Homo sapiens

<400> SEQUENCE: 250
acuuaaacgu ggauguacuu gcu                                                   23

<210> SEQ ID NO 251
<211> LENGTH: 23
<212> TYPE: RNA
<213> ORGANISM: Homo sapiens

<400> SEQUENCE: 251
uaagugcuuc cauguuuugg uga                                                   23

<210> SEQ ID NO 252
<211> LENGTH: 22
<212> TYPE: RNA
<213> ORGANISM: Homo sapiens

<400> SEQUENCE: 252
agaauugugg cuggacaucu gu                                                    22

<210> SEQ ID NO 253
<211> LENGTH: 23
<212> TYPE: RNA
<213> ORGANISM: Homo sapiens

```
<400> SEQUENCE: 253
uaggcagugu cauuagcuga uug                                    23

<210> SEQ ID NO 254
<211> LENGTH: 22
<212> TYPE: RNA
<213> ORGANISM: Homo sapiens

<400> SEQUENCE: 254
caaucacuaa cuccacugcc au                                     22

<210> SEQ ID NO 255
<211> LENGTH: 23
<212> TYPE: RNA
<213> ORGANISM: Homo sapiens

<400> SEQUENCE: 255
aggcagugua guuagcugau ugc                                    23

<210> SEQ ID NO 256
<211> LENGTH: 22
<212> TYPE: RNA
<213> ORGANISM: Homo sapiens

<400> SEQUENCE: 256
aaucacuaac cacacggcca gg                                     22

<210> SEQ ID NO 257
<211> LENGTH: 22
<212> TYPE: RNA
<213> ORGANISM: Homo sapiens

<400> SEQUENCE: 257
ugguuuaccg ucccacauac au                                     22

<210> SEQ ID NO 258
<211> LENGTH: 22
<212> TYPE: RNA
<213> ORGANISM: Homo sapiens

<400> SEQUENCE: 258 uauguggau gguaaaccgc uu                                      22

<210> SEQ ID NO 259
<211> LENGTH: 23
<212> TYPE: RNA
<213> ORGANISM: Homo sapiens

<400> SEQUENCE: 259
cagugcaaua guauugucaa agc                                    23

<210> SEQ ID NO 260
<211> LENGTH: 22
<212> TYPE: RNA
<213> ORGANISM: Homo sapiens

<400> SEQUENCE: 260
cacccguaga accgaccuug cg                                     22

<210> SEQ ID NO 261
<211> LENGTH: 22
<212> TYPE: RNA
<213> ORGANISM: Homo sapiens
```

```
<400> SEQUENCE: 261
caagcucgug ucugugdgguc cg                                           22

<210> SEQ ID NO 262
<211> LENGTH: 21
<212> TYPE: RNA
<213> ORGANISM: Homo sapiens

<400> SEQUENCE: 262 agggccccccc cucaauccug u                                            21

<210> SEQ ID NO 263
<211> LENGTH: 22
<212> TYPE: RNA
<213> ORGANISM: Homo sapiens

<400> SEQUENCE: 263
gagdguuggg uggaggcucu cc                                            22

<210> SEQ ID NO 264
<211> LENGTH: 21
<212> TYPE: RNA
<213> ORGANISM: Homo sapiens

<400> SEQUENCE: 264
acucuuuccc uguugcacua c                                             21

<210> SEQ ID NO 265
<211> LENGTH: 22
<212> TYPE: RNA
<213> ORGANISM: Homo sapiens

<400> SEQUENCE: 265
cagugcaaug augaaagggc au                                            22

<210> SEQ ID NO 266
<211> LENGTH: 22
<212> TYPE: RNA
<213> ORGANISM: Homo sapiens

<400> SEQUENCE: 266
uguaaacauc cuugacugga ag                                            22

<210> SEQ ID NO 267
<211> LENGTH: 22
<212> TYPE: RNA
<213> ORGANISM: Homo sapiens

<400> SEQUENCE: 267
cuuucagucg gauguuuaca gc                                            22

<210> SEQ ID NO 268
<211> LENGTH: 22
<212> TYPE: RNA
<213> ORGANISM: Homo sapiens

<400> SEQUENCE: 268
ccuauucuug auuacuuguu uc                                            22

<210> SEQ ID NO 269
<211> LENGTH: 22
<212> TYPE: RNA
```

```
<213> ORGANISM: Homo sapiens

<400> SEQUENCE: 269
uuaucagaau cuccaggggu ac                                            22

<210> SEQ ID NO 270
<211> LENGTH: 23
<212> TYPE: RNA
<213> ORGANISM: Homo sapiens

<400> SEQUENCE: 270 uccccaggu gugauucuga uuu                                            23

<210> SEQ ID NO 271
<211> LENGTH: 24
<212> TYPE: RNA
<213> ORGANISM: Homo sapiens

<400> SEQUENCE: 271
aauccuugga accuaggugu gagu                                          24

<210> SEQ ID NO 272
<211> LENGTH: 22
<212> TYPE: RNA
<213> ORGANISM: Homo sapiens

<400> SEQUENCE: 272
aacacaccua uucaaggauu ca                                            22

<210> SEQ ID NO 273
<211> LENGTH: 22
<212> TYPE: RNA
<213> ORGANISM: Homo sapiens

<400> SEQUENCE: 273
cggguggauc acgaugcaau uu                                            22

<210> SEQ ID NO 274
<211> LENGTH: 22
<212> TYPE: RNA
<213> ORGANISM: Homo sapiens

<400> SEQUENCE: 274
aauugcacgg uauccaucug ua                                            22

<210> SEQ ID NO 275
<211> LENGTH: 22
<212> TYPE: RNA
<213> ORGANISM: Homo sapiens

<400> SEQUENCE: 275
uaaugcCCCu aaaaauccuu au                                            22

<210> SEQ ID NO 276
<211> LENGTH: 22
<212> TYPE: RNA
<213> ORGANISM: Homo sapiens

<400> SEQUENCE: 276
agggacuuuc aggggcagcu gu                                            22

<210> SEQ ID NO 277
<211> LENGTH: 22
```

<212> TYPE: RNA
<213> ORGANISM: Homo sapiens

<400> SEQUENCE: 277
acuuuaacau ggaagugcuu uc                                    22

<210> SEQ ID NO 278
<211> LENGTH: 23
<212> TYPE: RNA
<213> ORGANISM: Homo sapiens

<400> SEQUENCE: 278
uaagugcuuc cauguuuuag uag                                   23

<210> SEQ ID NO 279
<211> LENGTH: 22
<212> TYPE: RNA
<213> ORGANISM: Homo sapiens

<400> SEQUENCE: 279
uuuaacaugg ggguaccugc ug                                    22

<210> SEQ ID NO 280
<211> LENGTH: 23
<212> TYPE: RNA
<213> ORGANISM: Homo sapiens

<400> SEQUENCE: 280
uaagugcuuc cauguuucag ugg                                   23

<210> SEQ ID NO 281
<211> LENGTH: 22
<212> TYPE: RNA
<213> ORGANISM: Homo sapiens

<400> SEQUENCE: 281
acuuuaacau ggaggcacuu gc                                    22

<210> SEQ ID NO 282
<211> LENGTH: 23
<212> TYPE: RNA
<213> ORGANISM: Homo sapiens

<400> SEQUENCE: 282
uaagugcuuc cauguuugag ugu                                   23

<210> SEQ ID NO 283
<211> LENGTH: 22
<212> TYPE: RNA
<213> ORGANISM: Homo sapiens

<400> SEQUENCE: 283
acuguugcua auaugcaacu cu                                    22

<210> SEQ ID NO 284
<211> LENGTH: 22
<212> TYPE: RNA
<213> ORGANISM: Homo sapiens

<400> SEQUENCE: 284
aauugcacuu uagcaauggu ga                                    22

<210> SEQ ID NO 285

```
<211> LENGTH: 21
<212> TYPE: RNA
<213> ORGANISM: Homo sapiens

<400> SEQUENCE: 285
aacauagagg aaauuccacg u                                             21

<210> SEQ ID NO 286
<211> LENGTH: 22
<212> TYPE: RNA
<213> ORGANISM: Homo sapiens

<400> SEQUENCE: 286
agaucgaccg uguuauauuc gc                                            22

<210> SEQ ID NO 287
<211> LENGTH: 21
<212> TYPE: RNA
<213> ORGANISM: Homo sapiens

<400> SEQUENCE: 287
aauaauacau gguugaucuu u                                             21

<210> SEQ ID NO 288
<211> LENGTH: 22
<212> TYPE: RNA
<213> ORGANISM: Homo sapiens

<400> SEQUENCE: 288
gccugcuggg guggaaccug gu                                            22

<210> SEQ ID NO 289
<211> LENGTH: 20
<212> TYPE: RNA
<213> ORGANISM: Homo sapiens

<400> SEQUENCE: 289
acucaaacug uggggggcacu                                              20

<210> SEQ ID NO 290
<211> LENGTH: 23
<212> TYPE: RNA
<213> ORGANISM: Homo sapiens

<400> SEQUENCE: 290
aagugccgcc aucuuugag ugu                                            23

<210> SEQ ID NO 291
<211> LENGTH: 23
<212> TYPE: RNA
<213> ORGANISM: Homo sapiens

<400> SEQUENCE: 291
aaagugcugc gacauuugag cgu                                           23

<210> SEQ ID NO 292
<211> LENGTH: 22
<212> TYPE: RNA
<213> ORGANISM: Homo sapiens

<400> SEQUENCE: 292
acucaaaaug ggggcgcuuu cc                                            22
```

-continued

```
<210> SEQ ID NO 293
<211> LENGTH: 23
<212> TYPE: RNA
<213> ORGANISM: Homo sapiens

<400> SEQUENCE: 293
gaagugcuuc gauuuugggg ugu                                              23

<210> SEQ ID NO 294
<211> LENGTH: 22
<212> TYPE: RNA
<213> ORGANISM: Homo sapiens

<400> SEQUENCE: 294
uuauaauaca accugauaag ug                                               22

<210> SEQ ID NO 295
<211> LENGTH: 22
<212> TYPE: RNA
<213> ORGANISM: Homo sapiens

<400> SEQUENCE: 295
cuuaucagau uguauuguaa uu                                               22

<210> SEQ ID NO 296
<211> LENGTH: 22
<212> TYPE: RNA
<213> ORGANISM: Homo sapiens

<400> SEQUENCE: 296
uuuguucguu cggcucgcgu ga                                               22

<210> SEQ ID NO 297
<211> LENGTH: 22
<212> TYPE: RNA
<213> ORGANISM: Homo sapiens

<400> SEQUENCE: 297
guagauucuc cuucuaugag ua                                               22

<210> SEQ ID NO 298
<211> LENGTH: 21
<212> TYPE: RNA
<213> ORGANISM: Homo sapiens

<400> SEQUENCE: 298
aucauagagg aaaauccacg u                                                21

<210> SEQ ID NO 299
<211> LENGTH: 22
<212> TYPE: RNA
<213> ORGANISM: Homo sapiens

<400> SEQUENCE: 299
agagguugcc cuuggugaau uc                                               22

<210> SEQ ID NO 300
<211> LENGTH: 22
<212> TYPE: RNA
<213> ORGANISM: Homo sapiens

<400> SEQUENCE: 300
aucacacaaa ggcaacuuuu gu                                               22
```

```
<210> SEQ ID NO 301
<211> LENGTH: 22
<212> TYPE: RNA
<213> ORGANISM: Homo sapiens

<400> SEQUENCE: 301
cuccugacuc cagguccugu gu                                              22

<210> SEQ ID NO 302
<211> LENGTH: 21
<212> TYPE: RNA
<213> ORGANISM: Homo sapiens

<400> SEQUENCE: 302
acuggacuug gagucagaag g                                               21

<210> SEQ ID NO 303
<211> LENGTH: 21
<212> TYPE: RNA
<213> ORGANISM: Homo sapiens

<400> SEQUENCE: 303
ugguagacua uggaacguag g                                               21

<210> SEQ ID NO 304
<211> LENGTH: 22
<212> TYPE: RNA
<213> ORGANISM: Homo sapiens

<400> SEQUENCE: 304
uauguaacau gguccacuaa cu                                              22

<210> SEQ ID NO 305
<211> LENGTH: 22
<212> TYPE: RNA
<213> ORGANISM: Homo sapiens

<400> SEQUENCE: 305
ugguugacca uagaacaugc gc                                              22

<210> SEQ ID NO 306
<211> LENGTH: 22
<212> TYPE: RNA
<213> ORGANISM: Homo sapiens

<400> SEQUENCE: 306
uauguaauau gguccacauc uu                                              22

<210> SEQ ID NO 307
<211> LENGTH: 22
<212> TYPE: RNA
<213> ORGANISM: Homo sapiens

<400> SEQUENCE: 307
uauacaaggg caagcucucu gu                                              22

<210> SEQ ID NO 308
<211> LENGTH: 22
<212> TYPE: RNA
<213> ORGANISM: Homo sapiens

<400> SEQUENCE: 308
gaaguuguuc gugguggauu cg                                              22
```

```
<210> SEQ ID NO 309
<211> LENGTH: 22
<212> TYPE: RNA
<213> ORGANISM: Homo sapiens

<400> SEQUENCE: 309
agaucagaag gugauugugg cu                                                  22

<210> SEQ ID NO 310
<211> LENGTH: 22
<212> TYPE: RNA
<213> ORGANISM: Homo sapiens

<400> SEQUENCE: 310
uuauaaagca augagacuga uu                                                  22

<210> SEQ ID NO 311
<211> LENGTH: 22
<212> TYPE: RNA
<213> ORGANISM: Homo sapiens

<400> SEQUENCE: 311
uccgucucag uuacuuuaua gc                                                  22

<210> SEQ ID NO 312
<211> LENGTH: 22
<212> TYPE: RNA
<213> ORGANISM: Homo sapiens

<400> SEQUENCE: 312
ucucugggcc ugugucuuag gc                                                  22

<210> SEQ ID NO 313
<211> LENGTH: 23
<212> TYPE: RNA
<213> ORGANISM: Homo sapiens

<400> SEQUENCE: 313
gcaaagcaca cggccugcag aga                                                 23

<210> SEQ ID NO 314
<211> LENGTH: 22
<212> TYPE: RNA
<213> ORGANISM: Homo sapiens

<400> SEQUENCE: 314
cuggcccucu cugcccuucc gu                                                  22

<210> SEQ ID NO 315
<211> LENGTH: 21
<212> TYPE: RNA
<213> ORGANISM: Homo sapiens

<400> SEQUENCE: 315
aggggugcua ucugugauug a                                                   21

<210> SEQ ID NO 316
<211> LENGTH: 23
<212> TYPE: RNA
<213> ORGANISM: Homo sapiens

<400> SEQUENCE: 316
```
ucucacacag aaaucgcacc cgu                                             23

<210> SEQ ID NO 317
<211> LENGTH: 21
<212> TYPE: RNA
<213> ORGANISM: Homo sapiens

<400> SEQUENCE: 317
gaacggcuuc auacaggagu u                                               21

<210> SEQ ID NO 318
<211> LENGTH: 22
<212> TYPE: RNA
<213> ORGANISM: Homo sapiens

<400> SEQUENCE: 318
cuccuauaug augccuuucu uc                                              22

<210> SEQ ID NO 319
<211> LENGTH: 22
<212> TYPE: RNA
<213> ORGANISM: Homo sapiens

<400> SEQUENCE: 319
aggugguccg uggcgcguuc gc                                              22

<210> SEQ ID NO 320
<211> LENGTH: 21
<212> TYPE: RNA
<213> ORGANISM: Homo sapiens

<400> SEQUENCE: 320
cacauuacac ggucgaccuc u                                               21

<210> SEQ ID NO 321
<211> LENGTH: 20
<212> TYPE: RNA
<213> ORGANISM: Homo sapiens

<400> SEQUENCE: 321
ccucugggcc cuuccuccag                                                 20

<210> SEQ ID NO 322
<211> LENGTH: 21
<212> TYPE: RNA
<213> ORGANISM: Homo sapiens

<400> SEQUENCE: 322
ucgaggagcu cacagucuag u                                               21

<210> SEQ ID NO 323
<211> LENGTH: 21
<212> TYPE: RNA
<213> ORGANISM: Homo sapiens

<400> SEQUENCE: 323
cuagacugaa gcuccuugag g                                               21

<210> SEQ ID NO 324
<211> LENGTH: 23
<212> TYPE: RNA
<213> ORGANISM: Homo sapiens

<400> SEQUENCE: 324
uauggcuuuu cauuccuaug uga                                              23

<210> SEQ ID NO 325
<211> LENGTH: 22
<212> TYPE: RNA
<213> ORGANISM: Homo sapiens

<400> SEQUENCE: 325
auguagggcu aaaagccaug gg                                               22

<210> SEQ ID NO 326
<211> LENGTH: 22
<212> TYPE: RNA
<213> ORGANISM: Homo sapiens

<400> SEQUENCE: 326
aaguucuguu auacacucag gc                                               22

<210> SEQ ID NO 327
<211> LENGTH: 22
<212> TYPE: RNA
<213> ORGANISM: Homo sapiens

<400> SEQUENCE: 327
ucagugcauc acagaacuuu gu                                               22

<210> SEQ ID NO 328
<211> LENGTH: 22
<212> TYPE: RNA
<213> ORGANISM: Homo sapiens

<400> SEQUENCE: 328
cuagguaugg ucccagggau cc                                               22

<210> SEQ ID NO 329
<211> LENGTH: 21
<212> TYPE: RNA
<213> ORGANISM: Homo sapiens

<400> SEQUENCE: 329
gccccugggc cuauccuaga a                                                21

<210> SEQ ID NO 330
<211> LENGTH: 23
<212> TYPE: RNA
<213> ORGANISM: Homo sapiens

<400> SEQUENCE: 330 cgcaucccu agggcauugg ugu                                               23

<210> SEQ ID NO 331
<211> LENGTH: 20
<212> TYPE: RNA
<213> ORGANISM: Homo sapiens

<400> SEQUENCE: 331
acugccccag gugcugcugg                                                  20

<210> SEQ ID NO 332
<211> LENGTH: 22
<212> TYPE: RNA
<213> ORGANISM: Homo sapiens

```
<400> SEQUENCE: 332
aacaauaucc uggugcugag ug                                    22

<210> SEQ ID NO 333
<211> LENGTH: 22
<212> TYPE: RNA
<213> ORGANISM: Homo sapiens

<400> SEQUENCE: 333
uccagcauca gugauuugu ug                                     22

<210> SEQ ID NO 334
<211> LENGTH: 23
<212> TYPE: RNA
<213> ORGANISM: Homo sapiens

<400> SEQUENCE: 334
ucccuguccu ccaggagcuc acg                                   23

<210> SEQ ID NO 335
<211> LENGTH: 23
<212> TYPE: RNA
<213> ORGANISM: Homo sapiens

<400> SEQUENCE: 335
ugagcgccuc gacgacagag ccg                                   23

<210> SEQ ID NO 336
<211> LENGTH: 23
<212> TYPE: RNA
<213> ORGANISM: Homo sapiens

<400> SEQUENCE: 336
ucaagagcaa uaacgaaaaa ugu                                   23

<210> SEQ ID NO 337
<211> LENGTH: 22
<212> TYPE: RNA
<213> ORGANISM: Homo sapiens

<400> SEQUENCE: 337
uuuuucauua uugcuccuga cc                                    22

<210> SEQ ID NO 338
<211> LENGTH: 22
<212> TYPE: RNA
<213> ORGANISM: Homo sapiens

<400> SEQUENCE: 338
uuuggucccc uucaaccagc ua                                    22

<210> SEQ ID NO 339
<211> LENGTH: 23
<212> TYPE: RNA
<213> ORGANISM: Homo sapiens

<400> SEQUENCE: 339
ccuaguaggu guccaguaag ugu                                   23

<210> SEQ ID NO 340
<211> LENGTH: 22
<212> TYPE: RNA
<213> ORGANISM: Homo sapiens
```

```
<400> SEQUENCE: 340
gcugacuccu aguccagggc uc                                        22

<210> SEQ ID NO 341
<211> LENGTH: 23
<212> TYPE: RNA
<213> ORGANISM: Homo sapiens

<400> SEQUENCE: 341
ugucugcccg caugccugcc ucu                                       23

<210> SEQ ID NO 342
<211> LENGTH: 20
<212> TYPE: RNA
<213> ORGANISM: Homo sapiens

<400> SEQUENCE: 342 auccuagaa auuguucaua                                            20

<210> SEQ ID NO 343
<211> LENGTH: 22
<212> TYPE: RNA
<213> ORGANISM: Homo sapiens

<400> SEQUENCE: 343
uagguaguuu ccuguuguug gg                                        22

<210> SEQ ID NO 344
<211> LENGTH: 22
<212> TYPE: RNA
<213> ORGANISM: Homo sapiens

<400> SEQUENCE: 344
ucgacagcac gacacugccu uc                                        22

<210> SEQ ID NO 345
<211> LENGTH: 22
<212> TYPE: RNA
<213> ORGANISM: Homo sapiens

<400> SEQUENCE: 345
acuggacuua gggucagaag gc                                        22

<210> SEQ ID NO 346
<211> LENGTH: 23
<212> TYPE: RNA
<213> ORGANISM: Homo sapiens

<400> SEQUENCE: 346
ugaggggcag agagcgagac uuu                                       23

<210> SEQ ID NO 347
<211> LENGTH: 23
<212> TYPE: RNA
<213> ORGANISM: Homo sapiens

<400> SEQUENCE: 347
agcucggucu gaggccccuc agu                                       23

<210> SEQ ID NO 348
<211> LENGTH: 22
<212> TYPE: RNA
```

```
<213> ORGANISM: Homo sapiens

<400> SEQUENCE: 348
cagcagcaau ucauguuuug aa                                              22

<210> SEQ ID NO 349
<211> LENGTH: 21
<212> TYPE: RNA
<213> ORGANISM: Homo sapiens

<400> SEQUENCE: 349
caaaacguga ggcgcugcua u                                               21

<210> SEQ ID NO 350
<211> LENGTH: 23
<212> TYPE: RNA
<213> ORGANISM: Homo sapiens

<400> SEQUENCE: 350
aaugacacga ucacucccgu uga                                             23

<210> SEQ ID NO 351
<211> LENGTH: 22
<212> TYPE: RNA
<213> ORGANISM: Homo sapiens

<400> SEQUENCE: 351
aucgggaaug ucguguccgc cc                                              22

<210> SEQ ID NO 352
<211> LENGTH: 23
<212> TYPE: RNA
<213> ORGANISM: Homo sapiens

<400> SEQUENCE: 352
uaaggugcau cuagugcagu uag                                             23

<210> SEQ ID NO 353
<211> LENGTH: 22
<212> TYPE: RNA
<213> ORGANISM: Homo sapiens

<400> SEQUENCE: 353
ugcccuaaau gccccuucug gc                                              22

<210> SEQ ID NO 354
<211> LENGTH: 23
<212> TYPE: RNA
<213> ORGANISM: Homo sapiens

<400> SEQUENCE: 354
caaagugcuc auagugcagg uag                                             23

<210> SEQ ID NO 355
<211> LENGTH: 22
<212> TYPE: RNA
<213> ORGANISM: Homo sapiens

<400> SEQUENCE: 355
acuguaguau gggcacuucc ag                                              22

<210> SEQ ID NO 356
<211> LENGTH: 22
```

<212> TYPE: RNA
<213> ORGANISM: Homo sapiens

<400> SEQUENCE: 356
uugcauaugu aggauguccc au                                          22

<210> SEQ ID NO 357
<211> LENGTH: 22
<212> TYPE: RNA
<213> ORGANISM: Homo sapiens

<400> SEQUENCE: 357
uaauacuguc ugguaaaacc gu                                          22

<210> SEQ ID NO 358
<211> LENGTH: 22
<212> TYPE: RNA
<213> ORGANISM: Homo sapiens

<400> SEQUENCE: 358
uggcagugua uuguuagcug gu                                          22

<210> SEQ ID NO 359
<211> LENGTH: 22
<212> TYPE: RNA
<213> ORGANISM: Homo sapiens

<400> SEQUENCE: 359
uuuugcgaug uguuccuaau au                                          22

<210> SEQ ID NO 360
<211> LENGTH: 21
<212> TYPE: RNA
<213> ORGANISM: Homo sapiens

<400> SEQUENCE: 360
ugucuugcag gccgucaugc a                                           21

<210> SEQ ID NO 361
<211> LENGTH: 22
<212> TYPE: RNA
<213> ORGANISM: Homo sapiens

<400> SEQUENCE: 361
caggucgucu ugcagggcuu cu                                          22

<210> SEQ ID NO 362
<211> LENGTH: 22
<212> TYPE: RNA
<213> ORGANISM: Homo sapiens

<400> SEQUENCE: 362
aucaugaugg gcuccucggu gu                                          22

<210> SEQ ID NO 363
<211> LENGTH: 22
<212> TYPE: RNA
<213> ORGANISM: Homo sapiens

<400> SEQUENCE: 363
aacacaccug guuaaccucu uu                                          22

<210> SEQ ID NO 364

```
<211> LENGTH: 22
<212> TYPE: RNA
<213> ORGANISM: Homo sapiens

<400> SEQUENCE: 364
aaaccguuac cauuacugag uu                                              22

<210> SEQ ID NO 365
<211> LENGTH: 22
<212> TYPE: RNA
<213> ORGANISM: Homo sapiens

<400> SEQUENCE: 365
aacuguuugc agaggaaacu ga                                              22

<210> SEQ ID NO 366
<211> LENGTH: 22
<212> TYPE: RNA
<213> ORGANISM: Homo sapiens

<400> SEQUENCE: 366
cucaucugca aagaaguaag ug                                              22

<210> SEQ ID NO 367
<211> LENGTH: 23
<212> TYPE: RNA
<213> ORGANISM: Homo sapiens

<400> SEQUENCE: 367
agguuacccg agcaacuuug cau                                             23

<210> SEQ ID NO 368
<211> LENGTH: 22
<212> TYPE: RNA
<213> ORGANISM: Homo sapiens

<400> SEQUENCE: 368
gaauguugcu cggugaaccc cu                                              22

<210> SEQ ID NO 369
<211> LENGTH: 23
<212> TYPE: RNA
<213> ORGANISM: Homo sapiens

<400> SEQUENCE: 369
acuucaccug guccacuagc cgu                                             23

<210> SEQ ID NO 370
<211> LENGTH: 21
<212> TYPE: RNA
<213> ORGANISM: Homo sapiens

<400> SEQUENCE: 370
aauauaacac agauggccug u                                               21

<210> SEQ ID NO 371
<211> LENGTH: 22
<212> TYPE: RNA
<213> ORGANISM: Homo sapiens

<400> SEQUENCE: 371
aucauagagg aaaauccaug uu                                              22
```

```
<210> SEQ ID NO 372
<211> LENGTH: 22
<212> TYPE: RNA
<213> ORGANISM: Homo sapiens

<400> SEQUENCE: 372
aagacgggag gaaagaaggg ag                                              22

<210> SEQ ID NO 373
<211> LENGTH: 21
<212> TYPE: RNA
<213> ORGANISM: Homo sapiens

<400> SEQUENCE: 373
ucacuccucu ccucccgucu u                                               21

<210> SEQ ID NO 374
<211> LENGTH: 22
<212> TYPE: RNA
<213> ORGANISM: Homo sapiens

<400> SEQUENCE: 374
ucaggcucag uccccucccg au                                              22

<210> SEQ ID NO 375
<211> LENGTH: 22
<212> TYPE: RNA
<213> ORGANISM: Homo sapiens

<400> SEQUENCE: 375
agaggcuggc cgugaugaau uc                                              22

<210> SEQ ID NO 376
<211> LENGTH: 22
<212> TYPE: RNA
<213> ORGANISM: Homo sapiens

<400> SEQUENCE: 376
gucauacacg gcucuccucu cu                                              22

<210> SEQ ID NO 377
<211> LENGTH: 22
<212> TYPE: RNA
<213> ORGANISM: Homo sapiens

<400> SEQUENCE: 377
uccuguacug agcugccccg ag                                              22

<210> SEQ ID NO 378
<211> LENGTH: 21
<212> TYPE: RNA
<213> ORGANISM: Homo sapiens

<400> SEQUENCE: 378
cggggcagcu caguacagga u                                               21

<210> SEQ ID NO 379
<211> LENGTH: 22
<212> TYPE: RNA
<213> ORGANISM: Homo sapiens

<400> SEQUENCE: 379
aaucauacag ggacauccag uu                                              22
```

```
<210> SEQ ID NO 380
<211> LENGTH: 21
<212> TYPE: RNA
<213> ORGANISM: Homo sapiens

<400> SEQUENCE: 380
cccagauaau ggcacucuca a                                              21

<210> SEQ ID NO 381
<211> LENGTH: 21
<212> TYPE: RNA
<213> ORGANISM: Homo sapiens

<400> SEQUENCE: 381
uugaaaggcu auuucuuggu c                                              21

<210> SEQ ID NO 382
<211> LENGTH: 22
<212> TYPE: RNA
<213> ORGANISM: Homo sapiens

<400> SEQUENCE: 382
gugacaucac auauacggca gc                                             22

<210> SEQ ID NO 383
<211> LENGTH: 20
<212> TYPE: RNA
<213> ORGANISM: Homo sapiens

<400> SEQUENCE: 383
ccauggaucu ccaggugggu                                                20

<210> SEQ ID NO 384
<211> LENGTH: 22
<212> TYPE: RNA
<213> ORGANISM: Homo sapiens

<400> SEQUENCE: 384
caaccuggag gacuccaugc ug                                             22

<210> SEQ ID NO 385
<211> LENGTH: 22
<212> TYPE: RNA
<213> ORGANISM: Homo sapiens

<400> SEQUENCE: 385 agugggggaac ccuuccauga gg                                            22

<210> SEQ ID NO 386
<211> LENGTH: 22
<212> TYPE: RNA
<213> ORGANISM: Homo sapiens

<400> SEQUENCE: 386
cuuaugcaag auucccuucu ac                                             22

<210> SEQ ID NO 387
<211> LENGTH: 21
<212> TYPE: RNA
<213> ORGANISM: Homo sapiens

<400> SEQUENCE: 387
gugucuuuug cucugcaguc a                                              21
```

<210> SEQ ID NO 388
<211> LENGTH: 22
<212> TYPE: RNA
<213> ORGANISM: Homo sapiens

<400> SEQUENCE: 388
ugagaacuga auuccauagg cu                                                22

<210> SEQ ID NO 389
<211> LENGTH: 22
<212> TYPE: RNA
<213> ORGANISM: Homo sapiens

<400> SEQUENCE: 389
ugcccugugg acucaguucu gg                                                22

<210> SEQ ID NO 390
<211> LENGTH: 22
<212> TYPE: RNA
<213> ORGANISM: Homo sapiens

<400> SEQUENCE: 390
uuccuaugca uauacuucuu ug                                                22

<210> SEQ ID NO 391
<211> LENGTH: 20
<212> TYPE: RNA
<213> ORGANISM: Homo sapiens

<400> SEQUENCE: 391
agagguauag ggcaugggaa                                                   20

<210> SEQ ID NO 392
<211> LENGTH: 23
<212> TYPE: RNA
<213> ORGANISM: Homo sapiens

<400> SEQUENCE: 392
aggaccugcg ggacaagauu cuu                                               23

<210> SEQ ID NO 393
<211> LENGTH: 22
<212> TYPE: RNA
<213> ORGANISM: Homo sapiens

<400> SEQUENCE: 393
uuguacaugg uaggcuuuca uu                                                22

<210> SEQ ID NO 394
<211> LENGTH: 22
<212> TYPE: RNA
<213> ORGANISM: Homo sapiens

<400> SEQUENCE: 394
ugaaggucua cugugugcca gg                                                22

<210> SEQ ID NO 395
<211> LENGTH: 23
<212> TYPE: RNA
<213> ORGANISM: Homo sapiens

<400> SEQUENCE: 395

```
ucuuggagua ggucauuggg ugg                                           23

<210> SEQ ID NO 396
<211> LENGTH: 21
<212> TYPE: RNA
<213> ORGANISM: Homo sapiens

<400> SEQUENCE: 396
cuggauggcu ccuccauguc u                                             21

<210> SEQ ID NO 397
<211> LENGTH: 22
<212> TYPE: RNA
<213> ORGANISM: Homo sapiens

<400> SEQUENCE: 397
ugaaacauac acgggaaacc uc                                            22

<210> SEQ ID NO 398
<211> LENGTH: 22
<212> TYPE: RNA
<213> ORGANISM: Homo sapiens

<400> SEQUENCE: 398
aaacaaacau ggugcacuuc uu                                            22

<210> SEQ ID NO 399
<211> LENGTH: 22
<212> TYPE: RNA
<213> ORGANISM: Homo sapiens

<400> SEQUENCE: 399
ugaguauuac auggccaauc uc                                            22

<210> SEQ ID NO 400
<211> LENGTH: 22
<212> TYPE: RNA
<213> ORGANISM: Homo sapiens

<400> SEQUENCE: 400
cgggguuuug agggcgagau ga                                            22

<210> SEQ ID NO 401
<211> LENGTH: 22
<212> TYPE: RNA
<213> ORGANISM: Homo sapiens

<400> SEQUENCE: 401
aacuggcccu caaagucccg cu                                            22

<210> SEQ ID NO 402
<211> LENGTH: 21
<212> TYPE: RNA
<213> ORGANISM: Homo sapiens

<400> SEQUENCE: 402
cagcagcaca cuguggutug u                                             21

<210> SEQ ID NO 403
<211> LENGTH: 22
<212> TYPE: RNA
<213> ORGANISM: Homo sapiens

<400> SEQUENCE: 403
```

```
caaaccacac uguguguuua ga                                                      22

<210> SEQ ID NO 404
<211> LENGTH: 23
<212> TYPE: RNA
<213> ORGANISM: Homo sapiens

<400> SEQUENCE: 404
aacauucauu guugucggug ggu                                                     23

<210> SEQ ID NO 405
<211> LENGTH: 23
<212> TYPE: RNA
<213> ORGANISM: Homo sapiens

<400> SEQUENCE: 405
cacucagccu ugagggcacu uuc                                                     23

<210> SEQ ID NO 406
<211> LENGTH: 22
<212> TYPE: RNA
<213> ORGANISM: Homo sapiens

<400> SEQUENCE: 406
aagugcuguc auagcugagg uc                                                      22

<210> SEQ ID NO 407
<211> LENGTH: 23
<212> TYPE: RNA
<213> ORGANISM: Homo sapiens

<400> SEQUENCE: 407
uuucaagcca gggggcguuu uuc                                                     23

<210> SEQ ID NO 408
<211> LENGTH: 21
<212> TYPE: RNA
<213> ORGANISM: Homo sapiens

<400> SEQUENCE: 408
aaagugcuuc cuuuuugagg g                                                       21

<210> SEQ ID NO 409
<211> LENGTH: 24
<212> TYPE: RNA
<213> ORGANISM: Homo sapiens

<400> SEQUENCE: 409
uucuccaaaa gaaagcacuu ucug                                                    24

<210> SEQ ID NO 410
<211> LENGTH: 22
<212> TYPE: RNA
<213> ORGANISM: Homo sapiens

<400> SEQUENCE: 410
gagugccuuc uuuuggagcg uu                                                      22

<210> SEQ ID NO 411
<211> LENGTH: 22
<212> TYPE: RNA
<213> ORGANISM: Homo sapiens
```

```
<400> SEQUENCE: 411
uucuccaaaa gggagcacuu uc                                        22

<210> SEQ ID NO 412
<211> LENGTH: 22
<212> TYPE: RNA
<213> ORGANISM: Homo sapiens

<400> SEQUENCE: 412
aagugccucc uuuuagagug uu                                        22

<210> SEQ ID NO 413
<211> LENGTH: 22
<212> TYPE: RNA
<213> ORGANISM: Homo sapiens

<400> SEQUENCE: 413
aagugcuucc uuuuagaggg uu                                        22

<210> SEQ ID NO 414
<211> LENGTH: 22
<212> TYPE: RNA
<213> ORGANISM: Homo sapiens

<400> SEQUENCE: 414
cucuagaggg aagcgcuuuc ug                                        22

<210> SEQ ID NO 415
<211> LENGTH: 22
<212> TYPE: RNA
<213> ORGANISM: Homo sapiens

<400> SEQUENCE: 415
aaagugcauc uuuuuagagg au                                        22

<210> SEQ ID NO 416
<211> LENGTH: 21
<212> TYPE: RNA
<213> ORGANISM: Homo sapiens

<400> SEQUENCE: 416
cuccagaggg aaguacuuuc u                                         21

<210> SEQ ID NO 417
<211> LENGTH: 22
<212> TYPE: RNA
<213> ORGANISM: Homo sapiens

<400> SEQUENCE: 417
aaagugcuuc ccuuuggacu gu                                        22

<210> SEQ ID NO 418
<211> LENGTH: 23
<212> TYPE: RNA
<213> ORGANISM: Homo sapiens

<400> SEQUENCE: 418
cucuugaggg aagcacuuuc ugu                                       23

<210> SEQ ID NO 419
<211> LENGTH: 22
<212> TYPE: RNA
<213> ORGANISM: Homo sapiens
```

```
<400> SEQUENCE: 419
gaaagugcuu ccuuuuagag gc                                      22

<210> SEQ ID NO 420
<211> LENGTH: 22
<212> TYPE: RNA
<213> ORGANISM: Homo sapiens

<400> SEQUENCE: 420
aaagugcauc cuuuuagagg uu                                      22

<210> SEQ ID NO 421
<211> LENGTH: 21
<212> TYPE: RNA
<213> ORGANISM: Homo sapiens

<400> SEQUENCE: 421
cuccagaggg augcacuuuc u                                       21

<210> SEQ ID NO 422
<211> LENGTH: 22
<212> TYPE: RNA
<213> ORGANISM: Homo sapiens

<400> SEQUENCE: 422
gaaggcgcuu cccuuuagag cg                                      22

<210> SEQ ID NO 423
<211> LENGTH: 23
<212> TYPE: RNA
<213> ORGANISM: Homo sapiens

<400> SEQUENCE: 423
gaacgcgcuu cccauagag ggu                                      23

<210> SEQ ID NO 424
<211> LENGTH: 22
<212> TYPE: RNA
<213> ORGANISM: Homo sapiens

<400> SEQUENCE: 424
cucuagaggg aagcacuuuc uc                                      22

<210> SEQ ID NO 425
<211> LENGTH: 21
<212> TYPE: RNA
<213> ORGANISM: Homo sapiens

<400> SEQUENCE: 425
gaaagcgcuu cucuuuagag g                                       21

<210> SEQ ID NO 426
<211> LENGTH: 21
<212> TYPE: RNA
<213> ORGANISM: Homo sapiens

<400> SEQUENCE: 426
aaagugcuuc cuuuuagagg g                                       21

<210> SEQ ID NO 427
<211> LENGTH: 22
<212> TYPE: RNA
```

```
<213> ORGANISM: Homo sapiens

<400> SEQUENCE: 427
caaagcgcuc cccuuuagag gu                                              22

<210> SEQ ID NO 428
<211> LENGTH: 22
<212> TYPE: RNA
<213> ORGANISM: Homo sapiens

<400> SEQUENCE: 428
cucuagaggg aagcacuuuc ug                                              22

<210> SEQ ID NO 429
<211> LENGTH: 22
<212> TYPE: RNA
<213> ORGANISM: Homo sapiens

<400> SEQUENCE: 429
aaagugcuuc cuuuuagagg gu                                              22

<210> SEQ ID NO 430
<211> LENGTH: 23
<212> TYPE: RNA
<213> ORGANISM: Homo sapiens

<400> SEQUENCE: 430
ucucuggagg gaagcacuuu cug                                             23

<210> SEQ ID NO 431
<211> LENGTH: 23
<212> TYPE: RNA
<213> ORGANISM: Homo sapiens

<400> SEQUENCE: 431
caaagcgcuu ucuuuagag ugu                                              23

<210> SEQ ID NO 432
<211> LENGTH: 22
<212> TYPE: RNA
<213> ORGANISM: Homo sapiens

<400> SEQUENCE: 432
cuacaaaggg aagcacuuuc uc                                              22

<210> SEQ ID NO 433
<211> LENGTH: 21
<212> TYPE: RNA
<213> ORGANISM: Homo sapiens

<400> SEQUENCE: 433
gaaggcgcuu cccuuuggag u                                               21

<210> SEQ ID NO 434
<211> LENGTH: 22
<212> TYPE: RNA
<213> ORGANISM: Homo sapiens

<400> SEQUENCE: 434
ccucuagaug gaagcacugu cu                                              22

<210> SEQ ID NO 435
<211> LENGTH: 22
```

```
<212> TYPE: RNA
<213> ORGANISM: Homo sapiens

<400> SEQUENCE: 435
aucgugcauc ccuuuagagu gu                                          22

<210> SEQ ID NO 436
<211> LENGTH: 22
<212> TYPE: RNA
<213> ORGANISM: Homo sapiens

<400> SEQUENCE: 436
caaagugccu cccuuuagag ug                                          22

<210> SEQ ID NO 437
<211> LENGTH: 22
<212> TYPE: RNA
<213> ORGANISM: Homo sapiens

<400> SEQUENCE: 437
aacgcacuuc ccuuuagagu gu                                          22

<210> SEQ ID NO 438
<211> LENGTH: 20
<212> TYPE: RNA
<213> ORGANISM: Homo sapiens

<400> SEQUENCE: 438
cuacaaaggg aagcccuuuc                                             20

<210> SEQ ID NO 439
<211> LENGTH: 22
<212> TYPE: RNA
<213> ORGANISM: Homo sapiens

<400> SEQUENCE: 439
aaagugcuuc ucuuuggugg gu                                          22

<210> SEQ ID NO 440
<211> LENGTH: 22
<212> TYPE: RNA
<213> ORGANISM: Homo sapiens

<400> SEQUENCE: 440
ucgugcaucc cuuuagagug uu                                          22

<210> SEQ ID NO 441
<211> LENGTH: 24
<212> TYPE: RNA
<213> ORGANISM: Homo sapiens

<400> SEQUENCE: 441
acaaagugcu ucccuuuaga gugu                                        24

<210> SEQ ID NO 442
<211> LENGTH: 22
<212> TYPE: RNA
<213> ORGANISM: Homo sapiens

<400> SEQUENCE: 442
aucuggaggu aagaagcacu uu                                          22

<210> SEQ ID NO 443
```

```
<211> LENGTH: 18
<212> TYPE: RNA
<213> ORGANISM: Homo sapiens

<400> SEQUENCE: 443
ugcuuccuuu cagagggu                                                   18

<210> SEQ ID NO 444
<211> LENGTH: 21
<212> TYPE: RNA
<213> ORGANISM: Homo sapiens

<400> SEQUENCE: 444
aaagcgcuuc ccuucagagu g                                               21

<210> SEQ ID NO 445
<211> LENGTH: 20
<212> TYPE: RNA
<213> ORGANISM: Homo sapiens

<400> SEQUENCE: 445
cugcaaaggg aagcccuuuc                                                 20

<210> SEQ ID NO 446
<211> LENGTH: 22
<212> TYPE: RNA
<213> ORGANISM: Homo sapiens

<400> SEQUENCE: 446
gaaagcgcuu cccuuugcug ga                                              22

<210> SEQ ID NO 447
<211> LENGTH: 21
<212> TYPE: RNA
<213> ORGANISM: Homo sapiens

<400> SEQUENCE: 447
caaagcgcuu cccuuuggag c                                               21

<210> SEQ ID NO 448
<211> LENGTH: 22
<212> TYPE: RNA
<213> ORGANISM: Homo sapiens

<400> SEQUENCE: 448
aucgugcauc cuuuuagagu gu                                              22

<210> SEQ ID NO 449
<211> LENGTH: 22
<212> TYPE: RNA
<213> ORGANISM: Homo sapiens

<400> SEQUENCE: 449
acaaagugcu ucccuuuaga gu                                              22

<210> SEQ ID NO 450
<211> LENGTH: 22
<212> TYPE: RNA
<213> ORGANISM: Homo sapiens

<400> SEQUENCE: 450
aaaaugguuc ccuuuagagu gu                                              22
```

```
<210> SEQ ID NO 451
<211> LENGTH: 22
<212> TYPE: RNA
<213> ORGANISM: Homo sapiens

<400> SEQUENCE: 451
aaagugcauc cuuuuagagu gu                                              22

<210> SEQ ID NO 452
<211> LENGTH: 23
<212> TYPE: RNA
<213> ORGANISM: Homo sapiens

<400> SEQUENCE: 452
uucucgagga aagaagcacu uuc                                             23

<210> SEQ ID NO 453
<211> LENGTH: 21
<212> TYPE: RNA
<213> ORGANISM: Homo sapiens

<400> SEQUENCE: 453
uuaagacuug cagugauguu u                                               21

<210> SEQ ID NO 454
<211> LENGTH: 22
<212> TYPE: RNA
<213> ORGANISM: Homo sapiens

<400> SEQUENCE: 454
aacaucacag caagucugug cu                                              22

<210> SEQ ID NO 455
<211> LENGTH: 23
<212> TYPE: RNA
<213> ORGANISM: Homo sapiens

<400> SEQUENCE: 455
uaauccuugc uaccugggug aga                                             23

<210> SEQ ID NO 456
<211> LENGTH: 22
<212> TYPE: RNA
<213> ORGANISM: Homo sapiens

<400> SEQUENCE: 456
augcaccugg gcaaggauuc ug                                              22

<210> SEQ ID NO 457
<211> LENGTH: 22
<212> TYPE: RNA
<213> ORGANISM: Homo sapiens

<400> SEQUENCE: 457
aauccuuugu cccuggguga ga                                              22

<210> SEQ ID NO 458
<211> LENGTH: 22
<212> TYPE: RNA
<213> ORGANISM: Homo sapiens

<400> SEQUENCE: 458
aaugcacccg ggcaaggauu cu                                              22
```

```
<210> SEQ ID NO 459
<211> LENGTH: 21
<212> TYPE: RNA
<213> ORGANISM: Homo sapiens

<400> SEQUENCE: 459
auccuugcua ucugggugcu a                                              21

<210> SEQ ID NO 460
<211> LENGTH: 22
<212> TYPE: RNA
<213> ORGANISM: Homo sapiens

<400> SEQUENCE: 460
aaugcaccug ggcaaggauu ca                                             22

<210> SEQ ID NO 461
<211> LENGTH: 23
<212> TYPE: RNA
<213> ORGANISM: Homo sapiens

<400> SEQUENCE: 461
uagcagcggg aacaguucug cag                                            23

<210> SEQ ID NO 462
<211> LENGTH: 22
<212> TYPE: RNA
<213> ORGANISM: Homo sapiens

<400> SEQUENCE: 462
agacccuggu cugcacucua uc                                             22

<210> SEQ ID NO 463
<211> LENGTH: 22
<212> TYPE: RNA
<213> ORGANISM: Homo sapiens

<400> SEQUENCE: 463
gggagccagg aaguauugau gu                                             22

<210> SEQ ID NO 464
<211> LENGTH: 22
<212> TYPE: RNA
<213> ORGANISM: Homo sapiens

<400> SEQUENCE: 464
cgucaacacu ugcugguuuc cu                                             22

<210> SEQ ID NO 465
<211> LENGTH: 18
<212> TYPE: RNA
<213> ORGANISM: Homo sapiens

<400> SEQUENCE: 465
uucacaggga ggugucau                                                  18

<210> SEQ ID NO 466
<211> LENGTH: 23
<212> TYPE: RNA
<213> ORGANISM: Homo sapiens

<400> SEQUENCE: 466
uaaauuucac cuuucugaga agg                                            23
```

<210> SEQ ID NO 467
<211> LENGTH: 21
<212> TYPE: RNA
<213> ORGANISM: Homo sapiens

<400> SEQUENCE: 467
uaaggcaccc uucugaguag a                                              21

<210> SEQ ID NO 468
<211> LENGTH: 21
<212> TYPE: RNA
<213> ORGANISM: Homo sapiens

<400> SEQUENCE: 468
uuuugcaccu uuuggaguga a                                              21

<210> SEQ ID NO 469
<211> LENGTH: 23
<212> TYPE: RNA
<213> ORGANISM: Homo sapiens

<400> SEQUENCE: 469
uacuccagag ggcgucacuc aug                                            23

<210> SEQ ID NO 470
<211> LENGTH: 23
<212> TYPE: RNA
<213> ORGANISM: Homo sapiens

<400> SEQUENCE: 470
ugauuguagc cuuuuggagu aga                                            23

<210> SEQ ID NO 471
<211> LENGTH: 21
<212> TYPE: RNA
<213> ORGANISM: Homo sapiens

<400> SEQUENCE: 471
uacugcagac aguggcaauc a                                              21

<210> SEQ ID NO 472
<211> LENGTH: 22
<212> TYPE: RNA
<213> ORGANISM: Homo sapiens

<400> SEQUENCE: 472
ugauugguac gucugugggu ag                                             22

<210> SEQ ID NO 473
<211> LENGTH: 22
<212> TYPE: RNA
<213> ORGANISM: Homo sapiens

<400> SEQUENCE: 473
uacucaggag aguggcaauc ac                                             22

<210> SEQ ID NO 474
<211> LENGTH: 21
<212> TYPE: RNA
<213> ORGANISM: Homo sapiens

<400> SEQUENCE: 474

-continued auugacacuu cugugaguag a                                      21

<210> SEQ ID NO 475
<211> LENGTH: 22
<212> TYPE: RNA
<213> ORGANISM: Homo sapiens

<400> SEQUENCE: 475
caugccuuga guguaggacc gu                                     22

<210> SEQ ID NO 476
<211> LENGTH: 22
<212> TYPE: RNA
<213> ORGANISM: Homo sapiens

<400> SEQUENCE: 476
ccucccacac ccaaggcuug ca                                     22

<210> SEQ ID NO 477
<211> LENGTH: 22
<212> TYPE: RNA
<213> ORGANISM: Homo sapiens

<400> SEQUENCE: 477
uaugugccuu uggacuacau cg                                     22

<210> SEQ ID NO 478
<211> LENGTH: 21
<212> TYPE: RNA
<213> ORGANISM: Homo sapiens

<400> SEQUENCE: 478
gcaguccaug ggcauauaca c                                      21

<210> SEQ ID NO 479
<211> LENGTH: 22
<212> TYPE: RNA
<213> ORGANISM: Homo sapiens

<400> SEQUENCE: 479
ggagaaauua uccuuggugu gu                                     22

<210> SEQ ID NO 480
<211> LENGTH: 22
<212> TYPE: RNA
<213> ORGANISM: Homo sapiens

<400> SEQUENCE: 480
auucugcauu uuuagcaagu uc                                     22

<210> SEQ ID NO 481
<211> LENGTH: 22
<212> TYPE: RNA
<213> ORGANISM: Homo sapiens

<400> SEQUENCE: 481
ucaguaaaug uuuauuagau ga                                     22

<210> SEQ ID NO 482
<211> LENGTH: 22
<212> TYPE: RNA
<213> ORGANISM: Homo sapiens

<400> SEQUENCE: 482
ucagcaaaca uuuauugugu gc                                      22

<210> SEQ ID NO 483
<211> LENGTH: 22
<212> TYPE: RNA
<213> ORGANISM: Homo sapiens

<400> SEQUENCE: 483
aaucguacag ggucauccac uu                                      22

<210> SEQ ID NO 484
<211> LENGTH: 21
<212> TYPE: RNA
<213> ORGANISM: Homo sapiens

<400> SEQUENCE: 484
gcgacccacu cuugguuucc a                                       21

<210> SEQ ID NO 485
<211> LENGTH: 21
<212> TYPE: RNA
<213> ORGANISM: Homo sapiens

<400> SEQUENCE: 485
aacaggugac ugguuagaca a                                       21

<210> SEQ ID NO 486
<211> LENGTH: 21
<212> TYPE: RNA
<213> ORGANISM: Homo sapiens

<400> SEQUENCE: 486
aaaacgguga gauuuuguuu u                                       21

<210> SEQ ID NO 487
<211> LENGTH: 21
<212> TYPE: RNA
<213> ORGANISM: Homo sapiens

<400> SEQUENCE: 487
gcuaguccug acucagccag u                                       21

<210> SEQ ID NO 488
<211> LENGTH: 22
<212> TYPE: RNA
<213> ORGANISM: Homo sapiens

<400> SEQUENCE: 488
agggacggga cgcggugcag ug                                      22

<210> SEQ ID NO 489
<211> LENGTH: 22
<212> TYPE: RNA
<213> ORGANISM: Homo sapiens

<400> SEQUENCE: 489
uauugcacuc gucccggccu cc                                      22

<210> SEQ ID NO 490
<211> LENGTH: 21
<212> TYPE: RNA
<213> ORGANISM: Homo sapiens

```
<400> SEQUENCE: 490
aggguaagcu gaaccucuga u                                              21

<210> SEQ ID NO 491
<211> LENGTH: 22
<212> TYPE: RNA
<213> ORGANISM: Homo sapiens

<400> SEQUENCE: 491
gaugagcuca uuguaauaug ag                                             22

<210> SEQ ID NO 492
<211> LENGTH: 22
<212> TYPE: RNA
<213> ORGANISM: Homo sapiens

<400> SEQUENCE: 492
auauuaccau uagcucaucu uu                                             22

<210> SEQ ID NO 493
<211> LENGTH: 23
<212> TYPE: RNA
<213> ORGANISM: Homo sapiens

<400> SEQUENCE: 493
guuugcacgg gugggccuug ucu                                            23

<210> SEQ ID NO 494
<211> LENGTH: 19
<212> TYPE: RNA
<213> ORGANISM: Homo sapiens

<400> SEQUENCE: 494
ugagcugcug uaccaaaau                                                 19

<210> SEQ ID NO 495
<211> LENGTH: 21
<212> TYPE: RNA
<213> ORGANISM: Homo sapiens

<400> SEQUENCE: 495
uaaaguaaau augcaccaaa a                                              21

<210> SEQ ID NO 496
<211> LENGTH: 22
<212> TYPE: RNA
<213> ORGANISM: Homo sapiens

<400> SEQUENCE: 496
caaaguuuaa gauccuugaa gu                                             22

<210> SEQ ID NO 497
<211> LENGTH: 20
<212> TYPE: RNA
<213> ORGANISM: Homo sapiens

<400> SEQUENCE: 497
aaaguagcug uaccauuugc                                                20

<210> SEQ ID NO 498
<211> LENGTH: 19
<212> TYPE: RNA
<213> ORGANISM: Homo sapiens
```

```
<400> SEQUENCE: 498
agguugacau acguuccc                                              19

<210> SEQ ID NO 499
<211> LENGTH: 19
<212> TYPE: RNA
<213> ORGANISM: Homo sapiens

<400> SEQUENCE: 499
aggcacggug ucagcaggc                                             19

<210> SEQ ID NO 500
<211> LENGTH: 19
<212> TYPE: RNA
<213> ORGANISM: Homo sapiens

<400> SEQUENCE: 500
gggcgccugu gaucccaac                                             19

<210> SEQ ID NO 501
<211> LENGTH: 23
<212> TYPE: RNA
<213> ORGANISM: Homo sapiens

<400> SEQUENCE: 501
aguauguucu uccaggacag aac                                        23

<210> SEQ ID NO 502
<211> LENGTH: 20
<212> TYPE: RNA
<213> ORGANISM: Homo sapiens

<400> SEQUENCE: 502
auguauaaau guauacacac                                            20

<210> SEQ ID NO 503
<211> LENGTH: 22
<212> TYPE: RNA
<213> ORGANISM: Homo sapiens

<400> SEQUENCE: 503
gaaaucaagc gugggugaga cc                                         22

<210> SEQ ID NO 504
<211> LENGTH: 21
<212> TYPE: RNA
<213> ORGANISM: Homo sapiens

<400> SEQUENCE: 504
gcgacccaua cuugguuuca g                                          21

<210> SEQ ID NO 505
<211> LENGTH: 21
<212> TYPE: RNA
<213> ORGANISM: Homo sapiens

<400> SEQUENCE: 505
aguuaaugaa uccuggaaag u                                          21

<210> SEQ ID NO 506
<211> LENGTH: 22
<212> TYPE: RNA
```

<213> ORGANISM: Homo sapiens

<400> SEQUENCE: 506
cgaaaacagc aauuaccuuu gc    22

<210> SEQ ID NO 507
<211> LENGTH: 21
<212> TYPE: RNA
<213> ORGANISM: Homo sapiens

<400> SEQUENCE: 507
ugaguuggcc aucugaguga g    21

<210> SEQ ID NO 508
<211> LENGTH: 20
<212> TYPE: RNA
<213> ORGANISM: Homo sapiens

<400> SEQUENCE: 508
guccgcucgg cgguggccca    20

<210> SEQ ID NO 509
<211> LENGTH: 24
<212> TYPE: RNA
<213> ORGANISM: Homo sapiens

<400> SEQUENCE: 509
cugaagugau guguaacuga ucag    24

<210> SEQ ID NO 510
<211> LENGTH: 23
<212> TYPE: RNA
<213> ORGANISM: Homo sapiens

<400> SEQUENCE: 510
ugagugugug ugugugagug ugu    23

<210> SEQ ID NO 511
<211> LENGTH: 22
<212> TYPE: RNA
<213> ORGANISM: Homo sapiens

<400> SEQUENCE: 511
cacgcucaug cacacaccca ca    22

<210> SEQ ID NO 512
<211> LENGTH: 19
<212> TYPE: RNA
<213> ORGANISM: Homo sapiens

<400> SEQUENCE: 512
gagccaguug gacaggagc    19

<210> SEQ ID NO 513
<211> LENGTH: 22
<212> TYPE: RNA
<213> ORGANISM: Homo sapiens

<400> SEQUENCE: 513
auucuaauuu cuccacgucu uu    22

<210> SEQ ID NO 514
<211> LENGTH: 22

```
<212> TYPE: RNA
<213> ORGANISM: Homo sapiens

<400> SEQUENCE: 514
aagaugugga aaaauuggaa uc                                              22

<210> SEQ ID NO 515
<211> LENGTH: 21
<212> TYPE: RNA
<213> ORGANISM: Homo sapiens

<400> SEQUENCE: 515
uagauaaaau auugguaccu g                                               21

<210> SEQ ID NO 516
<211> LENGTH: 21
<212> TYPE: RNA
<213> ORGANISM: Homo sapiens

<400> SEQUENCE: 516
cuucuugugc ucuaggauug u                                               21

<210> SEQ ID NO 517
<211> LENGTH: 23
<212> TYPE: RNA
<213> ORGANISM: Homo sapiens

<400> SEQUENCE: 517
uucauuuggu auaaaccgcg auu                                             23

<210> SEQ ID NO 518
<211> LENGTH: 22
<212> TYPE: RNA
<213> ORGANISM: Homo sapiens

<400> SEQUENCE: 518
uugagaauga ugaaucauua gg                                              22

<210> SEQ ID NO 519
<211> LENGTH: 21
<212> TYPE: RNA
<213> ORGANISM: Homo sapiens

<400> SEQUENCE: 519
ucuuguguuc ucuagaucag u                                               21

<210> SEQ ID NO 520
<211> LENGTH: 23
<212> TYPE: RNA
<213> ORGANISM: Homo sapiens

<400> SEQUENCE: 520
uuacaguugu ucaaccaguu acu                                             23

<210> SEQ ID NO 521
<211> LENGTH: 22
<212> TYPE: RNA
<213> ORGANISM: Homo sapiens

<400> SEQUENCE: 521
uaacugguug aacaacugaa cc                                              22

<210> SEQ ID NO 522
```

```
<211> LENGTH: 21
<212> TYPE: RNA
<213> ORGANISM: Homo sapiens

<400> SEQUENCE: 522
caaagaggaa ggucccauua c                                              21

<210> SEQ ID NO 523
<211> LENGTH: 22
<212> TYPE: RNA
<213> ORGANISM: Homo sapiens

<400> SEQUENCE: 523
uuaugguuug ccugggacug ag                                             22

<210> SEQ ID NO 524
<211> LENGTH: 19
<212> TYPE: RNA
<213> ORGANISM: Homo sapiens

<400> SEQUENCE: 524
ugggcguauc uguaugcua                                                 19

<210> SEQ ID NO 525
<211> LENGTH: 22
<212> TYPE: RNA
<213> ORGANISM: Homo sapiens

<400> SEQUENCE: 525
caaaacuggc aauuacuuuu gc                                             22

<210> SEQ ID NO 526
<211> LENGTH: 22
<212> TYPE: RNA
<213> ORGANISM: Homo sapiens

<400> SEQUENCE: 526
uaugcauugu auuuuaggu cc                                              22

<210> SEQ ID NO 527
<211> LENGTH: 21
<212> TYPE: RNA
<213> ORGANISM: Homo sapiens

<400> SEQUENCE: 527
uuuccauagg ugaugaguca c                                              21

<210> SEQ ID NO 528
<211> LENGTH: 22
<212> TYPE: RNA
<213> ORGANISM: Homo sapiens

<400> SEQUENCE: 528
aaaaguaauu gugguuuugg cc                                             22

<210> SEQ ID NO 529
<211> LENGTH: 22
<212> TYPE: RNA
<213> ORGANISM: Homo sapiens

<400> SEQUENCE: 529
caagaaccuc aguugcuuuu gu                                             22
```

```
<210> SEQ ID NO 530
<211> LENGTH: 21
<212> TYPE: RNA
<213> ORGANISM: Homo sapiens

<400> SEQUENCE: 530
uuggccacaa ugggguuagaa c                                                 21

<210> SEQ ID NO 531
<211> LENGTH: 22
<212> TYPE: RNA
<213> ORGANISM: Homo sapiens

<400> SEQUENCE: 531
ugagaaccac gucugcucug ag                                                 22

<210> SEQ ID NO 532
<211> LENGTH: 24
<212> TYPE: RNA
<213> ORGANISM: Homo sapiens

<400> SEQUENCE: 532
ucagaacaaa ugccgguucc caga                                               24

<210> SEQ ID NO 533
<211> LENGTH: 23
<212> TYPE: RNA
<213> ORGANISM: Homo sapiens

<400> SEQUENCE: 533
agugccugag ggaguaagag ccc                                                23

<210> SEQ ID NO 534
<211> LENGTH: 22
<212> TYPE: RNA
<213> ORGANISM: Homo sapiens

<400> SEQUENCE: 534
ugucuuacuc ccucaggcac au                                                 22

<210> SEQ ID NO 535
<211> LENGTH: 22
<212> TYPE: RNA
<213> ORGANISM: Homo sapiens

<400> SEQUENCE: 535
gagcuuauuc auaaaagugc ag                                                 22

<210> SEQ ID NO 536
<211> LENGTH: 21
<212> TYPE: RNA
<213> ORGANISM: Homo sapiens

<400> SEQUENCE: 536
uaauuuuaug uauaagcuag u                                                  21

<210> SEQ ID NO 537
<211> LENGTH: 20
<212> TYPE: RNA
<213> ORGANISM: Homo sapiens

<400> SEQUENCE: 537
agaccauggg uucucauugu                                                    20
```

```
<210> SEQ ID NO 538
<211> LENGTH: 22
<212> TYPE: RNA
<213> ORGANISM: Homo sapiens

<400> SEQUENCE: 538
uugugucaau augcgaugau gu                                              22

<210> SEQ ID NO 539
<211> LENGTH: 25
<212> TYPE: RNA
<213> ORGANISM: Homo sapiens

<400> SEQUENCE: 539
aggcaccagc caggcauugc ucagc                                           25

<210> SEQ ID NO 540
<211> LENGTH: 19
<212> TYPE: RNA
<213> ORGANISM: Homo sapiens

<400> SEQUENCE: 540
ugucucugcu ggguuucu                                                   19

<210> SEQ ID NO 541
<211> LENGTH: 21
<212> TYPE: RNA
<213> ORGANISM: Homo sapiens

<400> SEQUENCE: 541
gaagugugcc gugguguguc u                                               21

<210> SEQ ID NO 542
<211> LENGTH: 21
<212> TYPE: RNA
<213> ORGANISM: Homo sapiens

<400> SEQUENCE: 542
aagccugccc ggcuccucgg g                                               21

<210> SEQ ID NO 543
<211> LENGTH: 22
<212> TYPE: RNA
<213> ORGANISM: Homo sapiens

<400> SEQUENCE: 543
ugugucacuc gaugaccacu gu                                              22

<210> SEQ ID NO 544
<211> LENGTH: 22
<212> TYPE: RNA
<213> ORGANISM: Homo sapiens

<400> SEQUENCE: 544
uacgucaucg uugucaucgu ca                                              22

<210> SEQ ID NO 545
<211> LENGTH: 20
<212> TYPE: RNA
<213> ORGANISM: Homo sapiens

<400> SEQUENCE: 545
guugugucag uuuaucaaac                                                 20
```

<210> SEQ ID NO 546
<211> LENGTH: 22
<212> TYPE: RNA
<213> ORGANISM: Homo sapiens

<400> SEQUENCE: 546
aaaaguaauu gcgaguuuua cc                                        22

<210> SEQ ID NO 547
<211> LENGTH: 23
<212> TYPE: RNA
<213> ORGANISM: Homo sapiens

<400> SEQUENCE: 547
acuuacagac aagagccuug cuc                                       23

<210> SEQ ID NO 548
<211> LENGTH: 22
<212> TYPE: RNA
<213> ORGANISM: Homo sapiens

<400> SEQUENCE: 548
uggucuagga uuguuggagg ag                                        22

<210> SEQ ID NO 549
<211> LENGTH: 23
<212> TYPE: RNA
<213> ORGANISM: Homo sapiens

<400> SEQUENCE: 549
gacacgggcg acagcugcgg ccc                                       23

<210> SEQ ID NO 550
<211> LENGTH: 22
<212> TYPE: RNA
<213> ORGANISM: Homo sapiens

<400> SEQUENCE: 550
cacacacugc aauuacuuuu gc                                        22

<210> SEQ ID NO 551
<211> LENGTH: 19
<212> TYPE: RNA
<213> ORGANISM: Homo sapiens

<400> SEQUENCE: 551
aggcugcgga auucaggac                                            19

<210> SEQ ID NO 552
<211> LENGTH: 23
<212> TYPE: RNA
<213> ORGANISM: Homo sapiens

<400> SEQUENCE: 552
uaaaucccau ggugccuucu ccu                                       23

<210> SEQ ID NO 553
<211> LENGTH: 21
<212> TYPE: RNA
<213> ORGANISM: Homo sapiens

<400> SEQUENCE: 553
aaacuacuga aaaucaaaga u                                              21

<210> SEQ ID NO 554
<211> LENGTH: 21
<212> TYPE: RNA
<213> ORGANISM: Homo sapiens

<400> SEQUENCE: 554
guucaaaucc agaucuauaa c                                              21

<210> SEQ ID NO 555
<211> LENGTH: 25
<212> TYPE: RNA
<213> ORGANISM: Homo sapiens

<400> SEQUENCE: 555
aggggugguG uugggacagc uccgu                                          25

<210> SEQ ID NO 556
<211> LENGTH: 20
<212> TYPE: RNA
<213> ORGANISM: Homo sapiens

<400> SEQUENCE: 556
aggguguuuc ucucaucucu                                                20

<210> SEQ ID NO 557
<211> LENGTH: 21
<212> TYPE: RNA
<213> ORGANISM: Homo sapiens

<400> SEQUENCE: 557
ugagcuaaau gugugcuggg a                                              21

<210> SEQ ID NO 558
<211> LENGTH: 23
<212> TYPE: RNA
<213> ORGANISM: Homo sapiens

<400> SEQUENCE: 558
gcgaggaccc cucgggucu gac                                             23

<210> SEQ ID NO 559
<211> LENGTH: 25
<212> TYPE: RNA
<213> ORGANISM: Homo sapiens

<400> SEQUENCE: 559
gcugggcagg gcuucugagc uccuu                                          25

<210> SEQ ID NO 560
<211> LENGTH: 20
<212> TYPE: RNA
<213> ORGANISM: Homo sapiens

<400> SEQUENCE: 560
aggaauguuc cuucuuugcc                                                20

<210> SEQ ID NO 561
<211> LENGTH: 23
<212> TYPE: RNA
<213> ORGANISM: Homo sapiens

<400> SEQUENCE: 561

```
gaacgccugu ucuugccagg ugg                                            23

<210> SEQ ID NO 562
<211> LENGTH: 22
<212> TYPE: RNA
<213> ORGANISM: Homo sapiens

<400> SEQUENCE: 562
gggggucccc ggugcucgga uc                                             22

<210> SEQ ID NO 563
<211> LENGTH: 22
<212> TYPE: RNA
<213> ORGANISM: Homo sapiens

<400> SEQUENCE: 563
uccgagccug ggucucccuc uu                                             22

<210> SEQ ID NO 564
<211> LENGTH: 22
<212> TYPE: RNA
<213> ORGANISM: Homo sapiens

<400> SEQUENCE: 564
acucaaaacc cuucagugac uu                                             22

<210> SEQ ID NO 565
<211> LENGTH: 22
<212> TYPE: RNA
<213> ORGANISM: Homo sapiens

<400> SEQUENCE: 565
agucauugga ggguuugagc ag                                             22

<210> SEQ ID NO 566
<211> LENGTH: 22
<212> TYPE: RNA
<213> ORGANISM: Homo sapiens

<400> SEQUENCE: 566
aaaaguaauu gcgguuuuug cc                                             22

<210> SEQ ID NO 567
<211> LENGTH: 22
<212> TYPE: RNA
<213> ORGANISM: Homo sapiens

<400> SEQUENCE: 567
caaaaaucuc aauuacuuuu gc                                             22

<210> SEQ ID NO 568
<211> LENGTH: 22
<212> TYPE: RNA
<213> ORGANISM: Homo sapiens

<400> SEQUENCE: 568
agacuuccca uuugaaggug gc                                             22

<210> SEQ ID NO 569
<211> LENGTH: 23
<212> TYPE: RNA
<213> ORGANISM: Homo sapiens
```

```
<400> SEQUENCE: 569
aaacucuacu uguccuucug agu                                          23

<210> SEQ ID NO 570
<211> LENGTH: 24
<212> TYPE: RNA
<213> ORGANISM: Homo sapiens

<400> SEQUENCE: 570
gaccuggaca uguuugugcc cagu                                         24

<210> SEQ ID NO 571
<211> LENGTH: 20
<212> TYPE: RNA
<213> ORGANISM: Homo sapiens

<400> SEQUENCE: 571
auggagauag auauagaaau                                              20

<210> SEQ ID NO 572
<211> LENGTH: 21
<212> TYPE: RNA
<213> ORGANISM: Homo sapiens

<400> SEQUENCE: 572
ggcuagcaac agcgcuuacc u                                            21

<210> SEQ ID NO 573
<211> LENGTH: 21
<212> TYPE: RNA
<213> ORGANISM: Homo sapiens

<400> SEQUENCE: 573
acagucugcu gagguuggag c                                            21

<210> SEQ ID NO 574
<211> LENGTH: 23
<212> TYPE: RNA
<213> ORGANISM: Homo sapiens

<400> SEQUENCE: 574
aucccuugca ggggcuguug ggu                                          23

<210> SEQ ID NO 575
<211> LENGTH: 22
<212> TYPE: RNA
<213> ORGANISM: Homo sapiens

<400> SEQUENCE: 575
uaguaccagu accuuguguu ca                                           22

<210> SEQ ID NO 576
<211> LENGTH: 21
<212> TYPE: RNA
<213> ORGANISM: Homo sapiens

<400> SEQUENCE: 576
cacaagguau ugguauuacc u                                            21

<210> SEQ ID NO 577
<211> LENGTH: 21
<212> TYPE: RNA
<213> ORGANISM: Homo sapiens
```

-continued

<400> SEQUENCE: 577 aggggggaaag uucuauaguc c                                      21

<210> SEQ ID NO 578
<211> LENGTH: 22
<212> TYPE: RNA
<213> ORGANISM: Homo sapiens

<400> SEQUENCE: 578
gacuauagaa cuuccccccu ca                                      22

<210> SEQ ID NO 579
<211> LENGTH: 19
<212> TYPE: RNA
<213> ORGANISM: Homo sapiens

<400> SEQUENCE: 579
agcugucuga aaaugucuu                                          19

<210> SEQ ID NO 580
<211> LENGTH: 22
<212> TYPE: RNA
<213> ORGANISM: Homo sapiens

<400> SEQUENCE: 580
gugagucucu aagaaaagag ga                                      22

<210> SEQ ID NO 581
<211> LENGTH: 22
<212> TYPE: RNA
<213> ORGANISM: Homo sapiens

<400> SEQUENCE: 581
augcugacau auuuacuaga gg                                      22

<210> SEQ ID NO 582
<211> LENGTH: 21
<212> TYPE: RNA
<213> ORGANISM: Homo sapiens

<400> SEQUENCE: 582
ucuaguaaga guggcagucg a                                       21

<210> SEQ ID NO 583
<211> LENGTH: 21
<212> TYPE: RNA
<213> ORGANISM: Homo sapiens

<400> SEQUENCE: 583
uggguuuacg uugggagaac u                                       21

<210> SEQ ID NO 584
<211> LENGTH: 22
<212> TYPE: RNA
<213> ORGANISM: Homo sapiens

<400> SEQUENCE: 584
guucucccaa cguaagccca gc                                      22

<210> SEQ ID NO 585
<211> LENGTH: 22
<212> TYPE: RNA

```
<213> ORGANISM: Homo sapiens

<400> SEQUENCE: 585
aguauucugu accagggaag gu                                        22

<210> SEQ ID NO 586
<211> LENGTH: 21
<212> TYPE: RNA
<213> ORGANISM: Homo sapiens

<400> SEQUENCE: 586
agaccuggcc cagaccucag c                                         21

<210> SEQ ID NO 587
<211> LENGTH: 20
<212> TYPE: RNA
<213> ORGANISM: Homo sapiens

<400> SEQUENCE: 587
gugcauugcu guugcauugc                                           20

<210> SEQ ID NO 588
<211> LENGTH: 22
<212> TYPE: RNA
<213> ORGANISM: Homo sapiens

<400> SEQUENCE: 588
cagugccucg gcagugcagc cc                                        22

<210> SEQ ID NO 589
<211> LENGTH: 19
<212> TYPE: RNA
<213> ORGANISM: Homo sapiens

<400> SEQUENCE: 589
gugucugcuu ccuguggga                                            19

<210> SEQ ID NO 590
<211> LENGTH: 23
<212> TYPE: RNA
<213> ORGANISM: Homo sapiens

<400> SEQUENCE: 590
cuaauaguau cuaccacaau aaa                                       23

<210> SEQ ID NO 591
<211> LENGTH: 22
<212> TYPE: RNA
<213> ORGANISM: Homo sapiens

<400> SEQUENCE: 591
aaccagcacc ccaacuuugg ac                                        22

<210> SEQ ID NO 592
<211> LENGTH: 23
<212> TYPE: RNA
<213> ORGANISM: Homo sapiens

<400> SEQUENCE: 592
acuugggcac ugaaacaaug ucc                                       23

<210> SEQ ID NO 593
<211> LENGTH: 23
```

```
<212> TYPE: RNA
<213> ORGANISM: Homo sapiens

<400> SEQUENCE: 593
ugugcuugcu cgucccgccc gca                                            23

<210> SEQ ID NO 594
<211> LENGTH: 24
<212> TYPE: RNA
<213> ORGANISM: Homo sapiens

<400> SEQUENCE: 594 acuggggcu uucgggcucu gcgu                                            24

<210> SEQ ID NO 595
<211> LENGTH: 25
<212> TYPE: RNA
<213> ORGANISM: Homo sapiens

<400> SEQUENCE: 595
agggaucgcg ggcggguggc ggccu                                          25

<210> SEQ ID NO 596
<211> LENGTH: 23
<212> TYPE: RNA
<213> ORGANISM: Homo sapiens

<400> SEQUENCE: 596
aucgcugcgg uugcgagcgc ugu                                            23

<210> SEQ ID NO 597
<211> LENGTH: 21
<212> TYPE: RNA
<213> ORGANISM: Homo sapiens

<400> SEQUENCE: 597
augauccagg aaccugccuc u                                              21

<210> SEQ ID NO 598
<211> LENGTH: 24
<212> TYPE: RNA
<213> ORGANISM: Homo sapiens

<400> SEQUENCE: 598
aaagacauag gauagaguca ccuc                                           24

<210> SEQ ID NO 599
<211> LENGTH: 22
<212> TYPE: RNA
<213> ORGANISM: Homo sapiens

<400> SEQUENCE: 599
gucccucucc aaaugugucu ug                                             22

<210> SEQ ID NO 600
<211> LENGTH: 22
<212> TYPE: RNA
<213> ORGANISM: Homo sapiens

<400> SEQUENCE: 600
acuuguaugc uagcucaggu ag                                             22

<210> SEQ ID NO 601
```

```
<211> LENGTH: 19
<212> TYPE: RNA
<213> ORGANISM: Homo sapiens

<400> SEQUENCE: 601
aguguggcuu ucuuagagc                                             19

<210> SEQ ID NO 602
<211> LENGTH: 19
<212> TYPE: RNA
<213> ORGANISM: Homo sapiens

<400> SEQUENCE: 602
ucuaggcugg uacugcuga                                             19

<210> SEQ ID NO 603
<211> LENGTH: 19
<212> TYPE: RNA
<213> ORGANISM: Homo sapiens

<400> SEQUENCE: 603
aagcagcugc cucugaggc                                             19

<210> SEQ ID NO 604
<211> LENGTH: 21
<212> TYPE: RNA
<213> ORGANISM: Homo sapiens

<400> SEQUENCE: 604
guggcugcac ucacuuccuu c                                          21

<210> SEQ ID NO 605
<211> LENGTH: 19
<212> TYPE: RNA
<213> ORGANISM: Homo sapiens

<400> SEQUENCE: 605
aagugugcag ggcacuggu                                             19

<210> SEQ ID NO 606
<211> LENGTH: 22
<212> TYPE: RNA
<213> ORGANISM: Homo sapiens

<400> SEQUENCE: 606
aaaccugugu uguucaagag uc                                         22

<210> SEQ ID NO 607
<211> LENGTH: 21
<212> TYPE: RNA
<213> ORGANISM: Homo sapiens

<400> SEQUENCE: 607
aggaggcagc gcucucagga c                                          21

<210> SEQ ID NO 608
<211> LENGTH: 22
<212> TYPE: RNA
<213> ORGANISM: Homo sapiens

<400> SEQUENCE: 608
uuuaggauaa gcuugacuuu ug                                         22
```

```
<210> SEQ ID NO 609
<211> LENGTH: 21
<212> TYPE: RNA
<213> ORGANISM: Homo sapiens

<400> SEQUENCE: 609
aauggcgcca cuaggguugu g                                              21

<210> SEQ ID NO 610
<211> LENGTH: 22
<212> TYPE: RNA
<213> ORGANISM: Homo sapiens

<400> SEQUENCE: 610
aaaaguaauu gugguuuuug cc                                             22

<210> SEQ ID NO 611
<211> LENGTH: 22
<212> TYPE: RNA
<213> ORGANISM: Homo sapiens

<400> SEQUENCE: 611
caaaaaccac aguuucuuuu gc                                             22

<210> SEQ ID NO 612
<211> LENGTH: 24
<212> TYPE: RNA
<213> ORGANISM: Homo sapiens

<400> SEQUENCE: 612
ugccuggguc ucuggccugc gcgu                                           24

<210> SEQ ID NO 613
<211> LENGTH: 21
<212> TYPE: RNA
<213> ORGANISM: Homo sapiens

<400> SEQUENCE: 613
ucccacguug uggcccagca g                                              21

<210> SEQ ID NO 614
<211> LENGTH: 22
<212> TYPE: RNA
<213> ORGANISM: Homo sapiens

<400> SEQUENCE: 614
aggcggggcg ccgcgggacc gc                                             22

<210> SEQ ID NO 615
<211> LENGTH: 22
<212> TYPE: RNA
<213> ORGANISM: Homo sapiens

<400> SEQUENCE: 615
aggcagugua uuguuagcug gc                                             22

<210> SEQ ID NO 616
<211> LENGTH: 22
<212> TYPE: RNA
<213> ORGANISM: Homo sapiens

<400> SEQUENCE: 616
cagccacaac uacccugcca cu                                             22
```

```
<210> SEQ ID NO 617
<211> LENGTH: 21
<212> TYPE: RNA
<213> ORGANISM: Homo sapiens

<400> SEQUENCE: 617
guguugaaac aaucucuacu g                                              21

<210> SEQ ID NO 618
<211> LENGTH: 21
<212> TYPE: RNA
<213> ORGANISM: Homo sapiens

<400> SEQUENCE: 618
uaguagaccg uauagcguac g                                              21

<210> SEQ ID NO 619
<211> LENGTH: 22
<212> TYPE: RNA
<213> ORGANISM: Homo sapiens

<400> SEQUENCE: 619
uauguaacac gguccacuaa cc                                             22

<210> SEQ ID NO 620
<211> LENGTH: 22
<212> TYPE: RNA
<213> ORGANISM: Homo sapiens

<400> SEQUENCE: 620
uggugggccg cagaacaugu gc                                             22

<210> SEQ ID NO 621
<211> LENGTH: 22
<212> TYPE: RNA
<213> ORGANISM: Homo sapiens

<400> SEQUENCE: 621
uaugucugcu gaccaucacc uu                                             22

<210> SEQ ID NO 622
<211> LENGTH: 22
<212> TYPE: RNA
<213> ORGANISM: Homo sapiens

<400> SEQUENCE: 622
auaauacaug guuaaccucu uu                                             22

<210> SEQ ID NO 623
<211> LENGTH: 21
<212> TYPE: RNA
<213> ORGANISM: Homo sapiens

<400> SEQUENCE: 623
aauauuauac agucaaccuc u                                              21

<210> SEQ ID NO 624
<211> LENGTH: 21
<212> TYPE: RNA
<213> ORGANISM: Homo sapiens

<400> SEQUENCE: 624
ugacaacuau ggaugagcuc u                                              21
```

```
<210> SEQ ID NO 625
<211> LENGTH: 23
<212> TYPE: RNA
<213> ORGANISM: Homo sapiens

<400> SEQUENCE: 625
ggcagguucu cacccucucu agg                                           23

<210> SEQ ID NO 626
<211> LENGTH: 25
<212> TYPE: RNA
<213> ORGANISM: Homo sapiens

<400> SEQUENCE: 626
ggcggaggga aguagguccg uuggu                                         25

<210> SEQ ID NO 627
<211> LENGTH: 22
<212> TYPE: RNA
<213> ORGANISM: Homo sapiens

<400> SEQUENCE: 627
cuugguucag ggagggu ccc ca                                           22

<210> SEQ ID NO 628
<211> LENGTH: 22
<212> TYPE: RNA
<213> ORGANISM: Homo sapiens

<400> SEQUENCE: 628
uacccauugc auaucggagu ug                                            22

<210> SEQ ID NO 629
<211> LENGTH: 23
<212> TYPE: RNA
<213> ORGANISM: Homo sapiens

<400> SEQUENCE: 629
aucaacagac auuaauuggg cgc                                           23

<210> SEQ ID NO 630
<211> LENGTH: 23
<212> TYPE: RNA
<213> ORGANISM: Homo sapiens

<400> SEQUENCE: 630
ucggggauca ucaugucacg aga                                           23

<210> SEQ ID NO 631
<211> LENGTH: 22
<212> TYPE: RNA
<213> ORGANISM: Homo sapiens

<400> SEQUENCE: 631
ugugacagau ugauaacuga aa                                            22

<210> SEQ ID NO 632
<211> LENGTH: 22
<212> TYPE: RNA
<213> ORGANISM: Homo sapiens

<400> SEQUENCE: 632
```
uuugugaccu gguccacuaa cc                                              22

<210> SEQ ID NO 633
<211> LENGTH: 23
<212> TYPE: RNA
<213> ORGANISM: Homo sapiens

<400> SEQUENCE: 633
caagucuuau uugagcaccu guu                                             23

<210> SEQ ID NO 634
<211> LENGTH: 23
<212> TYPE: RNA
<213> ORGANISM: Homo sapiens

<400> SEQUENCE: 634
aggaagcccu ggaggggcug gag                                             23

<210> SEQ ID NO 635
<211> LENGTH: 21
<212> TYPE: RNA
<213> ORGANISM: Homo sapiens

<400> SEQUENCE: 635
uccgguucuc agggcuccac c                                               21

<210> SEQ ID NO 636
<211> LENGTH: 23
<212> TYPE: RNA
<213> ORGANISM: Homo sapiens

<400> SEQUENCE: 636
ugucacucgg cucggcccac uac                                             23

<210> SEQ ID NO 637
<211> LENGTH: 23
<212> TYPE: RNA
<213> ORGANISM: Homo sapiens

<400> SEQUENCE: 637
ugcaccaugg uugucugagc aug                                             23

<210> SEQ ID NO 638
<211> LENGTH: 23
<212> TYPE: RNA
<213> ORGANISM: Homo sapiens

<400> SEQUENCE: 638
ucugcucaua ccccaugguu ucu                                             23

<210> SEQ ID NO 639
<211> LENGTH: 19
<212> TYPE: RNA
<213> ORGANISM: Homo sapiens

<400> SEQUENCE: 639
gugaggacuc gggaggugg                                                  19

<210> SEQ ID NO 640
<211> LENGTH: 21
<212> TYPE: RNA
<213> ORGANISM: Homo sapiens

<400> SEQUENCE: 640
ccccaccucc ucucuccuca g                                      21

<210> SEQ ID NO 641
<211> LENGTH: 22
<212> TYPE: RNA
<213> ORGANISM: Homo sapiens

<400> SEQUENCE: 641
aaaagcuggg uugagagggc aa                                     22

<210> SEQ ID NO 642
<211> LENGTH: 20
<212> TYPE: RNA
<213> ORGANISM: Homo sapiens

<400> SEQUENCE: 642
aaaagcuggg uugagagggu                                        20

<210> SEQ ID NO 643
<211> LENGTH: 22
<212> TYPE: RNA
<213> ORGANISM: Homo sapiens

<400> SEQUENCE: 643
uuagggcccu ggcuccaucu cc                                     22

<210> SEQ ID NO 644
<211> LENGTH: 21
<212> TYPE: RNA
<213> ORGANISM: Homo sapiens

<400> SEQUENCE: 644
cuccguuugc cuguuucgcu g                                      21

<210> SEQ ID NO 645
<211> LENGTH: 22
<212> TYPE: RNA
<213> ORGANISM: Homo sapiens

<400> SEQUENCE: 645
ucaaaacuga ggggcauuuu cu                                     22

<210> SEQ ID NO 646
<211> LENGTH: 22
<212> TYPE: RNA
<213> ORGANISM: Homo sapiens

<400> SEQUENCE: 646
cuuggcaccu agcaagcacu ca                                     22

<210> SEQ ID NO 647
<211> LENGTH: 24
<212> TYPE: RNA
<213> ORGANISM: Homo sapiens

<400> SEQUENCE: 647
uugcagcugc cugggaguga cuuc                                   24

<210> SEQ ID NO 648
<211> LENGTH: 22
<212> TYPE: RNA
<213> ORGANISM: Homo sapiens

```
<400> SEQUENCE: 648
acccuaucaa uauugucucu gc                                            22

<210> SEQ ID NO 649
<211> LENGTH: 23
<212> TYPE: RNA
<213> ORGANISM: Homo sapiens

<400> SEQUENCE: 649
uagugcaaua uugcuuauag ggu                                           23

<210> SEQ ID NO 650
<211> LENGTH: 21
<212> TYPE: RNA
<213> ORGANISM: Homo sapiens

<400> SEQUENCE: 650
agaggauacc cuuuguaugu u                                             21

<210> SEQ ID NO 651
<211> LENGTH: 25
<212> TYPE: RNA
<213> ORGANISM: Homo sapiens

<400> SEQUENCE: 651
uaggcagugu auugcuagcg gcugu                                         25

<210> SEQ ID NO 652
<211> LENGTH: 23
<212> TYPE: RNA
<213> ORGANISM: Homo sapiens

<400> SEQUENCE: 652
uugcuaguug cacuccucuc ugu                                           23

<210> SEQ ID NO 653
<211> LENGTH: 22
<212> TYPE: RNA
<213> ORGANISM: Homo sapiens

<400> SEQUENCE: 653
ucuacaaagg aaagcgcuuu cu                                            22

<210> SEQ ID NO 654
<211> LENGTH: 22
<212> TYPE: RNA
<213> ORGANISM: Homo sapiens

<400> SEQUENCE: 654
ugagaccucu ggguucugag cu                                            22

<210> SEQ ID NO 655
<211> LENGTH: 23
<212> TYPE: RNA
<213> ORGANISM: Homo sapiens

<400> SEQUENCE: 655
cugggaucuc cggggucuug guu                                           23

<210> SEQ ID NO 656
<211> LENGTH: 22
<212> TYPE: RNA
<213> ORGANISM: Homo sapiens
```

```
<400> SEQUENCE: 656
acuccagccc cacagccuca gc                                              22

<210> SEQ ID NO 657
<211> LENGTH: 22
<212> TYPE: RNA
<213> ORGANISM: Homo sapiens

<400> SEQUENCE: 657
ggggcugggg ccggggccga gc                                              22

<210> SEQ ID NO 658
<211> LENGTH: 23
<212> TYPE: RNA
<213> ORGANISM: Homo sapiens

<400> SEQUENCE: 658
caguaacaaa gauucauccu ugu                                             23

<210> SEQ ID NO 659
<211> LENGTH: 20
<212> TYPE: RNA
<213> ORGANISM: Homo sapiens

<400> SEQUENCE: 659
gucccugagu guauguggug                                                 20

<210> SEQ ID NO 660
<211> LENGTH: 22
<212> TYPE: RNA
<213> ORGANISM: Homo sapiens

<400> SEQUENCE: 660
uucauucggc uguccagaug ua                                              22

<210> SEQ ID NO 661
<211> LENGTH: 21
<212> TYPE: RNA
<213> ORGANISM: Homo sapiens

<400> SEQUENCE: 661
auuugugcuu ggcucuguca c                                               21

<210> SEQ ID NO 662
<211> LENGTH: 22
<212> TYPE: RNA
<213> ORGANISM: Homo sapiens

<400> SEQUENCE: 662
gcagcagggu gaaacugaca ca                                              22

<210> SEQ ID NO 663
<211> LENGTH: 22
<212> TYPE: RNA
<213> ORGANISM: Homo sapiens

<400> SEQUENCE: 663
gcaggugcuc acuuguccuc cu                                              22

<210> SEQ ID NO 664
<211> LENGTH: 22
<212> TYPE: RNA
```

<213> ORGANISM: Homo sapiens

<400> SEQUENCE: 664
gcagagugca aacaauuuug ac	22

<210> SEQ ID NO 665
<211> LENGTH: 21
<212> TYPE: RNA
<213> ORGANISM: Homo sapiens

<400> SEQUENCE: 665
uggaggagaa ggaaggugau g	21

<210> SEQ ID NO 666
<211> LENGTH: 23
<212> TYPE: RNA
<213> ORGANISM: Homo sapiens

<400> SEQUENCE: 666
uccaguacca cgugucaggg cca	23

<210> SEQ ID NO 667
<211> LENGTH: 23
<212> TYPE: RNA
<213> ORGANISM: Homo sapiens

<400> SEQUENCE: 667
uggugcggag agggcccaca gug	23

<210> SEQ ID NO 668
<211> LENGTH: 20
<212> TYPE: RNA
<213> ORGANISM: Homo sapiens

<400> SEQUENCE: 668
cuguaugccc ucaccgcuca	20

<210> SEQ ID NO 669
<211> LENGTH: 24
<212> TYPE: RNA
<213> ORGANISM: Homo sapiens

<400> SEQUENCE: 669
agcagaagca gggagguucu ccca	24

<210> SEQ ID NO 670
<211> LENGTH: 22
<212> TYPE: RNA
<213> ORGANISM: Homo sapiens

<400> SEQUENCE: 670
ugcaacgaac cugagccacu ga	22

<210> SEQ ID NO 671
<211> LENGTH: 22
<212> TYPE: RNA
<213> ORGANISM: Homo sapiens

<400> SEQUENCE: 671
uauacaaggg cagacucucu cu	22

<210> SEQ ID NO 672
<211> LENGTH: 23

```
<212> TYPE: RNA
<213> ORGANISM: Homo sapiens

<400> SEQUENCE: 672
cgggucggag uuagcucaag cgg                                              23

<210> SEQ ID NO 673
<211> LENGTH: 21
<212> TYPE: RNA
<213> ORGANISM: Homo sapiens

<400> SEQUENCE: 673
cgcgggugcu uacugacccu u                                                21

<210> SEQ ID NO 674
<211> LENGTH: 21
<212> TYPE: RNA
<213> ORGANISM: Homo sapiens

<400> SEQUENCE: 674
cacugugucc uuucugcgua g                                                21

<210> SEQ ID NO 675
<211> LENGTH: 21
<212> TYPE: RNA
<213> ORGANISM: Homo sapiens

<400> SEQUENCE: 675
ccaccaccgu gucugacacu u                                                21

<210> SEQ ID NO 676
<211> LENGTH: 22
<212> TYPE: RNA
<213> ORGANISM: Homo sapiens

<400> SEQUENCE: 676
uuuugcaaua uguuccugaa ua                                               22

<210> SEQ ID NO 677
<211> LENGTH: 22
<212> TYPE: RNA
<213> ORGANISM: Homo sapiens

<400> SEQUENCE: 677
uugggaucau uuugcaucca ua                                               22

<210> SEQ ID NO 678
<211> LENGTH: 22
<212> TYPE: RNA
<213> ORGANISM: Homo sapiens

<400> SEQUENCE: 678
cugcccuggc ccgagggacc ga                                               22

<210> SEQ ID NO 679
<211> LENGTH: 21
<212> TYPE: RNA
<213> ORGANISM: Homo sapiens

<400> SEQUENCE: 679
uacuuggaaa ggcaucaguu g                                                21

<210> SEQ ID NO 680
```

```
<211> LENGTH: 22
<212> TYPE: RNA
<213> ORGANISM: Homo sapiens

<400> SEQUENCE: 680
ugcaacuuac cugagucauu ga                                              22

<210> SEQ ID NO 681
<211> LENGTH: 22
<212> TYPE: RNA
<213> ORGANISM: Homo sapiens

<400> SEQUENCE: 681
acacagggcu guugugaaga cu                                              22

<210> SEQ ID NO 682
<211> LENGTH: 21
<212> TYPE: RNA
<213> ORGANISM: Homo sapiens

<400> SEQUENCE: 682
uacucaaaaa gcugucaguc a                                               21

<210> SEQ ID NO 683
<211> LENGTH: 22
<212> TYPE: RNA
<213> ORGANISM: Homo sapiens

<400> SEQUENCE: 683
gacugacacc ucuuugggug aa                                              22

<210> SEQ ID NO 684
<211> LENGTH: 22
<212> TYPE: RNA
<213> ORGANISM: Homo sapiens

<400> SEQUENCE: 684
cacuggcucc uuucugggua ga                                              22

<210> SEQ ID NO 685
<211> LENGTH: 25
<212> TYPE: RNA
<213> ORGANISM: Homo sapiens

<400> SEQUENCE: 685
aaaggauucu gcugucgguc ccacu                                           25

<210> SEQ ID NO 686
<211> LENGTH: 22
<212> TYPE: RNA
<213> ORGANISM: Homo sapiens

<400> SEQUENCE: 686
uggugggcac agaaucugga cu                                              22

<210> SEQ ID NO 687
<211> LENGTH: 21
<212> TYPE: RNA
<213> ORGANISM: Homo sapiens

<400> SEQUENCE: 687
uuaauaucgg acaaccauug u                                               21
```

```
<210> SEQ ID NO 688
<211> LENGTH: 22
<212> TYPE: RNA
<213> ORGANISM: Homo sapiens

<400> SEQUENCE: 688
uauaccucag uuuuaucagg ug                                              22

<210> SEQ ID NO 689
<211> LENGTH: 21
<212> TYPE: RNA
<213> ORGANISM: Homo sapiens

<400> SEQUENCE: 689
ccuggaaaca cugagguugu g                                               21

<210> SEQ ID NO 690
<211> LENGTH: 22
<212> TYPE: RNA
<213> ORGANISM: Homo sapiens

<400> SEQUENCE: 690
uggauuucuu ugugaaucac ca                                              22

<210> SEQ ID NO 691
<211> LENGTH: 22
<212> TYPE: RNA
<213> ORGANISM: Homo sapiens

<400> SEQUENCE: 691
uggugguuua caaaguaauu ca                                              22

<210> SEQ ID NO 692
<211> LENGTH: 23
<212> TYPE: RNA
<213> ORGANISM: Homo sapiens

<400> SEQUENCE: 692
aaggagcuua caaucuagcu ggg                                             23

<210> SEQ ID NO 693
<211> LENGTH: 22
<212> TYPE: RNA
<213> ORGANISM: Homo sapiens

<400> SEQUENCE: 693
caacuagacu gugagcuucu ag                                              22

<210> SEQ ID NO 694
<211> LENGTH: 22
<212> TYPE: RNA
<213> ORGANISM: Homo sapiens

<400> SEQUENCE: 694
gugugcggaa augcuucugc ua                                              22

<210> SEQ ID NO 695
<211> LENGTH: 21
<212> TYPE: RNA
<213> ORGANISM: Homo sapiens

<400> SEQUENCE: 695
ugauauguuu gauauugggu u                                               21
```

```
<210> SEQ ID NO 696
<211> LENGTH: 22
<212> TYPE: RNA
<213> ORGANISM: Homo sapiens

<400> SEQUENCE: 696
ugcggggcua gggcuaacag ca                                              22

<210> SEQ ID NO 697
<211> LENGTH: 22
<212> TYPE: RNA
<213> ORGANISM: Homo sapiens

<400> SEQUENCE: 697
cuguugccac uaaccucaac cu                                              22

<210> SEQ ID NO 698
<211> LENGTH: 22
<212> TYPE: RNA
<213> ORGANISM: Homo sapiens

<400> SEQUENCE: 698
uccauuacac uacccugccu cu                                              22

<210> SEQ ID NO 699
<211> LENGTH: 22
<212> TYPE: RNA
<213> ORGANISM: Homo sapiens

<400> SEQUENCE: 699
aggcagcggg guguagugga ua                                              22

<210> SEQ ID NO 700
<211> LENGTH: 20
<212> TYPE: RNA
<213> ORGANISM: Homo sapiens

<400> SEQUENCE: 700
guagaggaga uggcgcaggg                                                 20

<210> SEQ ID NO 701
<211> LENGTH: 21
<212> TYPE: RNA
<213> ORGANISM: Homo sapiens

<400> SEQUENCE: 701
uccucuucuc ccuccuccca g                                               21

<210> SEQ ID NO 702
<211> LENGTH: 22
<212> TYPE: RNA
<213> ORGANISM: Homo sapiens

<400> SEQUENCE: 702
gugaacgggc gccaucccga gg                                              22

<210> SEQ ID NO 703
<211> LENGTH: 20
<212> TYPE: RNA
<213> ORGANISM: Homo sapiens

<400> SEQUENCE: 703
accaggaggc ugaggcccu                                                  20
```

<210> SEQ ID NO 704
<211> LENGTH: 21
<212> TYPE: RNA
<213> ORGANISM: Homo sapiens

<400> SEQUENCE: 704
gcaggaacuu gugagucucc u                                            21

<210> SEQ ID NO 705
<211> LENGTH: 22
<212> TYPE: RNA
<213> ORGANISM: Homo sapiens

<400> SEQUENCE: 705
aaacauucgc ggugcacuuc uu                                           22

<210> SEQ ID NO 706
<211> LENGTH: 22
<212> TYPE: RNA
<213> ORGANISM: Homo sapiens

<400> SEQUENCE: 706
auauaauaca accugcuaag ug                                           22

<210> SEQ ID NO 707
<211> LENGTH: 22
<212> TYPE: RNA
<213> ORGANISM: Homo sapiens

<400> SEQUENCE: 707
cuuagcaggu uguauuauca uu                                           22

<210> SEQ ID NO 708
<211> LENGTH: 20
<212> TYPE: RNA
<213> ORGANISM: Homo sapiens

<400> SEQUENCE: 708
cggcucuggg ucugugggga                                              20

<210> SEQ ID NO 709
<211> LENGTH: 23
<212> TYPE: RNA
<213> ORGANISM: Homo sapiens

<400> SEQUENCE: 709
cagugcaaug auauugucaa agc                                          23

<210> SEQ ID NO 710
<211> LENGTH: 22
<212> TYPE: RNA
<213> ORGANISM: Homo sapiens

<400> SEQUENCE: 710
aaaucucugc aggcaaaugu ga                                           22

<210> SEQ ID NO 711
<211> LENGTH: 22
<212> TYPE: RNA
<213> ORGANISM: Homo sapiens

<400> SEQUENCE: 711
auaagacgaa caaaagguuu gu                                    22

<210> SEQ ID NO 712
<211> LENGTH: 20
<212> TYPE: RNA
<213> ORGANISM: Homo sapiens

<400> SEQUENCE: 712
ggggagcugu ggaagcagua                                       20

<210> SEQ ID NO 713
<211> LENGTH: 25
<212> TYPE: RNA
<213> ORGANISM: Homo sapiens

<400> SEQUENCE: 713
cuagugaggg acagaaccag gauuc                                 25

<210> SEQ ID NO 714
<211> LENGTH: 23
<212> TYPE: RNA
<213> ORGANISM: Homo sapiens

<400> SEQUENCE: 714
gcagcagaga auaggacuac guc                                   23

<210> SEQ ID NO 715
<211> LENGTH: 20
<212> TYPE: RNA
<213> ORGANISM: Homo sapiens

<400> SEQUENCE: 715
agagucuugu gaugucuugc                                       20

<210> SEQ ID NO 716
<211> LENGTH: 22
<212> TYPE: RNA
<213> ORGANISM: Homo sapiens

<400> SEQUENCE: 716
uacugcagac guggcaauca ug                                    22

<210> SEQ ID NO 717
<211> LENGTH: 22
<212> TYPE: RNA
<213> ORGANISM: Homo sapiens

<400> SEQUENCE: 717
ugugcgcagg gagaccucuc cc                                    22

<210> SEQ ID NO 718
<211> LENGTH: 22
<212> TYPE: RNA
<213> ORGANISM: Homo sapiens

<400> SEQUENCE: 718
ugucuacuac uggagacacu gg                                    22

<210> SEQ ID NO 719
<211> LENGTH: 23
<212> TYPE: RNA
<213> ORGANISM: Homo sapiens

<400> SEQUENCE: 719
ccaguuaccg cuuccgcuac cgc 23

<210> SEQ ID NO 720
<211> LENGTH: 22
<212> TYPE: RNA
<213> ORGANISM: Homo sapiens

<400> SEQUENCE: 720
acaguagagg gaggaaucgc ag 22

<210> SEQ ID NO 721
<211> LENGTH: 22
<212> TYPE: RNA
<213> ORGANISM: Homo sapiens

<400> SEQUENCE: 721
auccgcgcuc ugacucucug cc 22

<210> SEQ ID NO 722
<211> LENGTH: 22
<212> TYPE: RNA
<213> ORGANISM: Homo sapiens

<400> SEQUENCE: 722
ugcccuuaaa ggugaaccca gu 22

<210> SEQ ID NO 723
<211> LENGTH: 24
<212> TYPE: RNA
<213> ORGANISM: Homo sapiens

<400> SEQUENCE: 723
uggggagcug aggcucuggg ggug 24

<210> SEQ ID NO 724
<211> LENGTH: 21
<212> TYPE: RNA
<213> ORGANISM: Homo sapiens

<400> SEQUENCE: 724
aaggcagggc ccccgcuccc c 21

<210> SEQ ID NO 725
<211> LENGTH: 23
<212> TYPE: RNA
<213> ORGANISM: Homo sapiens

<400> SEQUENCE: 725
cacccggcug ugugcacaug ugc 23

<210> SEQ ID NO 726
<211> LENGTH: 22
<212> TYPE: RNA
<213> ORGANISM: Homo sapiens

<400> SEQUENCE: 726
ucuucucugu uuuggccaug ug 22

<210> SEQ ID NO 727
<211> LENGTH: 21
<212> TYPE: RNA
<213> ORGANISM: Homo sapiens

<400> SEQUENCE: 727
cugacuguug ccguccucca g                                          21

<210> SEQ ID NO 728
<211> LENGTH: 22
<212> TYPE: RNA
<213> ORGANISM: Homo sapiens

<400> SEQUENCE: 728
aaauuauugu acaucggaug ag                                         22

<210> SEQ ID NO 729
<211> LENGTH: 21
<212> TYPE: RNA
<213> ORGANISM: Homo sapiens

<400> SEQUENCE: 729
auguaugugu gcaugugcau g                                          21

<210> SEQ ID NO 730
<211> LENGTH: 21
<212> TYPE: RNA
<213> ORGANISM: Homo sapiens

<400> SEQUENCE: 730
uugcucacug uucuucccua g                                          21

<210> SEQ ID NO 731
<211> LENGTH: 21
<212> TYPE: RNA
<213> ORGANISM: Homo sapiens

<400> SEQUENCE: 731
aagcauucuu ucauugguug g                                          21

<210> SEQ ID NO 732
<211> LENGTH: 22
<212> TYPE: RNA
<213> ORGANISM: Homo sapiens

<400> SEQUENCE: 732
uuuccggcuc gcguggugu gu                                          22

<210> SEQ ID NO 733
<211> LENGTH: 21
<212> TYPE: RNA
<213> ORGANISM: Homo sapiens

<400> SEQUENCE: 733
ccgucgccgc cacccgagcc g                                          21

<210> SEQ ID NO 734
<211> LENGTH: 23
<212> TYPE: RNA
<213> ORGANISM: Homo sapiens

<400> SEQUENCE: 734
gagggucuug ggagggaugu gac                                        23

<210> SEQ ID NO 735
<211> LENGTH: 27
<212> TYPE: RNA
<213> ORGANISM: Homo sapiens

```
<400> SEQUENCE: 735
cacuguaggu gauggugaga gugggca                                        27

<210> SEQ ID NO 736
<211> LENGTH: 23
<212> TYPE: RNA
<213> ORGANISM: Homo sapiens

<400> SEQUENCE: 736
ccugcagcga cuugauggcu ucc                                            23

<210> SEQ ID NO 737
<211> LENGTH: 22
<212> TYPE: RNA
<213> ORGANISM: Homo sapiens

<400> SEQUENCE: 737
guggguacgg cccagugggg gg                                             22

<210> SEQ ID NO 738
<211> LENGTH: 22
<212> TYPE: RNA
<213> ORGANISM: Homo sapiens

<400> SEQUENCE: 738
ugagccccug ugccgcccccc ag                                            22

<210> SEQ ID NO 739
<211> LENGTH: 26
<212> TYPE: RNA
<213> ORGANISM: Homo sapiens

<400> SEQUENCE: 739
gugagggcau gcaggccugg augggg                                         26

<210> SEQ ID NO 740
<211> LENGTH: 22
<212> TYPE: RNA
<213> ORGANISM: Homo sapiens

<400> SEQUENCE: 740
ucaccagccc uguguucccu ag                                             22

<210> SEQ ID NO 741
<211> LENGTH: 20
<212> TYPE: RNA
<213> ORGANISM: Homo sapiens

<400> SEQUENCE: 741
cgugccaccc uuuuccccag                                                20

<210> SEQ ID NO 742
<211> LENGTH: 21
<212> TYPE: RNA
<213> ORGANISM: Homo sapiens

<400> SEQUENCE: 742
gugggcgggg gcaggugugu g                                              21

<210> SEQ ID NO 743
<211> LENGTH: 20
<212> TYPE: RNA
```

<213> ORGANISM: Homo sapiens

<400> SEQUENCE: 743
ucacaccugc cucgccccccc                                             20

<210> SEQ ID NO 744
<211> LENGTH: 23
<212> TYPE: RNA
<213> ORGANISM: Homo sapiens

<400> SEQUENCE: 744
cucucaccac ugcccuccca cag                                          23

<210> SEQ ID NO 745
<211> LENGTH: 20
<212> TYPE: RNA
<213> ORGANISM: Homo sapiens

<400> SEQUENCE: 745
gugucugggc ggacagcugc                                              20

<210> SEQ ID NO 746
<211> LENGTH: 20
<212> TYPE: RNA
<213> ORGANISM: Homo sapiens

<400> SEQUENCE: 746
ugagcccugu ccucccgcag                                              20

<210> SEQ ID NO 747
<211> LENGTH: 22
<212> TYPE: RNA
<213> ORGANISM: Homo sapiens

<400> SEQUENCE: 747
ucggccugac cacccacccc ac                                           22

<210> SEQ ID NO 748
<211> LENGTH: 22
<212> TYPE: RNA
<213> ORGANISM: Homo sapiens

<400> SEQUENCE: 748
ccucuucccc uugucucucc ag                                           22

<210> SEQ ID NO 749
<211> LENGTH: 21
<212> TYPE: RNA
<213> ORGANISM: Homo sapiens

<400> SEQUENCE: 749
uccuucugcu ccgucccca g                                             21

<210> SEQ ID NO 750
<211> LENGTH: 20
<212> TYPE: RNA
<213> ORGANISM: Homo sapiens

<400> SEQUENCE: 750
cuuccucguc ugucugcccc                                              20

<210> SEQ ID NO 751
<211> LENGTH: 22

```
<212> TYPE: RNA
<213> ORGANISM: Homo sapiens

<400> SEQUENCE: 751
cuccugagcc auucugagcc uc                                          22

<210> SEQ ID NO 752
<211> LENGTH: 24
<212> TYPE: RNA
<213> ORGANISM: Homo sapiens

<400> SEQUENCE: 752
agccugauua aacacaugcu cuga                                        24

<210> SEQ ID NO 753
<211> LENGTH: 21
<212> TYPE: RNA
<213> ORGANISM: Homo sapiens

<400> SEQUENCE: 753
gugccagcug cagugggga g                                            21

<210> SEQ ID NO 754
<211> LENGTH: 21
<212> TYPE: RNA
<213> ORGANISM: Homo sapiens

<400> SEQUENCE: 754
cccggagcca ggaugcagcu c                                           21

<210> SEQ ID NO 755
<211> LENGTH: 22
<212> TYPE: RNA
<213> ORGANISM: Homo sapiens

<400> SEQUENCE: 755
gguggcccgg ccgugccuga gg                                          22

<210> SEQ ID NO 756
<211> LENGTH: 21
<212> TYPE: RNA
<213> ORGANISM: Homo sapiens

<400> SEQUENCE: 756
ucguggccug gucuccauua u                                           21

<210> SEQ ID NO 757
<211> LENGTH: 20
<212> TYPE: RNA
<213> ORGANISM: Homo sapiens

<400> SEQUENCE: 757
ucugcagggu uugcuuugag                                             20

<210> SEQ ID NO 758
<211> LENGTH: 21
<212> TYPE: RNA
<213> ORGANISM: Homo sapiens

<400> SEQUENCE: 758
uguucaugua gauguuuaag c                                           21

<210> SEQ ID NO 759
```

-continued

<211> LENGTH: 21
<212> TYPE: RNA
<213> ORGANISM: Homo sapiens

<400> SEQUENCE: 759
uggcagggag gcugggaggg g                                              21

<210> SEQ ID NO 760
<211> LENGTH: 18
<212> TYPE: RNA
<213> ORGANISM: Homo sapiens

<400> SEQUENCE: 760
ucagcuggcc cucauuuc                                                  18

<210> SEQ ID NO 761
<211> LENGTH: 20
<212> TYPE: RNA
<213> ORGANISM: Homo sapiens

<400> SEQUENCE: 761
ucacuguuca gacaggcgga                                                20

<210> SEQ ID NO 762
<211> LENGTH: 22
<212> TYPE: RNA
<213> ORGANISM: Homo sapiens

<400> SEQUENCE: 762
aaaaacugag acuacuuuug ca                                             22

<210> SEQ ID NO 763
<211> LENGTH: 22
<212> TYPE: RNA
<213> ORGANISM: Homo sapiens

<400> SEQUENCE: 763
aaaaguaauu gcggucuuug gu                                             22

<210> SEQ ID NO 764
<211> LENGTH: 22
<212> TYPE: RNA
<213> ORGANISM: Homo sapiens

<400> SEQUENCE: 764
ucugggcaac aaagugagac cu                                             22

<210> SEQ ID NO 765
<211> LENGTH: 21
<212> TYPE: RNA
<213> ORGANISM: Homo sapiens

<400> SEQUENCE: 765
ugcaggacca agaugagccc u                                              21

<210> SEQ ID NO 766
<211> LENGTH: 22
<212> TYPE: RNA
<213> ORGANISM: Homo sapiens

<400> SEQUENCE: 766
ugcuggauca gugguucgag uc                                             22

```
<210> SEQ ID NO 767
<211> LENGTH: 23
<212> TYPE: RNA
<213> ORGANISM: Homo sapiens

<400> SEQUENCE: 767
uggaguccag gaaucugcau uuu                                          23

<210> SEQ ID NO 768
<211> LENGTH: 19
<212> TYPE: RNA
<213> ORGANISM: Homo sapiens

<400> SEQUENCE: 768
uggauuuuug gaucaggga                                               19

<210> SEQ ID NO 769
<211> LENGTH: 24
<212> TYPE: RNA
<213> ORGANISM: Homo sapiens

<400> SEQUENCE: 769
uggcccugac ugaagaccag cagu                                         24

<210> SEQ ID NO 770
<211> LENGTH: 22
<212> TYPE: RNA
<213> ORGANISM: Homo sapiens

<400> SEQUENCE: 770
aaaaguacuu gcggauuuug cu                                           22

<210> SEQ ID NO 771
<211> LENGTH: 22
<212> TYPE: RNA
<213> ORGANISM: Homo sapiens

<400> SEQUENCE: 771 ugggguggucu ggagauuugu gc                                          22

<210> SEQ ID NO 772
<211> LENGTH: 22
<212> TYPE: RNA
<213> ORGANISM: Homo sapiens

<400> SEQUENCE: 772
ugugagguug gcauuguugu cu                                           22

<210> SEQ ID NO 773
<211> LENGTH: 21
<212> TYPE: RNA
<213> ORGANISM: Homo sapiens

<400> SEQUENCE: 773
uuaggccgca gaucugggug a                                            21

<210> SEQ ID NO 774
<211> LENGTH: 17
<212> TYPE: RNA
<213> ORGANISM: Homo sapiens

<400> SEQUENCE: 774
uucaaguaau ucaggug                                                 17
```

```
<210> SEQ ID NO 775
<211> LENGTH: 22
<212> TYPE: RNA
<213> ORGANISM: Homo sapiens

<400> SEQUENCE: 775
uucuggaauu cugugugagg ga                                              22

<210> SEQ ID NO 776
<211> LENGTH: 22
<212> TYPE: RNA
<213> ORGANISM: Homo sapiens

<400> SEQUENCE: 776
aaaaguauuu gcggguuuug uc                                              22

<210> SEQ ID NO 777
<211> LENGTH: 21
<212> TYPE: RNA
<213> ORGANISM: Homo sapiens

<400> SEQUENCE: 777
uugggacaua cuuaugcuaa a                                               21

<210> SEQ ID NO 778
<211> LENGTH: 22
<212> TYPE: RNA
<213> ORGANISM: Homo sapiens

<400> SEQUENCE: 778
uuuagagacg gggucuugcu cu                                              22

<210> SEQ ID NO 779
<211> LENGTH: 22
<212> TYPE: RNA
<213> ORGANISM: Homo sapiens

<400> SEQUENCE: 779
uuugaggcua cagugagaug ug                                              22

<210> SEQ ID NO 780
<211> LENGTH: 22
<212> TYPE: RNA
<213> ORGANISM: Homo sapiens

<400> SEQUENCE: 780
uuuucaacuc uaaugggaga ga                                              22

<210> SEQ ID NO 781
<211> LENGTH: 22
<212> TYPE: RNA
<213> ORGANISM: Homo sapiens

<400> SEQUENCE: 781
aacuggauca auuauaggag ug                                              22

<210> SEQ ID NO 782
<211> LENGTH: 19
<212> TYPE: RNA
<213> ORGANISM: Homo sapiens

<400> SEQUENCE: 782
aaaaacugua auuacuuuu                                                  19
```

```
<210> SEQ ID NO 783
<211> LENGTH: 26
<212> TYPE: RNA
<213> ORGANISM: Homo sapiens

<400> SEQUENCE: 783
aaguaguugg uuuguaugag augguu                                          26

<210> SEQ ID NO 784
<211> LENGTH: 21
<212> TYPE: RNA
<213> ORGANISM: Homo sapiens

<400> SEQUENCE: 784
aagugaucua aaggccuaca u                                               21

<210> SEQ ID NO 785
<211> LENGTH: 19
<212> TYPE: RNA
<213> ORGANISM: Homo sapiens

<400> SEQUENCE: 785
aauggauuuu uggagcagg                                                  19

<210> SEQ ID NO 786
<211> LENGTH: 22
<212> TYPE: RNA
<213> ORGANISM: Homo sapiens

<400> SEQUENCE: 786
acccgucccg uucguccccg ga                                              22

<210> SEQ ID NO 787
<211> LENGTH: 27
<212> TYPE: RNA
<213> ORGANISM: Homo sapiens

<400> SEQUENCE: 787
accuucuugu auaagcacug ugcuaaa                                         27

<210> SEQ ID NO 788
<211> LENGTH: 22
<212> TYPE: RNA
<213> ORGANISM: Homo sapiens

<400> SEQUENCE: 788
acgcccuucc cccccuucuu ca                                              22

<210> SEQ ID NO 789
<211> LENGTH: 21
<212> TYPE: RNA
<213> ORGANISM: Homo sapiens

<400> SEQUENCE: 789
acggugcugg auguggccuu u                                               21

<210> SEQ ID NO 790
<211> LENGTH: 21
<212> TYPE: RNA
<213> ORGANISM: Homo sapiens

<400> SEQUENCE: 790
```
acucuagcug ccaaaggcgc u    21

<210> SEQ ID NO 791
<211> LENGTH: 21
<212> TYPE: RNA
<213> ORGANISM: Homo sapiens

<400> SEQUENCE: 791
agagaagaag aucagccugc a    21

<210> SEQ ID NO 792
<211> LENGTH: 24
<212> TYPE: RNA
<213> ORGANISM: Homo sapiens

<400> SEQUENCE: 792
agccuggaag cuggagccug cagu    24

<210> SEQ ID NO 793
<211> LENGTH: 23
<212> TYPE: RNA
<213> ORGANISM: Homo sapiens

<400> SEQUENCE: 793
aggaugagca aagaaaguag auu    23

<210> SEQ ID NO 794
<211> LENGTH: 22
<212> TYPE: RNA
<213> ORGANISM: Homo sapiens

<400> SEQUENCE: 794
aggcauugac uucucacuag cu    22

<210> SEQ ID NO 795
<211> LENGTH: 21
<212> TYPE: RNA
<213> ORGANISM: Homo sapiens

<400> SEQUENCE: 795
agugaaugau ggguucugac c    21

<210> SEQ ID NO 796
<211> LENGTH: 21
<212> TYPE: RNA
<213> ORGANISM: Homo sapiens

<400> SEQUENCE: 796
aguuaggauu aggucgugga a    21

<210> SEQ ID NO 797
<211> LENGTH: 21
<212> TYPE: RNA
<213> ORGANISM: Homo sapiens

<400> SEQUENCE: 797
auauaugaug acuuagcuuu u    21

<210> SEQ ID NO 798
<211> LENGTH: 18
<212> TYPE: RNA
<213> ORGANISM: Homo sapiens

<400> SEQUENCE: 798
aucccaccuc ugccacca                                          18

<210> SEQ ID NO 799
<211> LENGTH: 22
<212> TYPE: RNA
<213> ORGANISM: Homo sapiens

<400> SEQUENCE: 799
aaaacuguaa uuacuuuugu ac                                     22

<210> SEQ ID NO 800
<211> LENGTH: 19
<212> TYPE: RNA
<213> ORGANISM: Homo sapiens

<400> SEQUENCE: 800
auggauaagg cuuuggcuu                                         19

<210> SEQ ID NO 801
<211> LENGTH: 22
<212> TYPE: RNA
<213> ORGANISM: Homo sapiens

<400> SEQUENCE: 801
augggugaau uuguagaagg au                                     22

<210> SEQ ID NO 802
<211> LENGTH: 22
<212> TYPE: RNA
<213> ORGANISM: Homo sapiens

<400> SEQUENCE: 802
augguacccu ggcauacuga gu                                     22

<210> SEQ ID NO 803
<211> LENGTH: 22
<212> TYPE: RNA
<213> ORGANISM: Homo sapiens

<400> SEQUENCE: 803
caaaaguaau uguggauuuu gu                                     22

<210> SEQ ID NO 804
<211> LENGTH: 21
<212> TYPE: RNA
<213> ORGANISM: Homo sapiens

<400> SEQUENCE: 804
caaagguauu ugugguuuuu g                                      21

<210> SEQ ID NO 805
<211> LENGTH: 22
<212> TYPE: RNA
<213> ORGANISM: Homo sapiens

<400> SEQUENCE: 805
caggaugugg ucaaguguug uu                                     22

<210> SEQ ID NO 806
<211> LENGTH: 22
<212> TYPE: RNA
<213> ORGANISM: Homo sapiens

```
<400> SEQUENCE: 806
ccaaaacugc aguuacuuuu gc                                    22

<210> SEQ ID NO 807
<211> LENGTH: 23
<212> TYPE: RNA
<213> ORGANISM: Homo sapiens

<400> SEQUENCE: 807
ccucagggcu guagaacagg gcu                                   23

<210> SEQ ID NO 808
<211> LENGTH: 21
<212> TYPE: RNA
<213> ORGANISM: Homo sapiens

<400> SEQUENCE: 808
ccuguugaag uguaaucccc a                                     21

<210> SEQ ID NO 809
<211> LENGTH: 18
<212> TYPE: RNA
<213> ORGANISM: Homo sapiens

<400> SEQUENCE: 809
cgggcguggu ggugggg                                          18

<210> SEQ ID NO 810
<211> LENGTH: 22
<212> TYPE: RNA
<213> ORGANISM: Homo sapiens

<400> SEQUENCE: 810
cuggacugag ccgugcuacu gg                                    22

<210> SEQ ID NO 811
<211> LENGTH: 23
<212> TYPE: RNA
<213> ORGANISM: Homo sapiens

<400> SEQUENCE: 811
cuggagauau ggaagagcug ugu                                   23

<210> SEQ ID NO 812
<211> LENGTH: 26
<212> TYPE: RNA
<213> ORGANISM: Homo sapiens

<400> SEQUENCE: 812
gaugaugaug gcagcaaauu cugaaa                                26

<210> SEQ ID NO 813
<211> LENGTH: 25
<212> TYPE: RNA
<213> ORGANISM: Homo sapiens

<400> SEQUENCE: 813
gggcgacaaa gcaagacucu uucuu                                 25

<210> SEQ ID NO 814
<211> LENGTH: 18
<212> TYPE: RNA
<213> ORGANISM: Homo sapiens
```

```
<400> SEQUENCE: 814
gucccuguuc aggcgcca                                              18

<210> SEQ ID NO 815
<211> LENGTH: 22
<212> TYPE: RNA
<213> ORGANISM: Homo sapiens

<400> SEQUENCE: 815
aaaaguaauc gcgguuuuug uc                                         22

<210> SEQ ID NO 816
<211> LENGTH: 17
<212> TYPE: RNA
<213> ORGANISM: Homo sapiens

<400> SEQUENCE: 816 guggggaga ggcuguc                                                17

<210> SEQ ID NO 817
<211> LENGTH: 20
<212> TYPE: RNA
<213> ORGANISM: Homo sapiens

<400> SEQUENCE: 817
uaaagagccc uguggagaca                                            20

<210> SEQ ID NO 818
<211> LENGTH: 17
<212> TYPE: RNA
<213> ORGANISM: Homo sapiens

<400> SEQUENCE: 818
uaagugcuuc caugcuu                                               17

<210> SEQ ID NO 819
<211> LENGTH: 17
<212> TYPE: RNA
<213> ORGANISM: Homo sapiens

<400> SEQUENCE: 819
uaauugcuuc cauguuu                                               17

<210> SEQ ID NO 820
<211> LENGTH: 22
<212> TYPE: RNA
<213> ORGANISM: Homo sapiens

<400> SEQUENCE: 820
uacguagaua uauauguauu uu                                         22

<210> SEQ ID NO 821
<211> LENGTH: 22
<212> TYPE: RNA
<213> ORGANISM: Homo sapiens

<400> SEQUENCE: 821
uagcaaaaac ugcaguuacu uu                                         22

<210> SEQ ID NO 822
<211> LENGTH: 22
<212> TYPE: RNA
```

<213> ORGANISM: Homo sapiens

<400> SEQUENCE: 822
aaaaguaauu gcggauuuug cc                                         22

<210> SEQ ID NO 823
<211> LENGTH: 22
<212> TYPE: RNA
<213> ORGANISM: Homo sapiens

<400> SEQUENCE: 823
uaguacugug cauaucaucu au                                         22

<210> SEQ ID NO 824
<211> LENGTH: 17
<212> TYPE: RNA
<213> ORGANISM: Homo sapiens

<400> SEQUENCE: 824
ucauauugcu ucuuucu                                               17

<210> SEQ ID NO 825
<211> LENGTH: 17
<212> TYPE: RNA
<213> ORGANISM: Homo sapiens

<400> SEQUENCE: 825
ucccuguucg ggcgcca                                               17

<210> SEQ ID NO 826
<211> LENGTH: 17
<212> TYPE: RNA
<213> ORGANISM: Homo sapiens

<400> SEQUENCE: 826
ucgccuccuc cucuccc                                               17

<210> SEQ ID NO 827
<211> LENGTH: 20
<212> TYPE: RNA
<213> ORGANISM: Homo sapiens

<400> SEQUENCE: 827
ucguuugccu uuuucugcuu                                            20

<210> SEQ ID NO 828
<211> LENGTH: 22
<212> TYPE: RNA
<213> ORGANISM: Homo sapiens

<400> SEQUENCE: 828
ucuauacaga cccuggcuuu uc                                         22

<210> SEQ ID NO 829
<211> LENGTH: 21
<212> TYPE: RNA
<213> ORGANISM: Homo sapiens

<400> SEQUENCE: 829
uggacugccc ugaucuggag a                                          21

<210> SEQ ID NO 830
<211> LENGTH: 25

```
<212> TYPE: RNA
<213> ORGANISM: Homo sapiens

<400> SEQUENCE: 830
ugggaacggg uuccggcaga cgcug                                    25

<210> SEQ ID NO 831
<211> LENGTH: 22
<212> TYPE: RNA
<213> ORGANISM: Homo sapiens

<400> SEQUENCE: 831
agaaggaaau ugaauucauu ua                                       22

<210> SEQ ID NO 832
<211> LENGTH: 22
<212> TYPE: RNA
<213> ORGANISM: Homo sapiens

<400> SEQUENCE: 832
cggaugagca aagaaagugg uu                                       22

<210> SEQ ID NO 833
<211> LENGTH: 17
<212> TYPE: RNA
<213> ORGANISM: Homo sapiens

<400> SEQUENCE: 833
ucccaccgcu gccaccc                                             17

<210> SEQ ID NO 834
<211> LENGTH: 18
<212> TYPE: RNA
<213> ORGANISM: Homo sapiens

<400> SEQUENCE: 834
gcaugggugg uucagugg                                            18

<210> SEQ ID NO 835
<211> LENGTH: 24
<212> TYPE: RNA
<213> ORGANISM: Homo sapiens

<400> SEQUENCE: 835
acuggcuagg gaaaaugauu ggau                                     24

<210> SEQ ID NO 836
<211> LENGTH: 23
<212> TYPE: RNA
<213> ORGANISM: Homo sapiens

<400> SEQUENCE: 836
uauucauuua ucccagccu aca                                       23

<210> SEQ ID NO 837
<211> LENGTH: 18
<212> TYPE: RNA
<213> ORGANISM: Homo sapiens

<400> SEQUENCE: 837
acguuggcuc uggugguug                                           18

<210> SEQ ID NO 838
```

```
<211> LENGTH: 22
<212> TYPE: RNA
<213> ORGANISM: Homo sapiens

<400> SEQUENCE: 838
acucggcgug gcgucggucg ug                                              22

<210> SEQ ID NO 839
<211> LENGTH: 22
<212> TYPE: RNA
<213> ORGANISM: Homo sapiens

<400> SEQUENCE: 839
uucacaagga ggugucauuu au                                              22

<210> SEQ ID NO 840
<211> LENGTH: 22
<212> TYPE: RNA
<213> ORGANISM: Homo sapiens

<400> SEQUENCE: 840
uucucaagga ggugucguuu au                                              22

<210> SEQ ID NO 841
<211> LENGTH: 18
<212> TYPE: RNA
<213> ORGANISM: Homo sapiens

<400> SEQUENCE: 841
cagggaggug aaugugau                                                   18

<210> SEQ ID NO 842
<211> LENGTH: 19
<212> TYPE: RNA
<213> ORGANISM: Homo sapiens

<400> SEQUENCE: 842
gaugaugcug cugaugcug                                                  19

<210> SEQ ID NO 843
<211> LENGTH: 17
<212> TYPE: RNA
<213> ORGANISM: Homo sapiens

<400> SEQUENCE: 843
ucucgcuggg gccucca                                                    17

<210> SEQ ID NO 844
<211> LENGTH: 21
<212> TYPE: RNA
<213> ORGANISM: Homo sapiens

<400> SEQUENCE: 844
uaggacacau ggucuacuuc u                                               21

<210> SEQ ID NO 845
<211> LENGTH: 24
<212> TYPE: RNA
<213> ORGANISM: Homo sapiens

<400> SEQUENCE: 845
ccagacagaa uucuaugcac uuuc                                            24
```

-continued

```
<210> SEQ ID NO 846
<211> LENGTH: 22
<212> TYPE: RNA
<213> ORGANISM: Homo sapiens

<400> SEQUENCE: 846
cucggcgcgg ggcgcgggcu cc                                              22

<210> SEQ ID NO 847
<211> LENGTH: 21
<212> TYPE: RNA
<213> ORGANISM: Homo sapiens

<400> SEQUENCE: 847
gcccuccgcc cgugcacccc g                                               21

<210> SEQ ID NO 848
<211> LENGTH: 22
<212> TYPE: RNA
<213> ORGANISM: Homo sapiens

<400> SEQUENCE: 848
gcccgcgugu ggagccaggu gu                                              22

<210> SEQ ID NO 849
<211> LENGTH: 22
<212> TYPE: RNA
<213> ORGANISM: Homo sapiens

<400> SEQUENCE: 849
aaaaccgucu aguuacaguu gu                                              22

<210> SEQ ID NO 850
<211> LENGTH: 23
<212> TYPE: RNA
<213> ORGANISM: Homo sapiens

<400> SEQUENCE: 850
cggcccgggc ugcugcuguu ccu                                             23

<210> SEQ ID NO 851
<211> LENGTH: 21
<212> TYPE: RNA
<213> ORGANISM: Homo sapiens

<400> SEQUENCE: 851
uccugcgcgu cccagaugcc c                                               21

<210> SEQ ID NO 852
<211> LENGTH: 23
<212> TYPE: RNA
<213> ORGANISM: Homo sapiens

<400> SEQUENCE: 852
ucauagcccu guacaaugcu gcu                                             23

<210> SEQ ID NO 853
<211> LENGTH: 19
<212> TYPE: RNA
<213> ORGANISM: Homo sapiens

<400> SEQUENCE: 853
aaaagcuggg uugagagga                                                  19
```

<210> SEQ ID NO 854
<211> LENGTH: 18
<212> TYPE: RNA
<213> ORGANISM: Homo sapiens

<400> SEQUENCE: 854
uccagugccc uccucucc                                                       18

<210> SEQ ID NO 855
<211> LENGTH: 27
<212> TYPE: RNA
<213> ORGANISM: Homo sapiens

<400> SEQUENCE: 855
auugaucauc gacacuucga acgcaau                                             27

<210> SEQ ID NO 856
<211> LENGTH: 18
<212> TYPE: RNA
<213> ORGANISM: Homo sapiens

<400> SEQUENCE: 856
ugaggcagua gauugaau                                                       18

<210> SEQ ID NO 857
<211> LENGTH: 21
<212> TYPE: RNA
<213> ORGANISM: Homo sapiens

<400> SEQUENCE: 857
cggcggggac ggcgauuggu c                                                   21

<210> SEQ ID NO 858
<211> LENGTH: 21
<212> TYPE: RNA
<213> ORGANISM: Homo sapiens

<400> SEQUENCE: 858
ugagugccgg ugccugcccu g                                                   21

<210> SEQ ID NO 859
<211> LENGTH: 22
<212> TYPE: RNA
<213> ORGANISM: Homo sapiens

<400> SEQUENCE: 859
cgcaggggcc gggugcucac cg                                                  22

<210> SEQ ID NO 860
<211> LENGTH: 21
<212> TYPE: RNA
<213> ORGANISM: Homo sapiens

<400> SEQUENCE: 860
ccaguccugu gccugccgcc u                                                   21

<210> SEQ ID NO 861
<211> LENGTH: 23
<212> TYPE: RNA
<213> ORGANISM: Homo sapiens

<400> SEQUENCE: 861
ugaguaccgc caugucuguu ggg                                                 23

<210> SEQ ID NO 862
<211> LENGTH: 20
<212> TYPE: RNA
<213> ORGANISM: Homo sapiens

<400> SEQUENCE: 862
caccaggcau uguggucucc                                               20

<210> SEQ ID NO 863
<211> LENGTH: 22
<212> TYPE: RNA
<213> ORGANISM: Homo sapiens

<400> SEQUENCE: 863
uacccagagc augcagugug aa                                            22

<210> SEQ ID NO 864
<211> LENGTH: 22
<212> TYPE: RNA
<213> ORGANISM: Homo sapiens

<400> SEQUENCE: 864 ucugccccu ccgcugcugc ca                                             22

<210> SEQ ID NO 865
<211> LENGTH: 22
<212> TYPE: RNA
<213> ORGANISM: Homo sapiens

<400> SEQUENCE: 865
cccugugccc ggcccacuuc ug                                            22

<210> SEQ ID NO 866
<211> LENGTH: 22
<212> TYPE: RNA
<213> ORGANISM: Homo sapiens

<400> SEQUENCE: 866
ggaggggucc cgcacuggga gg                                            22

<210> SEQ ID NO 867
<211> LENGTH: 22
<212> TYPE: RNA
<213> ORGANISM: Homo sapiens

<400> SEQUENCE: 867
accuugccuu gcugcccggg cc                                            22

<210> SEQ ID NO 868
<211> LENGTH: 20
<212> TYPE: RNA
<213> ORGANISM: Homo sapiens

<400> SEQUENCE: 868
ccccagggcg acgcggcggg                                               20

<210> SEQ ID NO 869
<211> LENGTH: 22
<212> TYPE: RNA
<213> ORGANISM: Homo sapiens

<400> SEQUENCE: 869
ucaggccagg cacaguggcu ca                                    22

<210> SEQ ID NO 870
<211> LENGTH: 19
<212> TYPE: RNA
<213> ORGANISM: Homo sapiens

<400> SEQUENCE: 870
accgugcaaa gguagcaua                                        19

<210> SEQ ID NO 871
<211> LENGTH: 25
<212> TYPE: RNA
<213> ORGANISM: Homo sapiens

<400> SEQUENCE: 871
cccccacaac cgcgcuugac uagcu                                 25

<210> SEQ ID NO 872
<211> LENGTH: 20
<212> TYPE: RNA
<213> ORGANISM: Homo sapiens

<400> SEQUENCE: 872
ccuccugccc uccuugcugu                                       20

<210> SEQ ID NO 873
<211> LENGTH: 22
<212> TYPE: RNA
<213> ORGANISM: Homo sapiens

<400> SEQUENCE: 873
cucccacugc uucacuugac ua                                    22

<210> SEQ ID NO 874
<211> LENGTH: 20
<212> TYPE: RNA
<213> ORGANISM: Homo sapiens

<400> SEQUENCE: 874
uguuuugaua acaguaaugu                                       20

<210> SEQ ID NO 875
<211> LENGTH: 23
<212> TYPE: RNA
<213> ORGANISM: Homo sapiens

<400> SEQUENCE: 875
guguuaauua aaccucuauu uac                                   23

<210> SEQ ID NO 876
<211> LENGTH: 23
<212> TYPE: RNA
<213> ORGANISM: Homo sapiens

<400> SEQUENCE: 876
cuguaauaua aauuuaauuu auu                                   23

<210> SEQ ID NO 877
<211> LENGTH: 22
<212> TYPE: RNA
<213> ORGANISM: Homo sapiens

<400> SEQUENCE: 877
uuggggaaac ggccgcugag ug                                                22

<210> SEQ ID NO 878
<211> LENGTH: 22
<212> TYPE: RNA
<213> ORGANISM: Homo sapiens

<400> SEQUENCE: 878
uagucccuuc cuugaagcgg uc                                                22

<210> SEQ ID NO 879
<211> LENGTH: 21
<212> TYPE: RNA
<213> ORGANISM: Homo sapiens

<400> SEQUENCE: 879
cgagccucaa gcaagggacu u                                                 21

<210> SEQ ID NO 880
<211> LENGTH: 22
<212> TYPE: RNA
<213> ORGANISM: Homo sapiens

<400> SEQUENCE: 880
agcuuccaug acuccugaug ga                                                22

<210> SEQ ID NO 881
<211> LENGTH: 22
<212> TYPE: RNA
<213> ORGANISM: Homo sapiens

<400> SEQUENCE: 881
caucagaauu cauggaggcu ag                                                22

<210> SEQ ID NO 882
<211> LENGTH: 21
<212> TYPE: RNA
<213> ORGANISM: Homo sapiens

<400> SEQUENCE: 882
gguucuuagc auaggagguc u                                                 21

<210> SEQ ID NO 883
<211> LENGTH: 21
<212> TYPE: RNA
<213> ORGANISM: Homo sapiens

<400> SEQUENCE: 883
ccucccaugc caagaacucc c                                                 21

<210> SEQ ID NO 884
<211> LENGTH: 21
<212> TYPE: RNA
<213> ORGANISM: Homo sapiens

<400> SEQUENCE: 884
uguucucuuu gccaaggaca g                                                 21

<210> SEQ ID NO 885
<211> LENGTH: 22
<212> TYPE: RNA
<213> ORGANISM: Homo sapiens

```
<400> SEQUENCE: 885
gcuggugcaa aaguaauggc gg                                        22

<210> SEQ ID NO 886
<211> LENGTH: 22
<212> TYPE: RNA
<213> ORGANISM: Homo sapiens

<400> SEQUENCE: 886
ucugcaagug ucagaggcga gg                                        22

<210> SEQ ID NO 887
<211> LENGTH: 21
<212> TYPE: RNA
<213> ORGANISM: Homo sapiens

<400> SEQUENCE: 887
ugacagcgcc cugccuggcu c                                         21

<210> SEQ ID NO 888
<211> LENGTH: 22
<212> TYPE: RNA
<213> ORGANISM: Homo sapiens

<400> SEQUENCE: 888
gagagcagug uguuugccu gg                                         22

<210> SEQ ID NO 889
<211> LENGTH: 22
<212> TYPE: RNA
<213> ORGANISM: Homo sapiens

<400> SEQUENCE: 889
gggacccagg gagagacgua ag                                        22

<210> SEQ ID NO 890
<211> LENGTH: 21
<212> TYPE: RNA
<213> ORGANISM: Homo sapiens

<400> SEQUENCE: 890
cuuccgcccc gccgggcguc g                                         21

<210> SEQ ID NO 891
<211> LENGTH: 19
<212> TYPE: RNA
<213> ORGANISM: Homo sapiens

<400> SEQUENCE: 891
ggggccuggc ggugggcgg                                            19

<210> SEQ ID NO 892
<211> LENGTH: 21
<212> TYPE: RNA
<213> ORGANISM: Homo sapiens

<400> SEQUENCE: 892
guuagggcca acaucucuug g                                         21

<210> SEQ ID NO 893
<211> LENGTH: 20
<212> TYPE: RNA
<213> ORGANISM: Homo sapiens
```

-continued

```
<400> SEQUENCE: 893 auaugguuu acuaguuggu                                            20

<210> SEQ ID NO 894
<211> LENGTH: 22
<212> TYPE: RNA
<213> ORGANISM: Homo sapiens

<400> SEQUENCE: 894
ugccuggaac auaguaggga cu                                        22

<210> SEQ ID NO 895
<211> LENGTH: 21
<212> TYPE: RNA
<213> ORGANISM: Homo sapiens

<400> SEQUENCE: 895
auaggacuca uauagugcca g                                         21

<210> SEQ ID NO 896
<211> LENGTH: 23
<212> TYPE: RNA
<213> ORGANISM: Homo sapiens

<400> SEQUENCE: 896
ugugacugca uuaugaaaau ucu                                       23

<210> SEQ ID NO 897
<211> LENGTH: 20
<212> TYPE: RNA
<213> ORGANISM: Homo sapiens

<400> SEQUENCE: 897
uggcuuuuaa cuuugauggc                                           20

<210> SEQ ID NO 898
<211> LENGTH: 21
<212> TYPE: RNA
<213> ORGANISM: Homo sapiens

<400> SEQUENCE: 898
cacagcaagu guagacaggc a                                         21

<210> SEQ ID NO 899
<211> LENGTH: 22
<212> TYPE: RNA
<213> ORGANISM: Homo sapiens

<400> SEQUENCE: 899
uaaauagagu aggcaaagga ca                                        22

<210> SEQ ID NO 900
<211> LENGTH: 22
<212> TYPE: RNA
<213> ORGANISM: Homo sapiens

<400> SEQUENCE: 900
guugggacaa gaggacgguc uu                                        22

<210> SEQ ID NO 901
<211> LENGTH: 17
<212> TYPE: RNA
```

```
<213> ORGANISM: Homo sapiens

<400> SEQUENCE: 901
cagagaauug uuuaauc                                              17

<210> SEQ ID NO 902
<211> LENGTH: 21
<212> TYPE: RNA
<213> ORGANISM: Homo sapiens

<400> SEQUENCE: 902
uucgcgggcg aaggcaaagu c                                         21

<210> SEQ ID NO 903
<211> LENGTH: 23
<212> TYPE: RNA
<213> ORGANISM: Homo sapiens

<400> SEQUENCE: 903
auggccaaaa cugcaguuau uuu                                       23

<210> SEQ ID NO 904
<211> LENGTH: 20
<212> TYPE: RNA
<213> ORGANISM: Homo sapiens

<400> SEQUENCE: 904
uagaggaagc uguggagaga                                           20

<210> SEQ ID NO 905
<211> LENGTH: 22
<212> TYPE: RNA
<213> ORGANISM: Homo sapiens

<400> SEQUENCE: 905
ugagggacag augccagaag ca                                        22

<210> SEQ ID NO 906
<211> LENGTH: 22
<212> TYPE: RNA
<213> ORGANISM: Homo sapiens

<400> SEQUENCE: 906
caucuggcau ccgucacaca ga                                        22

<210> SEQ ID NO 907
<211> LENGTH: 23
<212> TYPE: RNA
<213> ORGANISM: Homo sapiens

<400> SEQUENCE: 907
aucagggcuu guggaauggg aag                                       23

<210> SEQ ID NO 908
<211> LENGTH: 23
<212> TYPE: RNA
<213> ORGANISM: Homo sapiens

<400> SEQUENCE: 908
ucuggcaagu aaaaaacucu cau                                       23

<210> SEQ ID NO 909
<211> LENGTH: 22
```

```
<212> TYPE: RNA
<213> ORGANISM: Homo sapiens

<400> SEQUENCE: 909
gcaguagugu agagauuggu uu                                      22

<210> SEQ ID NO 910
<211> LENGTH: 21
<212> TYPE: RNA
<213> ORGANISM: Homo sapiens

<400> SEQUENCE: 910
uacccagucu ccggugcagc c                                       21

<210> SEQ ID NO 911
<211> LENGTH: 21
<212> TYPE: RNA
<213> ORGANISM: Homo sapiens

<400> SEQUENCE: 911
gcugcaccgg agacugggua a                                       21

<210> SEQ ID NO 912
<211> LENGTH: 23
<212> TYPE: RNA
<213> ORGANISM: Homo sapiens

<400> SEQUENCE: 912
ucgaggacug guggaagggc cuu                                     23

<210> SEQ ID NO 913
<211> LENGTH: 24
<212> TYPE: RNA
<213> ORGANISM: Homo sapiens

<400> SEQUENCE: 913
uggguagaga aggagcucag agga                                    24

<210> SEQ ID NO 914
<211> LENGTH: 22
<212> TYPE: RNA
<213> ORGANISM: Homo sapiens

<400> SEQUENCE: 914
uaaagaacuc uuaaaaccca au                                      22

<210> SEQ ID NO 915
<211> LENGTH: 19
<212> TYPE: RNA
<213> ORGANISM: Homo sapiens

<400> SEQUENCE: 915
acuggacuug gaggcagaa                                          19

<210> SEQ ID NO 916
<211> LENGTH: 23
<212> TYPE: RNA
<213> ORGANISM: Homo sapiens

<400> SEQUENCE: 916
ugauggauaa aagacuacau auu                                     23

<210> SEQ ID NO 917
```

```
<211> LENGTH: 22
<212> TYPE: RNA
<213> ORGANISM: Homo sapiens

<400> SEQUENCE: 917
ugccuaggcu gagacugcag ug                                              22

<210> SEQ ID NO 918
<211> LENGTH: 23
<212> TYPE: RNA
<213> ORGANISM: Homo sapiens

<400> SEQUENCE: 918
auacacauac acgcaacaca cau                                             23

<210> SEQ ID NO 919
<211> LENGTH: 23
<212> TYPE: RNA
<213> ORGANISM: Homo sapiens

<400> SEQUENCE: 919
cugacugaau agguaggguc auu                                             23

<210> SEQ ID NO 920
<211> LENGTH: 22
<212> TYPE: RNA
<213> ORGANISM: Homo sapiens

<400> SEQUENCE: 920
accugagguu gugcauuucu aa                                              22

<210> SEQ ID NO 921
<211> LENGTH: 24
<212> TYPE: RNA
<213> ORGANISM: Homo sapiens

<400> SEQUENCE: 921
ucuguagccu gggagcaaug gggu                                            24

<210> SEQ ID NO 922
<211> LENGTH: 24
<212> TYPE: RNA
<213> ORGANISM: Homo sapiens

<400> SEQUENCE: 922
uguggacagu gagguagagg gagu                                            24

<210> SEQ ID NO 923
<211> LENGTH: 23
<212> TYPE: RNA
<213> ORGANISM: Homo sapiens

<400> SEQUENCE: 923
uaggagcuca acagaugccu guu                                             23

<210> SEQ ID NO 924
<211> LENGTH: 22
<212> TYPE: RNA
<213> ORGANISM: Homo sapiens

<400> SEQUENCE: 924
agcuuuuggg aauucaggua gu                                              22
```

```
<210> SEQ ID NO 925
<211> LENGTH: 21
<212> TYPE: RNA
<213> ORGANISM: Homo sapiens

<400> SEQUENCE: 925
caaaagugau cgugguuuuu g                                              21

<210> SEQ ID NO 926
<211> LENGTH: 19
<212> TYPE: RNA
<213> ORGANISM: Homo sapiens

<400> SEQUENCE: 926
gagggcgggu ggaggagga                                                 19

<210> SEQ ID NO 927
<211> LENGTH: 22
<212> TYPE: RNA
<213> ORGANISM: Homo sapiens

<400> SEQUENCE: 927
aaggccuuuc ugaaccuuca ga                                             22

<210> SEQ ID NO 928
<211> LENGTH: 25
<212> TYPE: RNA
<213> ORGANISM: Homo sapiens

<400> SEQUENCE: 928
auaacauugu aaagcgcuuc uuucg                                          25

<210> SEQ ID NO 929
<211> LENGTH: 23
<212> TYPE: RNA
<213> ORGANISM: Homo sapiens

<400> SEQUENCE: 929
caaagacugc aauuacuuuu gcg                                            23

<210> SEQ ID NO 930
<211> LENGTH: 22
<212> TYPE: RNA
<213> ORGANISM: Homo sapiens

<400> SEQUENCE: 930
aggggaccaa agagauauau ag                                             22

<210> SEQ ID NO 931
<211> LENGTH: 22
<212> TYPE: RNA
<213> ORGANISM: Homo sapiens

<400> SEQUENCE: 931
auauaccugu ucggucucuu ua                                             22

<210> SEQ ID NO 932
<211> LENGTH: 24
<212> TYPE: RNA
<213> ORGANISM: Homo sapiens

<400> SEQUENCE: 932
agauauuuug aguguuugga auug                                           24
```

```
<210> SEQ ID NO 933
<211> LENGTH: 22
<212> TYPE: RNA
<213> ORGANISM: Homo sapiens

<400> SEQUENCE: 933
ggcgacaaaa cgagacccug uc                                              22

<210> SEQ ID NO 934
<211> LENGTH: 22
<212> TYPE: RNA
<213> ORGANISM: Homo sapiens

<400> SEQUENCE: 934
caugcuagga uagaaagaau gg                                              22

<210> SEQ ID NO 935
<211> LENGTH: 24
<212> TYPE: RNA
<213> ORGANISM: Homo sapiens

<400> SEQUENCE: 935
gguugggcag ugaggagggu guga                                            24

<210> SEQ ID NO 936
<211> LENGTH: 22
<212> TYPE: RNA
<213> ORGANISM: Homo sapiens

<400> SEQUENCE: 936
agcuacaguu acuuuugcac ca                                              22

<210> SEQ ID NO 937
<211> LENGTH: 22
<212> TYPE: RNA
<213> ORGANISM: Homo sapiens

<400> SEQUENCE: 937
uggaaaaaac uggugugugc uu                                              22

<210> SEQ ID NO 938
<211> LENGTH: 23
<212> TYPE: RNA
<213> ORGANISM: Homo sapiens

<400> SEQUENCE: 938
uuuguaugga uaugugugug uau                                             23

<210> SEQ ID NO 939
<211> LENGTH: 22
<212> TYPE: RNA
<213> ORGANISM: Homo sapiens

<400> SEQUENCE: 939
cuggggagau ccucgagguu gg                                              22

<210> SEQ ID NO 940
<211> LENGTH: 21
<212> TYPE: RNA
<213> ORGANISM: Homo sapiens

<400> SEQUENCE: 940 ggugggcaa ugggaucagg u                                                21
```

<210> SEQ ID NO 941
<211> LENGTH: 22
<212> TYPE: RNA
<213> ORGANISM: Homo sapiens

<400> SEQUENCE: 941
uguguuagaa uagggcaau aa										22

<210> SEQ ID NO 942
<211> LENGTH: 23
<212> TYPE: RNA
<213> ORGANISM: Homo sapiens

<400> SEQUENCE: 942
ggggaaagcg aguagggaca uuu									23

<210> SEQ ID NO 943
<211> LENGTH: 22
<212> TYPE: RNA
<213> ORGANISM: Homo sapiens

<400> SEQUENCE: 943
gauaucagcu caguaggcac cg									22

<210> SEQ ID NO 944
<211> LENGTH: 22
<212> TYPE: RNA
<213> ORGANISM: Homo sapiens

<400> SEQUENCE: 944
cagaagggga guugggagca ga									22

<210> SEQ ID NO 945
<211> LENGTH: 21
<212> TYPE: RNA
<213> ORGANISM: Homo sapiens

<400> SEQUENCE: 945
ccaggcucug cagugggaac u										21

<210> SEQ ID NO 946
<211> LENGTH: 22
<212> TYPE: RNA
<213> ORGANISM: Homo sapiens

<400> SEQUENCE: 946
aaagaucugg aagugggaga ca									22

<210> SEQ ID NO 947
<211> LENGTH: 22
<212> TYPE: RNA
<213> ORGANISM: Homo sapiens

<400> SEQUENCE: 947
uucagccagg cuagugcagu cu									22

<210> SEQ ID NO 948
<211> LENGTH: 22
<212> TYPE: RNA
<213> ORGANISM: Homo sapiens

<400> SEQUENCE: 948
aagggcuucc ucucugcagg ac       22

<210> SEQ ID NO 949
<211> LENGTH: 22
<212> TYPE: RNA
<213> ORGANISM: Homo sapiens

<400> SEQUENCE: 949
uaggauuaca agugucggcc ac       22

<210> SEQ ID NO 950
<211> LENGTH: 22
<212> TYPE: RNA
<213> ORGANISM: Homo sapiens

<400> SEQUENCE: 950
agagcugaga cuagaaagcc ca       22

<210> SEQ ID NO 951
<211> LENGTH: 23
<212> TYPE: RNA
<213> ORGANISM: Homo sapiens

<400> SEQUENCE: 951
cugauaagaa cagaggccca gau      23

<210> SEQ ID NO 952
<211> LENGTH: 23
<212> TYPE: RNA
<213> ORGANISM: Homo sapiens

<400> SEQUENCE: 952
uuagggagua gaaggguggg gag      23

<210> SEQ ID NO 953
<211> LENGTH: 22
<212> TYPE: RNA
<213> ORGANISM: Homo sapiens

<400> SEQUENCE: 953
uauaaaauga gggcaguaag ac       22

<210> SEQ ID NO 954
<211> LENGTH: 22
<212> TYPE: RNA
<213> ORGANISM: Homo sapiens

<400> SEQUENCE: 954
ugugacuuua agggaaaugg cg       22

<210> SEQ ID NO 955
<211> LENGTH: 22
<212> TYPE: RNA
<213> ORGANISM: Homo sapiens

<400> SEQUENCE: 955
agguggaugc aaugugaccu ca       22

<210> SEQ ID NO 956
<211> LENGTH: 23
<212> TYPE: RNA
<213> ORGANISM: Homo sapiens

<400> SEQUENCE: 956
cgcagacaau gccuacuggc cua                                               23

<210> SEQ ID NO 957
<211> LENGTH: 19
<212> TYPE: RNA
<213> ORGANISM: Homo sapiens

<400> SEQUENCE: 957
aucccaccac ugccaccau                                                    19

<210> SEQ ID NO 958
<211> LENGTH: 22
<212> TYPE: RNA
<213> ORGANISM: Homo sapiens

<400> SEQUENCE: 958
aggauuucag aaauacuggu gu                                                22

<210> SEQ ID NO 959
<211> LENGTH: 17
<212> TYPE: RNA
<213> ORGANISM: Homo sapiens

<400> SEQUENCE: 959
gaguucuaca gucagac                                                      17

<210> SEQ ID NO 960
<211> LENGTH: 22
<212> TYPE: RNA
<213> ORGANISM: Homo sapiens

<400> SEQUENCE: 960
uaggacugug cuuggcacau ag                                                22

<210> SEQ ID NO 961
<211> LENGTH: 22
<212> TYPE: RNA
<213> ORGANISM: Homo sapiens

<400> SEQUENCE: 961 cuggguucu gagacagaca gu                                                 22

<210> SEQ ID NO 962
<211> LENGTH: 24
<212> TYPE: RNA
<213> ORGANISM: Homo sapiens

<400> SEQUENCE: 962
agauguaugg aaucuguaua uauc                                              24

<210> SEQ ID NO 963
<211> LENGTH: 19
<212> TYPE: RNA
<213> ORGANISM: Homo sapiens

<400> SEQUENCE: 963 uggguuuug caguccuua                                                     19

<210> SEQ ID NO 964
<211> LENGTH: 22
<212> TYPE: RNA
<213> ORGANISM: Homo sapiens

```
<400> SEQUENCE: 964
aaaggaggaa auaggcaggc ca                                              22

<210> SEQ ID NO 965
<211> LENGTH: 23
<212> TYPE: RNA
<213> ORGANISM: Homo sapiens

<400> SEQUENCE: 965
gggaugguag accggugacg ugc                                             23

<210> SEQ ID NO 966
<211> LENGTH: 23
<212> TYPE: RNA
<213> ORGANISM: Homo sapiens

<400> SEQUENCE: 966
agguuguccg uggugaguuc gca                                             23

<210> SEQ ID NO 967
<211> LENGTH: 22
<212> TYPE: RNA
<213> ORGANISM: Homo sapiens

<400> SEQUENCE: 967
cccaauacac ggucgaccuc uu                                              22

<210> SEQ ID NO 968
<211> LENGTH: 23
<212> TYPE: RNA
<213> ORGANISM: Homo sapiens

<400> SEQUENCE: 968
uagugaguua gagaugcaga gcc                                             23

<210> SEQ ID NO 969
<211> LENGTH: 22
<212> TYPE: RNA
<213> ORGANISM: Homo sapiens

<400> SEQUENCE: 969
cggggagaga acgcagugac gu                                              22

<210> SEQ ID NO 970
<211> LENGTH: 19
<212> TYPE: RNA
<213> ORGANISM: Homo sapiens

<400> SEQUENCE: 970
acuggccugg gacuaccgg                                                  19

<210> SEQ ID NO 971
<211> LENGTH: 21
<212> TYPE: RNA
<213> ORGANISM: Homo sapiens

<400> SEQUENCE: 971
ugcacggcac uggggacacg u                                               21

<210> SEQ ID NO 972
<211> LENGTH: 17
<212> TYPE: RNA
<213> ORGANISM: Homo sapiens
```

```
<400> SEQUENCE: 972
ggggcgcggc cggaucg                                                  17

<210> SEQ ID NO 973
<211> LENGTH: 22
<212> TYPE: RNA
<213> ORGANISM: Homo sapiens

<400> SEQUENCE: 973
agaaggggug aaauuuaaac gu                                            22

<210> SEQ ID NO 974
<211> LENGTH: 25
<212> TYPE: RNA
<213> ORGANISM: Homo sapiens

<400> SEQUENCE: 974
cuuccagacg cuccgcccca cgucg                                         25

<210> SEQ ID NO 975
<211> LENGTH: 22
<212> TYPE: RNA
<213> ORGANISM: Homo sapiens

<400> SEQUENCE: 975 ugggggcggag cuuccggagg cc                                           22

<210> SEQ ID NO 976
<211> LENGTH: 23
<212> TYPE: RNA
<213> ORGANISM: Homo sapiens

<400> SEQUENCE: 976
aaaaguaacu gcgguuuuug ccu                                           23

<210> SEQ ID NO 977
<211> LENGTH: 19
<212> TYPE: RNA
<213> ORGANISM: Homo sapiens

<400> SEQUENCE: 977
aucgggcccu cggcgccgg                                                19

<210> SEQ ID NO 978
<211> LENGTH: 17
<212> TYPE: RNA
<213> ORGANISM: Homo sapiens

<400> SEQUENCE: 978
gcuucuguag uguaguc                                                  17

<210> SEQ ID NO 979
<211> LENGTH: 22
<212> TYPE: RNA
<213> ORGANISM: Homo sapiens

<400> SEQUENCE: 979
gccucucucg gagucgcucg ga                                            22

<210> SEQ ID NO 980
<211> LENGTH: 24
<212> TYPE: RNA
```

```
<213> ORGANISM: Homo sapiens

<400> SEQUENCE: 980 ugagggccu cagaccgagc uuuu                                              24

<210> SEQ ID NO 981
<211> LENGTH: 23
<212> TYPE: RNA
<213> ORGANISM: Homo sapiens

<400> SEQUENCE: 981
agaagaaggc ggucggucug cgg                                              23

<210> SEQ ID NO 982
<211> LENGTH: 23
<212> TYPE: RNA
<213> ORGANISM: Homo sapiens

<400> SEQUENCE: 982
ucaacaaaau cacugaugcu gga                                              23

<210> SEQ ID NO 983
<211> LENGTH: 23
<212> TYPE: RNA
<213> ORGANISM: Homo sapiens

<400> SEQUENCE: 983
ucagcaccag gauauuguug gag                                              23

<210> SEQ ID NO 984
<211> LENGTH: 22
<212> TYPE: RNA
<213> ORGANISM: Homo sapiens

<400> SEQUENCE: 984
caggcgucug ucuacguggc uu                                               22

<210> SEQ ID NO 985
<211> LENGTH: 21
<212> TYPE: RNA
<213> ORGANISM: Homo sapiens

<400> SEQUENCE: 985
ucacgcggag agauggcuuu g                                                21

<210> SEQ ID NO 986
<211> LENGTH: 20
<212> TYPE: RNA
<213> ORGANISM: Homo sapiens

<400> SEQUENCE: 986
uuggccaugg ggcugcgcgg                                                  20

<210> SEQ ID NO 987
<211> LENGTH: 23
<212> TYPE: RNA
<213> ORGANISM: Homo sapiens

<400> SEQUENCE: 987
agaggcuuug ugcggauacg ggg                                              23

<210> SEQ ID NO 988
<211> LENGTH: 21
```

<212> TYPE: RNA
<213> ORGANISM: Homo sapiens

<400> SEQUENCE: 988
cccuuggguc ugauggggua g                                               21

<210> SEQ ID NO 989
<211> LENGTH: 18
<212> TYPE: RNA
<213> ORGANISM: Homo sapiens

<400> SEQUENCE: 989
aaagcugggu ugagaagg                                                   18

<210> SEQ ID NO 990
<211> LENGTH: 23
<212> TYPE: RNA
<213> ORGANISM: Homo sapiens

<400> SEQUENCE: 990
uguggaaggu agacggccag aga                                             23

<210> SEQ ID NO 991
<211> LENGTH: 22
<212> TYPE: RNA
<213> ORGANISM: Homo sapiens

<400> SEQUENCE: 991
uggaagguag acggccagag ag                                              22

<210> SEQ ID NO 992
<211> LENGTH: 23
<212> TYPE: RNA
<213> ORGANISM: Homo sapiens

<400> SEQUENCE: 992 ugggacgua gcuggccaga cag                                              23

<210> SEQ ID NO 993
<211> LENGTH: 23
<212> TYPE: RNA
<213> ORGANISM: Homo sapiens

<400> SEQUENCE: 993
ucugggaggu uguagcagug gaa                                             23

<210> SEQ ID NO 994
<211> LENGTH: 22
<212> TYPE: RNA
<213> ORGANISM: Homo sapiens

<400> SEQUENCE: 994
uccugcguag gaucugagga gu                                              22

<210> SEQ ID NO 995
<211> LENGTH: 21
<212> TYPE: RNA
<213> ORGANISM: Homo sapiens

<400> SEQUENCE: 995
ggccagccac caggagggcu g                                               21

<210> SEQ ID NO 996

```
<211> LENGTH: 17
<212> TYPE: RNA
<213> ORGANISM: Homo sapiens

<400> SEQUENCE: 996
cgcgccgggc ccgggutt                                              17

<210> SEQ ID NO 997
<211> LENGTH: 18
<212> TYPE: RNA
<213> ORGANISM: Homo sapiens

<400> SEQUENCE: 997
cggggcggca ggggccuc                                              18

<210> SEQ ID NO 998
<211> LENGTH: 21
<212> TYPE: RNA
<213> ORGANISM: Homo sapiens

<400> SEQUENCE: 998
uaaaaacugc aauuacuuuc a                                          21

<210> SEQ ID NO 999
<211> LENGTH: 23
<212> TYPE: RNA
<213> ORGANISM: Homo sapiens

<400> SEQUENCE: 999
ggaggcgcag gcucggaaag gcg                                        23

<210> SEQ ID NO 1000
<211> LENGTH: 22
<212> TYPE: RNA
<213> ORGANISM: Homo sapiens

<400> SEQUENCE: 1000
guggaguccu ggggaaugga ga                                         22

<210> SEQ ID NO 1001
<211> LENGTH: 23
<212> TYPE: RNA
<213> ORGANISM: Homo sapiens

<400> SEQUENCE: 1001
agggacugcc uuaggagaaa guu                                        23

<210> SEQ ID NO 1002
<211> LENGTH: 22
<212> TYPE: RNA
<213> ORGANISM: Homo sapiens

<400> SEQUENCE: 1002
caccuugcgc uacucagguc ug                                         22

<210> SEQ ID NO 1003
<211> LENGTH: 17
<212> TYPE: RNA
<213> ORGANISM: Homo sapiens

<400> SEQUENCE: 1003
gggauaugaa gaaaaau                                               17
```

<210> SEQ ID NO 1004
<211> LENGTH: 22
<212> TYPE: RNA
<213> ORGANISM: Homo sapiens

<400> SEQUENCE: 1004
uucucaagag ggaggcaauc au                                              22

<210> SEQ ID NO 1005
<211> LENGTH: 21
<212> TYPE: RNA
<213> ORGANISM: Homo sapiens

<400> SEQUENCE: 1005
auugacaccu cugugagugg a                                               21

<210> SEQ ID NO 1006
<211> LENGTH: 22
<212> TYPE: RNA
<213> ORGANISM: Homo sapiens

<400> SEQUENCE: 1006
uggaagggag aagagcuuua au                                              22

<210> SEQ ID NO 1007
<211> LENGTH: 25
<212> TYPE: RNA
<213> ORGANISM: Homo sapiens

<400> SEQUENCE: 1007
gaacccauga gguugaggcu gcagu                                           25

<210> SEQ ID NO 1008
<211> LENGTH: 18
<212> TYPE: RNA
<213> ORGANISM: Homo sapiens

<400> SEQUENCE: 1008
cagugcaaug uuuuccuu                                                   18

<210> SEQ ID NO 1009
<211> LENGTH: 17
<212> TYPE: RNA
<213> ORGANISM: Homo sapiens

<400> SEQUENCE: 1009
augugggcuc aggcuca                                                    17

<210> SEQ ID NO 1010
<211> LENGTH: 16
<212> TYPE: RNA
<213> ORGANISM: Homo sapiens

<400> SEQUENCE: 1010
ugccuuccug ucugug                                                     16

<210> SEQ ID NO 1011
<211> LENGTH: 25
<212> TYPE: RNA
<213> ORGANISM: Homo sapiens

<400> SEQUENCE: 1011
acuggacuug gagucagaag agugg                                           25

<210> SEQ ID NO 1012
<211> LENGTH: 17
<212> TYPE: RNA
<213> ORGANISM: Homo sapiens

<400> SEQUENCE: 1012
cagccugaca ggaacag                                                  17

<210> SEQ ID NO 1013
<211> LENGTH: 17
<212> TYPE: RNA
<213> ORGANISM: Homo sapiens

<400> SEQUENCE: 1013
gggagucuac agcaggg                                                  17

<210> SEQ ID NO 1014
<211> LENGTH: 20
<212> TYPE: RNA
<213> ORGANISM: Homo sapiens

<400> SEQUENCE: 1014
ucccacuacu ucacuuguga                                               20

<210> SEQ ID NO 1015
<211> LENGTH: 18
<212> TYPE: RNA
<213> ORGANISM: Homo sapiens

<400> SEQUENCE: 1015
gcuggugaca ugagaggc                                                 18

<210> SEQ ID NO 1016
<211> LENGTH: 22
<212> TYPE: RNA
<213> ORGANISM: Homo sapiens

<400> SEQUENCE: 1016
cugggacagg aggaggaggc ag                                            22

<210> SEQ ID NO 1017
<211> LENGTH: 18
<212> TYPE: RNA
<213> ORGANISM: Homo sapiens

<400> SEQUENCE: 1017
ugggagcugg acuacuuc                                                 18

<210> SEQ ID NO 1018
<211> LENGTH: 17
<212> TYPE: RNA
<213> ORGANISM: Homo sapiens

<400> SEQUENCE: 1018
ccggcauguc cagggca                                                  17

<210> SEQ ID NO 1019
<211> LENGTH: 18
<212> TYPE: RNA
<213> ORGANISM: Homo sapiens

<400> SEQUENCE: 1019
ccaguguggc ucagcgag                                                 18

```
<210> SEQ ID NO 1020
<211> LENGTH: 17
<212> TYPE: RNA
<213> ORGANISM: Homo sapiens

<400> SEQUENCE: 1020
uucugagcug aggacag                                                        17

<210> SEQ ID NO 1021
<211> LENGTH: 18
<212> TYPE: RNA
<213> ORGANISM: Homo sapiens

<400> SEQUENCE: 1021
ccuagacacc uccaguuc                                                       18

<210> SEQ ID NO 1022
<211> LENGTH: 17
<212> TYPE: RNA
<213> ORGANISM: Homo sapiens

<400> SEQUENCE: 1022
uggagagaaa ggcagua                                                        17

<210> SEQ ID NO 1023
<211> LENGTH: 18
<212> TYPE: RNA
<213> ORGANISM: Homo sapiens

<400> SEQUENCE: 1023
cuggagucua ggauucca                                                       18

<210> SEQ ID NO 1024
<211> LENGTH: 19
<212> TYPE: RNA
<213> ORGANISM: Homo sapiens

<400> SEQUENCE: 1024
aauguuuuuu ccuguuucc                                                      19

<210> SEQ ID NO 1025
<211> LENGTH: 18
<212> TYPE: RNA
<213> ORGANISM: Homo sapiens

<400> SEQUENCE: 1025
ucccuggagu uucuucuu                                                       18

<210> SEQ ID NO 1026
<211> LENGTH: 16
<212> TYPE: RNA
<213> ORGANISM: Homo sapiens

<400> SEQUENCE: 1026
gcagcauuca uguccc                                                         16

<210> SEQ ID NO 1027
<211> LENGTH: 18
<212> TYPE: RNA
<213> ORGANISM: Homo sapiens

<400> SEQUENCE: 1027
```

```
gaaagagagc ugagugug                                    18

<210> SEQ ID NO 1028
<211> LENGTH: 19
<212> TYPE: RNA
<213> ORGANISM: Homo sapiens

<400> SEQUENCE: 1028
ggccuuguuc cugucccca                                   19

<210> SEQ ID NO 1029
<211> LENGTH: 20
<212> TYPE: RNA
<213> ORGANISM: Homo sapiens

<400> SEQUENCE: 1029
agcccccugg ccccaaaccc                                  20

<210> SEQ ID NO 1030
<211> LENGTH: 18
<212> TYPE: RNA
<213> ORGANISM: Homo sapiens

<400> SEQUENCE: 1030
ccgcuuucug agcuggac                                    18

<210> SEQ ID NO 1031
<211> LENGTH: 17
<212> TYPE: RNA
<213> ORGANISM: Homo sapiens

<400> SEQUENCE: 1031
ggugaggcua gcuggug                                     17

<210> SEQ ID NO 1032
<211> LENGTH: 18
<212> TYPE: RNA
<213> ORGANISM: Homo sapiens

<400> SEQUENCE: 1032
cucugggaaa ugggacag                                    18

<210> SEQ ID NO 1033
<211> LENGTH: 17
<212> TYPE: RNA
<213> ORGANISM: Homo sapiens

<400> SEQUENCE: 1033
cacugugggu acaugcu                                     17

<210> SEQ ID NO 1034
<211> LENGTH: 17
<212> TYPE: RNA
<213> ORGANISM: Homo sapiens

<400> SEQUENCE: 1034
ucccugagca aagccac                                     17

<210> SEQ ID NO 1035
<211> LENGTH: 18
<212> TYPE: RNA
<213> ORGANISM: Homo sapiens

<400> SEQUENCE: 1035
```

| | |
|---|---|
| gggauucugu agcuuccu | 18 |

<210> SEQ ID NO 1036
<211> LENGTH: 17
<212> TYPE: RNA
<213> ORGANISM: Homo sapiens

<400> SEQUENCE: 1036

| | |
|---|---|
| acauugccag ggaguuu | 17 |

<210> SEQ ID NO 1037
<211> LENGTH: 21
<212> TYPE: RNA
<213> ORGANISM: Homo sapiens

<400> SEQUENCE: 1037

| | |
|---|---|
| cugugggcuc agcgcguggg g | 21 |

<210> SEQ ID NO 1038
<211> LENGTH: 21
<212> TYPE: RNA
<213> ORGANISM: Homo sapiens

<400> SEQUENCE: 1038

| | |
|---|---|
| uuagcggugg accgcccugc g | 21 |

<210> SEQ ID NO 1039
<211> LENGTH: 18
<212> TYPE: RNA
<213> ORGANISM: Homo sapiens

<400> SEQUENCE: 1039

| | |
|---|---|
| cagccccaca gccucaga | 18 |

<210> SEQ ID NO 1040
<211> LENGTH: 20
<212> TYPE: RNA
<213> ORGANISM: Homo sapiens

<400> SEQUENCE: 1040

| | |
|---|---|
| cccugagacc cuaaccuuaa | 20 |

<210> SEQ ID NO 1041
<211> LENGTH: 18
<212> TYPE: RNA
<213> ORGANISM: Homo sapiens

<400> SEQUENCE: 1041

| | |
|---|---|
| aucugaccug augaaggu | 18 |

<210> SEQ ID NO 1042
<211> LENGTH: 18
<212> TYPE: RNA
<213> ORGANISM: Homo sapiens

<400> SEQUENCE: 1042

| | |
|---|---|
| ccagaggugg ggacugag | 18 |

<210> SEQ ID NO 1043
<211> LENGTH: 17
<212> TYPE: RNA
<213> ORGANISM: Homo sapiens -continued

<400> SEQUENCE: 1043
ccccgccacc gccuugg                                                    17

<210> SEQ ID NO 1044
<211> LENGTH: 22
<212> TYPE: RNA
<213> ORGANISM: Homo sapiens

<400> SEQUENCE: 1044 caguggguc uagggucag ga                                                22

<210> SEQ ID NO 1045
<211> LENGTH: 19
<212> TYPE: RNA
<213> ORGANISM: Homo sapiens

<400> SEQUENCE: 1045
cuuggggcau ggagucca                                                   19

<210> SEQ ID NO 1046
<211> LENGTH: 18
<212> TYPE: RNA
<213> ORGANISM: Homo sapiens

<400> SEQUENCE: 1046
agggcauguc caggggu                                                    18

<210> SEQ ID NO 1047
<211> LENGTH: 17
<212> TYPE: RNA
<213> ORGANISM: Homo sapiens

<400> SEQUENCE: 1047
ccugagaaaa gggccaa                                                    17

<210> SEQ ID NO 1048
<211> LENGTH: 23
<212> TYPE: RNA
<213> ORGANISM: Homo sapiens

<400> SEQUENCE: 1048
gccuggagcu acuccaccau cuc                                             23

<210> SEQ ID NO 1049
<211> LENGTH: 17
<212> TYPE: RNA
<213> ORGANISM: Homo sapiens

<400> SEQUENCE: 1049
caguguucag agaugga                                                    17

<210> SEQ ID NO 1050
<211> LENGTH: 19
<212> TYPE: RNA
<213> ORGANISM: Homo sapiens

<400> SEQUENCE: 1050
ggccacugag ucagcacca                                                  19

<210> SEQ ID NO 1051
<211> LENGTH: 18
<212> TYPE: RNA
<213> ORGANISM: Homo sapiens

```
<400> SEQUENCE: 1051
uugcacuugu cucaguga                                              18

<210> SEQ ID NO 1052
<211> LENGTH: 20
<212> TYPE: RNA
<213> ORGANISM: Homo sapiens

<400> SEQUENCE: 1052
uguuccucug ucucccagac                                            20

<210> SEQ ID NO 1053
<211> LENGTH: 19
<212> TYPE: RNA
<213> ORGANISM: Homo sapiens

<400> SEQUENCE: 1053
ggcuugcaug ggggacugg                                             19

<210> SEQ ID NO 1054
<211> LENGTH: 16
<212> TYPE: RNA
<213> ORGANISM: Homo sapiens

<400> SEQUENCE: 1054
aggaaacagg gaccca                                                16

<210> SEQ ID NO 1055
<211> LENGTH: 19
<212> TYPE: RNA
<213> ORGANISM: Homo sapiens

<400> SEQUENCE: 1055
cugugggcuc agcucuggg                                             19

<210> SEQ ID NO 1056
<211> LENGTH: 16
<212> TYPE: RNA
<213> ORGANISM: Homo sapiens

<400> SEQUENCE: 1056
cuaggaggcc uuggcc                                                16

<210> SEQ ID NO 1057
<211> LENGTH: 16
<212> TYPE: RNA
<213> ORGANISM: Homo sapiens

<400> SEQUENCE: 1057
uccagcucgg uggcac                                                16

<210> SEQ ID NO 1058
<211> LENGTH: 17
<212> TYPE: RNA
<213> ORGANISM: Homo sapiens

<400> SEQUENCE: 1058
gacauucaga cuaccug                                               17

<210> SEQ ID NO 1059
<211> LENGTH: 21
<212> TYPE: RNA
```

<213> ORGANISM: Homo sapiens

<400> SEQUENCE: 1059
auccccagau acaauggaca a					21

<210> SEQ ID NO 1060
<211> LENGTH: 21
<212> TYPE: RNA
<213> ORGANISM: Homo sapiens

<400> SEQUENCE: 1060
ggcuccuccu cucaggaugu g					21

<210> SEQ ID NO 1061
<211> LENGTH: 21
<212> TYPE: RNA
<213> ORGANISM: Homo sapiens

<400> SEQUENCE: 1061
gcaggcacag acagcccugg c					21

<210> SEQ ID NO 1062
<211> LENGTH: 18
<212> TYPE: RNA
<213> ORGANISM: Homo sapiens

<400> SEQUENCE: 1062
auucuaagug ccuuggcc					18

<210> SEQ ID NO 1063
<211> LENGTH: 17
<212> TYPE: RNA
<213> ORGANISM: Homo sapiens

<400> SEQUENCE: 1063
acucagucau ggucauu					17

<210> SEQ ID NO 1064
<211> LENGTH: 20
<212> TYPE: RNA
<213> ORGANISM: Homo sapiens

<400> SEQUENCE: 1064
ucagggaguc aggggagggc					20

<210> SEQ ID NO 1065
<211> LENGTH: 19
<212> TYPE: RNA
<213> ORGANISM: Homo sapiens

<400> SEQUENCE: 1065
gggggaagaa aaggugggg					19

<210> SEQ ID NO 1066
<211> LENGTH: 18
<212> TYPE: RNA
<213> ORGANISM: Homo sapiens

<400> SEQUENCE: 1066
cauucaacua gugauugu					18

<210> SEQ ID NO 1067
<211> LENGTH: 18

```
<212> TYPE: RNA
<213> ORGANISM: Homo sapiens

<400> SEQUENCE: 1067
guguucucug auggacag                                          18

<210> SEQ ID NO 1068
<211> LENGTH: 17
<212> TYPE: RNA
<213> ORGANISM: Homo sapiens

<400> SEQUENCE: 1068
cucagugacu caugugc                                           17

<210> SEQ ID NO 1069
<211> LENGTH: 17
<212> TYPE: RNA
<213> ORGANISM: Homo sapiens

<400> SEQUENCE: 1069
ccaauuacca cuucuuu                                           17

<210> SEQ ID NO 1070
<211> LENGTH: 18
<212> TYPE: RNA
<213> ORGANISM: Homo sapiens

<400> SEQUENCE: 1070
cagcaguccc uccccug                                           18

<210> SEQ ID NO 1071
<211> LENGTH: 18
<212> TYPE: RNA
<213> ORGANISM: Homo sapiens

<400> SEQUENCE: 1071
ggaucccggg gagggggg                                          18

<210> SEQ ID NO 1072
<211> LENGTH: 21
<212> TYPE: RNA
<213> ORGANISM: Homo sapiens

<400> SEQUENCE: 1072
gcaguucuga gcacaguaca c                                      21

<210> SEQ ID NO 1073
<211> LENGTH: 16
<212> TYPE: RNA
<213> ORGANISM: Homo sapiens

<400> SEQUENCE: 1073
cucuccuccc ggcuuc                                            16

<210> SEQ ID NO 1074
<211> LENGTH: 18
<212> TYPE: RNA
<213> ORGANISM: Homo sapiens

<400> SEQUENCE: 1074
cuaggggguu ugcccuug                                          18

<210> SEQ ID NO 1075
```

```
<210> SEQ ID NO 1075
<211> LENGTH: 21
<212> TYPE: RNA
<213> ORGANISM: Homo sapiens

<400> SEQUENCE: 1075
gaguguaguu cugagcagag c                                              21

<210> SEQ ID NO 1076
<211> LENGTH: 18
<212> TYPE: RNA
<213> ORGANISM: Homo sapiens

<400> SEQUENCE: 1076
uaaaauuugc auccagga                                                  18

<210> SEQ ID NO 1077
<211> LENGTH: 18
<212> TYPE: RNA
<213> ORGANISM: Homo sapiens

<400> SEQUENCE: 1077
gcggcgaguc cgacucau                                                  18

<210> SEQ ID NO 1078
<211> LENGTH: 17
<212> TYPE: RNA
<213> ORGANISM: Homo sapiens

<400> SEQUENCE: 1078 ugggcucag cgaguuu                                                    17

<210> SEQ ID NO 1079
<211> LENGTH: 18
<212> TYPE: RNA
<213> ORGANISM: Homo sapiens

<400> SEQUENCE: 1079
gggcucacau caccccau                                                  18

<210> SEQ ID NO 1080
<211> LENGTH: 17
<212> TYPE: RNA
<213> ORGANISM: Homo sapiens

<400> SEQUENCE: 1080
accccacucc ugguacc                                                   17

<210> SEQ ID NO 1081
<211> LENGTH: 19
<212> TYPE: RNA
<213> ORGANISM: Homo sapiens

<400> SEQUENCE: 1081
ucucccuuga gggcacuuu                                                 19

<210> SEQ ID NO 1082
<211> LENGTH: 17
<212> TYPE: RNA
<213> ORGANISM: Homo sapiens

<400> SEQUENCE: 1082
uugucugcug aguuucc                                                   17
```

```
<210> SEQ ID NO 1083
<211> LENGTH: 18
<212> TYPE: RNA
<213> ORGANISM: Homo sapiens

<400> SEQUENCE: 1083
ccccugggcc ggccuugg                                                 18

<210> SEQ ID NO 1084
<211> LENGTH: 19
<212> TYPE: RNA
<213> ORGANISM: Homo sapiens

<400> SEQUENCE: 1084
gcauugugca gggcuauca                                                19

<210> SEQ ID NO 1085
<211> LENGTH: 19
<212> TYPE: RNA
<213> ORGANISM: Homo sapiens

<400> SEQUENCE: 1085
ugcccuccuu ucuucccuc                                                19

<210> SEQ ID NO 1086
<211> LENGTH: 16
<212> TYPE: RNA
<213> ORGANISM: Homo sapiens

<400> SEQUENCE: 1086
uucagcagga acagcu                                                   16

<210> SEQ ID NO 1087
<211> LENGTH: 19
<212> TYPE: RNA
<213> ORGANISM: Homo sapiens

<400> SEQUENCE: 1087
ccugagaccc uaguuccac                                                19

<210> SEQ ID NO 1088
<211> LENGTH: 19
<212> TYPE: RNA
<213> ORGANISM: Homo sapiens

<400> SEQUENCE: 1088
ccucagauca gagccuugc                                                19

<210> SEQ ID NO 1089
<211> LENGTH: 18
<212> TYPE: RNA
<213> ORGANISM: Homo sapiens

<400> SEQUENCE: 1089
aauccuugcu accugggu                                                 18

<210> SEQ ID NO 1090
<211> LENGTH: 17
<212> TYPE: RNA
<213> ORGANISM: Homo sapiens

<400> SEQUENCE: 1090
ccaguuuucc caggauu                                                  17
```

<210> SEQ ID NO 1091
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: ribose

<400> SEQUENCE: 1091
gcauucaccg cgugccuuaa au                                              22

<210> SEQ ID NO 1092
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: ribose

<400> SEQUENCE: 1092
uuaaggcacg cggugaaugc ca                                              22

<210> SEQ ID NO 1093
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (19)..(20)
<223> OTHER INFORMATION: C3-spacer
<220> FEATURE:
<221> NAME/KEY: misc_feature
<222> LOCATION: (20)..(20)
<223> OTHER INFORMATION: 2'-O-methyl

<400> SEQUENCE: 1093
uaaggcacgc ggugaaugca                                                 20

<210> SEQ ID NO 1094
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1094
uaaggcacgc ggugaaugca                                                 20

<210> SEQ ID NO 1095
<211> LENGTH: 20

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1095
uaaggcacgc ggugaaucca                                               20

<210> SEQ ID NO 1096
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1096
uaaggcacgc ggugaagcca                                               20

<210> SEQ ID NO 1097
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1097
uaaggcacgc ggugaugcca                                               20

<210> SEQ ID NO 1098
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
```

```
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1098
uaaggcacgc ggugaugcca                                                     20

<210> SEQ ID NO 1099
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1099
uaaggcacgc gguaaugcca                                                     20

<210> SEQ ID NO 1100
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1100
uaaggcacgc gggaaugcca                                                     20

<210> SEQ ID NO 1101
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: C3-spacer
<220> FEATURE:
<221> NAME/KEY: misc_feature
```

<222> LOCATION: (19)..(20)
<223> OTHER INFORMATION: 2'-O-methyl

<400> SEQUENCE: 1101
uaaggcacgc gugaaugcca                                                        20

<210> SEQ ID NO 1102
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1102
uaaggcacgc gugaaugcca                                                        20

<210> SEQ ID NO 1103
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1103
uaaggcacgg gugaaugcca                                                        20

<210> SEQ ID NO 1104
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1104
uaaggcaccg gugaaugcca                                                        20

```
<210> SEQ ID NO 1105
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1105
uaaggcagcg gugaaugcca                                               20

<210> SEQ ID NO 1106
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1106
uaaggccgcg gugaaugcca                                               20

<210> SEQ ID NO 1107
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1107
uaaggacgcg gugaaugcca                                               20

<210> SEQ ID NO 1108
<211> LENGTH: 20
<212> TYPE: RNA
<213> ORGANISM: Artificial Sequence
<220> FEATURE:
<223> OTHER INFORMATION: Synthetic
```

-continued

```
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1108
uaagcacgcg gugaaugcca                                                    20

<210> SEQ ID NO 1109
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1109
uaagcacgcg gugaaugcca                                                    20

<210> SEQ ID NO 1110
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (2)..(3)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1110
uaggcacgcg gugaaugcca                                                    20

<210> SEQ ID NO 1111
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (1)..(2)
```

<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1111
uaggcacgcg gugaaugcca                                                    20

<210> SEQ ID NO 1112
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C6-spacer
<220> FEATURE:
<221> NAME/KEY: misc_feature
<222> LOCATION: (19)..(19)
<223> OTHER INFORMATION: 2'-O-methyl

<400> SEQUENCE: 1112
uaaggcacgc ggugaauga                                                     19

<210> SEQ ID NO 1113
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1113
uaaggcacgc ggugaauca                                                     19

<210> SEQ ID NO 1114
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1114
uaaggcacgc ggugaacca                                                19

<210> SEQ ID NO 1115
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1115
uaaggcacgc ggugagcca                                                19

<210> SEQ ID NO 1116
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1116
uaaggcacgc ggugugcca                                                19

<210> SEQ ID NO 1117
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1117
uaaggcacgc gguaugcca                                                19

<210> SEQ ID NO 1118
<211> LENGTH: 19
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1118
uaaggcacgc ggaaugcca                                                19

<210> SEQ ID NO 1119
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1119
uaaggcacgc ggaaugcca                                                19

<210> SEQ ID NO 1120
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1120
uaaggcacgc ugaaugcca                                                19

<210> SEQ ID NO 1121
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
```

```
<220> FEATURE:
<221> NAME/KEY: misc_feature
<222> LOCATION: (9)..(10)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1121
uaaggcacgg ugaaugcca                                                    19

<210> SEQ ID NO 1122
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1122
uaaggcacgg ugaaugcca                                                    19

<210> SEQ ID NO 1123
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: C6-spacer
<220> FEATURE:
<221> NAME/KEY: misc_feature
<222> LOCATION: (18)..(19)
<223> OTHER INFORMATION: 2'-O-methyl

<400> SEQUENCE: 1123
uaaggcacgg ugaaugcca                                                    19

<210> SEQ ID NO 1124
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: C6-spacer
<220> FEATURE:
<221> NAME/KEY: misc_feature
<222> LOCATION: (18)..(19)
```

<223> OTHER INFORMATION: 2'-O-methyl

<400> SEQUENCE: 1124
uaaggcgcgg ugaaugcca                                              19

<210> SEQ ID NO 1125
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides modified or unmodified as
      described
<220> FEATURE:
<221> NAME/KEY: misc_feature
<222> LOCATION: (1)..(1)
<223> OTHER INFORMATION: deoxy
<220> FEATURE:
<221> NAME/KEY: misc_feature
<222> LOCATION: (1)..(1)
<223> OTHER INFORMATION: inverted abasic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: deoxy
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: deoxy
<220> FEATURE:
<221> NAME/KEY: misc_feature
<222> LOCATION: (18)..(18)
<223> OTHER INFORMATION: 2'-deoxy-2'-fluoro
<220> FEATURE:

```
<221> NAME/KEY: misc_feature
<222> LOCATION: (19)..(19)
<223> OTHER INFORMATION: deoxy
<220> FEATURE:
<221> NAME/KEY: misc_feature
<222> LOCATION: (21)..(21)
<223> OTHER INFORMATION: inverted abasic

<400> SEQUENCE: 1125
guaugaccga cuacgcguat t                                              21

<210> SEQ ID NO 1126
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1126
uacgcguagu cggucauacu u                                              21
```

```
<210> SEQ ID NO 1127
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: ribose

<400> SEQUENCE: 1127
uuaaggcacg cggugaaugc ca                                              22

<210> SEQ ID NO 1128
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: ribose
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1128
uaaggcacgc ggugaaugcc a                                               21

<210> SEQ ID NO 1129
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1129
uaaggcacgc ggugaaugcc a                                               21

<210> SEQ ID NO 1130
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides modified or unmodified as
      described
<220> FEATURE:
<221> NAME/KEY: misc_feature
<222> LOCATION: (1)..(3)
<223> OTHER INFORMATION: deoxy
```

```
<220> FEATURE:
<221> NAME/KEY: misc_feature
<222> LOCATION: (1)..(1)
<223> OTHER INFORMATION: inverted abasic
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: deoxy
<220> FEATURE:
<221> NAME/KEY: misc_feature
<222> LOCATION: (7)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: deoxy
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic

<400> SEQUENCE: 1130
aggucaucca ugacaacuut t                                              21

<210> SEQ ID NO 1131
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
```

```
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-O-methyl
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1131
aaguugucau ggaugaccuu u                                              21

<210> SEQ ID NO 1132
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides modified or unmodified as
      described
<220> FEATURE:
<221> NAME/KEY: misc_feature
<222> LOCATION: (1)..(19)
<223> OTHER INFORMATION: ribose

<400> SEQUENCE: 1132
uccagauugu ccgcaacuat t                                              21

<210> SEQ ID NO 1133
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides modifed or unmodified as
      described
<220> FEATURE:
<221> NAME/KEY: misc_feature
<222> LOCATION: (1)..(19)
<223> OTHER INFORMATION: ribose

<400> SEQUENCE: 1133
uaguugcgga caaucuggat t                                              21

<210> SEQ ID NO 1134
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: ribose

<400> SEQUENCE: 1134
```

```
gcauucaccg cgugccuuaa u                                              21

<210> SEQ ID NO 1135
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1135
uuaagagaag ccuuacuggu u                                              21

<210> SEQ ID NO 1136
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1136
uuaagagaag ccuucugguu                                                20

<210> SEQ ID NO 1137
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1137
uuaagagaag ccuuaugguu                                                20

<210> SEQ ID NO 1138
<211> LENGTH: 20
<212> TYPE: RNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1138
uuaagagaag ccuuacgguu                                                  20

<210> SEQ ID NO 1139
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1139
uuaagagaag ccuuacuguu                                                  20

<210> SEQ ID NO 1140
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1140
uuaagagaag ccuuacuguu                                                  20

<210> SEQ ID NO 1141
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
```

```
<220> FEATURE:
<221> NAME/KEY: misc_feature
<222> LOCATION: (19)..(20)
<223> OTHER INFORMATION: 2'-O-methyl

<400> SEQUENCE: 1141
uuucaauugu augugagguu                                                    20

<210> SEQ ID NO 1142
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1142
auggauuccu ucaggacguu                                                    20

<210> SEQ ID NO 1143
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1143
uuacuuugac agucauacuu                                                    20

<210> SEQ ID NO 1144
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1144
```
uuugggacga auguaugcuu                                              20

<210> SEQ ID NO 1145
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1145
uuagaauagu ugaggaacuu                                              20

<210> SEQ ID NO 1146
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1146
auuggcuguu agaaugcguu                                              20

<210> SEQ ID NO 1147
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1147
ucuccauuca uuccuaucuu                                              20

<210> SEQ ID NO 1148
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1148
uuugcuucau uauaggaguu                                              20

<210> SEQ ID NO 1149
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1149
uuuugcuuca uuauagggou                                              20

<210> SEQ ID NO 1150
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1150
ugaggacuug agggcugcuu                                              20

<210> SEQ ID NO 1151
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:

```
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1151
aaauuuguua guuagagguu                                               20

<210> SEQ ID NO 1152
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1152
gcugcacucc uucugcuguu                                               20

<210> SEQ ID NO 1153
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1153
ucaaauucua uuaucucuuu                                               20

<210> SEQ ID NO 1154
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl
```

<400> SEQUENCE: 1154
aaccuugaua ucuuugaguu                                          20

<210> SEQ ID NO 1155
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1155
acaucauuau cuguaaucuu                                          20

<210> SEQ ID NO 1156
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1156
ugcagcaagc ugcugaaguu                                          20

<210> SEQ ID NO 1157
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1157
uugaucuaaa ugcauugguu                                          20

<210> SEQ ID NO 1158

```
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1158
aacaaaguau uugacacguu                                               20

<210> SEQ ID NO 1159
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1159
uccuauacug gcuucuaguu                                               20

<210> SEQ ID NO 1160
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1160
uuaagagaag ccuucugguu                                               20

<210> SEQ ID NO 1161
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1161
aaucaaauga uugcuuuuuu                                              20

<210> SEQ ID NO 1162
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1162
uucaguguga ugacacuguu                                              20

<210> SEQ ID NO 1163
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1163
ugguauucag ugugaugcuu                                              20

<210> SEQ ID NO 1164
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
```

```
<221> NAME/KEY: misc_feature
<222> LOCATION: (19)..(20)
<223> OTHER INFORMATION: 2'-O-methyl

<400> SEQUENCE: 1164
uugguauuca gugugauauu                                               20

<210> SEQ ID NO 1165
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1165
uucccucuaa uuuguacguu                                               20

<210> SEQ ID NO 1166
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1166
ugguauuucc auuaagucuu                                               20

<210> SEQ ID NO 1167
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1167
aagcugaacu ugugaucauu                                               20
```

<210> SEQ ID NO 1168
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1168
ugauuaaucu ugauuuccuu                                              20

<210> SEQ ID NO 1169
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1169
uuuauaguag ucuacaaguu                                              20

<210> SEQ ID NO 1170
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1170
uuucaauugu augugagauu                                              20

<210> SEQ ID NO 1171
<211> LENGTH: 20
<212> TYPE: RNA
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1171
auggauuccu ucaggacuuu                                           20

<210> SEQ ID NO 1172
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1172
uuacuuugac agucauacuu                                           20

<210> SEQ ID NO 1173
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1173
uuugggacga auguaugcuu                                           20

<210> SEQ ID NO 1174
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature

```
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1174
uuagaauagu ugaggaaguu                                                    20

<210> SEQ ID NO 1175
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1175
auuggcuguu agaaugcuuu                                                    20

<210> SEQ ID NO 1176
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1176
ucuccauuca uuccuauauu                                                    20

<210> SEQ ID NO 1177
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl
```

```
<400> SEQUENCE: 1177
uuugcuucau uauaggaguu                                                    20

<210> SEQ ID NO 1178
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1178
uuuugcuuca uuauaggauu                                                    20

<210> SEQ ID NO 1179
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1179
ugaggacuug agggcugguu                                                    20

<210> SEQ ID NO 1180
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1180
aaauuuguua guuagagauu                                                    20

<210> SEQ ID NO 1181
<211> LENGTH: 20
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1181
gcugcacucc uucugcuuuu                                          20

<210> SEQ ID NO 1182
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1182
ucaaauucua uuaucucauu                                          20

<210> SEQ ID NO 1183
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1183
aaccuugaua ucuuugacuu                                          20

<210> SEQ ID NO 1184
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
```

```
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1184
acaucauuau cuguaauuuu                                         20

<210> SEQ ID NO 1185
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1185
ugcagcaagc ugcugaauuu                                         20

<210> SEQ ID NO 1186
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1186
uugaucuaaa ugcauuguuu                                         20

<210> SEQ ID NO 1187
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
```

```
<222> LOCATION: (19)..(20)
<223> OTHER INFORMATION: 2'-O-methyl

<400> SEQUENCE: 1187
uugaucuaaa ugcauuguuu                                                   20

<210> SEQ ID NO 1188
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1188
uccuauacug gcuucuauuu                                                   20

<210> SEQ ID NO 1189
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1189
auuucaggaa uuguuaaauu                                                   20

<210> SEQ ID NO 1190
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1190
aaucaaauga uugcuuuguu                                                   20
```

```
<210> SEQ ID NO 1191
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1191
uucaguguga ugacacuuuu                                                  20

<210> SEQ ID NO 1192
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1192
ugguauucag ugugaugauu                                                  20

<210> SEQ ID NO 1193
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1193
uugguauuca gugugauguu                                                  20

<210> SEQ ID NO 1194
<211> LENGTH: 20
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1194
uucccucuaa uuuguacuuu                                              20

<210> SEQ ID NO 1195
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1195
ugguauuucc auuaaguuuu                                              20

<210> SEQ ID NO 1196
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1196
aagcugaacu ugugaucauu                                              20

<210> SEQ ID NO 1197
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
```

```
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1197
ugauuaaucu ugauuucuuu                                               20

<210> SEQ ID NO 1198
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: C3-spacer
<220> FEATURE:
<221> NAME/KEY: misc_feature
<222> LOCATION: (19)..(20)
<223> OTHER INFORMATION: 2'-O-methyl

<400> SEQUENCE: 1198
uuuauaguag ucuacaaauu                                               20

<210> SEQ ID NO 1199
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1199
uuucaauugu augugagagu u                                             21

<210> SEQ ID NO 1200
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1200
auggauuccu ucaggacugu u                                             21

<210> SEQ ID NO 1201
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1201
uuacuuugac agucauaccu u                                              21

<210> SEQ ID NO 1202
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1202
uuugggacga auguaugccu u                                              21

<210> SEQ ID NO 1203
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1203
uuagaauagu ugaggaagcu u                                              21

<210> SEQ ID NO 1204
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: 2'-deoxy-2'-fluoro
<220> FEATURE:
<221> NAME/KEY: misc_feature
<222> LOCATION: (21)..(22)
<223> OTHER INFORMATION: 2'-O-methyl

<400> SEQUENCE: 1204
auuggcuguu agaaugcugu u                                              21

<210> SEQ ID NO 1205
<211> LENGTH: 21
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1205
ucuccauuca uuccuauacu u                                              21

<210> SEQ ID NO 1206
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1206
uuugcuucau uauaggaggu u                                              21

<210> SEQ ID NO 1207
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1207
uuuugcuuca uuauaggagu u                                              21

<210> SEQ ID NO 1208
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1208
ugaggacuug agggcuggcu u                                              21

<210> SEQ ID NO 1209
<211> LENGTH: 21
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1209
aaauuuguua guuagagagu u                                       21

<210> SEQ ID NO 1210
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1210
gcugcacucc uucugcuugu u                                       21

<210> SEQ ID NO 1211
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1211
ucaaauucua uuaucucauu u                                       21

<210> SEQ ID NO 1212
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1212
aaccuugaua ucuuugacgu u                                       21

<210> SEQ ID NO 1213
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1213
acaucauuau cuguaauucu u                                     21

<210> SEQ ID NO 1214
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1214
ugcagcaagc ugcugaaugu u                                     21

<210> SEQ ID NO 1215
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1215
uugaucuaaa ugcauugugu u                                     21

<210> SEQ ID NO 1216
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1216
aacaaaguau uugacacggu u                                     21
```

```
<210> SEQ ID NO 1217
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1217
uccuauacug gcuucuaugu u                                             21

<210> SEQ ID NO 1218
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1218
auuucaggaa uuguuaaagu u                                             21

<210> SEQ ID NO 1219
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1219
aaucaaauga uugcuuuguu u                                             21

<210> SEQ ID NO 1220
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1220
uucaguguga ugacacuugu u                                             21
```

```
<210> SEQ ID NO 1221
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1221
ugguauucag ugugaugacu u                                          21

<210> SEQ ID NO 1222
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1222
uugguauuca gugugaugau u                                          21

<210> SEQ ID NO 1223
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1223
uucccucuaa uuuguacugu u                                          21

<210> SEQ ID NO 1224
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1224
ugguauuucc auuaaguucu u                                          21
```

```
<210> SEQ ID NO 1225
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1225
aagcugaacu ugugaucaau u                                         21

<210> SEQ ID NO 1226
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1226
ugauuaaucu ugauuucucu u                                         21

<210> SEQ ID NO 1227
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 1227
uuuauaguag ucuacaaagu u                                         21
```